United States Patent
Roche et al.

(10) Patent No.: US 11,992,424 B2
(45) Date of Patent: May 28, 2024

(54) MEASUREMENT SYSTEM FOR A SELECTION OF AT LEAST ONE PROSTHETIC COMPONENT OF A SHOULDER JOINT DURING SURGERY

(71) Applicants: Chris Roche, Gainesville, FL (US); Alexander Greene, Gainesville, FL (US); Jonathan Trousdale, Davie, FL (US); Joseph DeCerce, Fort Lauderdale, FL (US)

(72) Inventors: Chris Roche, Gainesville, FL (US); Alexander Greene, Gainesville, FL (US); Jonathan Trousdale, Davie, FL (US); Joseph DeCerce, Fort Lauderdale, FL (US)

(73) Assignees: HOWMEDICA OSTEONICS CORP., Mahwa, NJ (US); EXACTECH, INC., Gainesville, FL (US)

( * ) Notice: Subject to any disclaimer, the term of this patent is extended or adjusted under 35 U.S.C. 154(b) by 233 days.

(21) Appl. No.: 16/951,771

(22) Filed: Nov. 18, 2020

(65) Prior Publication Data
US 2021/0137703 A1 May 13, 2021

Related U.S. Application Data

(63) Continuation-in-part of application No. 16/592,355, filed on Oct. 3, 2019, now Pat. No. 11,684,492, and (Continued)

(51) Int. Cl.
A61F 2/46 (2006.01)
A61F 2/30 (2006.01)
A61F 2/40 (2006.01)

(52) U.S. Cl.
CPC ........ *A61F 2/4657* (2013.01); *A61F 2/30749* (2013.01); *A61F 2/4612* (2013.01); (Continued)

(58) Field of Classification Search
CPC .... A61F 2/4657; A61F 2/4684; A61F 2/4014; A61F 2/4081; A61F 2002/4029; (Continued)

(56) References Cited

U.S. PATENT DOCUMENTS

| | | |
|---|---|---|
| 6,379,386 B1 | 4/2002 | Resch et al. |
| 6,530,957 B1 | 3/2003 | Jack |

(Continued)

*Primary Examiner* — Kevin T Truong
*Assistant Examiner* — Diana Jones
(74) *Attorney, Agent, or Firm* — Bookoff McAndrews, PLLC

(57) ABSTRACT

A selection system comprises a ring, a plurality of shims, a measurement device, and at least one glenoid component. The ring is configured to couple to a humerus. A shim of the plurality of shims is configured to couple to the ring. The measurement device is configured to couple to the shim. Each shim of the plurality of shims has a different height when coupled to the ring. The selection system generates measurement data to support the selection of at least one prosthetic component for a shoulder joint in a surgical environment. The shoulder joint geometry can be adjusted by changing shims, changing glenoid component or both. The selection system is removed after the selection of the final prosthetic components for the shoulder joint. The final prosthetic components are installed in the shoulder joint. The measurement device is placed in the shoulder joint and measurement data is generated to verify performance.

11 Claims, 50 Drawing Sheets

Related U.S. Application Data a continuation-in-part of application No. 16/592,409, filed on Oct. 3, 2019, now Pat. No. 11,534,315, and a continuation-in-part of application No. 16/592,443, filed on Oct. 3, 2019, now Pat. No. 11,660,211.

(60) Provisional application No. 62/742,179, filed on Oct. 5, 2018, provisional application No. 62/742,207, filed on Oct. 5, 2018.

(52) U.S. Cl.
CPC ...... *A61F 2/4684* (2013.01); *A61F 2002/302* (2013.01); *A61F 2002/30245* (2013.01); *A61F 2002/30649* (2013.01); *A61F 2002/4007* (2013.01); *A61F 2002/4085* (2013.01); *A61F 2002/4633* (2013.01); *A61F 2002/4666* (2013.01)

(58) Field of Classification Search
CPC ............. A61F 2002/4666; A61B 34/10; A61B 2034/105; A61B 2034/108
See application file for complete search history.

(56) References Cited

U.S. PATENT DOCUMENTS

| | | |
|---|---|---|
| 6,676,705 B1 | 1/2004 | Wolf |
| 6,776,799 B2 | 8/2004 | Ball et al. |
| 7,309,360 B2 | 12/2007 | Tornier et al. |
| 7,621,961 B2 | 11/2009 | Stone |
| 7,780,681 B2 | 8/2010 | Sarin et al. |
| 7,918,892 B2 | 4/2011 | Huebner |
| 8,078,254 B2 | 12/2011 | Murphy |
| 8,096,933 B2 | 1/2012 | Kelman |
| 8,109,942 B2 | 2/2012 | Carson |
| 8,241,296 B2 | 8/2012 | Wasielewski |
| 8,273,093 B2 | 9/2012 | Klotz et al. |
| 8,486,070 B2 | 7/2013 | Morgan et al. |
| 8,494,805 B2 | 7/2013 | Roche et al. |
| 8,647,387 B2 | 2/2014 | Winslow |
| 8,974,467 B2 | 3/2015 | Stone |
| 9,011,549 B2 | 4/2015 | Splieth et al. |
| 9,017,335 B2 | 4/2015 | Stiehl |
| 9,301,812 B2 | 4/2016 | Kehres et al. |
| 9,414,927 B2 | 8/2016 | Iannotti et al. |
| 9,452,055 B2 | 9/2016 | Lappin |
| 9,572,682 B2 | 2/2017 | Aghazadeh |
| 9,622,869 B2 | 4/2017 | Nerot et al. |
| 9,649,160 B2 | 5/2017 | van der Walt et al. |
| 9,962,266 B2 | 5/2018 | Humphrey |
| 10,034,759 B2 | 7/2018 | Deransart et al. |
| 2004/0230199 A1 | 11/2004 | Jansen et al. |
| 2006/0224088 A1 | 10/2006 | Roche |
| 2007/0179625 A1 | 8/2007 | Ekholm et al. |
| 2008/0146969 A1 | 6/2008 | Kurtz |
| 2009/0030349 A1 | 1/2009 | Cowin |
| 2009/0125117 A1 | 5/2009 | Paradis |
| 2009/0171370 A1 | 7/2009 | Yoon et al. |
| 2010/0023068 A1 | 1/2010 | Bouttens et al. |
| 2010/0137871 A1 | 6/2010 | Borja |
| 2013/0053904 A1 | 2/2013 | Penenberg |
| 2013/0066323 A1 | 3/2013 | Nycz et al. |
| 2013/0090737 A1* | 4/2013 | Flaherty .............. A61F 2/30749 623/19.13 |
| 2014/0135658 A1 | 5/2014 | Hladio et al. |
| 2014/0135773 A1 | 5/2014 | Stein et al. |
| 2014/0330105 A1 | 11/2014 | Roche |
| 2015/0238691 A1* | 8/2015 | Boyden .................... A61B 5/11 604/66 |
| 2015/0297354 A1 | 10/2015 | Walch et al. |
| 2015/0297362 A1 | 10/2015 | Singh et al. |
| 2017/0007330 A1* | 1/2017 | Britton ................. A61B 5/4528 |
| 2017/0079799 A1 | 3/2017 | Smith et al. |
| 2017/0079803 A1 | 3/2017 | Lang |
| 2018/0116805 A1* | 5/2018 | Johannaber ............ A61B 34/25 |
| 2018/0161168 A1* | 6/2018 | Johannaber ............ A61B 34/20 |

\* cited by examiner

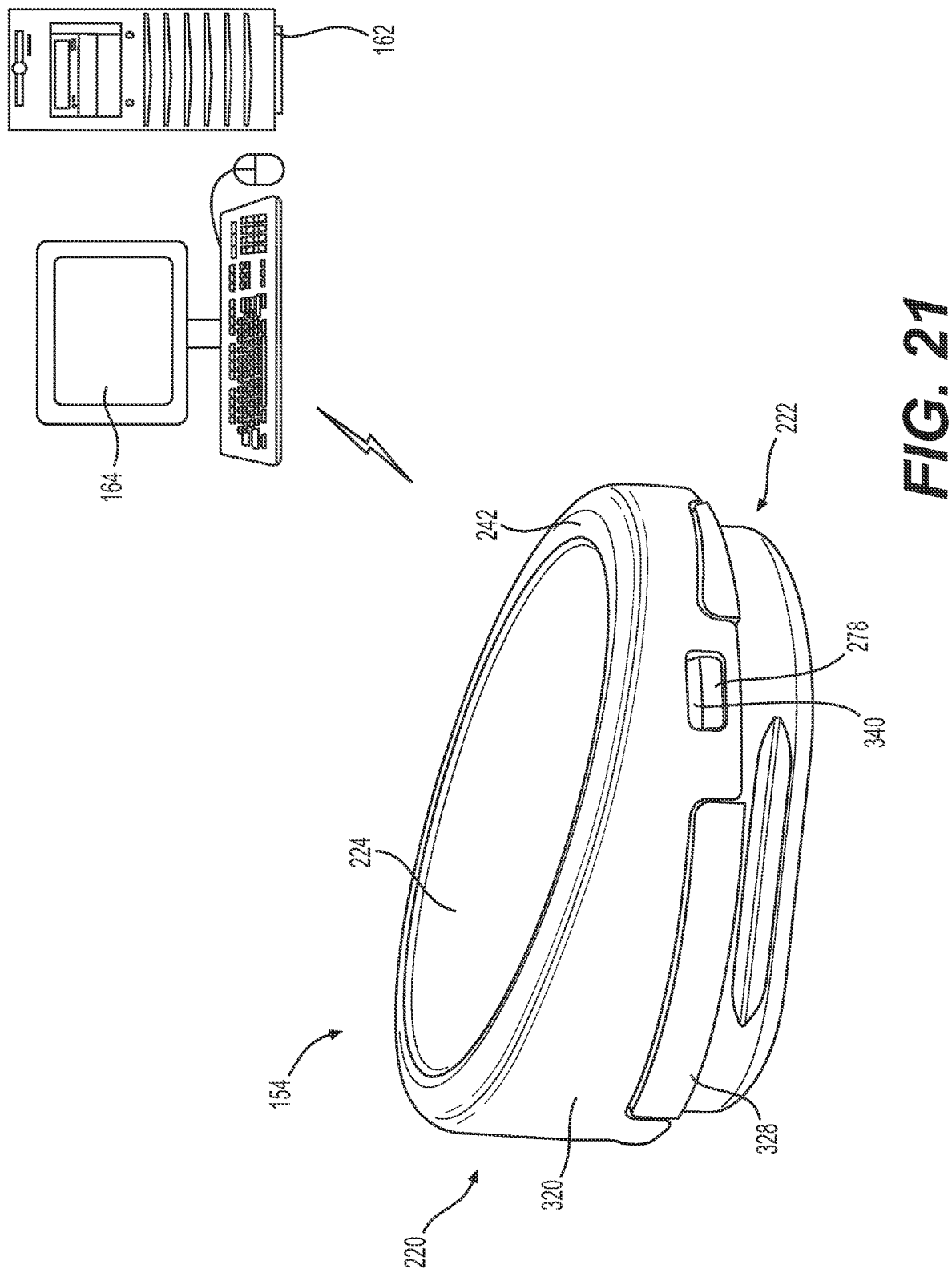

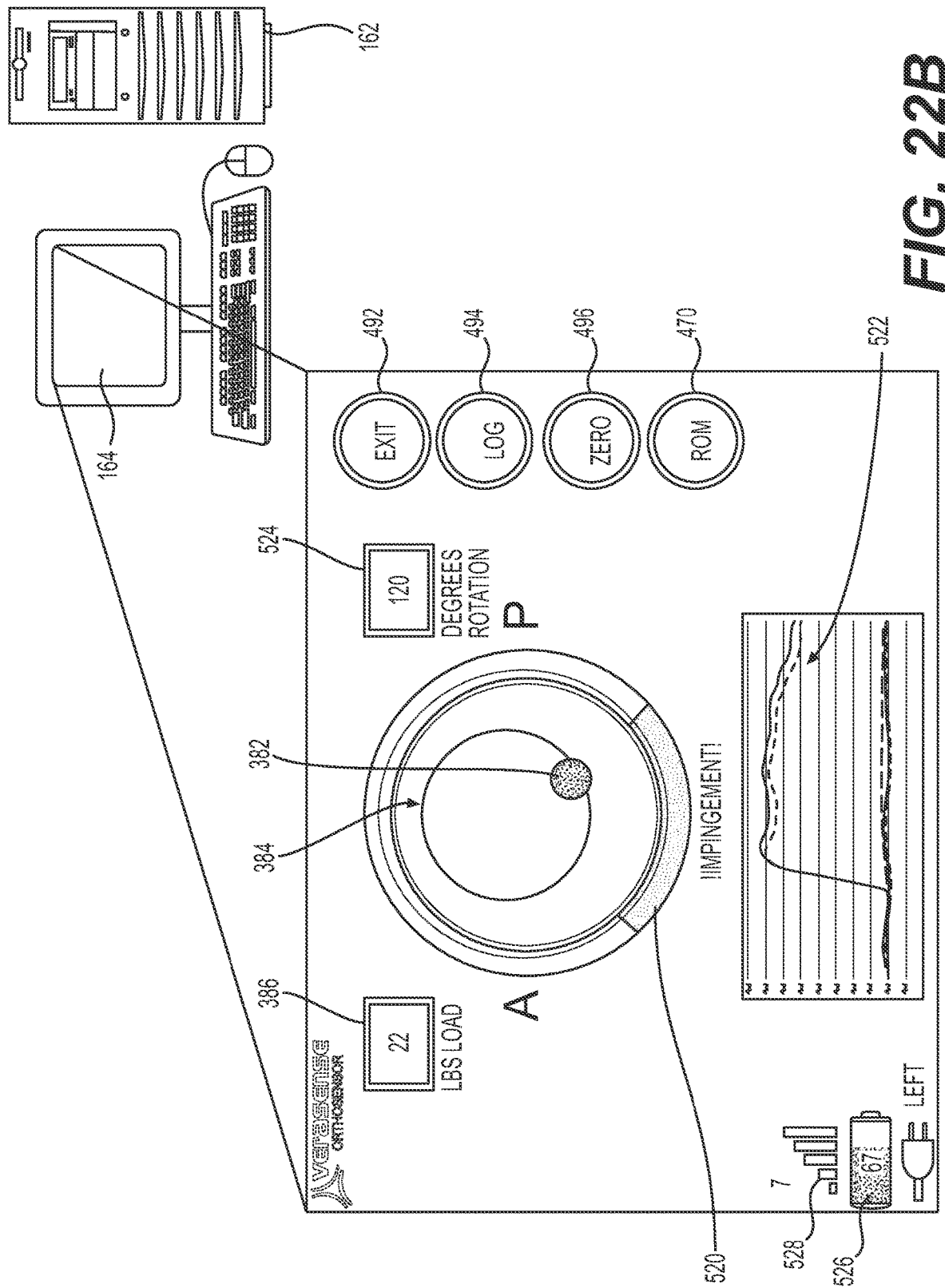

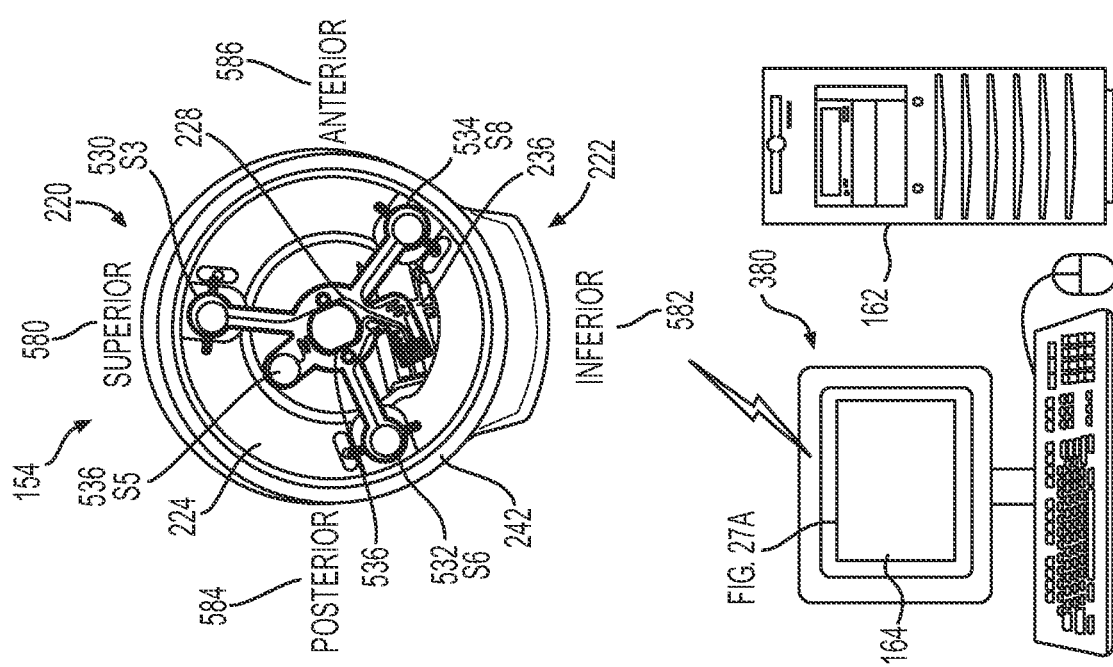

EQUATION 2) $\phi_s = 0.768 \, rad \, (44°)$

EQUATION 3) $\phi_1 = \frac{\pi}{2}, \phi_2 = \frac{11\pi}{6}, \phi_3 = \frac{7\pi}{6}$ EQUATION 4) $\hat{s}_i = \begin{bmatrix} -\cos(\phi_i)\sin(\theta_s) \\ -\sin(\phi_i)\sin(\theta_s) \\ -\cos(\theta_s) \end{bmatrix}$ $\hat{s}_1 = (0, -0.695, -0.719)$ (top sensor)
$\hat{s}_2 = (-0.602, 0.347, -0.719)$ (top sensor)
$\hat{s}_3 = (0.602, 0.347, -0.719)$ (top sensor)

EQUATION 5) $\vec{S}_i = S\hat{S}_i$

EQUATION 6) $\vec{F}_r = \vec{S}_1 + \vec{S}_2 + \vec{S}_2$

EQUATION 7) $\vec{F}_a = -\vec{F}_r$

EQUATION 8) $\begin{bmatrix} F_{ax} \\ F_{ay} \\ F_{az} \end{bmatrix} = -\begin{bmatrix} S_{1x} & S_{2x} & S_{3x} \\ S_{1y} & S_{2y} & S_{3y} \\ S_{1z} & S_{2z} & S_{3z} \end{bmatrix} \begin{bmatrix} S_1 \\ S_2 \\ S_3 \end{bmatrix}$ EQUATION 9) $\|\vec{F}_{all}\| = \sqrt{F_{ax}^2 + F_{ay}^2 + F_{az}^2}$ EQUATION 10) $\vec{P}_a = r * \dfrac{\vec{F}_a}{\|\vec{F}_a\|}$ EQUATION 11) $(x_a, y_a) = (p_{ax}, p_{ay})$

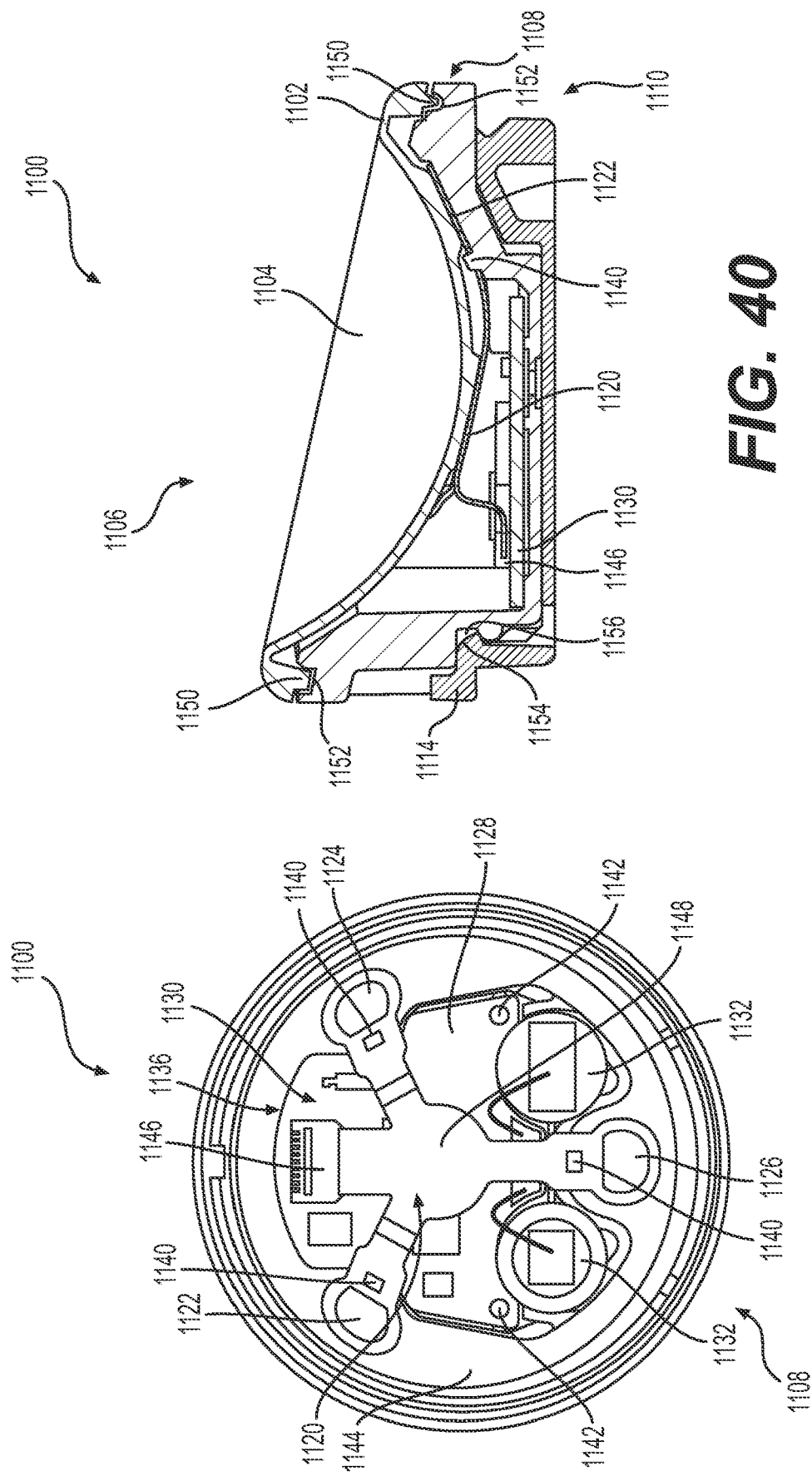

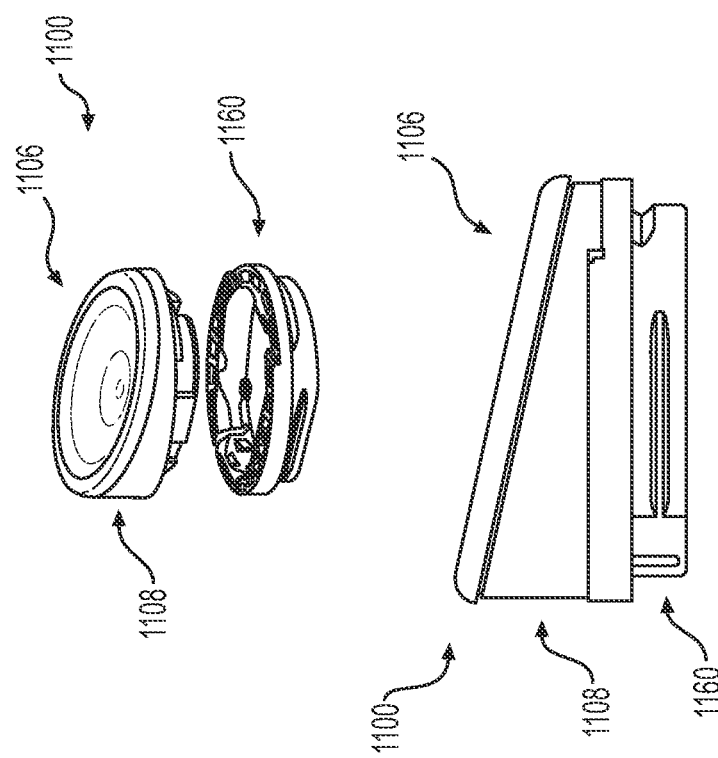
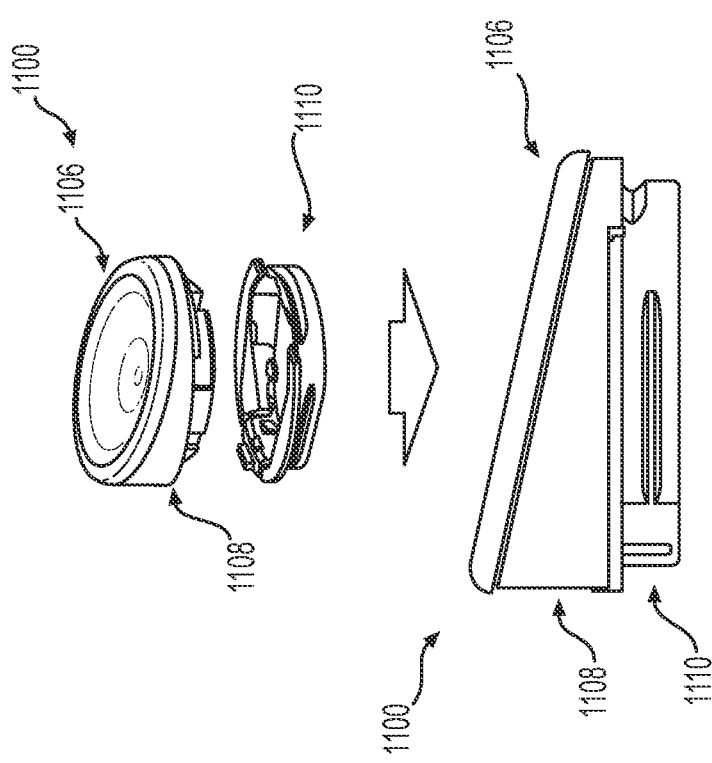

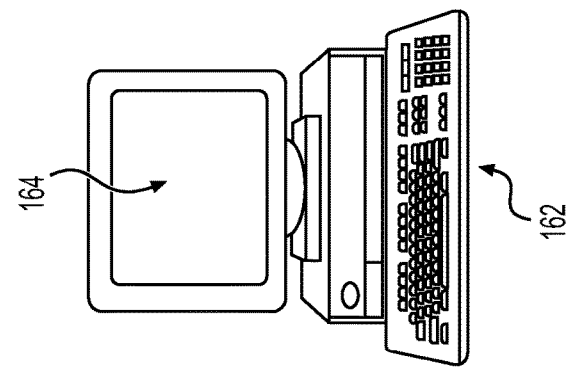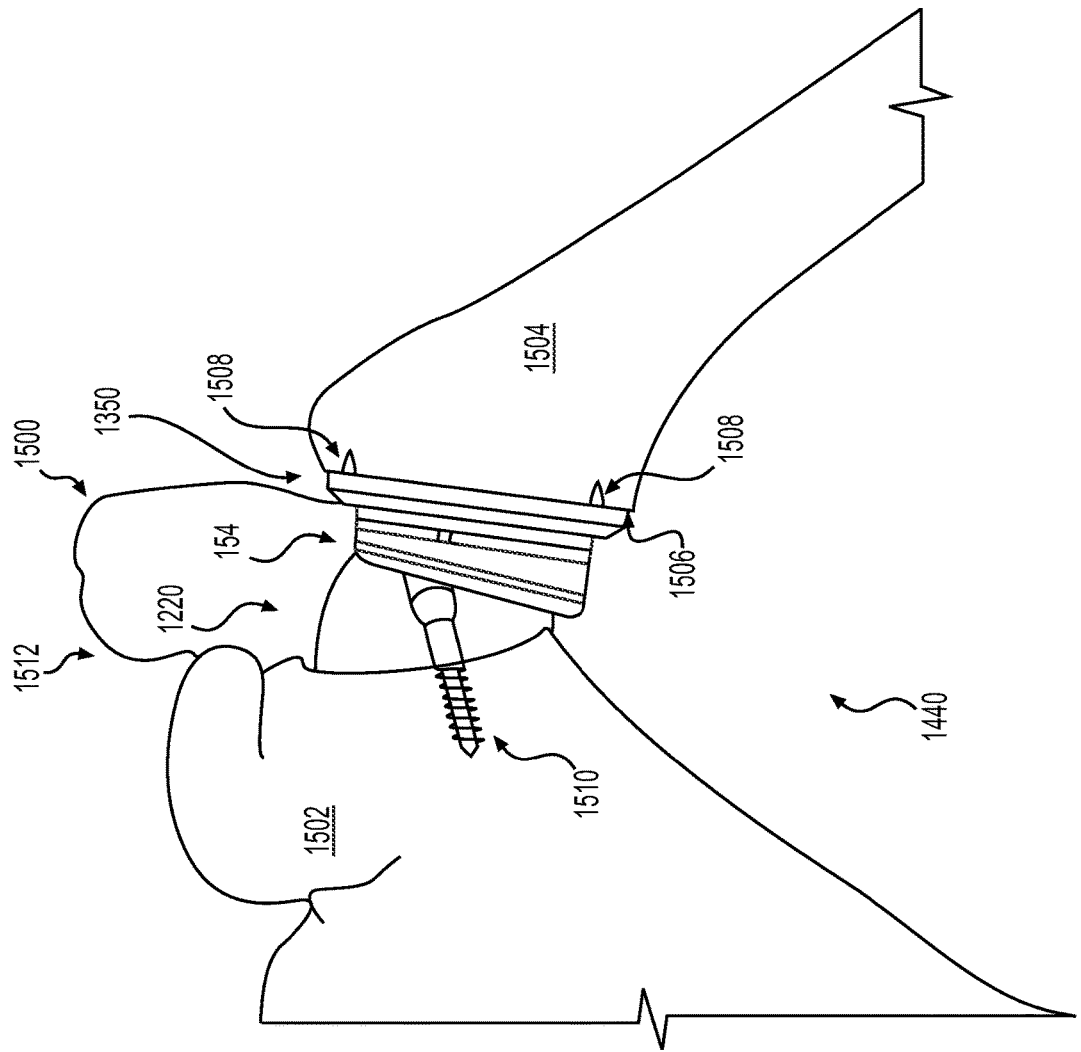
FIG. 53

US 11,992,424 B2

MEASUREMENT SYSTEM FOR A SELECTION OF AT LEAST ONE PROSTHETIC COMPONENT OF A SHOULDER JOINT DURING SURGERY

FIELD OF THE INVENTION

The invention relates in general to medical and surgical devices and more particularly to parameter measurement related to the musculoskeletal system.

BACKGROUND OF THE INVENTION

The musculoskeletal system of a mammal is subject to breakdown due to many factors such as environment, genetics, diet, usage, and aging. A joint of the musculoskeletal system typically comprises two or more bones that move in relation to one another. Movement is enabled by muscle tissue and tendons attached to the joint. Ligaments hold and stabilize the one or more joint bones positionally. Cartilage is a wear surface that prevents bone-to-bone contact, distributes load, and lowers friction.

There has been substantial growth in the repair of the human musculoskeletal system. In general, prosthetic orthopedic joints have evolved over time using animal studies, empirical evidence, simulation data, mechanical prototypes, and patient data. The tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance. It would be of great benefit to provide quantitative measurement data in real-time to support installation of prosthetic components or prosthetic joints.

BRIEF DESCRIPTION OF THE DRAWINGS

FIG. 21 is an illustration of the measurement device in accordance with an example embodiment;

FIG. 22B is an illustration of the GUI indicating impingement in accordance with an example embodiment;

FIG. 27B is an illustration of the measurement device transmitting measurement data to the computer and displaying the measurement data on the display in accordance with an example embodiment;

FIG. 39 is a view of a cavity of a bottom housing of the measurement device in accordance with an example embodiment;

FIG. 40 is a cross-sectional view of the measurement device in accordance with an example embodiment;

FIG. 41A illustrates the measurement device with first shim in accordance with an example embodiment;

FIG. 41B illustrates the measurement device with a second shim in accordance with an example embodiment;

FIG. 53 is an illustration of the selection system in a shoulder joint in accordance with an example embodiment;

DETAILED DESCRIPTION OF EMBODIMENTS

Figure 2:
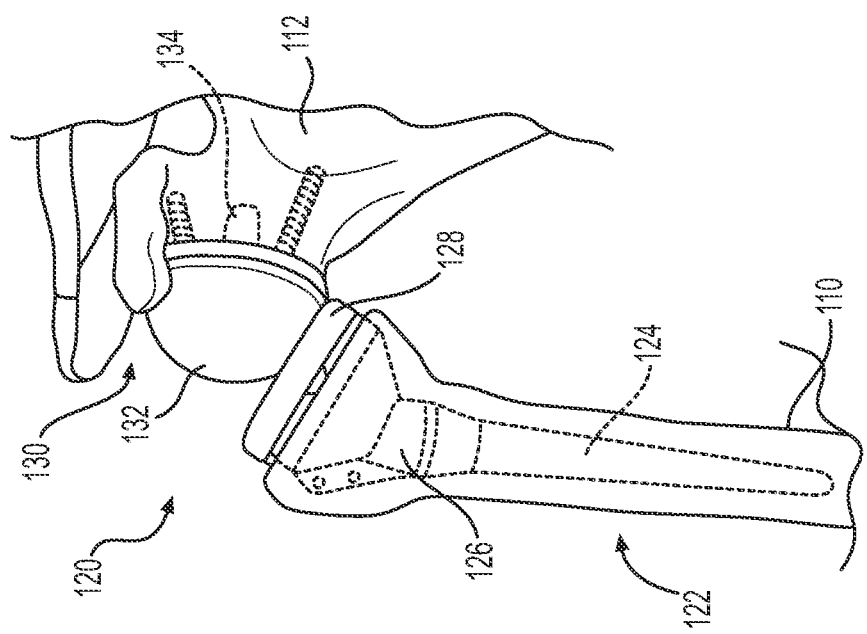
FIG. 2 is an illustration of a prosthetic shoulder joint in accordance with an example embodiment.

The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device.

The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, and MEMs devices) can be used within the scope of the embodiments described.

At least one embodiment is directed to a kinetic orthopedic measurement system to aid a surgeon in determining real time alignment, range of motion, loading, impingement, and contact point of orthopedic implants. Although the system is generic to any orthopedic surgery (e.g., spinal, shoulder, knee, hip, ankle, wrist, finger, toe, bone, musculoskeletal, etc.) the following examples deal with shoulder surgery as a non-limiting example of an embodiment of the invention.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading on the shoulder joint, contact and congruency through a full range of motion, and information regarding impingement.

In general, kinetics is the study of the effect of forces upon the motion of a body or system of bodies. Disclosed herein is a system for kinetic assessment of the musculoskeletal system. The kinetic system can be for the installation of prosthetic components or for monitoring and assessment of permanently installed components to the musculoskeletal system. For example, installation of a prosthetic component can require one or more bone surface to be prepared to receive a device or component. The kinetic system is designed to take quantitative measurements of at least the load, position of load, or alignment with the forces being applied to the joint similar to that of a final joint installation. The sensed measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. The physical parameter or parameters of interest can include, but are not limited to, measurement of alignment, load, force, pressure, position, displacement, density, viscosity, pH, spurious accelerations, color, movement, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the measurement device are illustrative only and do not limit use for other parts of a body. The measurement device can be a tool, equipment, implant, or prosthesis that measures at least one parameter or supports installation of prosthetic components to the musculoskeletal system. The measurement device can be used on bone, the knee, hip, ankle, spine, shoulder, hand, wrist, foot, fingers, toes, and other areas of the musculoskeletal system. In general, the principles disclosed herein are meant to be adapted for use in all locations of the musculoskeletal system.

At least one embodiment is directed to a system for adjusting or monitoring a contact position of a musculoskeletal joint for stability comprising: a prosthetic component configured to rotate after being coupled to a bone; a sensored prosthesis having an articular surface where the sensored prosthesis is configured to couple to the prosthetic component, where the sensored prosthesis has a plurality of load sensors coupled to the articular surface and a position measurement system configured to measure position, slope, rotation, or trajectory, and a remote system configured to wirelessly receive quantitative measurement data from the sensored prosthesis where the remote system is configured to display the articular surface, where the remote system is configured to display position of applied load to the articular surface, and where the remote system is configured to report impingement as the musculoskeletal joint is moved through a range of motion (ROM).

In general, the joint measurement system disclosed herein is directed to and can be used for any ball and socket joint of a musculoskeletal system. Typically, a first bone terminates in a ball-shaped surface and fits within a second bone having a cup that receives the ball. The first bone is motivated by muscle, tendon, ligament, and tissue to move the first bone such that the ball of the first bone rotates within the cup of the second bone. A ball and socket joint has some of the widest range of motions of different joints within the musculoskeletal system. For example, the shoulder joint and the hip joint are ball and socket joints. The shoulder joint and the hip joint are synovial joints having synovial fluid. The examples disclosed herein below are for a shoulder joint system such as a reverse prosthetic shoulder joint or a standard prosthetic shoulder joint. The reverse prosthetic shoulder and the standard shoulder have a cup and a ball as part of the joint system. The measurement device including the electronic circuitry and sensors can be adapted for either the curved surface of the cup or the curved surface of the ball of the shoulder joint system. All of the shoulder joint examples disclosed herein can be also be used and sized for a hip. The measurement device disclosed herein can be adapted for either a curved surface of the acetabular cup of the hip or it can be adapted for a curved surface of a ball of a femoral head.

Figure 1:
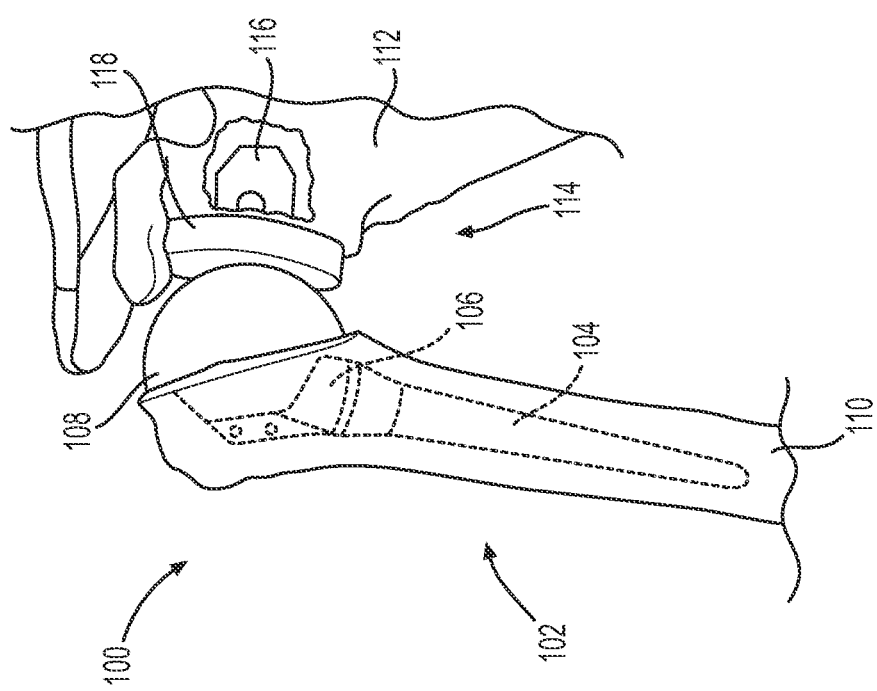
FIG. 1 is an illustration of a prosthetic shoulder joint in accordance with an example embodiment.

FIG. 1 is an illustration of a prosthetic shoulder joint 100 in accordance with an example embodiment. The natural shoulder joint supports a wide range of motion (ROM) when compared to other joints of the musculoskeletal system. The shoulder joint comprises a humerus, a scapula, coracoid process, acromion, and a clavicle. The shoulder joint is encapsulated by a synovial membrane that produces synovial fluid that lubricates the shoulder joint and circulates nutrients to the area. The scapula includes a glenoid cavity. The glenoid cavity has a curved surface. The proximal end of the humerus has a humeral head having a curved surface that couples to the glenoid cavity to support movement and establishes the range of motion of the shoulder joint. A humeral neck extends from the humerus and couples to the humeral head at a predetermined angle. Muscles, tendons and ligaments couple to the humerus, scapula, and clavicle to hold the shoulder joint in place and to move the humerus in relation to the scapula.

Prosthetic shoulder joint 100 comprises a humeral prosthesis 102 and a glenoid prosthesis 114. Humeral prosthesis 102 includes a stem 104, a neck 106, and a head 108. Head 108 has an exterior curved surface configured to support movement of prosthetic shoulder joint 100. In one embodiment, the exterior curved surface is convex. The proximal end of a humerus 110 is cut to receive humeral prosthesis 102. Stem 104 is inserted into the medullary cavity of humerus 110 to couple humeral prosthesis 102 to humerus 110.

Glenoid prosthesis 114 comprises a glenoid structure 118 and retaining structure 116. The glenoid cavity on scapula 112 is prepared to receive glenoid prosthesis 114. Retaining structure 116 of glenoid prosthesis 114 is configured to couple to scapula 112 to retain glenoid structure 118. In one embodiment, glenoid structure 118 replaces the glenoid cavity. Glenoid structure 118 has an external curved surface. Glenoid structure 118 is configured to couple to head 108 of humeral prosthesis 102 to support movement of prosthetic shoulder joint 100. In one embodiment, the external curved surface of glenoid structure is concave. The external curved surface of glenoid structure 118 is low friction to support movement under load by humeral prosthesis 102.

In one embodiment, glenoid prosthesis 114 is a trialing device that includes a trial measurement device. After measurements have been taken with the trial measurement device the trialing device is removed and a permanent prosthesis is installed. Alternatively, glenoid prosthesis 114 can comprise a tray coupled to retaining structure 116. A bearing having an articular surface is configured to couple to the tray. In one embodiment, the bearing can be removed from the tray and replaced with the trial measurement device. A further example is a removable humeral head 108 that can be replaced with the trial measurement device. In one embodiment, the trial measurement device on humeral prosthesis 102 can operate separately or in conjunction with the trial measurement device that replaces glenoid structure 118. In general, the trial measurement device will have at least one sensor configured to measure a parameter. The trial measurement device will have an external curved surface and dimensions similar to glenoid prosthesis 114 or humeral prosthesis 102. In one embodiment, measurements taken by the trial measurement device will relate to prosthetic shoulder joint 100 range of motion and stability.

FIG. 2 is an illustration of a prosthetic shoulder joint 120 in accordance with an example embodiment. Prosthetic shoulder joint 120 is also known as a reverse prosthetic shoulder joint. Prosthetic shoulder joint 120 comprises a humeral prosthesis 122 and a glenoid prosthesis 130. Humeral prosthesis 122 comprises a stem 124, a neck 126, and a humeral liner 128. A proximal end of a humerus 110 is cut to receive humeral prosthesis 122. Stem 124 is inserted into the medullary cavity of humerus 110.

Glenoid prosthesis 130 comprises a glenoid sphere 132 and a retaining structure 134. The glenoid cavity of a scapula 112 is prepared for receiving glenoid prosthesis 130. Retaining structure 134 of glenoid prosthesis 130 is configured to couple to scapula 112 to retain and hold glenoid sphere 132 in a position to couple to humeral prosthesis 122. In one embodiment, glenoid sphere 132 is configured to couple to a surface of scapula 112 to replace the glenoid cavity. Glenoid sphere 132 has a curved surface configured to couple to humeral liner 128 of humeral prosthesis 122. Prosthetic shoulder joint 120 is a reverse shoulder because a glenoid sphere that corresponds to a humeral head of the humerus is coupled to the scapula. Also, humeral liner 128 which corresponds to the glenoid cavity of scapula 112 is instead coupled to humerus 110. Thus, the articulating surfaces have been reversed. In one embodiment, an external curved surface of humeral liner 128 is concave. In one embodiment, the external curved surface of glenoid sphere 132 is convex to couple to the humeral liner 128 and support movement of prosthetic shoulder joint 120. The external curved surface of humeral liner 128 supports loading and is low friction to support movement of prosthetic shoulder joint 120.

In one embodiment, humeral liner 128 can be removed and replaced with a trial measurement device. The trial measurement device can be coupled to the neck of humeral prosthesis 122. For example, neck 126 of humeral prosthesis 122 can terminate in a tray configured to receive humeral liner 128. Humeral liner 128 is configured to be removable and replaced with the trial measurement device. The trial measurement device will have at least one sensor configured to measure a parameter. The trial measurement device will have an external curved surface and dimensions similar to humeral liner 128. In one embodiment, measurements taken by the trial measurement device will relate to movement, loading, and stability of humeral prosthesis 122 in prosthetic shoulder joint 130. In one embodiment, glenoid sphere 132 can be removed and replaced with a second trial measurement device having at least one sensor. In one embodiment, the second trial measurement device can be used instead of the first trial measurement device for assessing prosthetic shoulder joint 130. In one embodiment, the first and second trial measurement devices can both be used to provide measurement data for assessing prosthetic shoulder joint 130. Final prosthetic components are installed after using the first or second trial measurement devices. In one embodiment, one or more of the final prosthetic components can have at least one sensor for measuring a parameter.

Figure 3:
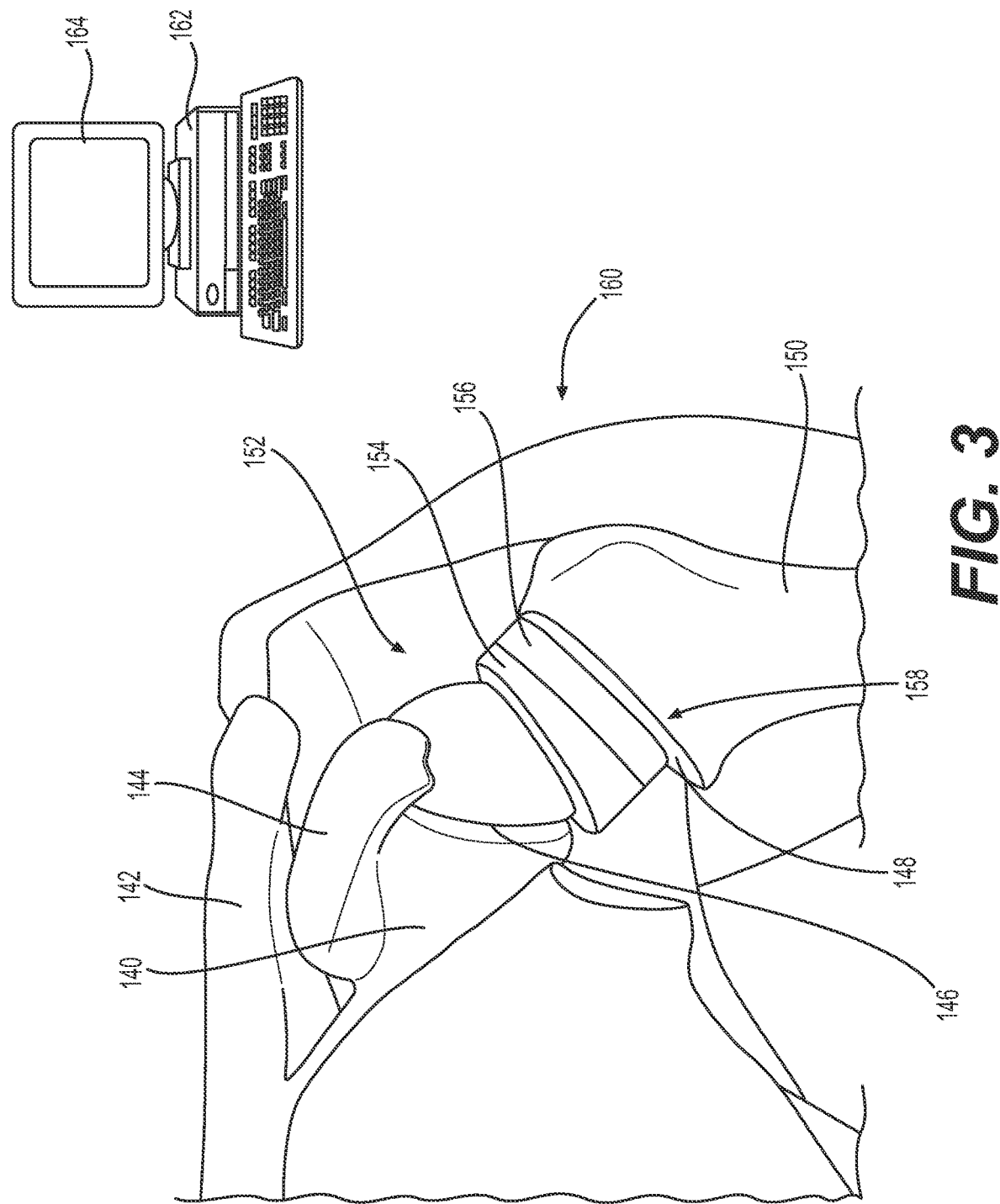
FIG. 3 is an illustration of a measurement device in a shoulder joint system in accordance with an example embodiment.

FIG. 3 is an illustration of a measurement device 154 in a shoulder joint system 160 in accordance with an example embodiment. In the example embodiment, a reverse shoulder joint is illustrated in the musculoskeletal system. Shoulder joint system 160 comprises computer 162, glenoid sphere 152, and humeral prosthesis 158 including measurement device 154. A glenoid sphere 152 is shown coupled to a prepared bone surface of scapula 140. The clavicle 142 and coracoid process 144 are shown in relation to the placement of glenoid sphere 152. In one embodiment, the glenoid cavity of scapula 140 is prepared to receive glenoid sphere 152. As shown, glenoid sphere 152 couples to a prepared bone surface 146 of scapula 140. Glenoid sphere 152 can have an anchor or stem to support attachment to scapula 140. In one embodiment, screws are used to couple glenoid sphere 152 to scapula 140. Glenoid sphere 152 has an external curved surface configure to couple to measurement device 154. In the example, glenoid sphere 152 has a convex surface.

In one embodiment, a humeral prosthesis 158 is configured to couple to a humerus 150. The proximal end of humerus 150 is cut to have a prepared bone surface 148 for receiving humeral prosthesis 158. The humeral liner has a low friction surface and is configured to support movement of shoulder joint system 160. The humeral liner is configured to couple humeral tray 156. In the example, the humeral liner is configured to be removable from humeral prosthesis 158 and is removed in FIG. 3. Measurement device 154 replaces the humeral liner in humeral tray 156. In one embodiment, measurement device 154 is configured to be dimensionally equivalent to the humeral liner. In one embodiment, the external curved surface of measurement device 154 is concave and figured to couple to the external curved surface of glenoid sphere 152. Measurement device 154 comprises at least one sensor and electronic circuitry configured to control a measurement process and transmit measurement data to a computer 162 in proximity to shoulder joint system 160. In one embodiment, measurement device 154 can further include a position measurement system configured to measure position or movement. The at least one sensor will measure parameters of interest to support installation of shoulder joint system 160. Typically, computer 162 is in an operating room outside the surgical field where shoulder joint system 160 is being installed. A display 164 includes a graphical user interface (GUI) that supports presenting measurement data in a graphical manner where an operating team can rapidly assimilate the measurement data to verify, adjust or make changes that improve the installation.

In general, at least one component in shoulder joint system 160 has measurement capability. In the example, shoulder joint system 160 is a reverse shoulder system having measurement device 154. Measurement device 154 can be adapted for use in a standard shoulder joint system comprising a humeral prosthesis and a glenoid prosthesis. Sensors can also be placed in one or both of the humeral prosthesis and glenoid prosthesis of the standard shoulder joint system. Measurement device 154 is not limited to shoulder arthroplasty. Measurement device 154 can be adapted for use for hip, knee, spine, bone, ankle, wrist, fingers, toes, and other parts of the musculoskeletal system.

Quantitative measurement data is needed to kinetically assess and optimize a shoulder joint during surgery. Measurement device 154 delivers quantitative measurement data to a surgeon or surgical team in real-time that support adjustment of the tension on different soft tissues that enable the shoulder and affect range of motion of the shoulder. In one embodiment, measurement device 154 is a temporary or trialing device that is dimensionally substantially equivalent to a corresponding permanent prosthesis. The permanent prosthesis that replaces measurement device 154 in the final prosthetic joint will measure similar to the measurement data provided by measurement device 154.

Shoulder joint system 160 is taken through a range of motion (ROM) that is measured by measurement device 154. For example, a position of humerus 150, a load magnitude applied to measurement device 154 by glenoid sphere 152, and a contact point where glenoid sphere 152 couples to measurement device 154 can be measured in real-time through the ROM. Scapular notching is a common complication in a shoulder joint installation. Notching is caused by repetitive contact between humeral prosthesis 158 and the inferior scapular neck that causes an osteolytic reaction which results in polyethylene debris. Adjustments to shoulder joint system 160 can be made when impingement is detected to prevent scapular notching from occurring. The range of motion and loading is monitored to determine whether to adjust tensions on various soft tissue elements enabling the shoulder movement. Adjustments to the soft tissue using the quantitative measurement data can reduce or eliminate impingement, create more stability in the shoulder joint, and increase a range of motion of the shoulder. More specifically, stability is enhanced by using measurements to reduce implant malpositioning, improve subscapularis quality, and adjust muscle tensioning of the shoulder joint. Proper compressive forces of the soft tissue at the glenohumeral joint were found to significant improve stability in a reverse total shoulder arthroplasty. Moreover, prosthesis designs which lateralize the humerus are inherently more stable because they better tension the rotator cuff and achieve more deltoid wrapping.

Figure 4A:
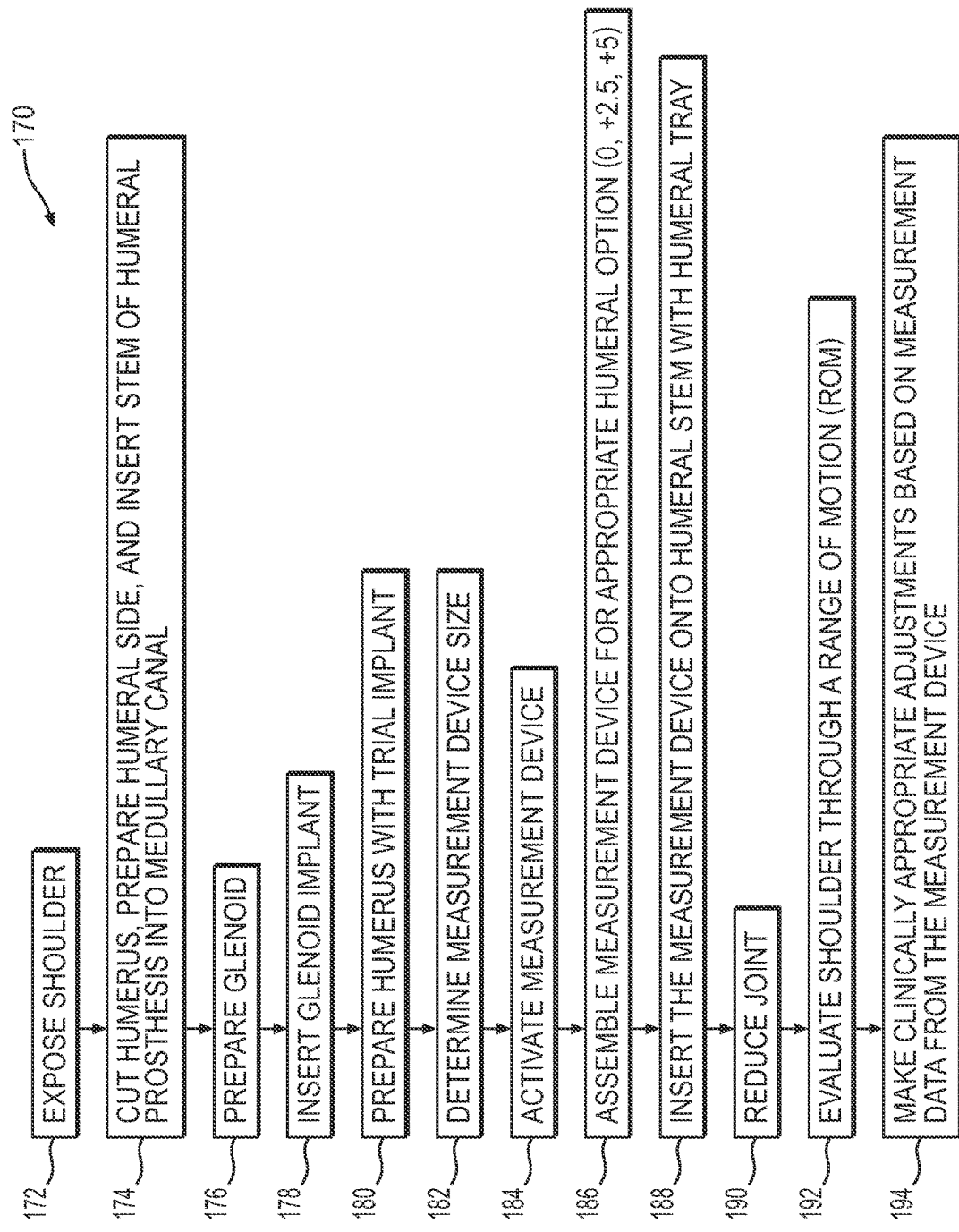
FIG. 4A is a flow diagram for a shoulder joint installation using the measurement device of FIG. 3 in accordance with an example embodiment.

FIG. 4A is a flow diagram 170 for a shoulder joint installation using measurement device 154 of FIG. 3 in accordance with an example embodiment. In the example, the measurement device disclosed in flow diagram 170 corresponds to measurement device 154 and is configured to fit into a humeral prosthesis. The measurement device includes at least one sensor and is configured to measure at least one parameter. In one embodiment, the measurement device transmits measurement data to a computer. The measurement data can be reviewed in real-time on a display coupled to the computer. In one embodiment, the measurement device is also compatible with tensioning devices to allow functionality earlier in the surgery such as immediately after a humeral cut. The measurement device supports different size musculoskeletal systems and shoulder joint systems where a single measurement device can support a substantial portion of the population. In one embodiment, the measurement device can be inserted into a humeral trial and implant without special tools. Similarly, the measurement device can be removed from the humeral trial and implant without special tools.

All steps may not be listed, for example steps known in the art that can be used in the method. Also, the steps listed herein do not imply a specific order and may be practiced in different orders depending on the application. In a step 172, the shoulder is exposed to gain access to the humerus. In a step 174, the proximal end of the humerus is cut to prepare a humeral side. In one embodiment, the cut is made at a predetermined angle. In one embodiment, a prepared bone surface of the humerus is configured to receive a humeral prosthesis. The stem of the humeral prosthesis is inserted into the medullary canal of the humerus and placed in a predetermined position. The humeral prosthesis may also include a stem protector. In a step 176, the glenoid prosthesis is prepared for implantation. In one embodiment, one or more bone cuts or bone modifications are made to the scapula for receiving the glenoid prosthesis. In a step 178, the glenoid prosthesis is inserted and coupled to the scapula. In a step 180, a trial implant is coupled to the humerus. In a step 182, a measurement device size is determined for the shoulder application. In one embodiment, different sized measurement devices can be provided for selection. Alternatively, different adapters can be provided to assemble the measurement device for the appropriate size. In a step 184, the measurement device is activated. In a step 186, the measurement device is assembled for an appropriate humeral option. The measurement device is configured to be adjusted such that a humeral neck angle of the humeral prosthesis can be changed. For example, different offsets can be chosen such as (0, 2.5, or 5 degrees) to affect a range of motion of the shoulder joint. In a step 188, a humeral tray and the measurement device are coupled to the humeral stem of the humeral prosthesis. Thus, the glenoid prosthesis and the humeral prosthesis with the measurement device have been installed respectively to the scapula and the humerus. In a step 190, the shoulder is reduced. The shoulder is in place with the measurement device sending measurement data to the computer. The display couples to the computer to display the measurement data in real-time to a surgeon or surgical team.

In a step 192, the shoulder is evaluated through a range of motion (ROM). In one embodiment, the shoulder is moved through one or more predetermined motions to indicate through measurement data, any issues with the prosthetic shoulder joint installation. The measurement device transmits measurement data from the one or more sensors in the measurement device to the computer. The measurement data is displayed in real-time to the surgeon or surgical team. In one embodiment, some of the measurement data is processed by the computer and displayed graphically on the display of the computer to support rapid assimilation of the measurement data by the surgical team. In a step 194, clinically appropriate adjustments are made based on measurement data from the measurement device.

Figure 4B:
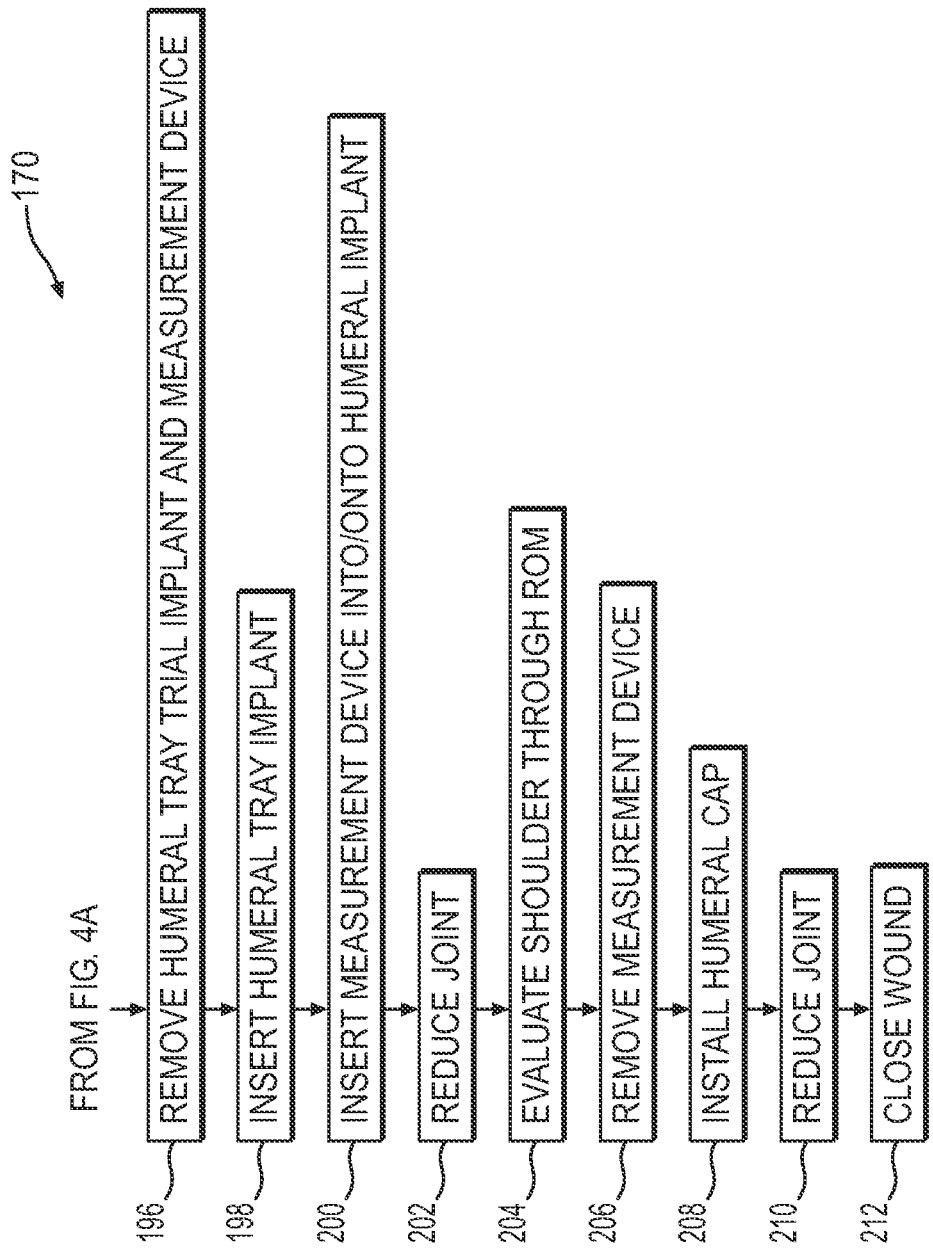
FIG. 4B is a continuation of the flow diagram from FIG. 4A for the shoulder joint installation using the measurement device of FIG. 3 in accordance with an example embodiment.

FIG. 4B is a continuation of flow diagram 170 from FIG. 4A for the shoulder joint installation using measurement device 154 of FIG. 3 in accordance with an example embodiment. In a step 196, the humeral tray trial implant and the measurement device is removed from the humeral prosthesis. In a step 198, a humeral tray implant is installed onto the humeral prosthesis. In one embodiment, the humeral tray implant is a final implant and not a trialing device. In a step 200, the insert measurement device is coupled to the humeral prosthesis. In one embodiment, the measurement device is coupled to the humeral tray implant. In one embodiment, the trialing implant is dimensionally similar to the humeral tray implant such that measurement data taken with the measurement device in the humeral tray should be substantially equal to the measurement data taken when the measurement device was in the trial implant. In a step 202, the shoulder joint is reduced.

In a step 204, the shoulder is moved through a ROM. The measurement device transmits measurement data to the computer and is displayed on the display. The measurement data is reviewed by the surgeon or surgical team to verify the previous clinically appropriate adjustments using the permanent humeral tray implant coupled to the humeral prosthesis. In one embodiment, further clinically appropriate adjustments can be made to refine or improve the shoulder joint based on the ROM results and quantitative measurement data. In a step 206, the measurement device is removed from the permanent humeral tray implant. In one embodiment, the measurement device is a disposable device that is disposed of after the surgery is completed. In a step 208, a humeral liner is coupled to the humeral tray implant. The humeral liner has a curved surface that is configured to couple to the glenoid implant. The humeral liner is dimensionally substantially equal to the measurement device. The humeral liner has a low friction surface that can withstand the loading applied to the shoulder over a range of motion. In a step 210, the shoulder joint is reduced. In a step 212, the wound is closed with the permanent shoulder prosthetic components in place. The permanent shoulder will perform equivalently to that measured and adjusted with the measurement device.

Figure 5:
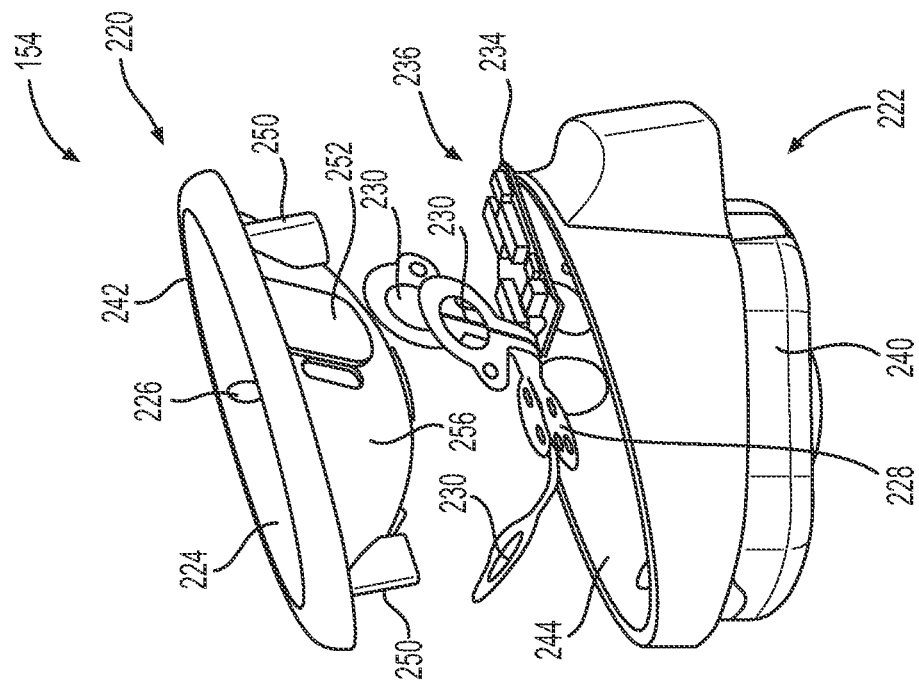
FIG. 5 is an exploded view of the measurement device illustrating components in accordance with an example embodiment.

FIG. 5 is an exploded view of measurement device 154 illustrating components in accordance with an example embodiment. In general, measurement device 154 generates quantitative measurement data targeted on clinical parameters that effect outcomes, impingement, stability, and range of motion of the joint. In the example, measurement device 154 is configured to be used in a shoulder joint and more specifically in a reverse shoulder joint. Measurement device 154 is configured to measure a functional load range and a maximum load range representative of loading seen in a reverse shoulder joint. Measurement device 154 is configured to detect and report joint forces related to a glenoid sphere coupling to a humeral liner when the shoulder joint is being trialed. Measurement device 154 includes sensors to detect motion and orientation of a humeral prosthesis. Measurement device 154 is configured to detect inferior impingement on a humeral liner. Measurement device 154 is configured to measure superior impingement on the humeral liner. Measurement device supports an understanding of the soft tissues coupled to the shoulder joint, what soft tissues need to be evaluated and the consequences of adjusting the soft tissue. In one embodiment, the tension of the different soft tissues coupled to the shoulder joint can be evaluated and individually be adjusted within a predetermined range that results in optimal stability. Measurement device 154 is configured to couple to a computer having a display. In one embodiment, the computer and display are within the operating room in view of the surgical team to report the measurement data from measurement device 154. Typically, the computer and the display are placed outside the sterile field of the operating room. Measurement device 154 includes a low power transceiver to support communications within the operating room but highly attenuated signals outside the operating room. The communication can be secure by encrypting the transmission to prevent the measurement data from being read.

Measurement device 154 and the computer provide load and motion data with minimal lag or delay. In one embodiment, lag or delay is typically less than 2 seconds. In one embodiment, measurement device 154 is designed for a single use and is provided in sterile packaging. In one embodiment, a power source within measurement device 154 has sufficient power for a single use but cannot power a second usage. In one embodiment, measurement device 154 cannot be opened to replace the power source. In one embodiment, a functional life for measurement device 154 is approximately an hour to several hours in a surgical environment. Measurement device 154 comprises biocompatible materials. In one embodiment, measurement device 154 is tested and calibrated before sterile packaging to ensure optimal performance.

Measurement device 154 comprises an upper housing 220 and a bottom housing 222. Upper housing 220 and bottom housing 222 are configured to couple together to form a hermetically sealed enclosure. Sensors 230, electronic circuitry 236, and PC board 234 are hermetically sealed within the enclosure. In the example, upper housing 220 has an exterior curved surface 224 configured to couple to an external curved surface of a glenoid sphere to support movement of the shoulder joint. Upper housing 220 further includes a rim 242 that couples to external curved surface 224. In one embodiment, upper housing 220 and bottom housing 222 have corresponding retaining features to hold upper housing 220 to bottom housing 222. Alternatively, screws can be placed through openings 226 to couple upper housing 220 to bottom housing 222. Bottom housing 222 has a mounting structure 240 configured to couple to a humeral tray of the humeral prosthesis. Glue or an adhesive may also be used to couple upper housing 220 to bottom housing 222. Mounting structure 240 aligns and retains the enclosure to the humeral prosthesis. Bottom housing 222 includes openings 254 configured to receive structures from upper housing 220. Openings 254 terminate to a reinforced area that is configured to receive the screws to hold upper housing 220 to bottom housing 222. A flexible interconnect 228 is configured to couple to printed circuit (PC) board 234. Flexible interconnect 228 couples sensors 230 to electronic circuitry 236. In one embodiment, electronic components are mounted to PC board 234. PC Board 234 includes interconnect to couple the electronic components to form an electronic circuit configured to control a measurement process and transmit measurement data.

In one embodiment, sensors 230 are formed in flexible interconnect 228. Sensors 230 can be replicated accurately and have similar characteristics when formed at the same time in or on flexible interconnect 228. A reference sensor 232 can also be formed in or on flexible interconnect 228. For example, sensors 230 can be load sensors. The load sensors can be an elastic capacitor, a MEMs device, mechanical structure, hydraulic structure, pneumatic structure, strain gauge, a transducer, or a piezo-structure. The load sensors when coupled to a load convert the load to an electrical signal that is provided through flexible interconnect 228 to electronic circuitry 236. Alternatively, sensors 230 can be discrete sensors that are coupled to flexible interconnect 228. In the example, sensors 230 as load sensors are elastic capacitors, MEMs devices, or piezo-structures. Sensors 230 couple between upper housing 220 and bottom housing 222. In one embodiment, sensors 230 couple to raised regions 238 on an interior surface 244 of bottom housing 222. Raised regions 238 each have a surface that is not co-planar to interior surface 244 of the bottom housing. In one embodiment, there are an equal number of sensors 230 as raised regions 238. For example, three load sensors are used to measure loading applied to external curved surface 224. A load applied to surface 224 of upper housing 226 by the glenoid sphere of the shoulder joint is configured to compress sensors 230. In one embodiment, screws in openings 226 that couple upper housing 220 to bottom housing 222 can be adjusted to preload sensors 230 thereby placing sensors 230 in a linear operating region for the load range applied to measurement device 154. Measurement device 154 can also be placed through a calibration process to ensure optimal performance where each sensor can be measured and correction applied to sensor measurement to ensure linear operation over a load range. The corrections are stored in memory where they can be used to correct each sensor of the system.

Figure 6:
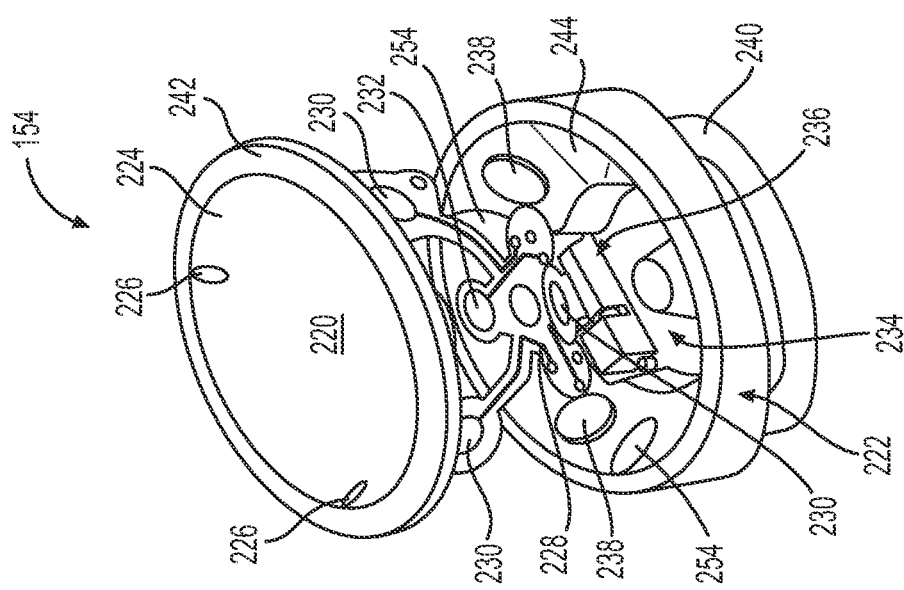
FIG. 6 is an exploded side view of the measurement device in accordance with an example embodiment.

FIG. 6 is an exploded side view of measurement device 154 in accordance with an example embodiment. In one embodiment, the side view shows that upper housing 220 couples to bottom housing 222 at a predetermined angle relative to a bottom surface of mounting structure 240. Electronic circuitry 236, PC board 234, flexible interconnect 228, and sensors 230 are housed in the enclosure formed by upper housing 220 and bottom housing 222. In one embodiment, electronic circuitry 236 and PC board 234 are placed within a cavity within the interior of bottom housing 222. Flexible interconnect 228 couples to a connector mounted on PC board 234 to couples sensors 230 to electronic circuitry 236. An interior surface 256 of upper housing 220 includes raised regions 252. Raised regions 252 are sensor pads configured to couple to sensors 230. Raised regions 252 each have a surface that is not co-planar with interior surface 256 of upper housing 220. In one embodiment, there are an equal number of raised regions 252 as sensors 230.

Upper housing 220 can be coupled to lower housing 222 by screws, retaining features, adhesive, welding, electrical means, magnetic means or other sealing and fastening methodologies. Upper housing 220 and lower housing 222 can comprise a polymer, ceramic, metal, metal alloy, or material that can support loading of a musculoskeletal joint and provides a low friction surface. In one embodiment, the material comprising upper housing 220 is low friction such that external curved surface 224 is low friction. Alternatively, a low friction coating can be bonded or applied to upper housing 220 to provide a low friction external curved surface 224. In the example shown herein above, upper housing 220 couples to lower housing 222 by screws. Upper housing 220 includes structures 250 corresponding to openings 254 of FIG. 5. In one embodiment, structures 250 are cylindrical in shape. A screw placed through an opening 226 couples through a corresponding structure 250. Structure 250 is a reinforced region of upper housing 220 configured to receive a screw. In one embodiment, structures 250 aligns upper housing 220 to bottom housing 222. Upper housing 220 aligns to bottom housing 222 such that structures 250 of upper housing 220 couple into openings 254 on surface 244 of bottom housing 222. In one embodiment, openings 254 terminate to a reinforced region of bottom housing 222. Screws couple through structures 250 and into the reinforced region in bottom housing 222 to hold upper housing 220 to bottom housing 222. As mentioned previously, the screws can be adjusted to seal the enclosure and preload sensors 230 for optimal performance.

Figure 7:
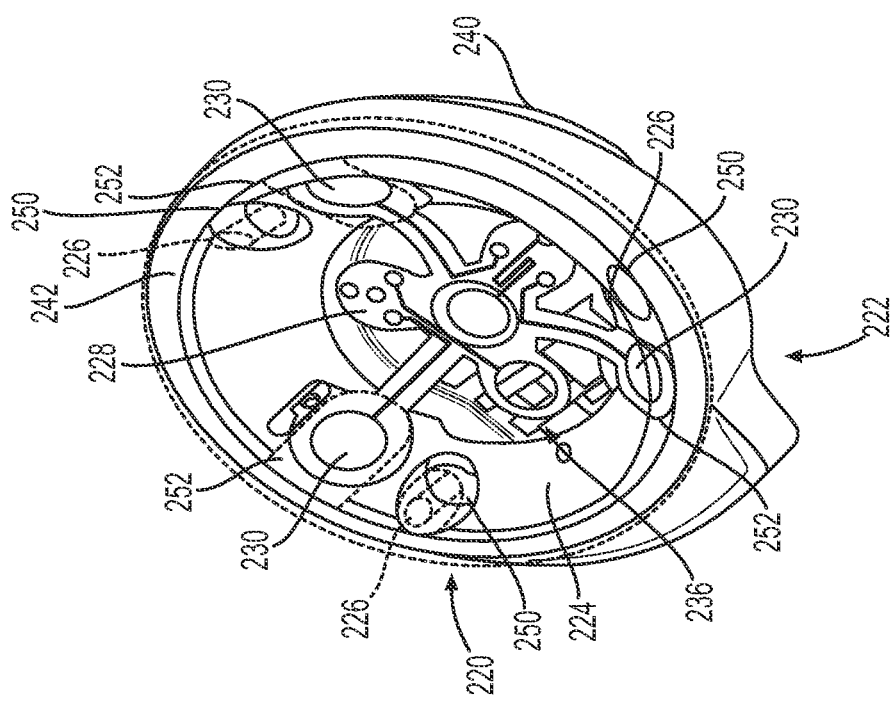
FIG. 7 is an illustration of the upper housing coupled to the bottom housing in accordance with an example embodiment.

FIG. 7 is an illustration of upper housing 220 coupled to bottom housing 222 in accordance with an example embodiment. Upper housing 220 is a transparent to show underlying electronic circuitry 236, flexible interconnect 228, and sensors 230. Screws are placed in openings 226 and couple to bottom housing 222 to hold upper housing 220 to bottom housing 222. In one embodiment, three screws are used to hold upper housing 220 to bottom housing 222.

Sensors 230 are shown coupling to raised regions 252 of upper housing 220. Referring briefly to FIG. 6, raised regions 252 are formed on interior surface 256 of upper housing 220. Referring briefly to FIG. 5, sensors 230 also couple to raised regions 238 on interior surface 244 of bottom housing 222. In one embodiment, raised regions 252 and raised regions 238 have an area greater than or equal to the area of sensors 230. Flexible interconnect 228 couples sensors 230 to electronic circuitry 236 within the enclosure. In one embodiment, sensors 230 comprise three sensors configured to measure loading applied to external curved surface 224 of upper housing 220. In one embodiment, the three sensors are equidistant from one another and located adjacent to rim 242 of upper housing 220 underlying external curved surface 224. Each sensor 230 is located at a predetermined location on external curved surface 224. A pressure applied to surface 224 of upper housing 220 compresses sensors 230 between raised regions 252 and raised regions 238 at the predetermined locations. The measurement data from sensors 230 are transmitted from measurement device 154 to computer 162 shown in FIG. 3 within the operating room. The calibration data can be used to adjust the measured output of sensors 230 at measurement device 154 prior to transmission or at computer 162 of FIG. 3. Computer 162 includes a display 164 configured to provide information related to the measurement data. In one embodiment, computer 162 is configured to calculate a load magnitude at a contact point on external curved surface 224 from the measurement data from sensors 230. In the example, the contact point is an area or region of external curved surface 224 that couples to the glenoid sphere of a reverse shoulder joint. Computer 162 further calculates the position of the contact point on external curved surface 224 from the measurement data from sensors 230 and the locations of sensors on external curved surface 224. In one embodiment, the measurement data can include data from a position or motion measurement system. The position or motion measurement system is part of electronic circuitry 236. In one embodiment, the position measurement system comprises one or more inertial sensors. Data from the position measurement system can be used to support the calculations and presentations performed by computer 162 and displayed on display 164.

Sensors 230 can be tested and calibrated prior to packaging and sterilizing measurement device 154 to further linearize the output. As part of the calibration process the screws can be torqued to different values to pre-load sensors 230. The pre-loading of sensors 230 can support operation of sensors 230 in a linear region of operation. The calibration data can be stored in memory as part of electronic circuitry 236 and used to correct non-linearities of sensors 230 to provide more accurate measurement data. In the calibration process sensors will be zeroed or measure zero when the external curved surface 224 is unloaded.

Figure 8:
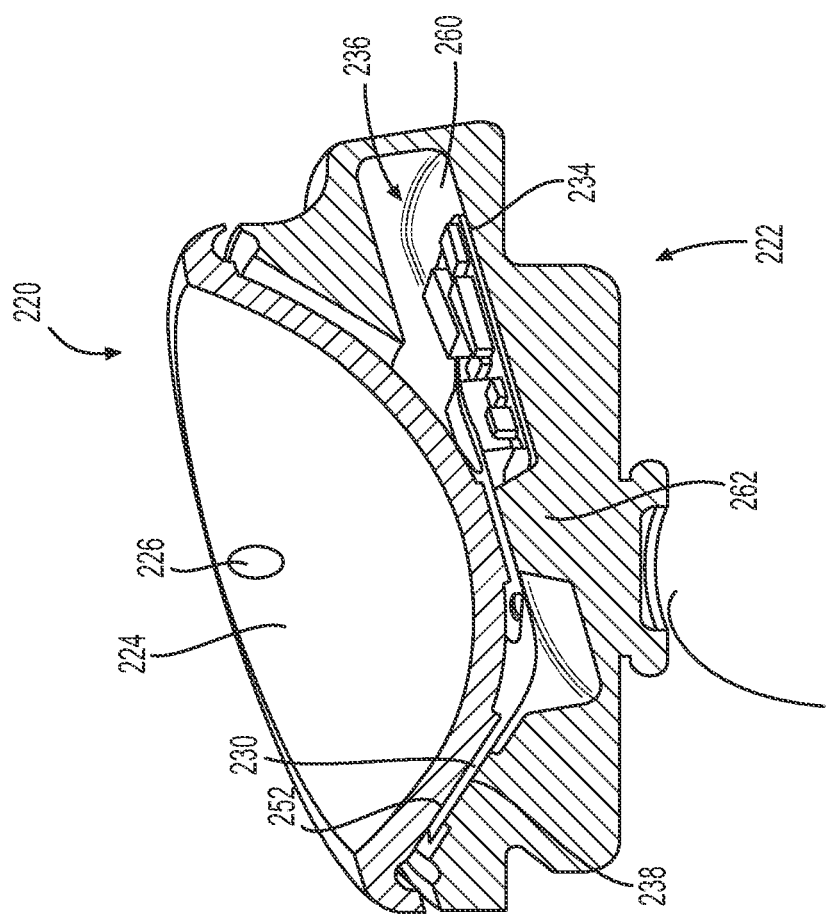
FIG. 8 is a cross-section of the measurement device in accordance with an example embodiment.

FIG. 8 is a cross-section of measurement device 154 in accordance with an example embodiment. A cavity 260 is formed when upper housing 220 couples to bottom housing 222. Electronic circuitry 236 on printed circuit board 234 is placed in cavity 260. Cavity 260 includes at least one retaining device to align and retain electronic circuitry 236 and PC board 234. In one embodiment, sensors 230 are formed in or on flexible interconnect 238. Flexible interconnect 238 is patterned or formed to place sensors 230 at predetermined locations. As shown, flexible interconnect 238 locates sensor 230 couples between raised region 252 on upper housing 222 and raised region 238 on bottom housing 222. In one embodiment, a support structure 262 can extend from bottom housing 222 towards upper housing 220 to retain flexible interconnect 238 centrally within measurement device 154.

Figure 9:
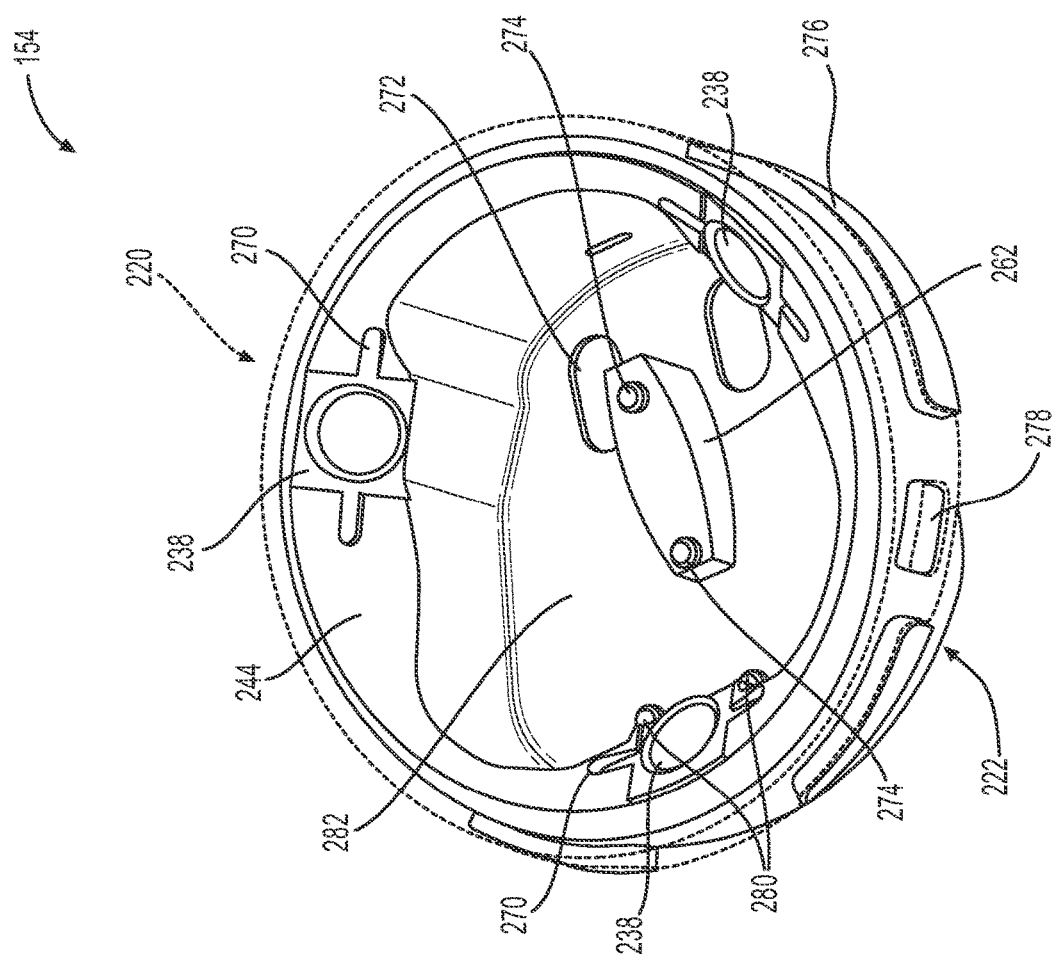
FIG. 9 is an illustration of mechanical features of the enclosure of the measurement device in accordance with an example embodiment.

FIG. 9 is an illustration of mechanical features of the enclosure of measurement device 154 in accordance with an example embodiment. Measurement device 154 comprises an upper housing 220 and a bottom housing 222 that forms an enclosure for electronic circuitry and one or more sensors. As shown, upper housing 220 comprises a transparent material to show underlying features in bottom housing 222. In one embodiment, upper housing 220 and bottom housing 222 comprises a biocompatible material. In one embodiment, upper housing 220 and bottom housing 222 can be molded or 3D printed with a polymer material.

Raised regions 238 are formed on interior surface 244 of bottom housing 222. Raised regions 238 are sensor platforms that extend above interior surface 244 of bottom housing 222. In one embodiment, each raised region 238 couples to a corresponding sensor. In the example, three raised regions 238 are formed on interior surface 244. In one embodiment, sensors 230 are capacitors approximately 4 millimeters in diameter formed in flexible interconnect 228. In one embodiment, a capacitor can be formed by a first interconnect and a second interconnect separated by a dielectric material within flexible interconnect 228. In one embodiment, the dielectric material can be polyimide. In one embodiment, the capacitor can be shielded to minimize parasitic coupling of capacitance or signals to the capacitor.

In one embodiment, raised regions 238 are greater than or equal to 4 millimeters to support sensors 230. A sensor snap 270 is a cutout on interior surface 244 of bottom housing 222 in proximity to raised regions 238. The cutout of sensor snap 270 supports retaining sensor 230 on a corresponding raised region 238.

A solder hole 272 is a cutout in bottom housing 222 to accommodate interconnect that is used to couple batteries within the enclosure. A flex snap 274 is a retaining feature configured to retain flexible interconnect 228 shown in FIG. 6 to bottom housing 222. In one embodiment, flex snaps 274 comprises one or more columns that are formed on support structure 262. Flexible interconnect 228 has one or more openings corresponding to the one or more columns. Flex snaps 274 are pressed through corresponding openings of flexible interconnect 228 to align and retain flexible interconnect 228 to support structure 262. In one embodiment, flexible interconnect 228 is suspended above a rigid cutout 282 of bottom housing 222. In one embodiment, rigid cutout 282 is a large cutout area in bottom housing 222. Electronic circuitry 236 and PC board 234 as shown in FIG. 8 can be placed in rigid cutout 282. Rigid snap 280 is a retaining feature configured to retain PC board 234 to bottom housing 222. In one embodiment, rigid snap 280 can be one or more columns configured to couple through one or more openings in PC board 234 to align and retain PC board 234. In one embodiment, upper housing 220 and bottom housing 222 have retaining features to couple upper housing 222 to bottom housing 222. In one embodiment, an O-ring is used to hermetically seal the enclosure. In one embodiment, the O-ring circumferentially couples to bottom housing 222. In one embodiment, the O-ring locks into bottom housing 222. In one embodiment, a housing snap 278 is one or more male retaining features on an exterior of bottom housing 222. Housing snaps 278 couples through one or more corresponding openings on upper housing 220 to align and retain upper housing 220 to bottom housing 222. In one embodiment, the O-ring is made of flexible material and compresses to seal a surface of upper housing 220 and a surface of bottom housing 222 when retained by housing snap 278. Flexible O-ring compresses and seals the surface of upper housing 220 and the surface of bottom housing 222. A compressed O-ring applies a force that holds housing snaps 278 within the corresponding openings in upper housing 220. Tray rim 276 is an extrusion on bottom housing 222 that couples to a humeral tray 156 of a humeral prosthesis 158 as shown in FIG. 3 and transfers loading applied to measurement device 154 to the humeral tray.

Figure 10:
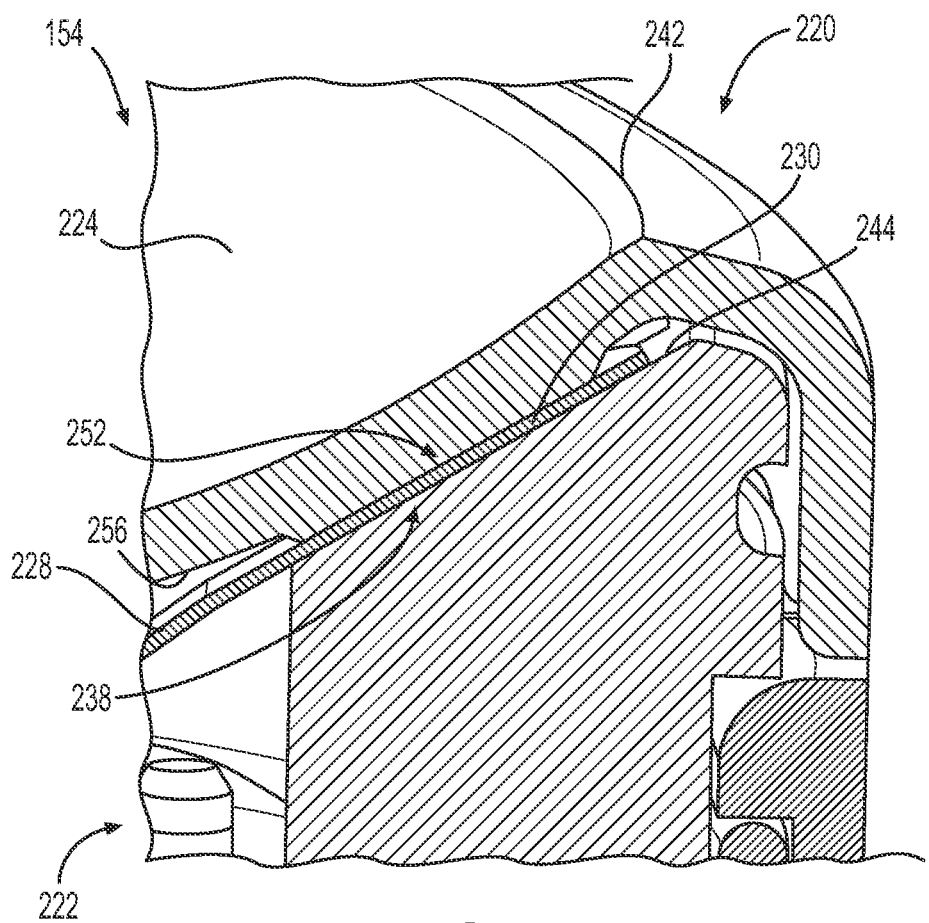
FIG. 10 is a cross-sectional view of part of the enclosure illustrating the sensor between the upper housing and the bottom housing in accordance with an example embodiment.

FIG. 10 is a cross-sectional view of part of the enclosure illustrating sensor 230 between upper housing 220 and bottom housing 222 in accordance with an example embodiment. In the example, external curved surface 224 of upper housing 220 couples to an external curved surface of glenoid sphere 152 as shown in FIG. 3. In one embodiment, sensor 230 is an elastic capacitive sensor integrated into flexible interconnect 228 as shown in FIG. 7. In one embodiment, the elastic capacitive sensor is approximately 0.012 inches thick. Sensor 230 is located adjacent to rim 242 of upper housing 220 underlying external curved surface 224 to maximize an area of measurement. The elastic capacitive sensor is engaged after assembly of upper housing 220 and bottom housing 222. A gap of 0.010 inches thick is designed into upper housing 220 and bottom housing 222 to pre-load sensor 230 when upper housing 220 and bottom housing 222 are coupled together. In one embodiment, raised region 252 on interior surface 256 of upper housing 220 is flat. Sensor 230 couples to raised region 252. In one embodiment, raised region 238 on interior surface 244 is also flat. Sensor 230 couples to raised region 238. In the example, sensor 230 is coupled between raised regions 252 and 238 respectively of upper housing 220 and bottom housing 220 such that sensor 230 is compressed by 0.002 inches when upper housing 220 is coupled to bottom housing 222. It has been found that the flat surface of raised regions 252 and 238 reduces hysteresis of sensors 230 thereby leading to more accurate load measurement. It has been further found that surface roughness affects load measurement. In one embodiment, the flat surfaces are formed smooth to improve measurement consistency.

Figure 11:
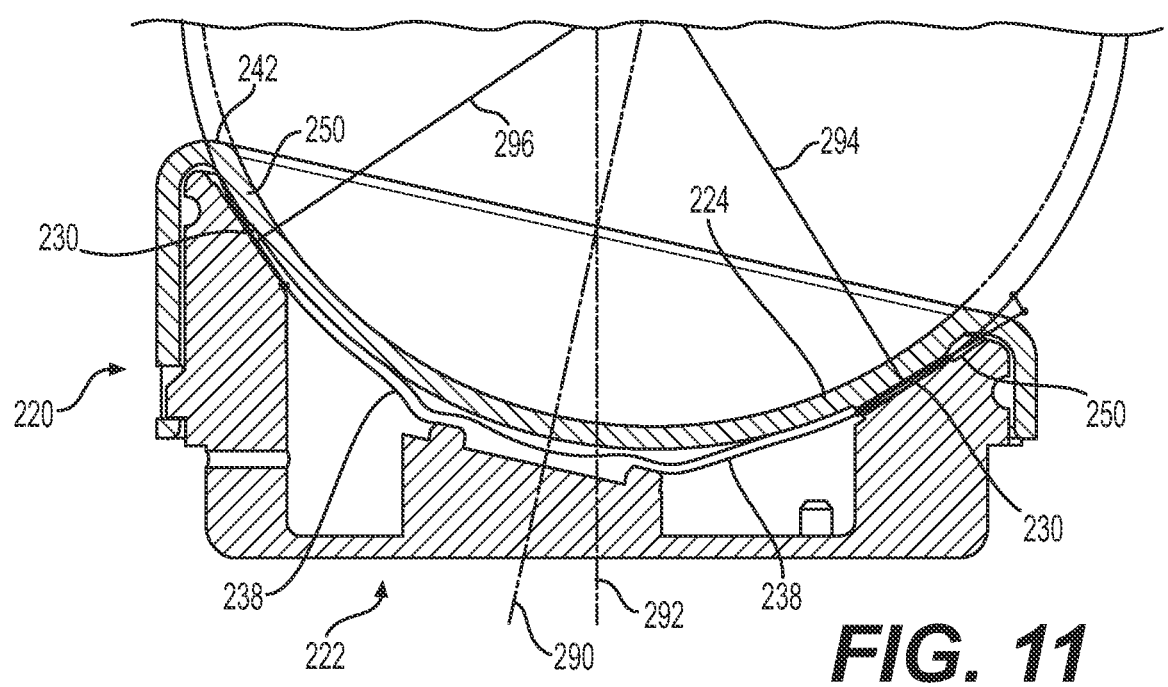
FIG. 11 is a cross-sectional view of the measurement device illustrating the external curved surface of the upper housing in accordance with an example embodiment.

FIG. 11 is a cross-sectional view of measurement device 154 illustrating external curved surface 224 of upper housing 220 in accordance with an example embodiment. Curved surface 224 is configured to couple to the external curved surface of glenoid sphere 152 as shown in FIG. 3. In one embodiment, sensors 230 comprise three sensors underlying upper housing 220. The three sensors are located underlying external curved surface 224 near rim 242 of upper housing 220. The three sensors are spaced equidistant from one another. In one embodiment, raised regions 252 and 238 respectively on upper housing 220 and bottom housing 222 are located in proximity to rim 242 to locate sensor 230 as high as possible around external curved surface 224 of upper housing 220. Placing sensors 230 near rim 242 maximizes the sensing area that can be measured on external curved surface 224. In one embodiment, the three sensors are placed 44 degrees from a gleno-sphere axis 290. An axis 292 of external curved surface 224 is shown relative to gleno-sphere axis 290. In the example, arrows 294 and 296 are 44 degrees from gleno-sphere axis 290 and indicate a location of sensors 230.

Figure 12:
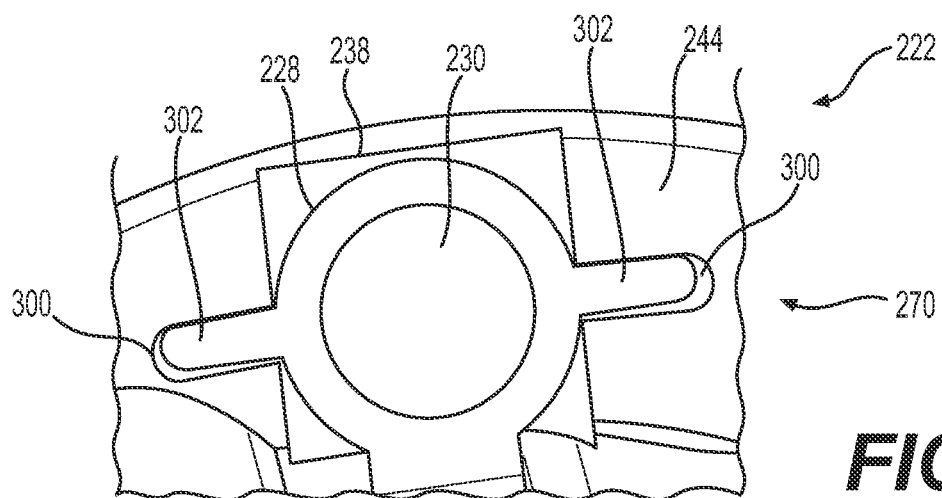
FIG. 12 is an illustration of a sensor snap formed in the bottom housing in accordance with an example embodiment.

FIG. 12 is an illustration of sensor snap 270 formed in bottom housing 222 in accordance with an example embodiment. Sensor snap 270 comprises cutouts 300 and wings 302. Sensors 230 are coupled to bottom housing 222 in a manner to prevent movement during measurement. Any movement of sensors 230 will introduce error to the measurement data. In the example, movement of the elastic capacitor sensors formed in flexible interconnect 228 creates fluctuations in the capacitive measurements. In one embodiment, wings 302 are formed in flexible interconnect 228 on opposing sides of sensor 230. Cutouts 300 are formed in interior surface 244 of bottom housing 222. Cutouts 300 correspond to wings 302 formed in proximity to sensor 230. Wings 302 press-fit into cutouts 300, to align and retain sensor 230 on raised region 238, and prevent movement of sensor 230 during measurement. Press fitting wings 302 into cutouts 300 have the added benefit of reducing assembly time. As an alternative to cutouts 300, posts can be formed extending from internal surface 244 of bottom housing 222. The posts would be formed on opposing sides of sensor 230 in proximity to sensor 230. The posts would couple to corresponding openings in flexible interconnect 228 to align, retain, and prevent movement of sensor 230 on raised region 238. A further measure to prevent movement would be to glue sensor 230 to raised region 238, glue wings 302 into cutouts 300, or glue both sensor 230 and wings 302 respectively to raised region 238 and cutouts 300.

Figure 13:
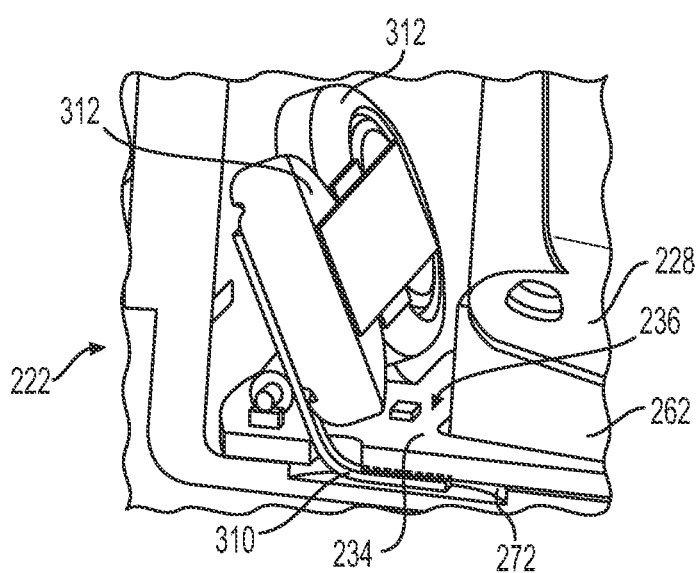
FIG. 13 is a cross-sectional view of the bottom housing illustrating a solder hole in accordance with an example embodiment.

FIG. 13 is a cross-sectional view of bottom housing 222 illustrating solder hole 272 in accordance with an example embodiment. Solder hole 272 is a cutout in bottom housing 222 for a solder battery connection 310 to couple to PC board 234. As shown, solder hole 272 underlies PC board 234. Solder battery connection 310 couples batteries 312 to a bottom surface of PC board 234 to power electronic circuitry 236. In one embodiment, solder hole 272 allows PC board 234 to lie flat on an interior bottom surface of bottom housing 222. Solder hole 272 positions batteries 312 to allow coupling of flexible interconnect 223 to support structure 262.

Figure 14:
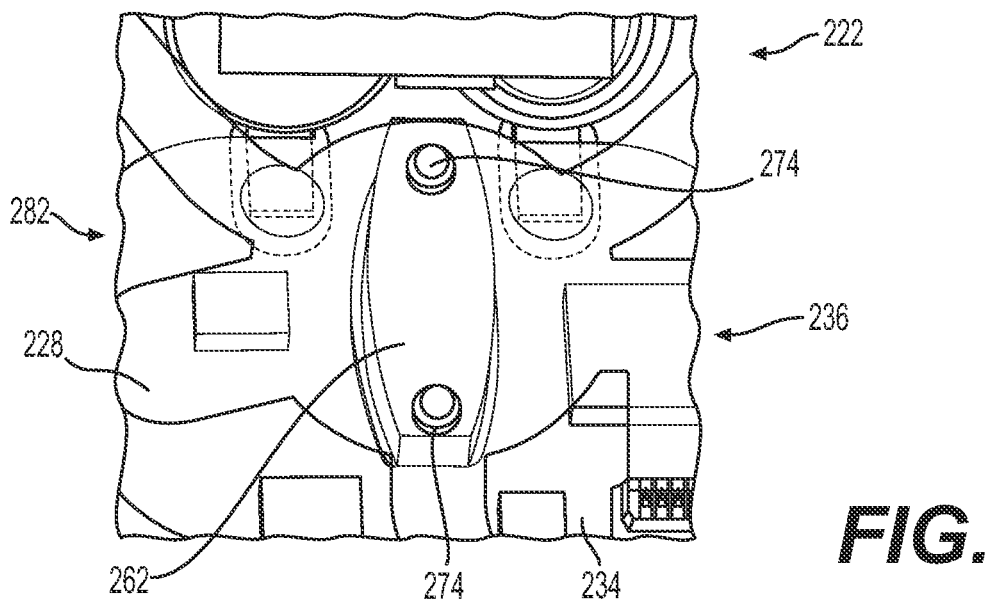
FIG. 14 is an illustration of the support structure in the bottom housing configured to couple to the flexible interconnect in accordance with an example embodiment.

FIG. 14 is an illustration of support structure 262 in bottom housing 222 configured to couple to flexible interconnect 228 in accordance with an example embodiment. In one embodiment, support structure 262 extends from an interior bottom surface of bottom housing 222. Support structure 262 is centrally located in rigid cutout 282 as shown in FIG. 9. In one embodiment flexible interconnect 228 is rigidly coupled to support structure 262. Support structure 262 includes flex snaps 274. Flex snaps 274 are columns extending from support structure 262. Flexible interconnect 228 has openings corresponding to flex snaps 274. In one embodiment, flex snaps 274 are oversized or larger than the openings in interconnect 228. The openings of flexible interconnect 228 are pushed on flex snaps 274 which press fits flexible interconnect to support structure 262.

Alternatively, pins can be used to couple flexible interconnect 228 to support structure 262. Both support structure 262 and flexible interconnect 228 have openings. Pins can be used to couple through the openings in flexible interconnect 228 and into the openings in support structure 262. In one embodiment, the pins forcibly couple to the openings of support structure 262 as an interference fit to retain flexible interconnect 228 to support structure 262. An adhesive could also be used to hold the pins to support structure 262.

In one embodiment, a surface of support structure 262 is not planar or parallel to the bottom surface of bottom housing 222. In the example, the surface of support structure 262 places flexible interconnect 228 at a 12.5 degree angle relative to the bottom surface of bottom housing 222. The angle places flexible interconnect 228 in a position to support placement of sensors 230 as shown in FIG. 7. Support structure 262 also places a connector of flexible interconnect 228 in a position to couple to a connector on PC board 234. In one embodiment, flexible interconnect 228 is suspended above the bottom surface of bottom housing 222.

Figure 15:
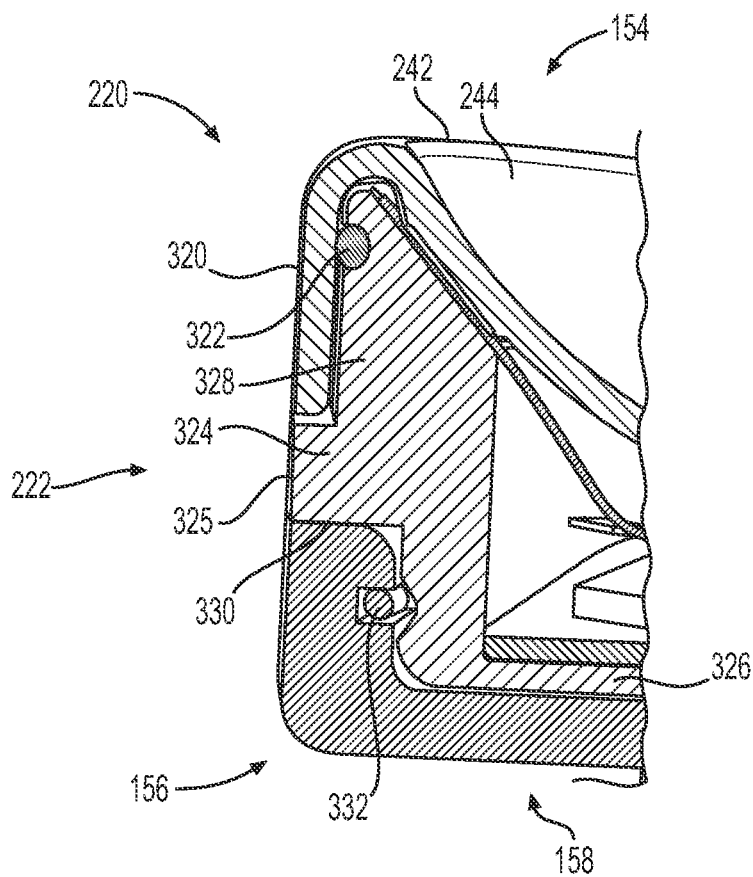
FIG. 15 is a cross-sectional view of a portion of the upper housing, the bottom housing, and the humeral tray in accordance with an example embodiment.

FIG. 15 is a cross-sectional view of a portion of upper housing 220, bottom housing 222, and humeral tray 156 in accordance with an example embodiment. In the example, bottom housing 222 couples to humeral tray 156 of humeral prosthesis 158. Humeral tray 156 typically comprises a metal such as stainless steel or titanium. Bottom housing 222 can have a retaining feature that couples to a corresponding retaining feature of humeral tray 156 such that measurement device 154 is retained but removable from humeral tray 156. In the example, loading on external curved surface 244 of upper housing 220 is transferred through sensors 230 as shown in FIG. 7 to bottom housing 222. The load distribution to sensors 230 can be unequal depending on the trajectory of the force to external curved surface 244. The loading couples through bottom housing 222 and is distributed to humeral tray 156.

Upper housing 220 includes a sidewall 320 configured to couple to a sidewall 328 of bottom housing 222. Sidewall 320 overlies a portion of sidewall 328 of bottom housing 222 when upper housing 220 is coupled to bottom housing 222. In one embodiment, bottom housing 222 has an O-ring 322 fitted around a circumferential groove in sidewall 328 of bottom housing 222. O-ring 322 is configured to hermetically seal the enclosure. In one embodiment, O-ring 322 is compressed when sidewall 320 of upper housing 220 overlies sidewall 328 of bottom housing 222. As previously mentioned, coupling upper housing 220 to bottom housing 222 pre-loads sensors 230 that corresponds to an external curved surface 244 being unloaded.

Sidewall 328 of bottom housing 222 can have a protrusion 325 extending partially or circumferentially from sidewall 328. In one embodiment, a first ledge of protrusion 325 couples to sidewall 320 of upper housing 220 from above protrusion 325. In one embodiment, a second ledge of protrusion 325 couples to a rim 330 of humeral tray 156 from below protrusion 325. In one embodiment, loading is applied to external curved surface 244, through load the load sensors, to sidewall 328 of bottom housing 222 to rim 330 and a surface of humeral tray 156 to distribute loading applied to measurement device 154 and to humeral prosthesis 158. Humeral tray 156 can have an O-ring 332 that aligns, retains, and seals a portion of bottom housing 222 to humeral tray 156. In one embodiment, bottom housing 222 can have a corresponding groove that accommodates O-ring 332 when measurement device 154 is pressed into humeral tray 156.

Figure 16:
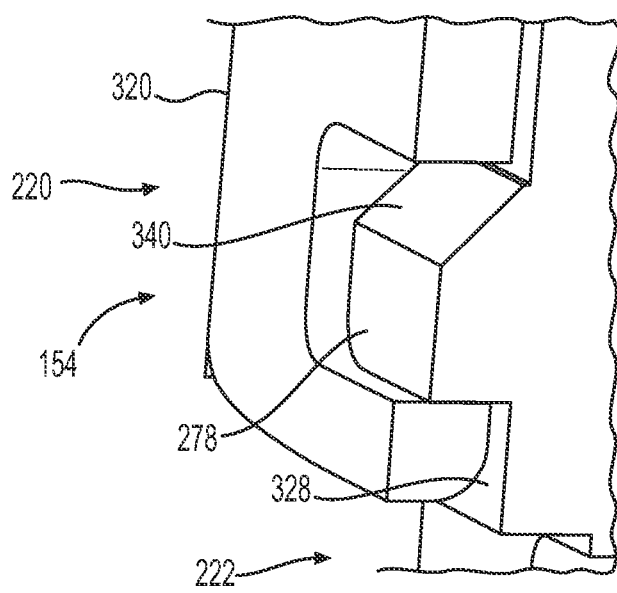
FIG. 16 is an illustration of a housing snap on the measurement device to couple the upper housing to the bottom housing in accordance with an example embodiment.

FIG. 16 is an illustration of housing snap 278 on measurement device 154 to couple upper housing 220 to bottom housing 222 in accordance with an example embodiment. Housing snap 278 comprises a protrusion extending from sidewall 328 of bottom housing 222. In one embodiment, sidewall 320 of upper housing 220 is designed to flex. In one embodiment, sidewall 320 has an opening configured to receive housing snap 278 to retain upper housing 220 to bottom housing 222. In one embodiment, upper housing 220 slides onto bottom housing 222 such that sidewall 320 of upper housing 220 overlies sidewall 328 of bottom housing 222. Upper housing 220 and bottom housing 222 are compressed together until the housing snap 278 on sidewall 328 couples through the corresponding opening in sidewall 320 of upper housing 220. In one embodiment, the housing snap 278 has an angled or sloped wall 340 that facilitates sidewall 320 to flex and slide over the protrusion until housing snap 278 engages with the corresponding opening. In one embodiment, more than one housing snap 278 is used to retain upper housing 220 to bottom housing 222. Alternatively, upper housing 220 can be screwed to bottom housing 222 as disclosed in FIGS. 5-7.

Figure 17:
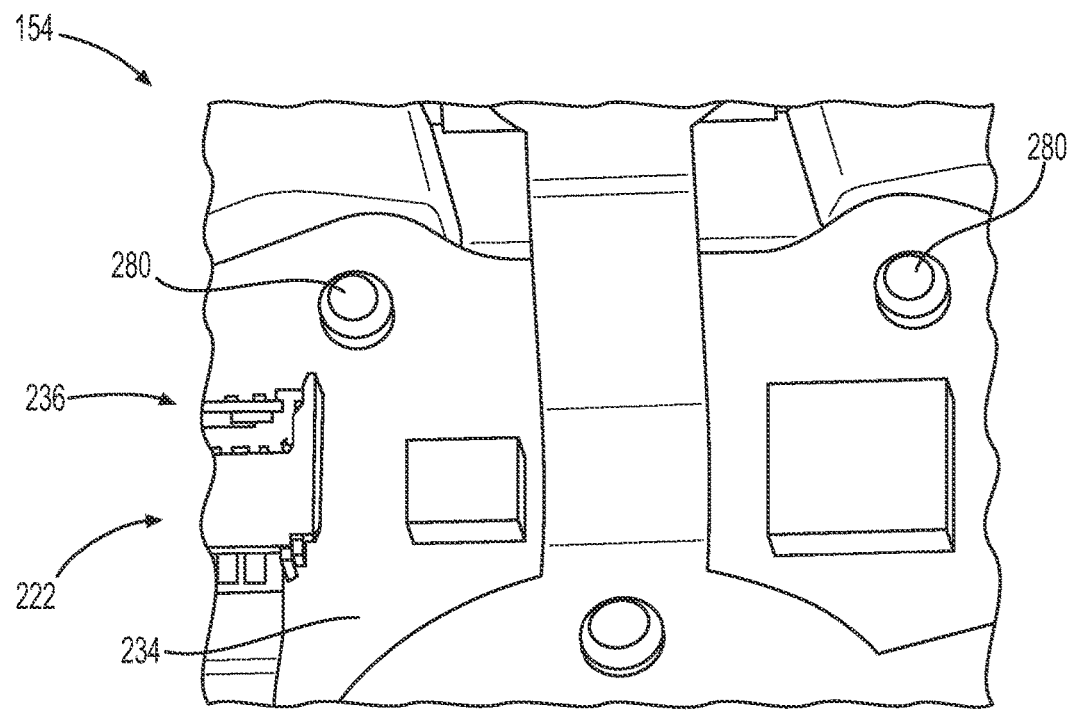
FIG. 17 is an illustration of rigid snaps extending from the bottom housing in accordance with an example embodiment.

FIG. 17 is an illustration of rigid snaps 280 extending from bottom housing 222 in accordance with an example embodiment. Rigid snaps 280 are press fit columns extending from the interior bottom surface of bottom housing 222. In one embodiment, rigid snaps 280 correspond to undersized openings in PC board 234. In the example, PC board 234 is a multi-layer rigid printed circuit board that interconnects electronic circuitry 236 to form a circuit or system to control a measurement process and transmit measurement from measurement device 154. Rigid snaps 280 are aligned to openings in PC board 234. Pressure is applied to PC board 234 until rigid snaps 280 couple through the corresponding openings in PC board 234. Rigid snaps 280 align and retain PC board 234 within the enclosure. More specifically, rigid snaps 280 prevent movement of PC board 234 while in the shoulder joint. Movement of PC board 234 can introduce movement to leads or flexible interconnect coupling to PC board 234 thereby affecting measurement.

Figure 18:
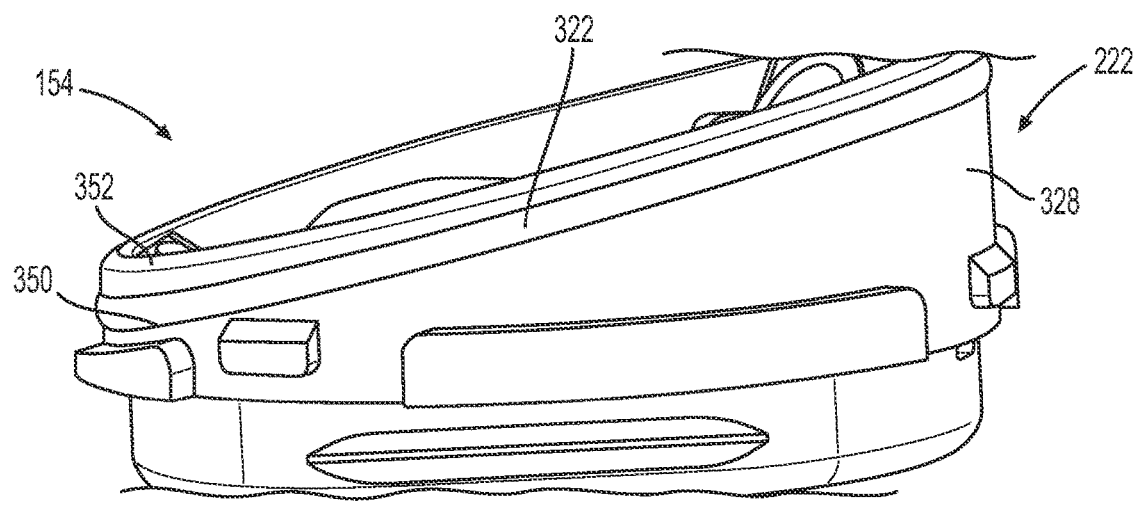
FIG. 18 is an illustration of the O-ring in the measurement device in accordance with an example embodiment.

FIG. 18 is an illustration of O-ring 322 in measurement devices 154 in accordance with an example embodiment. Bottom housing 222 has a rim 352. Sidewall 328 of bottom housing 222 can have a groove 350 around the perimeter to retain an O-ring 322 below rim 352. In one embodiment, O-ring 322 has a durometer of approximately shore 40. Rim 242 of upper housing 220 overlies O-ring 322 when upper housing 220 couples to bottom housing 222 as shown in FIG. 15. O-ring 322 hermetically seals the enclosure and prevents the ingress of gas, liquids, or solids from entering measurement device 154. Load measurement by measurement device 154 is unaffected by O-ring 322.

Figure 19:
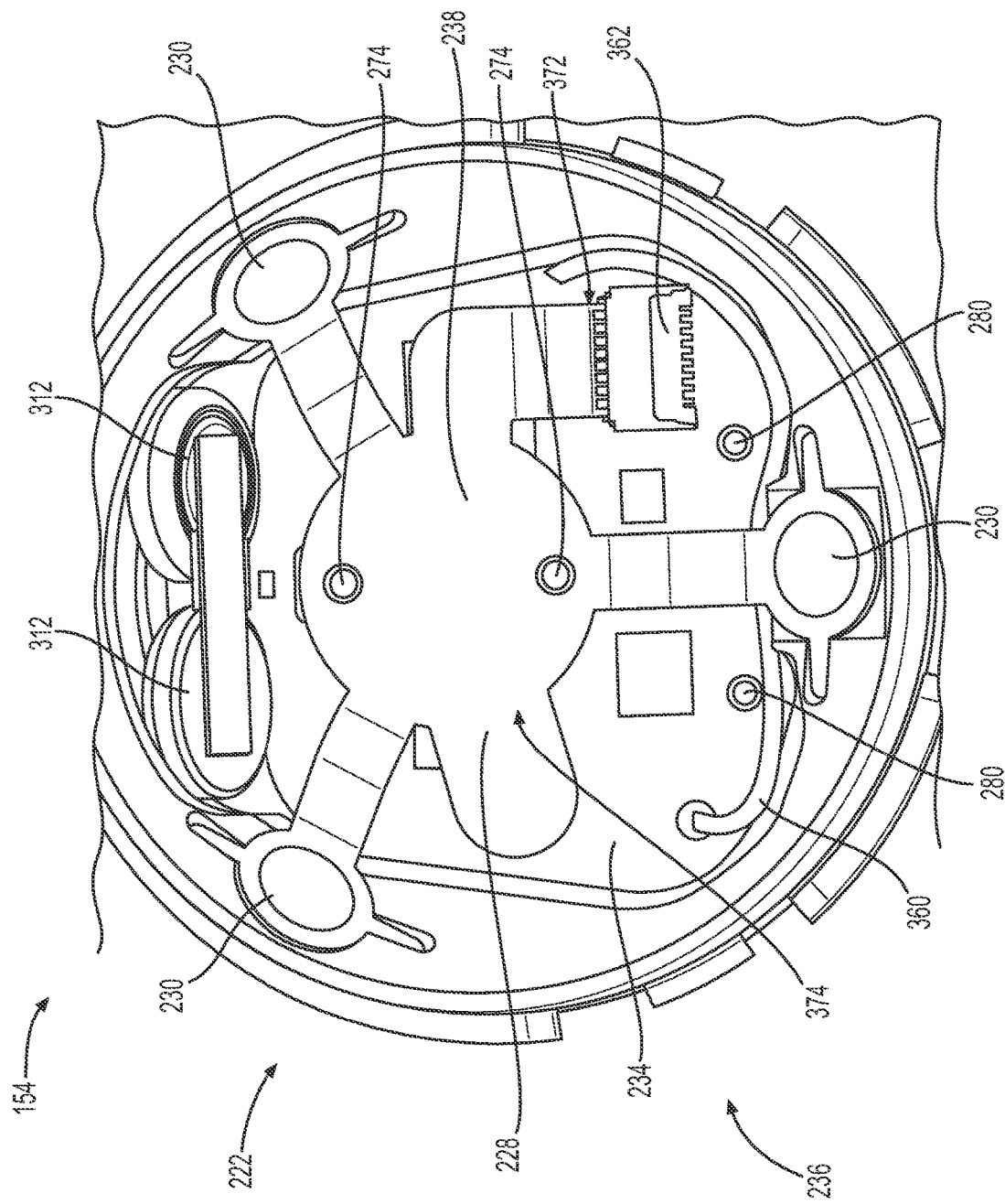
FIG. 19 is an illustration of the bottom housing with the electronic circuitry in accordance with an example embodiment.

FIG. 19 is an illustration of bottom housing 222 with electronic circuitry 236 in accordance with an example embodiment. In one embodiment, PC board 234 is a rigid printed circuit board coupled to the interior bottom surface of bottom housing 222 through rigid snaps 280. Electronic circuitry 236 comprises electronic components such as processors, digital signal processors, digital logic circuitry, interface circuitry, analog circuitry, buffers, amplifiers, radio frequency circuitry, sensors, passive components, and other circuitry. The electronic components can be mounted to PC board 234. PC board 234 has multiple layers of interconnect to couple the electronic components to form a circuit that controls a measurement process and transmits measurement data. Flexible interconnect 228 couples sensors 230 to PC board 234. In one embodiment, flexible interconnect 228 is suspended above PC board 234 and couples to flex plug 362 mounted on PC board 234. Flex snaps 274 couple through openings in flexible interconnect 228 to retain, align, and prevent movement of flexible interconnect 228. Flexible interconnect 228 does not have any angled bends because they have been observed to cause sensor anomalies and errant data. In one embodiment, flexible interconnect 228 has a shielding layer 374 to shield sensors 230 and interconnect. Shielding layer 374 is a grounded copper layer that is external to the sensor ground that has showed significant noise improvement. Flexible interconnect 228 has a plug 372 that couples to a flex plug 362 that couples to PC board 234. Flex plug 362 couples sensors 230 to electronic circuitry 236. Batteries 312 couple to PC board 234 via an interconnect 310 that underlies PC board 234 in solder hole 312 as shown in FIG. 13. In one embodiment, batteries 312 are configured to power measurement device 154 for a single operation. An antenna 360 couples to a transceiver circuit on PC board 234. Antenna 360 transmits measurement data from measurement device 154 within the operating room to computer 162 as shown in FIG. 3 to provide the measurement data for use by a surgeon in real-time. In one embodiment, measurement device 154 is disposed of in an appropriate manner after the shoulder surgery is completed.

Figure 20:
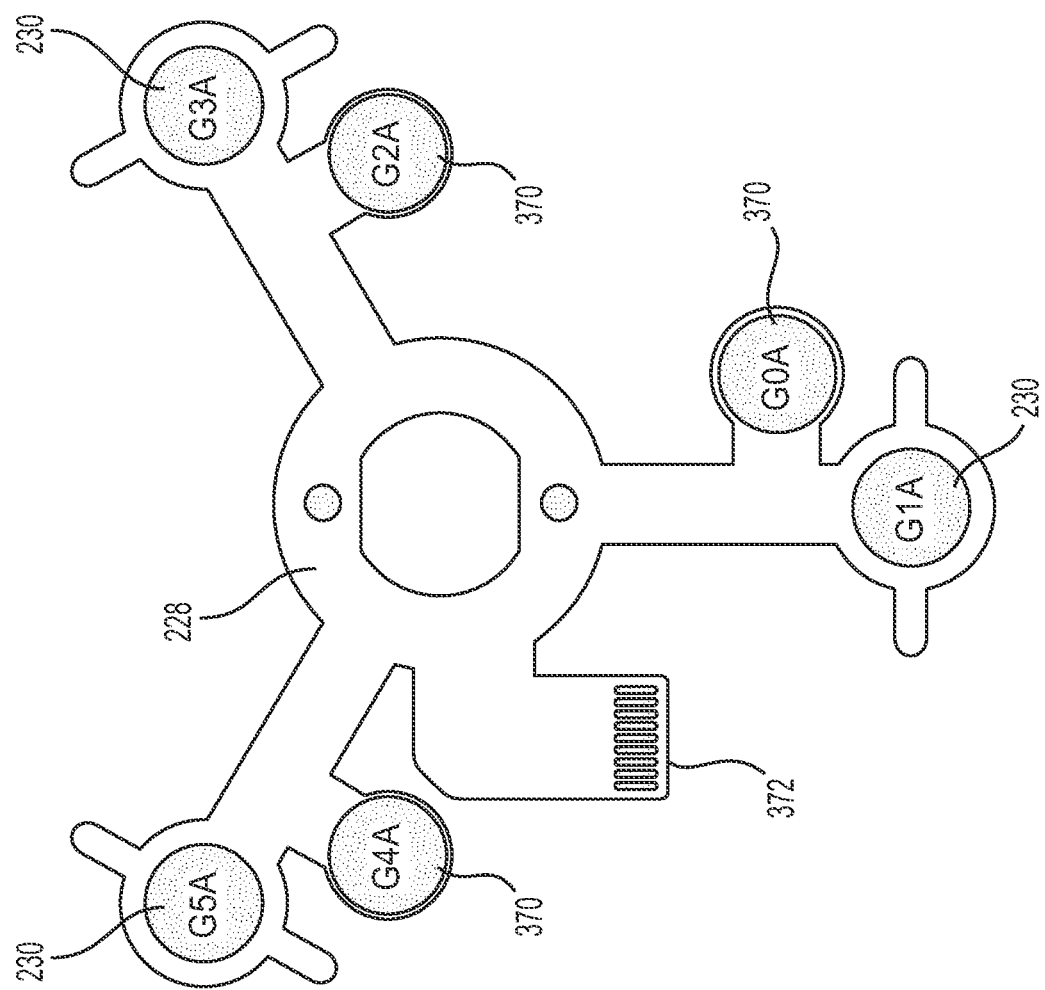
FIG. 20 is an illustration of the flexible interconnect in accordance with an example embodiment.

FIG. 20 is an illustration of flexible interconnect 228 in accordance with an example embodiment. Flexible interconnect 228 includes sensors 230 configured to measure a force, pressure, or load applied to the measurement device. Sensors 230 can be coupled to flexible interconnect 228 or formed as part of flexible interconnect 228. In one embodiment, sensors 230 are capacitors formed in flexible interconnect 228 using two or more layers of interconnect. The capacitors comprise a first metal region and a second metal region separated by a dielectric material. In one embodiment, the capacitors are shielded to prevent noise coupling and to reduce parasitic coupling. In one embodiment, the capacitors comprise more than one capacitor coupled in series or coupled in parallel. In one embodiment, the capacitors can comprise more than one dielectric layer. In general, the capacitors are elastic over a range of operation seen by a shoulder joint. Sensors 230 couple through interconnect in flexible interconnect 228 to a plug 372. Plug 372 is configured to couple to flex plug 362 on PC board 234 as shown in FIG. 19. In one embodiment, one or more reference sensors 370 are coupled to or formed in flexible interconnect 228. Reference sensors 370 are not configured to measure loading applied to the measurement device. Reference sensors 370 are formed identically to sensors 230. In one embodiment, reference sensors 370 are located near sensors 230 to ensure strong temperature and noise compensation for sensors 230. If a single reference sensor 370 is used it can be located in an area substantially equidistant from sensors 370. Alternatively, the single reference sensor 370 can be placed in proximity to one of sensors 370. In one embodiment, there is a reference sensor 370 for each sensor 230.

FIG. 21 is an illustration of measurement device 154 in accordance with an example embodiment. In general, a load applied by a prosthetic component coupled to external curved surface 224 will have no path to ground except through the plurality of sensors measuring loading in measurement device 154. In one embodiment, there will be no parallel paths to apply or dilute loading in measurement device 154. Measurement device 154 is designed to operate under a maximum load that is applied to external curved surface 224 during installation into a prosthetic joint or when installed in the prosthetic joint. A compression strength of measurement device 154 can accept the maximum load without impacting the load path and accept the maximum load without plastic deformation. In one embodiment, measurement device 154 is configured to withstand torque applied during a humeral reduction. Measurement device 154 has a form factor that matches a target trial implant for the prosthetic joint.

Upper housing 220 is coupled to bottom housing 222 to form the enclosure for housing the power source, electronic circuitry, and one or more sensors. The power source can be a passive storage device, battery, or other means of providing power. Alternatively, power can be wired, inductively or RF coupled to measurement device 154. The power source has sufficient energy to power the electronic circuitry and sensors for a single joint arthroplasty. Upper housing 220 is retained by one or more housing snap 278 on sidewall 328 of bottom housing 222 coupling through an opening in sidewall 320 of upper housing 220. Housing snap 278 has an angled or sloped wall 340 that facilitates sidewall 320 of upper housing 220 to flex and slide over housing snap 278 until housing snap 278 couples through the opening in sidewall 320 of upper housing 220 to retain upper housing 220 to bottom housing 222. In the example, housing snap 278 is configured to keep housing 220 proximate to sensor engagement without applying a load when coupled to housing 222.

In the example, measurement device 154 couples to the humeral prosthesis. External curved surface 224 couples to a glenoid sphere coupled to a scapula to support movement of a shoulder. In one embodiment, measurement device uses three sensors to measure load and position of load on external curved surface 224. In one embodiment, at least one reference sensor can also be used to improve the accuracy of the load measurements from each sensor. The interface between the external curved surface 224 and sensors 230 is fully constrained. In one embodiment, the sensing configuration of measurement device 154 uses exactly three load sensors for full constraint if sensors 230 are oriented towards a center of curvature of external curved surface 224 such that all force vectors pass through a same point with no moments to balance. In one embodiment, measurement device 154 measures loading applied to external curved surface 224 in a range of 10-60 lbs. for the shoulder application. The accuracy of the measured load magnitude is 3.5 lbs. or less. In one embodiment, the range and accuracy can be adjusted by changing parameters of the capacitor sensor such as dielectric thickness or sensor area. The measured capacitance value correlates to loading applied to external curved surface 224. Alternatively, different sensor types such as a MEMs, strain gauge, or piezo-sensor could be used in place of the capacitor. Measure device 154 can be operated with a safe overload of 200 percent of the maximum load range. In the example, the position of applied load or contact point of the glenoid sphere on external curved surface 224 has an accuracy of 2 millimeter and 2 degrees or less. This accuracy is given for reference and can be changed or improved depending on the application and requirements of the measurement device. The shoulder joint can be moved through a range of motion and measurement device 154 will provide measurement data in real-time. The measurement data is transmitted to computer 162 in the operating room where computer 162 receives and processes the measurement data and displays the measurement data on display 164 in a form that can be rapidly assimilated by the surgeon and surgical team to support validation or adjustment with quantitative measurement data.

Figure 22A:
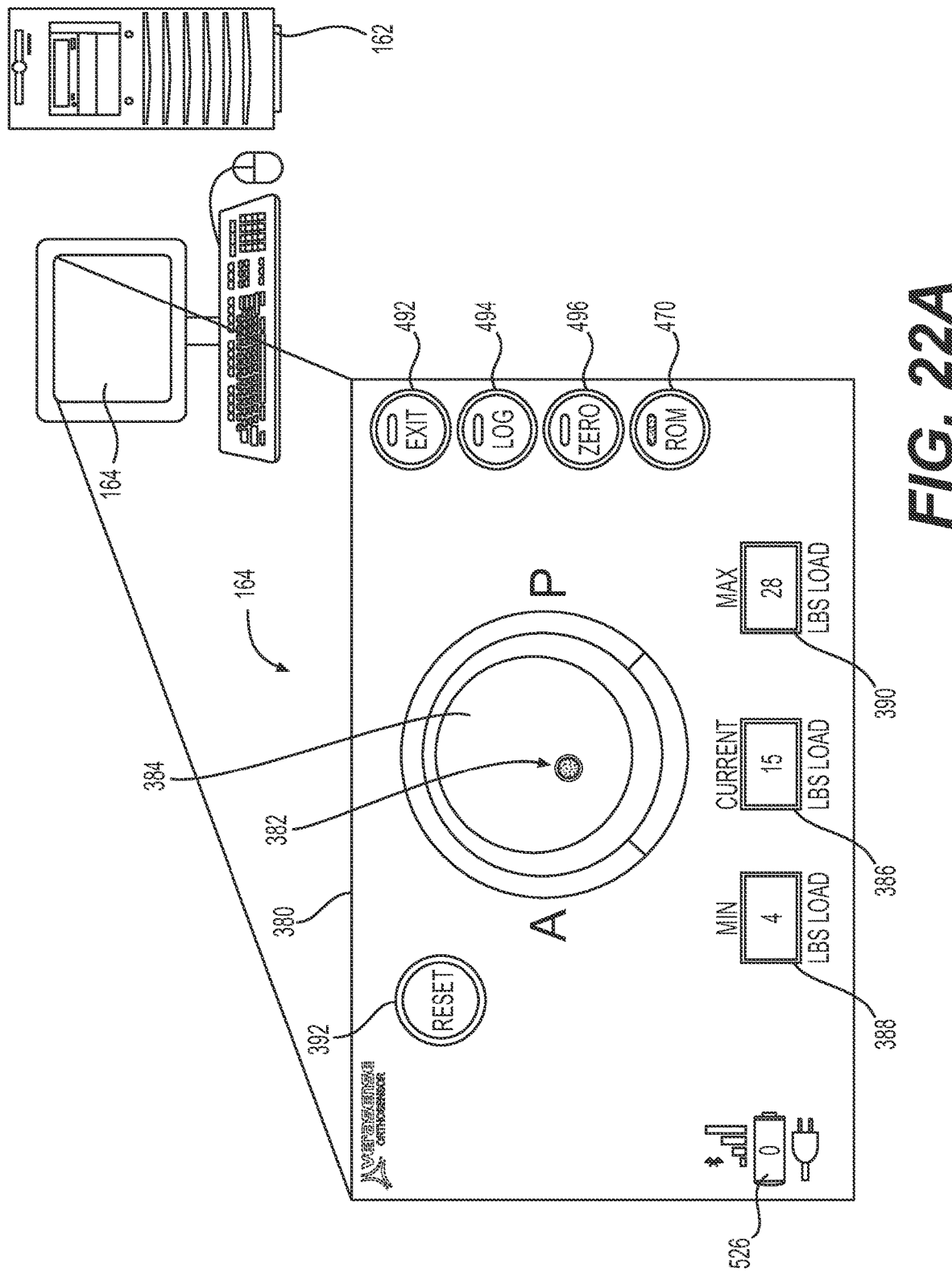
FIG. 22A is an illustration of a GUI on the display of the computer in accordance with an example embodiment.

FIG. 22A is an illustration of a GUI 380 on display 164 of computer 162 in accordance with an example embodiment. Measurement device 154 is in a shoulder joint and transmitting measurement data as shown in FIG. 3. Components of FIGS. 3, 7, 8, 9, and 21 may be referred to in the discussion herein below to relate operation of measurement device 154 to what is displayed in GUI 380. In general, a surgeon moves the shoulder through a free range of motion to generate measurement data to determine stability of the shoulder joint. The measurement data from the sensors in measurement device 154 is transmitted to computer 162. Computer 162 processes the information and displays the information in a manner where quantitative measurement data can be rapidly assimilated by the surgeon or surgical team. The measurement data can be displayed or it can be presented graphically or audibly.

A picture of a portion of measurement device 154 is displayed on display 164. In the example, a surface 384 is displayed on display 164 that corresponds to external curved surface 224 as shown in FIG. 21. In one embodiment, display 164 depicts a curved surface of a ball or socket prosthetic joint system. In one embodiment, radial measurement data from load sensors at predetermined locations as disclosed in FIGS. 29A-31 herein below is used to determine contact point 384 on display 164. In other words, the movement of contact point 384 is not measured, depicted, or calculated for display 164 as a planar measurement but illustrates movement on a curved surface. Display 164 can further add measurement data or graphics to disclose movement of contact point 384 on external curved surface 224. In one embodiment, movement of contact point 384 will be non-linear. In one embodiment, display 164 may display a three dimensional type of animation to illustrate to a surgeon or surgical team a location of contact point 384 on external curved surface 224. This allows the surgeon to understand loading or location on a ball or cup of a prosthetic joint system. Alternatively, more than one view or different orientations of external curved surface 224 can be provided on display 164 to better illustrate a location of contact point 384 on external curved surface 224. In a reverse shoulder joint, external curved surface 224 couples to a glenoid sphere. A contact point 382 or load centroid location is represented on GUI 380 where the glenoid sphere applies loading to external curved surface 224 of measurement device 154. Contact point 382 is shown on surface 384 of GUI 380. A display box 386 discloses the load magnitude in real-time on GUI 380 as the shoulder joint is moved through the range of motion. In one embodiment, computer 162 or measurement device 154 can include software having a force location and load magnitude algorithm that calculates contact point 382 and load magnitude as displayed in display box 386 from the measurement data received from measurement device 154. In the example, the measurement data comprises information from three sensors measuring loading applied to external curved surface 224, at least one reference sensor, and a position measurement system. The position measurement system is configured to measure position or motion. In one embodiment, the position measurement system is configured to be housed in measurement device 154. In one embodiment, the position measurement system is an inertial measurement unit (IMU). Computer 162 or measurement device 154 can further have quaternion and range of motion algorithms to support measurement of movement and position. Calibration information can be accessed for the IMU or load sensors and used with the force location, load magnitude, and impingement measurements. In one embodiment, calibration information or calibration data corresponds to test measurements on measurement device 154. In one embodiment, the calibration data can be stored on non-volatile memory such as EEPROM within measurement device 154. As the shoulder joint is moved through a predetermined range of motion there will be a minimum load magnitude measured at a first location and a maximum load magnitude measured at a second location on surface 384 for the predetermined range of motion. The minimum load magnitude is indicated in display box 388 on GUI 380 that is continuously updated should a lower value occur. Similarly, the maximum load magnitude is indicated in display box 390 on GUI 380 that is continuously updated. In one embodiment, force vector data can be used to detect impingement. GUI 380 will notify the surgeon or surgical team when impingement is detected by audible, visual, or haptic means. In one embodiment, the IMU comprises one or more inertial sensors and is housed in measurement device 154. The IMU can track position, motion, and can also be used in conjunction with the force vector data or alone to determine impingement.

In the example, an exit button 492, a LOG button 494, a zero button 496, a reset button 392, and a ROM button 470 are provided on GUI 380. In one embodiment, exit button 492 toggles between connecting measurement device 154 and disconnecting measurement 154 from computer 162. In one embodiment, exit button 492 will indicate when measurement device 154 is coupled to computer 162. In one embodiment, enabling LOG button 494 logs data for 10 seconds. In one embodiment, enabling zero button 496 zeroes load data offsets. In one embodiment, enabling reset button 392 resets display box 388 and display box 390 to the current load magnitude value. In one embodiment, enabling ROM button 370 initiates a range of motion test. ROM button 370 further initializes the IMU for the range of motion test. Battery indicator 526 indicates an amount of power left in the power source. In the example, the power source is one or more batteries and battery indicator 526 indicates the percentage of power remaining in the batteries of measurement device 154 or provide an estimation of an operating time of measurement device 154 based on the average current drain from the batteries. GUI 380 further includes a tracking function that displays dynamic motion of contact point 382 through the full range of motion to evaluate joint kinetics. GUI 380 can also indicate or leave a location trace where loading exceeds a predetermined threshold.

FIG. 22B is an illustration of GUI 380 indicating impingement in accordance with an example embodiment. Components of FIGS. 3, 7, 8, 9, and 21 may be referred to in the discussion herein below to relate operation of measurement device 154 to what is displayed in GUI 380. GUI 380 shows contact point 382 on surface 384 corresponding to the contact point on surface 224 of measurement device 154. In the example, contact point 382 is calculated from quantitative measurement data from measurement device 154 and is updated in real-time as the shoulder joint is moved through a range of motion.

Measurement device 154 couples to computer 162 that can be indicated on GUI 380. An indicator 528 on GUI 380 shows the signal strength of the wireless connection to measurement device 154. A signal strength is displayed on indicator 528 that provides an indication of the connection and ability to transfer measurement data to computer 162. In one embodiment, the wireless connection is a Bluetooth low energy connection that opens a connection dialog between computer 162 any Bluetooth devices. Computer 162 is used to select measurement device 154 for connection and initiates the wireless connection. In one embodiment, calibration data and device information from measurement device 154 is downloaded to computer 162. Measurement device 154 couples to computer 162 and begins to stream measurement data. In one embodiment, GUI 380 zeroes any load data and then begins showing a measured load magnitude at contact point 382 in display box 386.

In a first step, the ROM button 470 is enabled preparing for measurement device 154 to measure the shoulder joint as it is moved through a predetermined range of motion. The position measurement system is enabled for measurement. In the example, the position measurement system is an inertial measurement unit. In a second step, the shoulder joint is held motionless at zero degrees adduction for 5 seconds. In a third step, GUI 380 is configured to display a notification to begin movement in abduction. In a fourth step, during the movement, the degrees of rotation and plot will be updating. In a fifth step, at the end of the movement (e.g. full abduction) the user will hold the arm motionless. In a sixth step, measurement data will be captured during the movement and ROM button 470 will indicate that the measurement has ended. In one embodiment, ROM button 470 will change color when the measurement has ended.

Impingement occurs when a prosthetic joint impinges on bone or soft tissue. In the example, scapular notching occurs when the prosthetic shoulder joint impacts bone as some point in the range of motion. Scapular notching typically occurs during an adduction movement. Impingement may also occur in the soft tissue around the prosthetic shoulder joint. Soft tissue impingement is often called acromial impingement. Impingement information can be displayed on GUI 380. In one embodiment, a rim 520 is used to show if impingement occurs and approximately where the impingement occurs. A portion of rim 520 will be highlighted by a color change or a gray scale change on the portion of rim 520 in proximity to where the impingement occurs. In one embodiment, the portion of rim 520 in proximity to the impingement will turn red when impingement is detected. In one embodiment, a plot 522 is displayed on GUI 380. Plot 522 shows range of motion angles versus loading for contact point 382.

Figure 23:
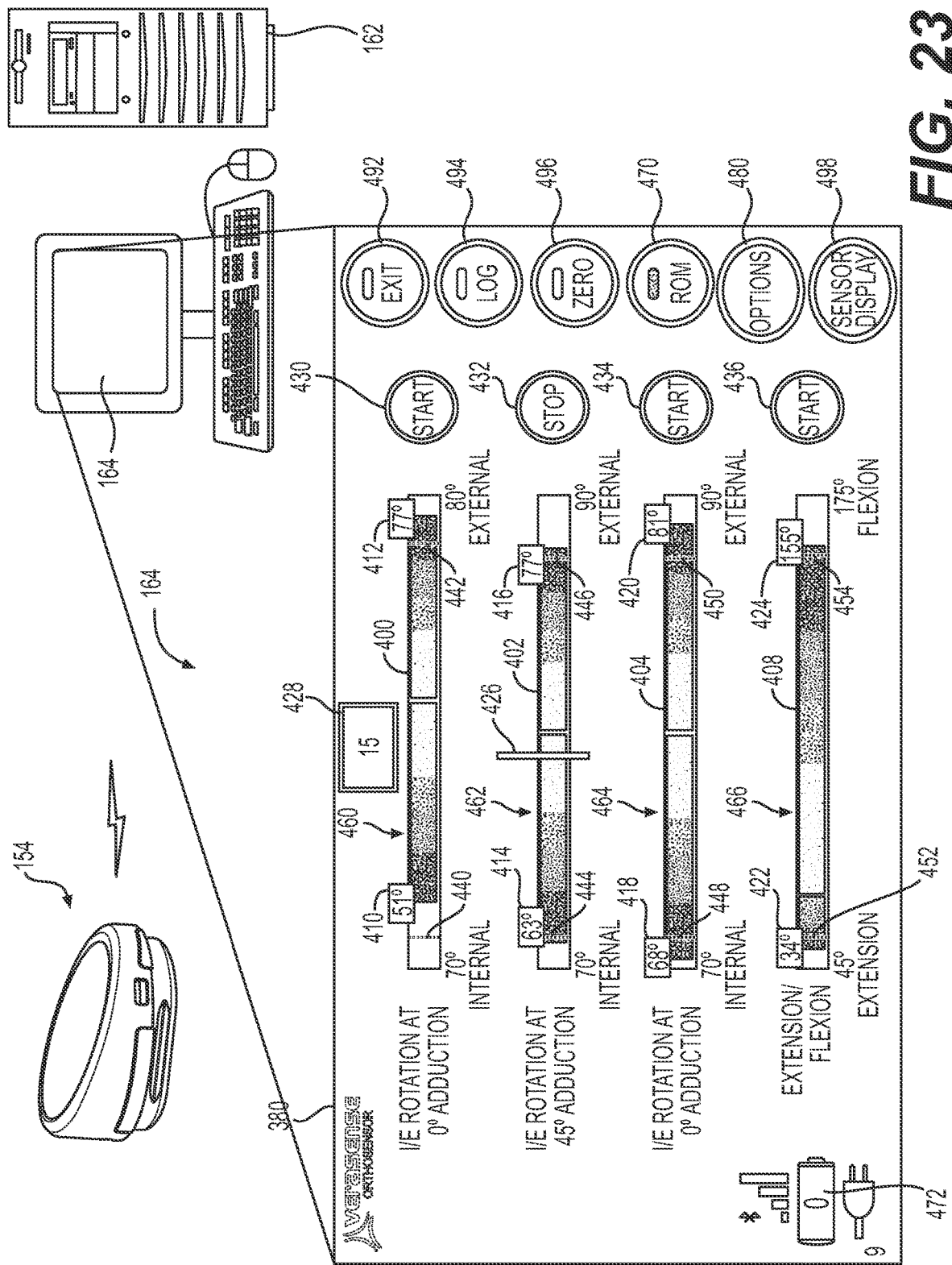
FIG. 23 is an illustration of the GUI on the display coupled to the computer displaying sensor information related to range of motion from the measurement device in accordance with an example embodiment.

FIG. 23 is an illustration of GUI 380 on display 164 coupled to computer 162 displaying sensor information related to range of motion from measurement device 154 in accordance with an example embodiment. In the example, measurement device 154 is in the reverse shoulder joint as shown in FIG. 3. Components of FIGS. 3, 7, 8, 9, and 21 may be referred to in the discussion herein below to relate operation of measurement device 154 to what is displayed in GUI 380. The measurement data comprises data from sensors 230 coupled at predetermined positions in measurement device 154 to measure loading applied to external curved surface 224. In one embodiment, the predetermined positions of sensors 230 are used to calculate the position of load and the magnitude of load applied to external curved surface 224. In one embodiment, the measurement data can further comprise information from the position measurement system. In one embodiment, the position measurement system comprises one or more inertial measurement units for tracking position and motion.

Computer 162 converts measurement data from measurement device 154 to a graphical form that a surgeon or surgical team can rapidly assess a status of the shoulder joint. A display box on GUI 380 can be used to provide numerical information related to a parameter measurement. In the example, the shoulder joint can be moved through specific or predetermined range of motions. A motion bar is used to provide information on a predetermined range of motion. The motion bar is a tool of GUI 380 that allows the surgeon to rapidly assess the movement to determine if the shoulder joint functions with known norms or could use further optimization to affect loading or range of motion. Alternatively, a round graphic can be used with a rim and indicator which rotates around it to read for the angle. As shown, four motion bars are displayed on GUI 380. Each motion bar corresponds to a specific movement of the shoulder joint. In the shoulder example each motion bar will indicate a maximum range of motion for an internal motion and an external motion for the specific movement. As shown, the internal motion maximum is indicated on a left side of the motion bar and a numerical value for the maximum internal motion is listed below the motion bar on the left side. The external motion maximum is indicated on a right side of the motion bar and a numerical value for the maximum internal motion is listed below the motion bar on the right side. A center or zero between internal and external motion is indicated by a bar central to the motion bar. In general, the actual range of motion as the surgeon moves the installed prosthetic joint with measurement device 154 will be less than the internal motion maximum or the external motion maximum. A first display box will indicate the numerical load magnitude applied to measurement device 154. A second display box indicates the maximum range of motion (in degrees) achieved by internal movement of the prosthetic joint (by the surgeon) relative to the internal motion maximum. The second display box is placed on the left side of the motion bar and above the motion bar. A third display box indicates the maximum range of motion (in degrees) achieved by external movement of the prosthetic joint (by the surgeon) relative to the external motion maximum. The third display box is placed on the right side of the motion bar and above the motion bar.

The motion bar in GUI 380 graphically displays the same information as the display boxes but in a manner that can be rapidly assimilated to reduce an assessment time. In one embodiment, the surgeon can use the motion bars to determine if the loading and range of motion is within an acceptable range without looking at numerical values. As mentioned previously, the motion bar length indicates a range maximum from internal motion maximum to external motion maximum. The range of motion of the movement by the surgeon of the prosthetic joint can be indicated by a color scale region within the motion bar. The range of motion of the movement of the surgeon can also be indicated by a grey scale region within the motion bar. A color scale can be used in within the motion bar to indicate the magnitude of loading at different points within the range of motion. The color scale can be a load magnitude or correspond to a predetermined load magnitude range over the range of motion. Similarly, the grey in the grey scale region can indicate the magnitude of loading. Each shade of grey can be a load magnitude or correspond to a predetermined load magnitude range. In one embodiment, the surgeon does not need to know the absolute load magnitude at each point over the range of motion but that the load magnitudes are within a predetermined range over the range of motion. The surgeon can "at a glance" determine that the color within the motion bar is correct or that the loading or range of motion is incorrect. In one embodiment, the color or color scale corresponds to an acceptable predetermined range of the load magnitude for the shoulder joint based on clinical evidence that provides optimum performance. In one embodiment, the colors or shades of gray displayed in the motion bar indicate a pattern that the surgeon is looking for over a specific movement of the prosthetic joint. For example, the color scale or grey scale can change as the movement moves to the internal or external maximum. For example, the surgeon can view a grey scale indicating optimal loading over a predetermined range centered between the internal and external movement. Moving outside the predetermined range towards the maximum internal movement or the maximum external movement results in increased or decreased loading that is less than optimal. In general, the surgeon can "at a glance" determine where the optimal loading occurs and at where it is located in the range of motion. The motion bar can also indicate loading or range of motion issues that need to be addressed. For example, adjustments can be made if the loading is non-symmetric about the internal/external movement center, if the optimal loading range does not cover a sufficient range of movement, or if there are loading problems at the extremes. Alternatively, the colors or shades of gray are chosen to allow the surgeon to rapidly assess where the load magnitude is outside the predetermined range and at what range in the movement (e.g. internal motion or external motion) the load magnitude is outside the predetermined range. For example, green can indicate the load magnitude is within a predetermined range. Yellow/Orange can indicate the load magnitude is bordering on being outside the predetermined range. Red can indicate that the load magnitude is higher than acceptable. Blue can indicate that the load magnitude is lower than acceptable. Thus, the surgeon does not need to review numbers but at a glance can determine if the load magnitude over the range of motion is acceptable or needs to be adjusted. The surgeon can then make adjustments such as soft tissue tensioning, modifying a bone surface, changing position of the implant, or shimming the implant to change the load magnitude to be within the predetermined range to name but a few.

Typically, the surgeon is trying to achieve an acceptable range of motion for the internal motion and the external motion of a particular movement of the joint. In one embodiment, the acceptable range of motion can be indicated by dashed lines on the motion bar. A first dashed line is indicated on the internal motion side of the bar. A second dashed line is indicated on the external motion side of the bar. The surgeon can determine at a glance of the motion bar if the color scale region or the grey scale region overlies the dashed lines or falls short of the acceptable range of motion (defined by the dashed lines) for the internal motion or external motion of the joint movement. Thus, GUI 380 supports rapid assessment of the joint status as it relates to the range of motion and loading over the range of motion.

In one embodiment, computer 162 can analyze the measurement data and provide a detailed workflow of the corrections or adjustments to achieve the desired range of motion and loading for the kinetic assessment of the prosthetic joint.

In the example of a shoulder joint, a ROM button 470 is enabled on GUI 380 to initiate a range of motion measurement. Display 164 can be operated via touch screen, remote control, audio control, keyboard, or other device. In the example, GUI 380 shows four motion bars on display 164 after ROM button 470 is enabled. The four motion bars are a motion bar 400, a motion bar 402, a motion bar 404, and a motion bar 406. Each motion bar has a start/stop button for initiating or stopping a measurement. Although four motion bars are shown in the example, more or less can be displayed depending on the application or joint type. In the example, motion bar 400, motion bar 402, motion bar 404, and motion bar 406 respectively have a start/stop button 430, a start/stop button 432, a start/stop button 434, and a start stop button 436. Each motion bar represents a type of movement for a prosthetic shoulder joint that is measured. Motion bar 400 represents a movement comprising internal/external rotation at zero degrees abduction. Motion bar 402 represents a movement comprising internal/external rotation at 45 degrees abduction. Motion bar 404 represents a movement comprising internal/external rotation at zero degrees adduction. Motion bar 404 represents movement of the shoulder joint in extension and flexion.

In the example, start/stop button 432 is enabled to begin a measurement. In one embodiment, all other range of motion tests are disabled when start/stop button 432 is enabled. In one embodiment, starting a new test will reset or redo a finished test. A bar 426 appears across motion bar 402 to indicate position of the shoulder joint within the range of motion of the selected movement. The shoulder joint is moved through the internal/external rotation at 45 degrees abduction. GUI 380 further includes display boxes 414 and 416 in proximity to and above motion bar 402. GUI 380 also displays a maximum rotation of internal rotation (70 degrees) and the maximum rotation of external rotation (90 degrees) shown respectively at a left end and below motion bar 402 and at a right end and below motion bar 402. Realistically, maximum rotation or maximum movement both internal and external is not often achievable for joint installations. An acceptable range of movement for the installed shoulder joint is indicated by dashed line 444 corresponding to internal rotation of the shoulder joint at 45 degrees abduction and dashed lines 446 corresponding to external rotation of the shoulder joint at 45 degrees abduction. The actual measured movement range from internal to external corresponds to the color scale region or the gray scale region 462 within motion bar 402. Note that gray scale region 462 overlies dashed line 444 on the left side of motion bar 402 and overlies dashed line 446 on the right side of motion bar 402. Gray scale region 462 indicates that the installed prosthetic shoulder joint has an acceptable range of motion for internal/external rotation at 45 degrees abduction. Gray scale region 462 also indicates the loading over the range of motion of the shoulder joint at 45 degrees abduction. The loading applied at the current location is also shown in display box 428. The gray scale used in gray scale region 462 indicates loading at different points in the range of motion. The surgeon can review gray scale region 462 at a glance to determine if the loading is correct around the movement center between internal and external rotation, if the loading is correct for a sufficient range of motion around the movement center, and behavior or transition of the loading to the internal rotation maximum and the external rotation maximum of the shoulder joint. The surgeon can then perform adjustments to change the loading profile and range of motion indicated by motion bar 402. As mentioned previously, computer 162 can provide a work flow that provides the adjustments that can be monitored in real-time to produce change in the measurement data related to motion bar 402 to produce more optimal loading and range of motion.

Motion bar 400, 404, and 406 are disabled during the shoulder range of motion measurement with the internal/external rotation at 45 degrees abduction for motion bar 402 of GUI 380. Motion bar 400 measures a shoulder range of motion having an internal/external rotation at zero degrees abduction when start/stop button 430 is enabled. In the example, the maximum internal rotation is 70 degrees and the maximum external rotation is 80 degrees for motion bar 400. Dashed lines 440 and 442 respectively indicate an acceptable range of motion for the internal/external rotation at zero degrees abduction. Dashed line 440 couples through motion bar 400 on the left side corresponding to internal rotation. Dashed line 442 couples through motion bar 400 on the right side corresponding to external rotation. The color scale or gray scale region 460 is shown in motion bar 400. The measured range of motion of the internal rotation at zero degrees adduction is indicated in display box 410 on GUI 380. Similarly, the measured range of motion of the external rotation at zero degrees abduction is indicated in display box 412.

Motion bar 404 measures a shoulder range of motion having an internal/external rotation at zero degrees adduction when start/stop button 434 is enabled. In the example, the maximum internal rotation is 70 degrees and the maximum external rotation is 90 degrees for motion bar 404. Dashed lines 448 and 450 respectively indicate an acceptable range of motion for the internal/external rotation at zero degrees adduction. Dashed line 448 couples through motion bar 404 on the left side corresponding to internal rotation. Dashed line 450 couples through motion bar 400 on the right side corresponding to external rotation. The color scale or gray scale region 464 is shown in motion bar 404. The measured range of motion of the internal rotation at zero degrees adduction is indicated in display box 418 on GUI 380. Similarly, the measured range of motion of the external rotation at zero degrees adduction is indicated in display box 420.

Motion bar 408 measures a shoulder range of motion in extension and flexion when start/stop button 436 is enabled. In the example, the maximum extension is 45 degrees and the maximum flexion is 175 degrees for motion bar 408. Dashed lines 452 and 454 respectively indicate an acceptable range of motion for extension and flexion of the shoulder joint. Dashed line 452 couples through motion bar 408 on the left side corresponding to the shoulder joint in extension. Dashed line 454 couples through motion bar 408 on the right side corresponding to the shoulder joint in flexion. The color scale or gray scale region 466 is shown in motion bar 408. The measured range of motion of the shoulder joint in extension is indicated in display box 422 on GUI 380. Similarly, the measured range of motion of the shoulder joint in flexion is indicated in display box 424.

Figure 24:
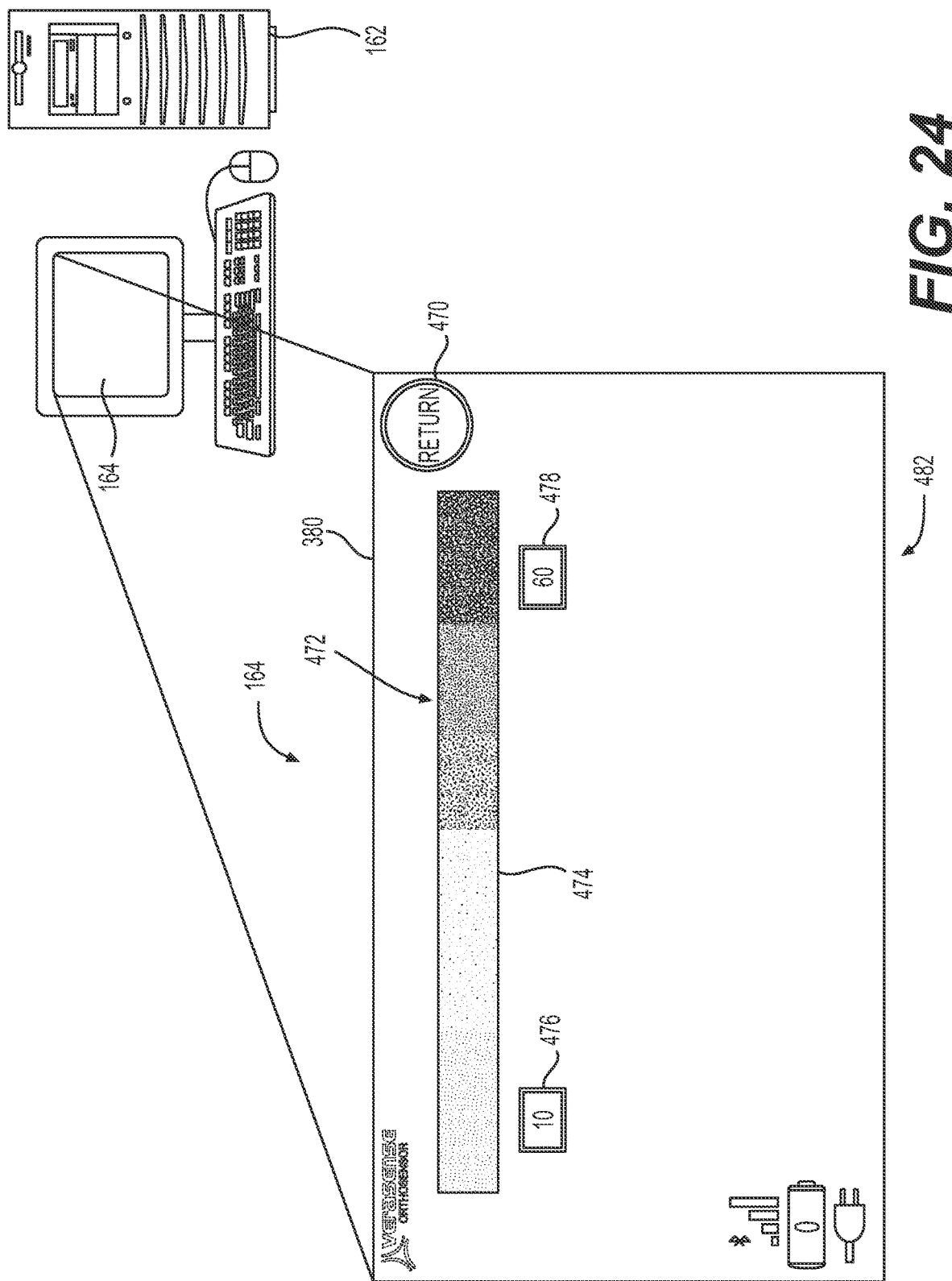
FIG. 24 is an illustration of an option screen in accordance with an example embodiment.

FIG. 24 is an illustration of an option screen 482 in accordance with an example embodiment. Referring briefly to FIG. 23, an options button 480 is pressed on GUI 380 and returns option screen 482. Option screen 482 allows the user to change a color scale 472 or gray scale region in motion bar 474 that relates color scale 472 or gray scale to measured loading of the joint. Display boxes 476 and 478 respectively indicate a low and a high load value for color scale 472 or gray scale region. In one embodiment, there are four values for setting load range for each color or gray shade. In one embodiment, if a gradient map is selected to indicate loading, a used or acceptable value of loading should be a mid-point of color range 472 or gray scale. In one embodiment, if a solid map is selected to indicate loading, a used value should represent maximum loading for that color range or gray scale. The selected color scale 472 or grey scale range will take effect after exiting options screen 482. In one embodiment, a redo of the test will result in redrawing motion bar 474 with the new color range or gray scale entered in option screen 384 after enabling return button 470.

Figure 25:
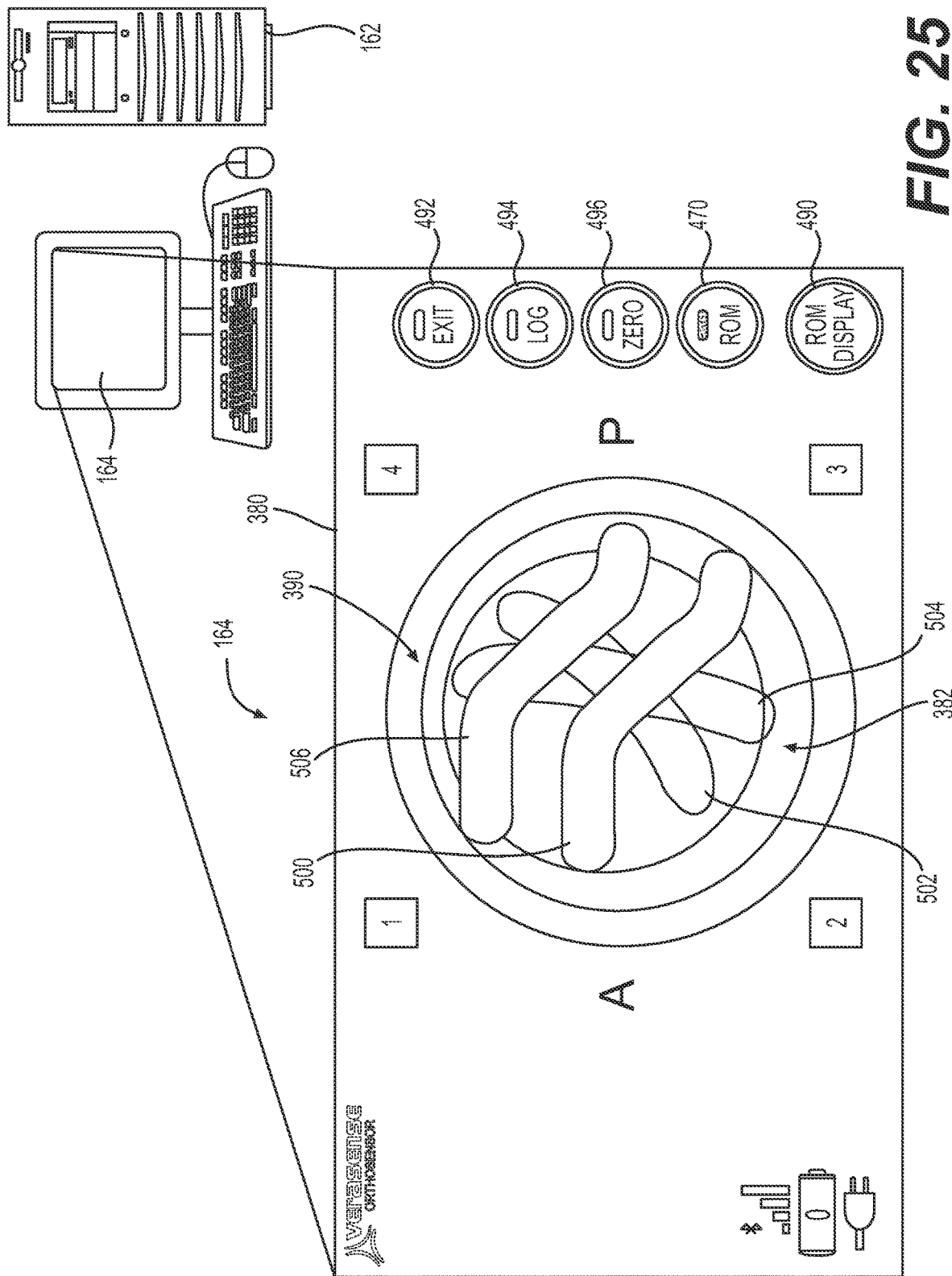
FIG. 25 is an illustration of a range of motion (ROM) overlay on the GUI 380 in accordance with an example embodiment.

FIG. 25 is an illustration of a range of motion (ROM) overlay 390 on GUI 380 in accordance with an example embodiment. Referring briefly to FIG. 23, the shoulder joint is taken through four different motions and the measurement data stored. Enabling the ROM display button 490 displays ROM overlay 390. In the example, GUI 380 graphically displays the movement of contact point 382 to external curved surface 384 on GUI 380 for each of the four different shoulder joint movements measured in FIG. 23. As previously mentioned, contact point 382 corresponds to the contact point of the glenoid sphere on external curved surface 224 of the shoulder joint. Contact point 382 is calculated from measurement data from load sensors or the IMU in measurement device 154 as shown in FIG. 21. The movement of contact point 382 for a predetermined movement is called a load track. In one embodiment, this is not an active screen or real-time measurement. ROM overlay 390 uses stored measurement data from each of the movements. A load track 500 corresponds to the internal and external movement at zero degrees abduction. A load track 502 corresponds to the internal and external movement at 45 degrees abduction. A load track 504 corresponds to the internal and external movement at zero degrees adduction. A load track 506 corresponds to the movement in extension and flexion of the shoulder joint. Thus, the movement of contact point 382 can be understood for each different movement that is measured and used to determine if a problem may exist in the pattern of movement and the load magnitude at specific points in the movement. In one embodiment, the loading value can be indicated across a load track by color scale or gray scale shade. In one embodiment, computer 162 can analyze the load tracks and provide a workflow to correct or optimize the shoulder joint based on the quantitative measurement data.

Figure 26:
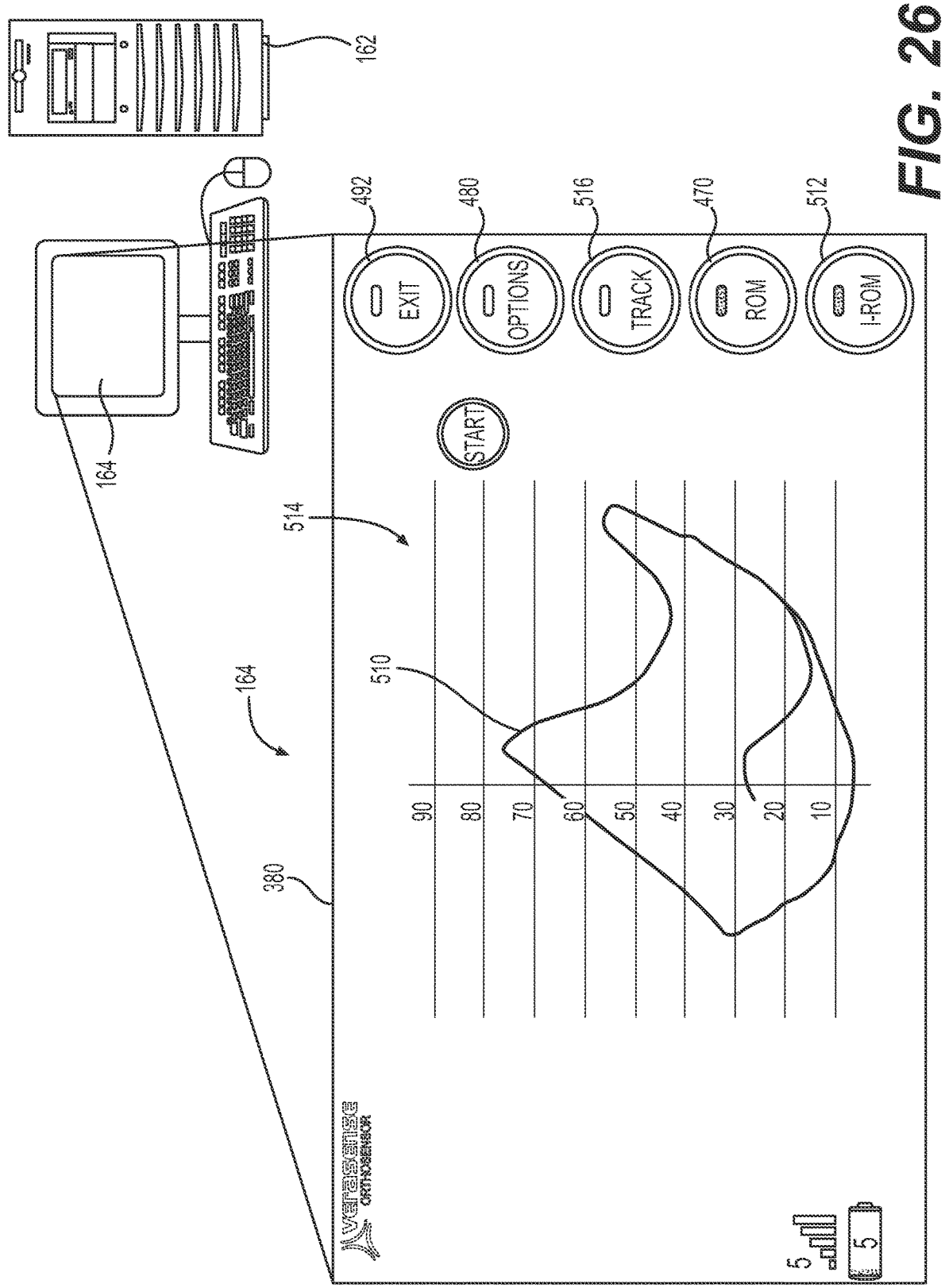
FIG. 26 is an illustration of the GUI showing an impingement range of motion assessment in accordance with an example embodiment.

FIG. 26 is an illustration of GUI 380 showing an impingement range of motion assessment in accordance with an example embodiment. Enabling I-ROM button 512 produces a graph 514 where trace 510 is continuously active. In one embodiment, the arm and shoulder joint is moved in a "windmill" motion. Trace 510 corresponds to a position of the humerus relative to adduction (graph Y-axis-humerus Z-axis) and horizontal flexion (graph X-axis, humerus Y-axis) is rendered. Track button 516 can be toggled to collect trace data or reset trace for a new data collection. In one embodiment, the measurement ignores the internal/external rotation of the arm. Furthermore, the area covered by trace 510 are the limits of abduction/adduction and horizontal flexion.

Figure 27A:
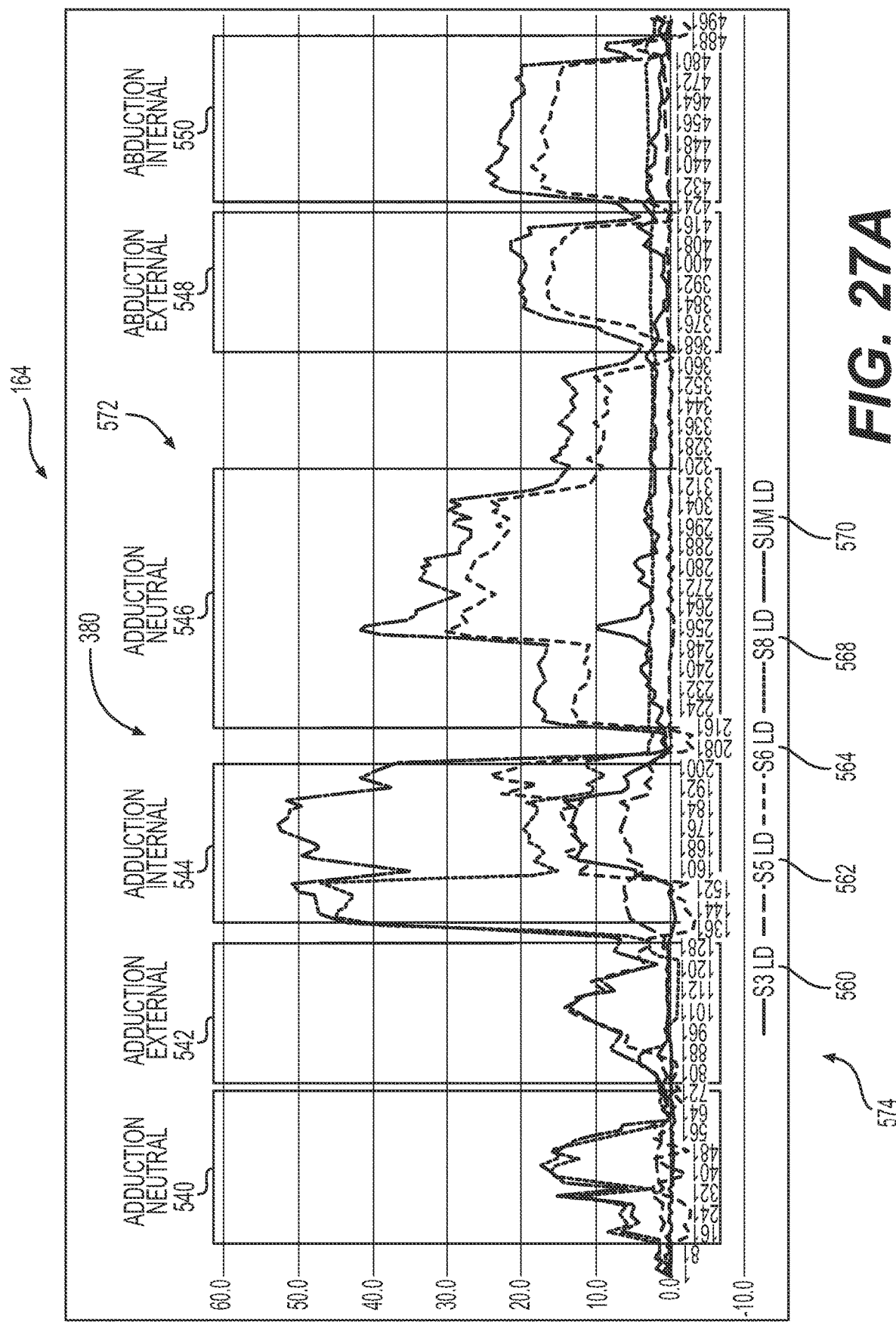
FIG. 27A is an illustration of measurement data from the measurement device in accordance with an example embodiment.

FIG. 27A is an illustration of measurement data from measurement device 154 in accordance with an example embodiment. FIG. 27B is an illustration of measurement device 154 transmitting measurement data to computer 162 and displaying the measurement data on display 164 in accordance with an example embodiment. Display 164 includes GUI 380 to support rapid assimilation of measurement data. Housing 220 is made transparent to show placement of electronic circuitry 236 and sensors 530, 532, and 534. Sensors 530, 532, and 534 underlie external curved surface 224 of housing 220. In one embodiment, measurement device 154 shows orientation when placed in a shoulder joint such as a superior position 580, an inferior position 582, an anterior position 586, and a posterior position 584. Sensor seating is configured to orient sensors 530, 532, and 534 toward a center of curvature of external curved surface 224. Sensors 530, 532, and 534 correspond to sensors 230 as shown in FIG. 19 but are individually identified to disclose placement or location within measurement device 154 relative to superior position 580, inferior position 582, anterior position 586, and posterior position 584 in the shoulder joint. Sensors 530, 532, and 534 are respectively labeled S3, S6, and S8 on measurement device 154. Measurement device 154 also has a reference sensor 536 labeled S5. As previously mentioned, sensors 530, 532, and 534 are spaced equidistant from each other and located as close to rim 242 as possible to maximize the measurement area. As shown, sensor 530 is located in proximity to superior position 580. Sensor 532 is located between posterior position 584 and inferior position 582. Sensor 534 is located between anterior position 586 and inferior position 582. Thus, measurement data from each sensor can be correlated to the movement to better understand how shoulder position affects loading. Measurement data from sensors 530, 532, 534, reference sensor 536 is transmitted wirelessly to computer 162. The measurement data from sensors 530, 532, and 534 is used to calculate a load magnitude and a contact point by computer 162 on external curved surface 224 of measurement device 154 of FIG. 21. Display 164 coupled to computer 162 can display the load magnitude and the contact point for viewing by the surgeon and surgical team.

In the example, a shoulder implant is installed in a shoulder of a patient. Measurement device 154 is inserted in the shoulder joint and powered on. The shoulder is moved through predetermined range of motions. The measurement data from measurement device 154 is captured by computer 162. In one embodiment, the shoulder can be forced from a neutral position to impingement. Display 164 provides a graph 572 showing load data from sensors 530, 532, 534, reference sensor 536, and a sum of sensors 530, 532, and 534 as the shoulder joint is moved through different predetermined motions. Graph 572 is illustrative of what a surgeon or surgical might see if the measurement data from each sensor was provided graphically. Sensors 530, 562, 564, and 568 are represented by different colors, gray scale shades, or patterned lines on graph 572 as indicated by a legend 574. In legend 574, sensor key 560 illustrates measurement data on graph 572 related to sensor 530 (S3). Sensor key 562 illustrates measurement data on graph 572 related to reference sensor 536 (S5) in proximity to superior position 580 of measurement device 154. Sensor key 564 illustrates measurement data on graph 572 related to sensor 532 (S6) between posterior position 584 and inferior position 582 of measurement device 154. Sensor key 568 illustrates measurement data on graph 572 related to sensor 534 (S8) between anterior position 586 and inferior position 582 of measurement device 154. Finally, a sum key 570 illustrates measurement data on graph 572 related to a sum of load measurement data related to sensors 530 (S3), 532 (S6), and 534(S8).

Box 540 of graph 572 corresponds to a neutral shoulder rotation in adduction. Measurement data from sensors 530

(S3), 532 (S6), and 534(S8) indicate that sensor 534 is more heavily loaded than sensors 530 (S3) and sensor 532 (S6) during the neutral shoulder rotation in adduction. Reference sensor 536 (S5) is not loaded in the example. The loading on sensor 534 (S8) varies between 5 lbs. to 17 lbs. during the neutral shoulder rotation in adduction. Sum 570 looks similar to sensor 534 (S8) during the neutral shoulder rotation in adduction because the load contributions of sensors 530 (S3) and 532 (S6) are small. In general, the surgeon can see graphically where the loading occurs relative to the movement and what each sensor is measuring in the neutral shoulder rotation in adduction.

Box 542 of graph 572 corresponds to an external shoulder rotation in adduction. Measurement data from sensors 530 (S3), 532 (S6), and 534(S8) indicate that sensors 530 (S3) and sensor 534 (S8) have a loading less than sensor 532 (S6) during the external shoulder rotation in adduction. Reference sensor 536 (S5) is not loaded in the example. The loading on sensor 532 (S6) varies between 7 lbs. to 15 lbs. during the external shoulder rotation in adduction. Sum 570 looks similar to sensor 532 (S6) during the external shoulder rotation in adduction because the load contributions of sensors 530 (S3) and 535 (S8) are small. In general, the surgeon can see graphically where the loading occurs relative to the movement and what each sensor is measuring in the external shoulder rotation in adduction.

Box 544 of graph 572 corresponds to an internal shoulder rotation in adduction. Measurement data from sensors 530 (S3), 532 (S6), and 534(S8) indicate that all sensors 530 (S3), sensor 532 (S6), and sensor 534 (S8) have significant loading of greater than 10 lbs. during the internal shoulder rotation in adduction. Reference sensor 536 (S5) is noisy during this measurement having a loading as high as 5 lbs. during the measurement. As previously mentioned, these are just example graphs of measurements. In the initial part of the internal shoulder rotation in adduction, sensor 534 (S8) has a reading of greater than 40 lbs. where it is greatly reduced to under 20 lbs. thereafter. Conversely, the initial part of the internal shoulder rotation in adduction, sensors 530 (S3) and 532 (S6) have a reading of no loading and a loading of greater than 10 lbs. thereafter. The loading on sensor 532 (S6) varies between 7 lbs. to 15 lbs. during the external shoulder rotation in adduction. Sum 570 combines the loading of sensors 530 (S3), 532 (S6), and 534 (S8) during the internal shoulder rotation in adduction which exceeds 50 lbs. in portions of the rotation. In general, the surgeon can see graphically where the loading occurs relative to the movement and what each sensor is measuring in the internal shoulder rotation in adduction.

Box 546 of graph 572 corresponds to a neutral shoulder rotation in abduction. Measurement data from sensors 530 (S3), 532 (S6), and 534(S8) indicate that sensors 530 (S3) and sensor 534 (S8) are loaded less than sensor 532 (S6) during the neutral shoulder rotation in abduction. Reference sensor 536 (S5) is unloaded. The loading on sensor 532 (S6) varies between 12 lbs. to greater than 40 lbs. during the neutral shoulder rotation in abduction. Sum 570 looks similar to sensor 532 (S6) during the neutral shoulder rotation in abduction but load components of sensors 530 (S3) and 534 (S8) do contribute such that sum 570 does not overlap sensor key 564 during the neutral shoulder rotation in abduction. In general, the surgeon can see graphically where the loading occurs relative to the movement and what each sensor is measuring in the neutral shoulder rotation in abduction.

Box 548 of graph 572 corresponds to an external shoulder rotation in abduction. Measurement data from sensors 530 (S3), 532 (S6), and 534 (S8) indicate that sensors 530 (S3) and sensor 534 (S8) are loaded less than sensor 532 (S6) during the external shoulder rotation in abduction. Reference sensor 524 (S5) is unloaded. The loading on sensor 532 (S6) varies between 13-16 lbs. during the external shoulder rotation in abduction. Sum 570 looks similar to load data from sensor 532 (S6) during the external shoulder rotation in abduction but differs because loading from sensors 530 (S3) and 534 (S8) are added. In general, the surgeon can see graphically where the loading occurs relative to the movement and what each sensor is measuring in the external shoulder rotation in abduction.

Box 550 of graph 572 corresponds to an internal shoulder rotation in abduction. Measurement data from sensors 530 (S3), 532 (S6), and 534 (S8) indicate that sensors 530 (S3) and sensor 534 (S8) are loaded less than sensor 532 (S6) during internal shoulder rotation in abduction. Reference sensor 524 (S5) is unloaded. The loading coupled to sensor 532 (S6) varies between 15-19 lbs. during the internal shoulder rotation in abduction. Sum 570 looks similar to load data from sensor 532 (S6) during the external shoulder rotation in abduction but differs because loading from sensors 530 (S3) and 534 (S8) are added. In general, the surgeon can see graphically where the loading occurs relative to the movement and what each sensor is measuring in the internal shoulder rotation in abduction.

Figure 28:
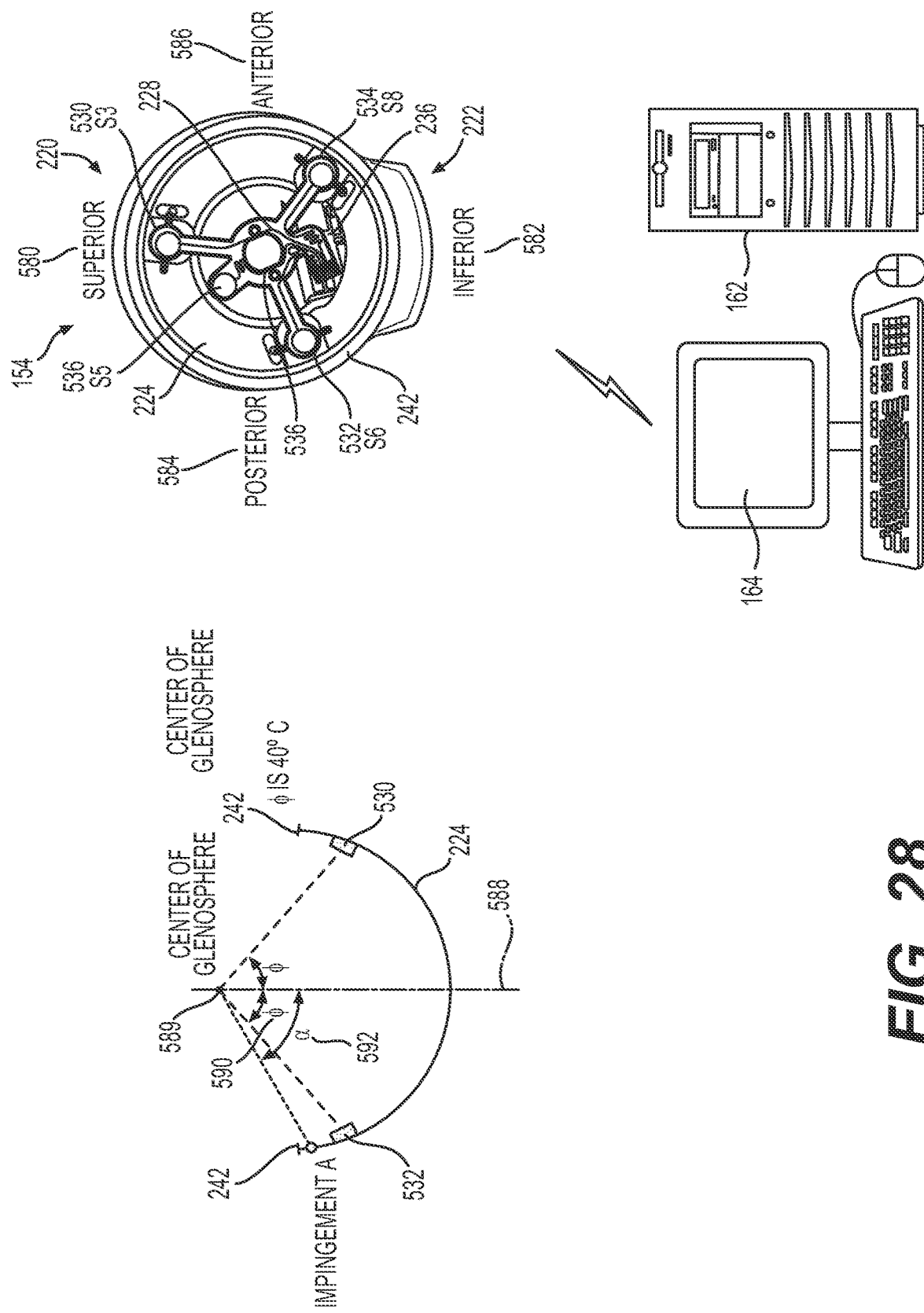
FIG. 28 illustrates a cross-sectional view of the external curved surface of the measurement device as shown in FIG. 21 in accordance with an example embodiment.

FIG. 28 illustrates a cross-sectional view of external curved surface 224 of measurement device 154 as shown in FIG. 21 in accordance with an example embodiment. In the example, three sensors are used to measure loading and position of load where the glenoid sphere contacts and loads external curved surface 224. The three sensors are equidistant from one another. Sensor 530 and sensor 532 are shown in the cross-sectional view. A center 589 of the glenoid sphere is shown with an axis 588 of the glenoid sphere indicated by a dashed line. Sensor 530 is an angle $\phi$ from axis 588 of the glenoid sphere. Similarly, sensor 532 is an angle $\phi$ from axis 588 of the glenoid sphere. In one embodiment, impingement is detected when a measured force angle $\alpha$ is greater than the angle $\phi$. Alternatively, impingement can be detected when the measured force angle $\alpha$ does not correlate to the assumptions such as the applied force is normal to external curved surface 224, the reaction forces are detected to the center of rotation, there are no moment arms, and simple force balancing applies. In one embodiment, the position measurement system or an IMU can be used to measure a first angle $\alpha$. A second angle $\alpha$ can be measured with the measurement data from the three sensors. The first and second angle $\alpha$ can be compared to one another as a redundancy check or to determine if the measurement is outside the angle $\phi$ to determine impingement.

Figure 29A:
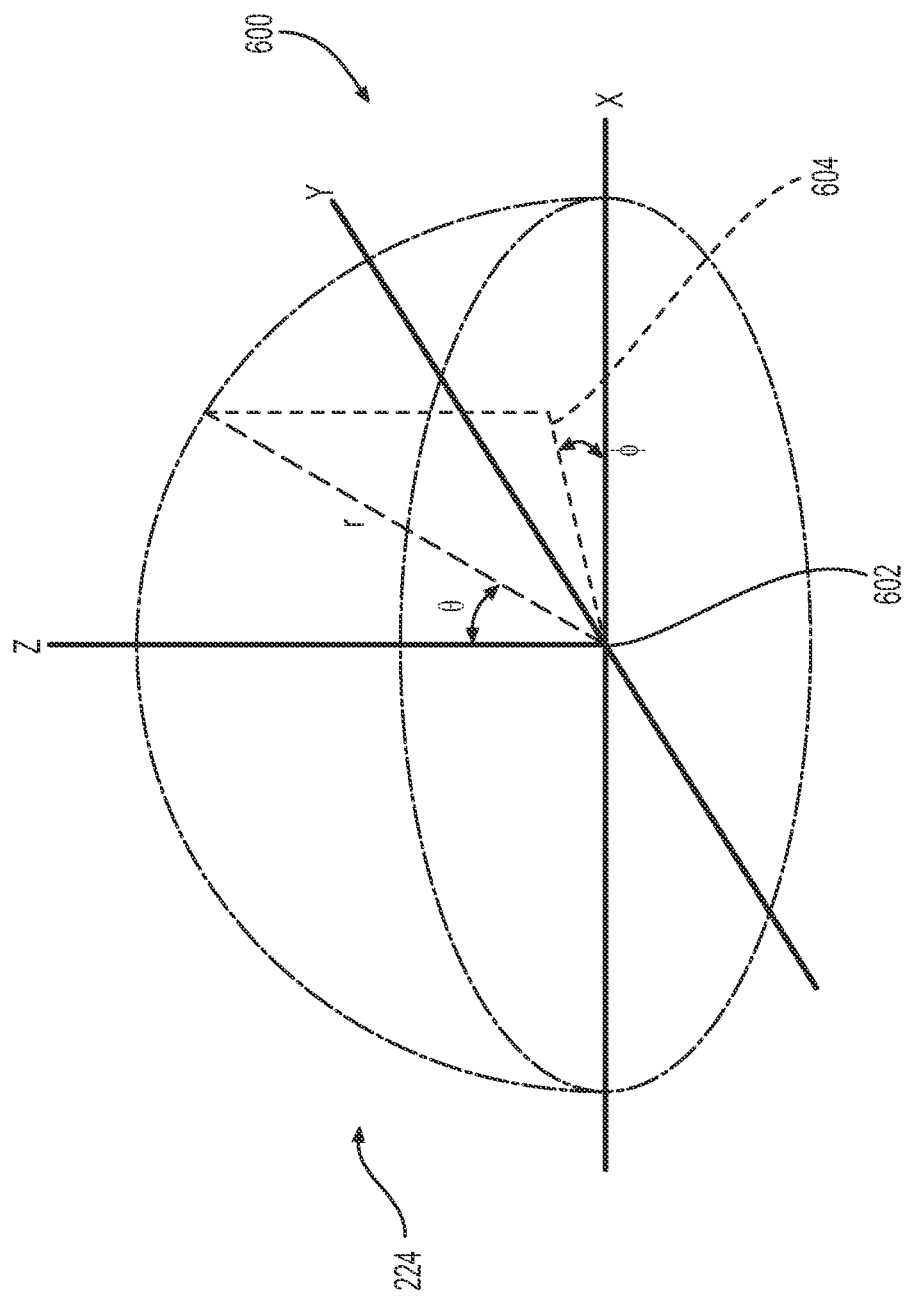
FIG. 29A is an illustration of a spherical coordinate system for calculating force and position in accordance with an example embodiment.

FIG. 29A is an illustration of a spherical coordinate system 600 for calculating force and position in accordance with an example embodiment. In one embodiment, spherical coordinate system 600 is natural and can be used to mathematically describe external curved surface 224 of measurement device 154 as shown in FIG. 21. External curved surface 224 of measurement device 154 couples to a prosthetic component of a joint and is configured to support movement of the joint. In the example, an origin 602 of spherical coordinate system 600 is the center of curvature of external curved surface 224. The positive Z-axis extends from origin 602 to external curved surface 224 intersecting a plane equidistant from each sensor coupled to external curved surface 224. A point in spherical coordinate system 600 can be defined by a radius r, an angle $\theta$, and an angle $\phi$ as shown in FIG. 29A. In the example, the radius r is a radius of curvature of curved surface 224. Theta ($\theta$) is an angle measured from radius r to the Z-axis. Phi (φ) is an angle measured from the X-axis and dashed line 604. Dashed line 604 can be calculated by the equation 1 r×sin(φ) on FIG. 29A. Dashed line 604 is on the X-Y plane. Note that an external curved surface that is convex (a ball of the joint instead of the cup) can be modeled similarly.

Figure 29B:
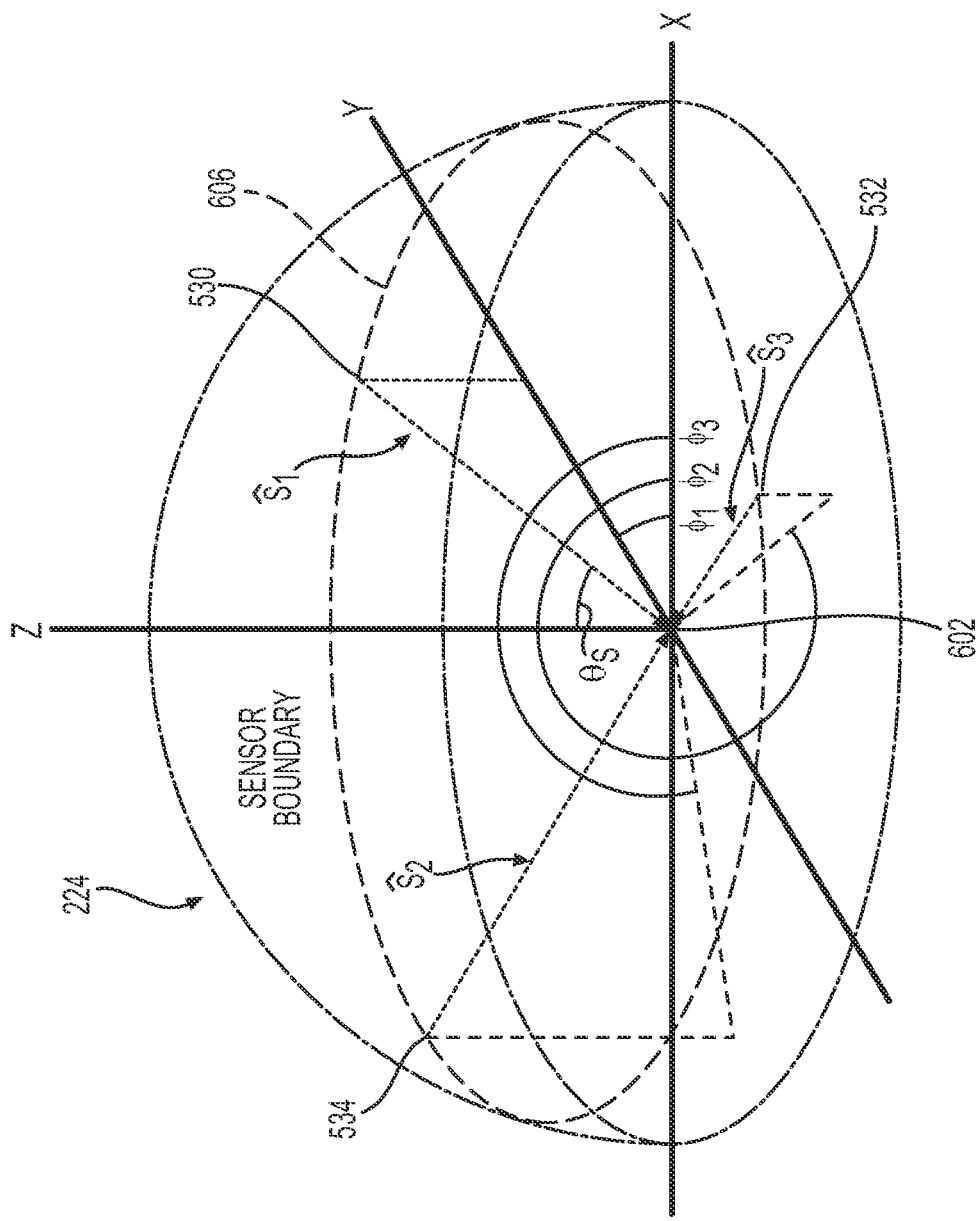
FIG. 29B is an example of force and position calculations related to sensor location in accordance with an example embodiment.

FIG. 29B is an example of force and position calculations related to sensor location in accordance with an example embodiment. Referring briefly to FIG. 27B, sensors 530, 532, and 534 are configured to measure a force, pressure, or load applied to external curved surface 224 of measurement device 154. As mentioned previously, the sensor locations and the force and position calculations can correspond to either a ball shaped prosthetic component or a cup shaped prosthetic component. In general, sensors 530, 532, and 534 are placed equidistant from each other and have a maximum radius of circle on external curved surface 224 defined by sensors 530, 532, and 534. Referring briefly to FIG. 27B and FIG. 29B sensor 530 is located in proximity to superior position 580 which is called herein as a top sensor of measurement device 154. Sensor 532 is between posterior position 584 and inferior position 582 which is called a bottom left sensor herein. Sensor 534 is between anterior position 586 and inferior position 582 which is called a bottom right sensor herein. In the example, radius r is given a value of 0.748 inches for a prototype measurement device 154. Sensors 530, 532, and 534 are located as close to the X-Y plane on curved surface 224 as possible to maximize the measurement area on external curved surface 224.

In the example, the radial position of sensors 530, 532, and 534 are described in equation 2 of FIG. 29B. The angle $\theta_s$ is an angle measured from the Z-axis such that each sensor 530, 532, and 534 is located on dashed circle 606. The angular positions of sensors 530, 532, and 534 are defined in equation 3 of FIG. 29B. The angular position is relative to the X-axis. Sensor 530 is located at $\phi_1 = \pi/2$ on dashed circle 606. Sensor 534 is located at $\phi_2 = 11\pi/6$ on dashed circle 606. Sensor 532 is located at $\phi_3 = 7\pi/6$ on dashed circle 606. In one embodiment, a sensor unit vector represents the direction from the sensor to origin 602. The sensor unit vector is the assumed direction of the sensor reaction force. The equation for the unit vectors related to sensors 530, 532, and 534 are defined by equation 4 where sensors 530, 534, and 532 respectively correspond to unit vector $\hat{S}_1$, $\hat{S}_2$, and $\hat{S}_3$ on FIG. 29B. Sensor 530 has a unit vector $\hat{S}_1 = (0, -0.695, -0.719)$ in polar coordinates which is the top sensor as shown in FIG. 27B. Sensor 534 has a unit vector $\hat{S}_2 = (-0.602, 0.347, 0.719)$ in polar coordinates which is the bottom right sensor as shown in FIG. 27B. Sensor 532 has a unit vector $\hat{S}_3 = (0.602, 0.347, -0.719)$ in polar coordinates which is the bottom left sensor as shown in FIG. 27B.

Figure 30:
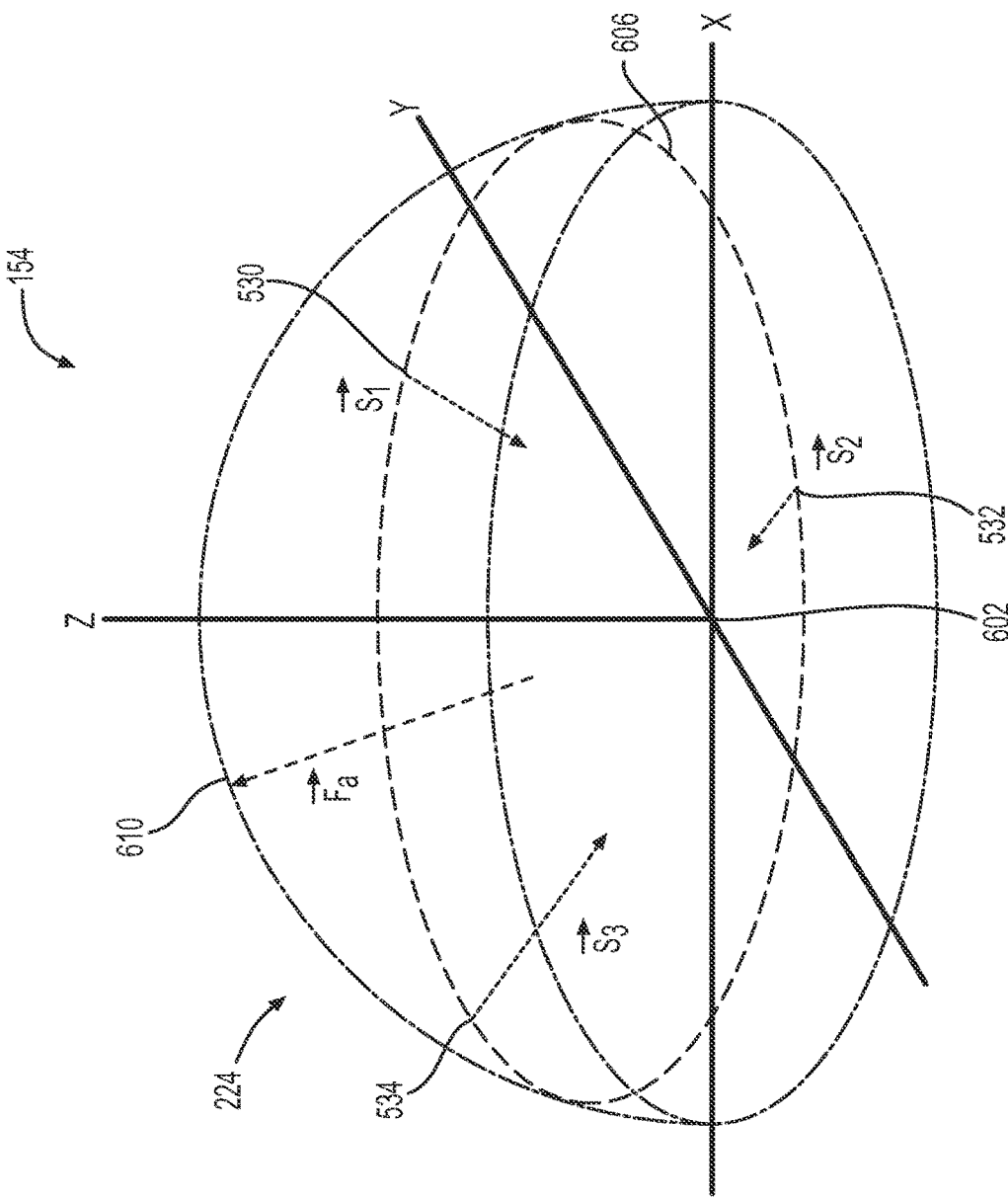
FIG. 30 is a diagram showing a force magnitude calculation from measurement data from the sensors in accordance with an example embodiment.

FIG. 30 is a diagram showing a force magnitude calculation from measurement data from sensors 530, 532, and 534 in accordance with an example embodiment. The force magnitude calculation can be used for a measurement device as a ball or a measurement device as a cup. Thus, measurement device 154 can be implement for a reverse shoulder, regular shoulder, femoral head of a femoral prosthetic component of a hip, or an acetabular cup of a hip. It is assumed in the calculation of the force magnitude and position of applied force that there is no friction on external curved surface 224 of measurement device 154 as shown in FIG. 21. The interface between external curved surface 224 and sensors 530, 532, and 534 as shown in FIG. 27B are fully constrained. In one embodiment, only sensors 530, 532, and 534 are used for full constraint if sensors 530, 532, and 534 are oriented towards the center of curvature of external curved surface 224 such that all force vectors pass through the same point and there are no moments to balance. Reaction force vectors are assumed to be normal to external curved surface 224, and therefore pass through the same point in space at origin 602 that is the center of curvature. In general, sensors 530, 534, and 532 measures loading applied to external curved surface 224 where a scalar reaction force is respectively represented by $S_1$, $S_2$, and $S_3$ for the above listed sensors. Reaction force vectors $\vec{S}_1$, $\vec{S}_2$, and $\vec{S}_3$ are given by equation 5 of FIG. 30 where i is 1, 2, or 3 respectively corresponds to sensors 530 (top sensor), 534 (bottom right sensor), and 532 (bottom left sensor). As mentioned previously, reaction force vectors $\vec{S}_1$, $\vec{S}_2$, and $\vec{S}_3$ couple through origin 602. The total reaction force $\vec{F}_r$ is given by equation 6 of FIG. 30 which is the sum of the reaction force vectors $\vec{S}_1$, $\vec{S}_2$, and $\vec{S}_3$. A balance of forces requires that the applied force vector $\vec{F}_a$ applied to external curved surface 224 is equal to the negative of the total reaction force $\vec{F}_r$ as shown in equation 7 of FIG. 30. Applied force vector $\vec{F}_a$ couples to a contact point 610 on external curved surface 224 of measurement device 154. In the reverse shoulder joint example, contact point 610 corresponds to a location where a glenoid sphere applies a force, pressure, or load to measurement device 154 for the measurement data from sensors 530, 532, and 534. Applied force vector $\vec{F}_a$ also couples through origin 602 if the tail is extended. The combined force magnitude can be broken down into X-axis, Y-axis, and Z-axis force components measured by load sensors 530, 532, and 534 as shown by equation 8 of FIG. 30 that corresponds to equation 7. The load magnitude applied to external curved surface 224 can be calculated from the measurement data from sensors and more specifically from $F_{ax}$, $F_{ay}$, and $F_{az}$ previously calculated in equation 8 from the scalar reaction forces of sensors 530, 532, and 534 broken into X-axis, Y-axis, and Z-axis components and summed. The reported load measured using measurement data from sensors 530, 532, and 534 is $\|\vec{F}_a\|$ and can be calculated by equation 9 of FIG. 30 which is the square root of the sum of the squares of $F_{ax}$, $F_{ay}$, and $F_{az}$ calculated. Thus, the load magnitude at contact point 610 can be calculated in real-time from the measurement data from sensors 530, 532, and 534.

Figure 31:
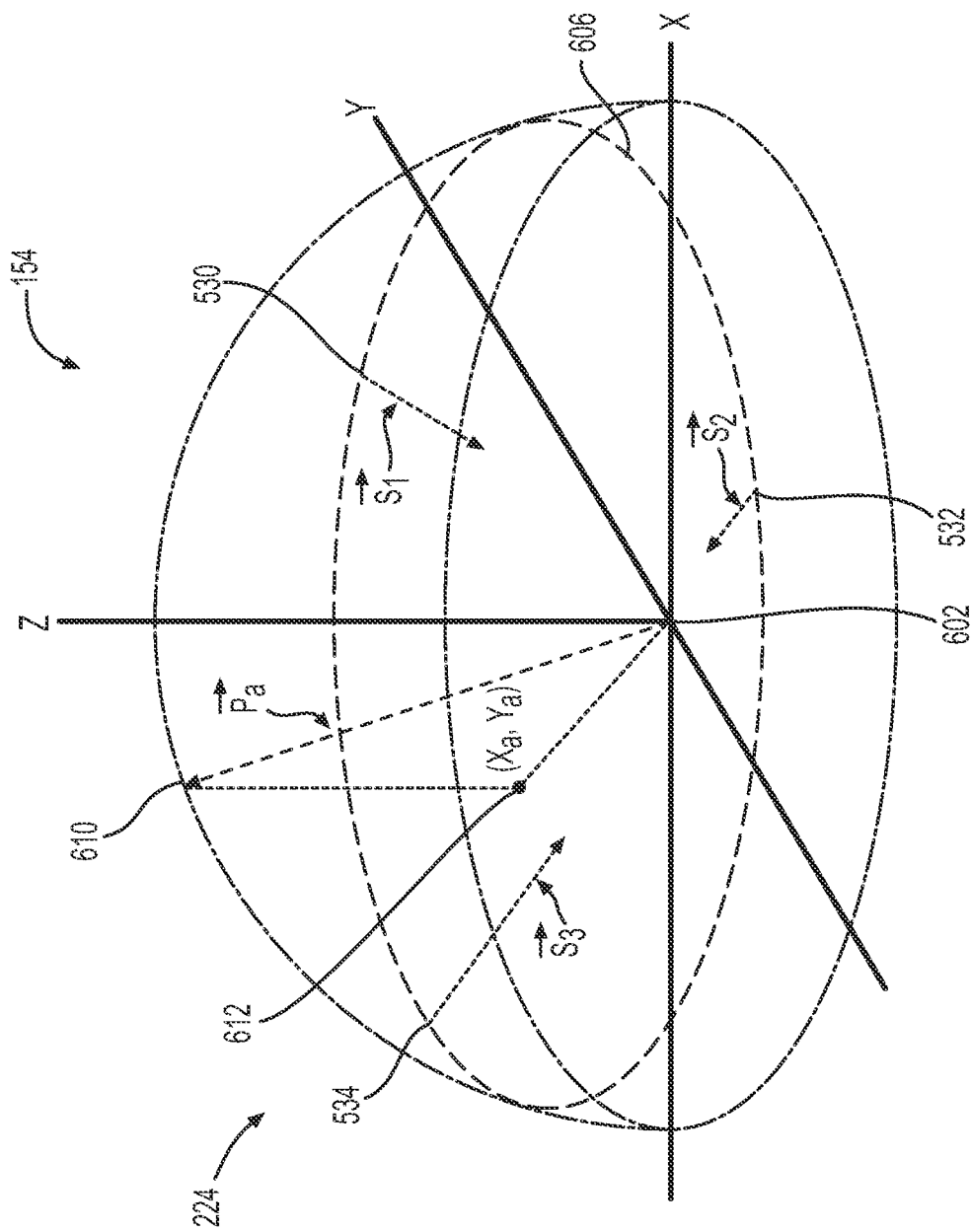
FIG. 31 is a diagramming showing a position of applied load calculation on the external curved surface of the measurement device using measurement data from the sensors in accordance with an example embodiment.

FIG. 31 is a diagram showing a position of applied load calculation on external curved surface 224 of measurement device 154 using measurement data from sensors 530, 532, and 534 in accordance with an example embodiment. Referring briefly to FIG. 22A, contact point 382 is indicated on surface 384 of GUI 380 and display 164. Note that surface 384 is a two-dimensional image of a three dimensional curved surface. Accurate placement of a contact point on a two dimensional image of a three dimensional curved surface is disclosed herein below for GUI 380. In the example, the point of load application in $R^3$ is projected onto the X-Y plane to display load position. In the example, a point 612 $(x_a, y_a)$ is the projected load position on the X-Y plane. In one embodiment, the applied force vector $\vec{F}_a$ is converted to a positional vector $\vec{P}_a$ with the same direction and magnitude of r as shown in equation 10 of FIG. 31. Positional vector $\vec{P}_a$ couples to external curved surface 224 at contact point 610 and also couples through origin 602. The projection of $\vec{P}_a$ onto the X-Y plane is given by equation 11 which is $(x_a, y_a)=(P_{ax}, P_{ay})$. Thus, contact point 610 can be accurately represented on a two-dimensional display for view by the surgeon or surgical team in real-time.

In one embodiment, measurement data from force sensors 530, 532, and 534 are used to detect impingement corresponding to FIG. 22B. For example, impingement caused repeatable load spikes peripherally. Load spikes of 10-30 lbs. occur near an impingement point are captured in the measurement data and used to detect impingement. A force magnitude and contact point where a prosthetic component couples external curved surface 224 of measurement device 154 is calculated from measurement data from sensors 530, 532, and 534 as disclosed herein above. A position measurement system can also provide measurement data to support the force magnitude and contact point measurement. In the example certain assumptions are made in the calculations. Sensors 530, 532, and 534 are placed equidistant from one another at positions that maximize the radius of circle defined by the sensors. Sensors 530, 532, and 534 are oriented such that sensor reaction forces are directed to a center of curvature of external curved surface 224. In one embodiment, it is assumed that no frictional forces or negligible frictional forces occur on external curved surface 224 or at a sensor interface. In one embodiment, reaction force vectors are assumed to be normal to external curved surface 224 and therefore pass through the center of curvature of external curved surface 224. There can only be specific combination of forces possible when utilizing one or more of the assumptions disclosed herein above when calculating the load magnitude and the contact point using the forces applied to sensors 530, 532, and 534. In one embodiment, force combinations that are outside the one or more assumptions can mean that the measured force or measured forces by sensors 530, 532, and 534 are not normal to external curved surface 224 of measurement device 154. Alternatively, the force vector may not pass through the center of curvature of external curved surface 224. Any combination of forces measured by sensors 530, 532, and 534 outside the possible combinations determined by one or more assumptions disclosed herein should be reviewed or considered as impingement. Furthermore, time based analysis of the load data from sensors 530, 532, and 534 can be used and correlated against known impingement to detect impingement. As mentioned previously, abrupt changes in the measured load vector also equates to impingement. In one embodiment, the position measurement system such as an IMU (inertial measurement unit) can be used to monitor movement and correlate against known joint movement for a particular motion to detect abnormalities that indicate impingement. The joint geometry may also be susceptible to impingement in specific directions. If so, predetermined movements can be performed on the joint to determine if impingement occurs and adjustments made based on quantitative measurement data.

Figure 32:
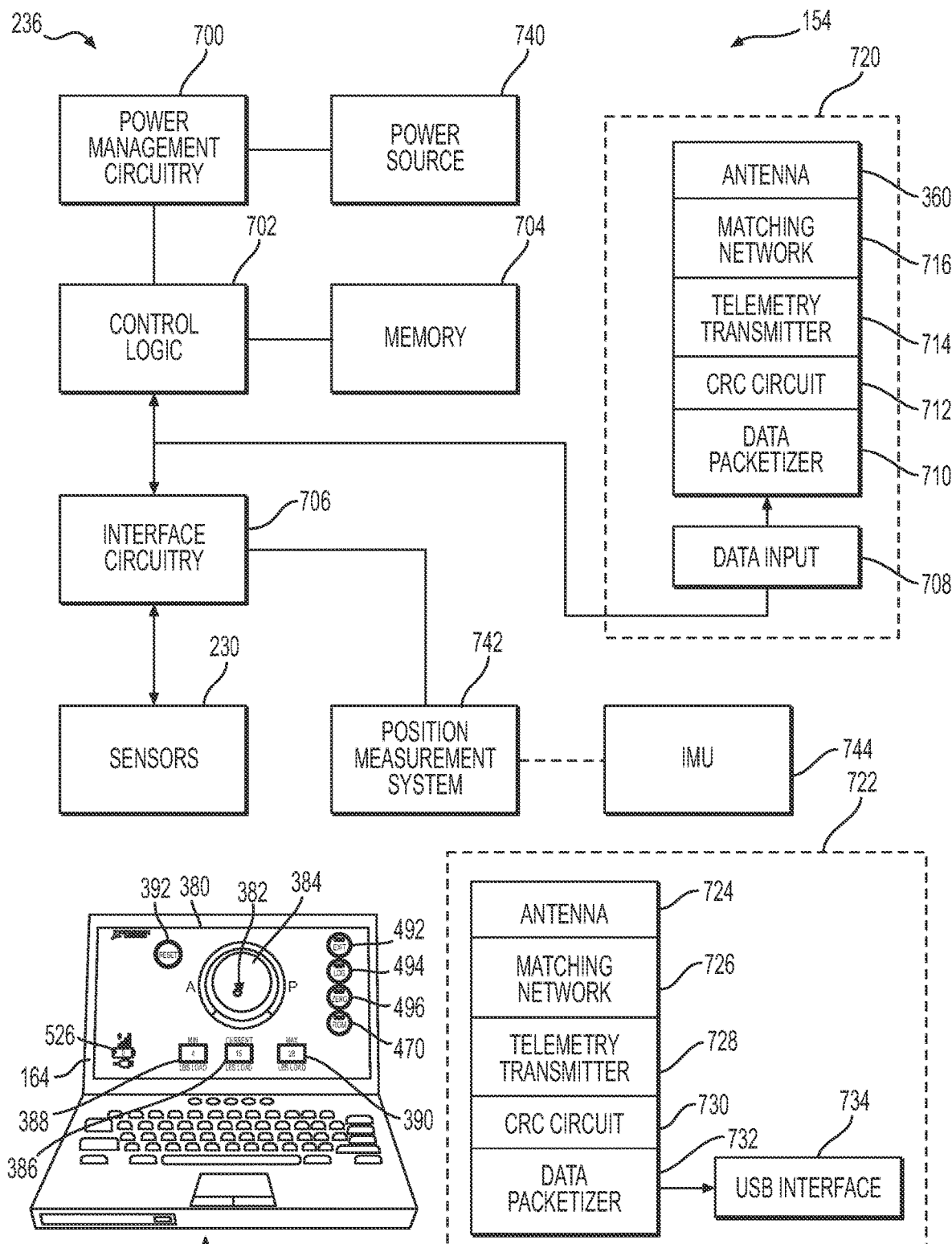
FIG. 32 is a block diagram of the electronic circuitry in the measurement device in accordance with an example embodiment.

FIG. 32 is a block diagram of electronic circuitry 236 in measurement device 154 in accordance with an example embodiment. In general, electronic circuitry 236 couples to one or more sensors to measure one or more parameters. Components of FIGS. 3, 5-21 may be referred to in the discussion herein below to relate operation of measurement device 154 to electronic circuitry 236. The sensors can measure parameters such as, height, length, width, tilt/slope, position, orientation, load magnitude, force, pressure, contact point location, displacement, density, viscosity, pH, light, color, sound, optical, vascular flow, visual recognition, humidity, alignment, position, rotation, inertial sensing, turbidity, bone density, fluid viscosity, strain, angular deformity, vibration, torque, elasticity, motion, acceleration, infection, pain, and temperature to name but a few. In the example, electronic circuitry 236 is configured to control a measurement process, receive measurement data from sensors 230, receive measurement data from position measurement system 742, and transmit the measurement data to computer 162 for further analysis and feedback. More specifically, sensors 230 measure a force, pressure, or load at predetermined locations of external curved surface 224. Sensors 230 at the predetermined locations comprise sensor 530, 532, and 534 as shown in FIG. 27B. Position measurement system 742 measures position, movement, rotation, velocity, acceleration, or distance. In one embodiment, position measurement system comprises an inertial measurement unit (IMU) 744 configured to measure 9 degrees of freedom. IMU 744 can comprise one or more inertial sensors. In one embodiment, sensors 230 and position measurement system 742 is housed in measurement device 154.

Electronic circuitry 236 comprises power management circuitry 700, control logic 702, memory 704, interface circuitry 706, position measurement system 742, and wireless communication circuitry 720. A power source 740 couples to electronic circuitry 236 to power a measurement process. Power source 740 can be an inductor, super capacitor, storage cell, wired power, wireless power, solar cell, energy harvesting device, or other energy storage medium. In one embodiment, power source 740 comprises batteries 312. Electronic circuitry 236 further includes a transceiver that can be positioned on or within, or engaged with, or attached or affixed to or within, a wide range of physical systems including, but not limited to instruments, equipment, devices, prosthetic components, or other physical systems for use on or in human bodies and configured for sensing and communicating parameters of interest in real time. Electronic circuitry 236 is coupled together to form an electronic system using multiple layers of interconnect on printed circuit board 234. Flexible interconnect 228 can be used to couple electronic circuitry 236 to sensors 230 that are remotely located.

Electronic circuitry 236 can be configured to provide two-way communication between measurement device 154 and computer 162. In one embodiment, measurement device 154 provides quantitative measurement data related to a shoulder joint installation. Measurement device 154 is configured to provide quantitative measurement data related to load magnitude, position of applied load, position, and rotation. The measurement data from measurement device 154 is used by computer 162 in a kinematic assessment to support installation of prosthetic components to ensure optimal loading, balance, stability, alignment, range of motion, and reduce impingement that improves performance and reliability based on clinical evidence.

Power source 740 provides power to electronic circuitry 236 and sensors 230. The power source 740 can be temporary or permanent. In one embodiment, the power source is not rechargeable. Measurement device 154 is disposable after a single use and the power in batteries 312 are insufficient for a second surgery. Measurement device 154 would be destroyed or disposed of after being used. Alternatively, power source 740 could be rechargeable. Measurement device 154 would be sterilized before being reused. Charging of power source 740 can comprise wired energy transfer or short-distance wireless energy transfer. A charging power source to recharge power source 740 can include, but is not limited to, a battery or batteries, an alternating current power supply, a radio frequency receiver, an electromagnetic induction coil, a photoelectric cell or cells, a thermocouple or thermocouples, or a transducer energy transfer. In one embodiment, energy transfer to power source 740 could be allowed for the single application scenario if power source 740 has insufficient energy to finish the surgery. Furthermore, measurement device 154 can utilize power management circuitry 700 to minimize the power drain of power source 740 while in use or when electronic circuitry 236 is idling.

As previously mentioned, power source 740 in measurement device 154 comprises batteries 312. Batteries 312 can be recharged by the methods disclosed herein above. Alternatively, power source 740 can be a super capacitor, an inductor, or other energy storage device. An external charging source can be coupled wirelessly to the rechargeable battery, capacitor, or inductive energy storage device through an electromagnetic induction coil by way of inductive charging. The charging operation can be controlled by power management circuitry 700 within electronic circuitry 236. In one embodiment, power management circuit 700 supports operation of measurement device 154 during charging thereby allowing the surgery to continue if a low charge on power source 740 is detected. For example, power can be transferred to batteries 312, capacitive energy storage device, or inductive energy storage device by way of efficient step-up and step-down voltage conversion circuitry. This conserves operating power of circuit blocks at a minimum voltage level to support the required level of performance.

Power management circuitry 700 is configured to operate under severe power constraints. In one embodiment, power management circuitry 700 controls power up, power down, and minimizes power usage during operation. The power management circuitry 700 is configured to reduce power dissipation during operation of the system. The power management circuitry 700 can turn off or reduce the power delivered to circuits that are not being used in a specific operation. Similarly, if the system is idle and not being used, the power management circuitry 700 can put other unused circuitry in a sleep mode that awakens prior to the next measurement being made. Power management circuitry 700 can include one or more voltage regulation circuits that provide a plurality of different stable voltages to electronic circuitry 236 and sensors 230.

In one configuration, a charging operation of power source 740 can further serve to communicate downlink data to electronic circuitry. For instance, downlink control data can be modulated onto the energy source signal and thereafter demodulated from an inductor in electronic circuitry 230. This can serve as a more efficient way for receiving downlink data instead of configuring an internal transceiver within electronic circuitry 230 for both uplink and downlink operation. As one example, downlink data can include updated control parameters that measurement device 154 uses when making a measurement, such as external positional information or for recalibration purposes. It can also be used to download a serial number or other identification data.

Control logic 702 controls a measurement process or sequence that engages the sensors, converts the measurement data into a useable format, and transmits the information. Control logic 702 can comprise digital circuitry, a microcontroller, a microprocessor, an ASIC (Application Specific Integrated Circuit), a DSP (Digital Signal Processing), a gate array implementation, a standard cell implementation, and other circuitry. Control logic 702 couples to memory 704. Memory 704 is configured to store measurement data, software routines, diagnostics/test routines, calibration data, calibration algorithms, workflows, and other information or programs. In one embodiment, one or more sensors may be continuously enabled and sampled periodically to control logic 702. Control logic 702 controls the measurement process, stores the measurement data in memory, or transmit the measurement data in real-time. Control logic 702 can include dedicated ports that couple to a sensor to continuously receive measurement data or receive updated measurements at high sample rates. Alternatively, control logic 702 can select a sensor to be measured. For example, multiple sensors can be coupled to control logic 702 via a multiplexer. Control logic 702 controls which sensor is coupled through the multiplexer to sample and output the measurement data. Multiplexed measurement data works well when the measurement data is not critical or can be sampled occasionally as needed. Control logic 702 can also select and receive measurement data from different sensors in a sequence or simultaneously through parallel channels. Control logic 702 can be configured to monitor the measurement data from a sensor but transmit measurement data only when a change occurs in the measurement data. Furthermore, control logic 702 can modify the measurement data prior to transmitting the measurement data to computer 162. For example, the measurement data can be corrected for non-linearity using calibration data. In one embodiment, a microcontroller with Bluetooth low energy (BLE) is used with an analog to digital converter to convert analog values to digital.

Interface circuitry 706 couples between sensors 230 and control logic 702. Interface circuitry 706 supports conversion of a sensor output to a form that can be received by computer 162. Interface circuitry 706 comprises digital circuitry and analog circuitry. The analog circuitry can include multiplexers, amplifiers, buffers, comparators, filters, passive components, analog to digital converters, and digital to analog converters to name but a few. In one embodiment interface circuitry 706 uses one or more multiplexers to select a sensor for providing measurement data to control logic 702. Control logic 702 is configured to provide control signals that enable the multiplexer to select the sensor for measurement. The multiplexer can be enabled to deliver the measurement data to control logic 702, memory 704, or to be transmitted. Typically, at least one analog to digital conversion or digital to analog conversion of the measurement data occurs via the interface circuitry 706.

Sensors 230 couple through interface circuitry 706 to control logic 702. Alternatively, interface circuitry 706 can couple directly to circuitry for transmitting measurement data as it is measured. The physical parameter or parameters of interest measured by sensors 230 are force, pressure, or load as disclosed herein but sensors 230 can further include other sensors that measure height, length, width, tilt/slope, position, orientation, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Often, a measured parameter is used in conjunction with another measured parameter to make a kinetic and qualitative assessment. In joint reconstruction, portions of the musculoskeletal system are prepared to receive prosthetic components. Preparation includes bone cuts or bone shaping to mate with one or more prosthesis. Parameters can be evaluated relative to orientation, stability, alignment, impingement, direction, displacement, or position as well as movement, rotation, or acceleration along an axis or combination of axes by wireless sensing modules or devices positioned on or within a body, instrument, appliance, vehicle, equipment, or other physical system.

Sensors 230 can directly or indirectly measure a parameter of interest. For example, a load sensor in measurement device 154 can comprise a capacitor, a piezo-sensor, or a MEMs sensor that can compress as loading is applied to the load sensor. Measuring load with a capacitor is an indirect form of sensing as the capacitance value of the capacitor will change with the amount of loading applied to the capacitor. The capacitive measurement data can be sent to computer 162 for further processing. Computer 162 can include software and calibration data related to the elastic capacitors. The load measurement data can be converted from capacitance values to load measurements. Computer 162 can store calibration data that can be used to curve fit and compensate for non-linear output of a sensor over a range of operation. Furthermore, the individual sensor measurement can be combined to produce other measurement data by computer 162. In keeping with the example of load measurement data, the individual load measurement data can be combined or assessed to determine a location where the load is applied to a surface to which the load sensors couple. The measurement data can be displayed on a display that supports a surgeon rapidly assimilating the measurement data. For example, the calculated measurement data on the location of applied load to a surface may have little or no meaning to a surgeon. Conversely, an image of the surface being loaded with a contact point displayed on the surface can be rapidly assimilated by the surgeon to determine if there is an issue with the contact point.

In one embodiment, shoulder joint system 160 transmits and receives information wirelessly. Wireless operation reduces clutter within the surgical area, wired distortion of, or limitations on, measurements caused by the potential for physical interference by, or limitations imposed by, cables connecting a device with an internal power with data collection, storage, or display equipment in an operating room environment. Electronic circuitry 236 includes wireless communication circuitry 720. In one embodiment, wireless communication circuitry 720 is configured for short range telemetry and battery operation. Typically, measurement device 154, and computer 162 are located in an operating room such that the transmission of measurement data from measurement device 156 to computer 162 is less than 10 meters. As illustrated, the exemplary communications system comprises wireless communication circuitry 720 of measurement device 154 and receiving system wireless communication circuitry 722 of computer 162. Wireless communications circuitry 720 comprises, but is not limited to, the antenna 360, a matching network 716, the telemetry transceiver 714, a CRC circuit 712, a data packetizer 710, and a data input 708. Wireless communication circuitry 720 can include more or less than the number of components shown and are not limited to those shown or the order of the components.

Similarly, computer 162 includes wireless communication circuitry 722. Wireless communication circuitry 722 comprises an antenna 724, a matching network 726, a telemetry receiver 728, a CRC circuit 730, and a data packetizer 732. Notably, other interface systems can be directly coupled to the data packetizer 732 for processing and rendering sensor data. In general, electronic circuitry 236 couples to sensors 230 and is configured to transmit quantitative measurement data to computer 162 in real-time to process, display, analyze, and provide feedback. Measurement device 154 includes a plurality of load sensors configured to measure loads applied to external curved surface 224. Measurement device 154 further includes an inertial measurement unit comprising one or more inertial sensors and other parameter measurement sensors as listed herein above. The measurement data from the plurality of load sensors and the inertial sensors is transmitted to computer 162. Computer 162 can calculate a load magnitude applied to external curved surface 224 from the plurality of load sensors. In the example, three load sensors are used for the measurement. Computer 162 can further calculate a position of applied load (contact point) to external curved surface 224 of measurement device 154. Measurement device 154 can further use measurement data from position measurement system 742 to monitor position and movement of measurement device 154 or a prosthetic component. The position or tracking data from position measurement system 742 is also sent to computer 162. The results can also be displayed on display 164 of computer 162. In one embodiment, measurement data from position measurement system 742 can be used to measure range of motion, alignment, and impingement. In one embodiment, the transmission of the measurement data from different sensors or components can be sent on different channels or the measurement data can be sent at different times on the same channel.

As mentioned previously, wireless communication circuitry comprises data input 708, data packetizer 710, CRC circuit 712 telemetry transmitter 714, matching network 716, and antenna 718. In general, measurement data from sensors 230 is provided to data input 708 of wireless communication circuitry 720. In one embodiment, the measurement data from sensors 230 can come directly from interface circuitry 706, from memory 704, from control logic 702, or from a combination of paths to data input 708. In one embodiment, measurement data can be stored in memory 704 prior to being provided to data input 708. Data packetizer 710 assembles the measurement data into packets and includes sensor information received or processed by control logic 702. Control logic 702 can comprise specific modules for efficiently performing core signal processing functions of the measurement device 154. Control logic 702 provides the further benefit of reducing the form factor to meet dimensional requirements for integration into measurement device 154.

In general, measurement data from measurement device 154 is encrypted. In one embodiment, the output of data packetizer 710 couples to the input of CRC circuit 712. CRC circuit 712 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The output of CRC circuit 712 couples to the input of telemetry transceiver 714. The telemetry transceiver 714 then transmits the CRC encoded data packet through the matching network 716 by way of the antenna 360. Telemetry transceiver 714 can increase a carrier frequency in one or more steps and add the information or measurement data from measurement device 154 to the carrier frequency. The matching network 716 provides an impedance match for achieving optimal communication power efficiency between telemetry transmitter 714 and antenna 360.

Antenna 360 can be integrated with components of the measurement device 154 to provide the radio frequency transmission. The substrate for the antenna 360 and electrical connections with the electronic circuitry 236 can further include the matching network 716. In one embodiment, the antenna 360 and a portion of the matching network 716 can be a wire or formed in printed circuit board 234 that interconnects the components that comprise electronic circuitry 236. This level of integration of the antenna and electronics enables reductions in the size and cost of wireless equipment. Potential applications may include, but are not limited to any type musculoskeletal equipment or prosthetic components where a compact antenna can be used. This includes disposable modules or devices as well as reusable modules or devices and modules or devices for long-term use.

The process for receiving wireless communication circuitry 722 is the opposite of the sending process. Antenna 724 receives transmitted measurement data from wireless communication circuitry 720 Wireless communication circuitry 720 can transmit at low power such that receiving wireless communication circuitry 722 must be in proximity, for example within 10 meters to receive measurement data. Antenna 724 couples to matching network 726 that efficiently couples the measurement data to telemetry transmitter circuit 728. The measurement data can be sent on a carrier signal that supports wireless transmission. The measurement data is stripped off from the carrier signal by telemetry transmitter 728. The measurement data is received by CRC circuit 730 from telemetry transmitter 728. CRC circuit 730 performs a cyclic redundancy check algorithm to verify that the measurement data has not been corrupted during transmission. The CRC circuit 730 provides the checked measurement data to data packetizer 732. Data packetizer 732 reassembles the measurement data where it is provided to USB interface 734. USB interface 734 provides the measurement data to computer 162 for further processing.

It should be noted that the measuring, transmitting, receiving, and processing of the measurement data can be performed in real-time for use by a surgeon to support installation of a shoulder joint. In one embodiment, computer 162 displays at least a portion of one prosthetic component. In the example, external curved surface 224 and rim 242 of measurement device 154 is displayed on display 164 coupled to computer 162. Measurement data from sensors 230 and position measurement system 742 is used to calculate a load magnitude and a position of applied load on external curved surface 224 of measurement device 154. The location of each load sensor is known relative to external curved surface 224. The position of applied load can be calculated using the location information from each load sensor and the load magnitude at each location by computer 162 as disclosed in detail herein above. The position of applied load is also called contact point 382 on GUI 380 of display 164. Similarly, the load magnitude at contact point 382 can be calculated from the three load sensors and the three load sensor locations. Typically, the shoulder joint is moved through a predetermine range of motion. The minimum load, the maximum load, and the load at the current location is displayed on GUI 380 respectively in display boxes 380, 390, and 386. The amount of rotation or range of motion can also be indicated. These measurements are measured or calculated in real-time. Rim 242 can also be highlighted to indicate impingement during the predetermined range of motion. In one embodiment, rim 242 will high light an area of rim 242 in proximity to the measured impingement. Adjustments can be performed that affect alignment, loading, position of load, rotation, or other parameters and monitored in real-time on display 164. The adjustments can support optimization after the measured parameters are within specification to fine tune the prosthetic component installation with quantitative measurement data.

Figure 33:
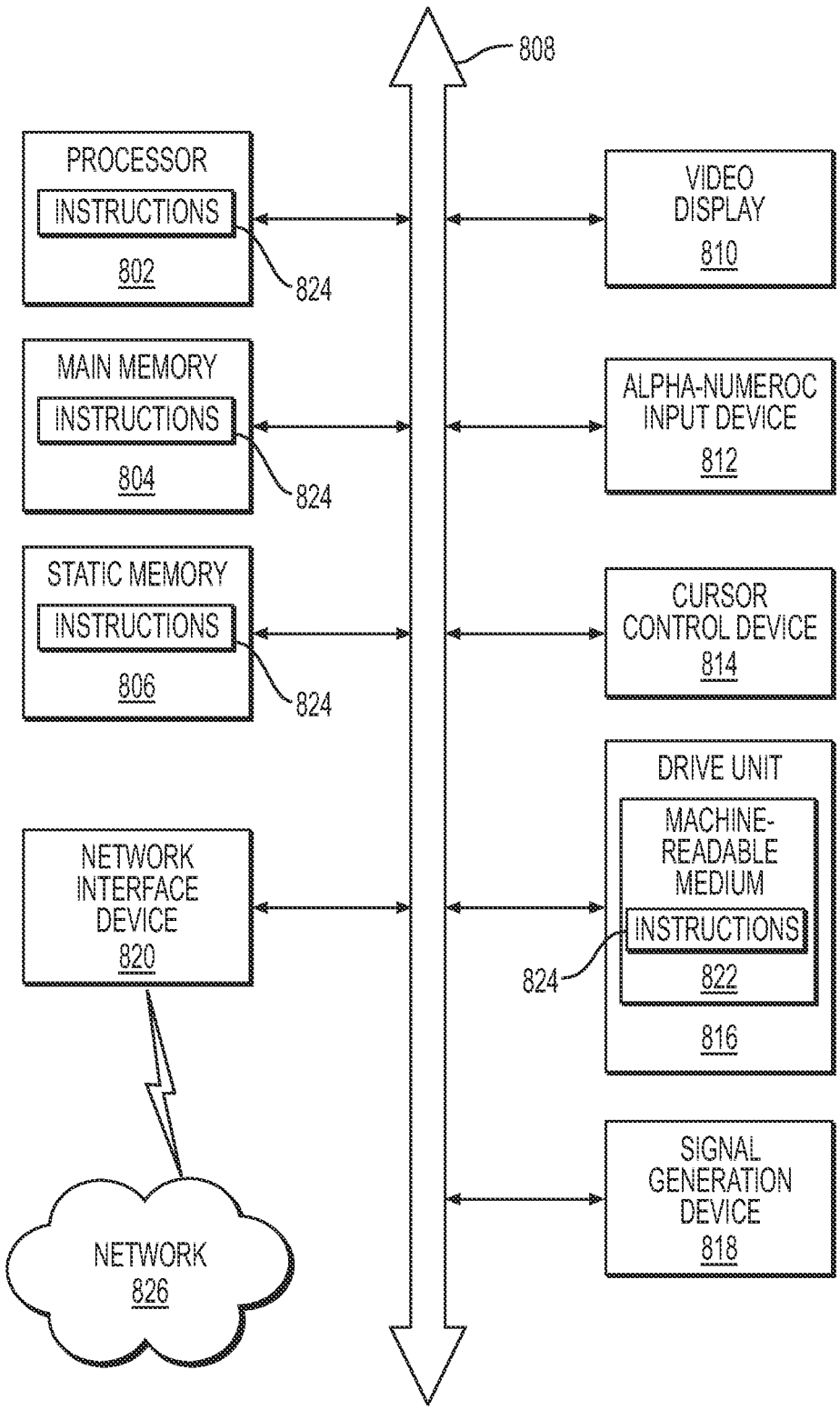
FIG. 33 is a block diagram of the system or computer in accordance with an example embodiment.

FIG. 33 is a block diagram of the system or computer in accordance with an example embodiment. The exemplary diagrammatic representation of a machine, system, or computer in the form of a system 800 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 800 may include a processor 802 (e.g., a central processing unit (CPU), a graphics processing unit (GPU, or both), a main memory 804 and a static memory 806, which communicate with each other via a bus 808. System 800 may further include a video display unit 810 (e.g., a liquid crystal display (LCD), a flat panel, a solid state display, or a cathode ray tube (CRT)). System 800 may include an input device 812 (e.g., a keyboard), a cursor control device 814 (e.g., a mouse), a disk drive unit 816, a signal generation device 818 (e.g., a speaker or remote control) and a network interface device 820.

The disk drive unit 816 can be other types of memory such as flash memory and may include a machine-readable medium 822 on which is stored one or more sets of instructions 824 (e.g., software) embodying any one or more of the methodologies or functions described herein, including those methods illustrated above. Instructions 824 may also reside, completely or at least partially, within the main memory 804, the static memory 806, and/or within the processor 802 during execution thereof by the system 800. Main memory 804 and the processor 802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 824, or that which receives and executes instructions 824 from a propagated signal so that a device connected to a network environment 820 can send or receive voice, video or data, and to communicate over the network 826 using the instructions 824. The instructions 824 may further be transmitted or received over the network 826 via the network interface device 820.

While the machine-readable medium 822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 34:
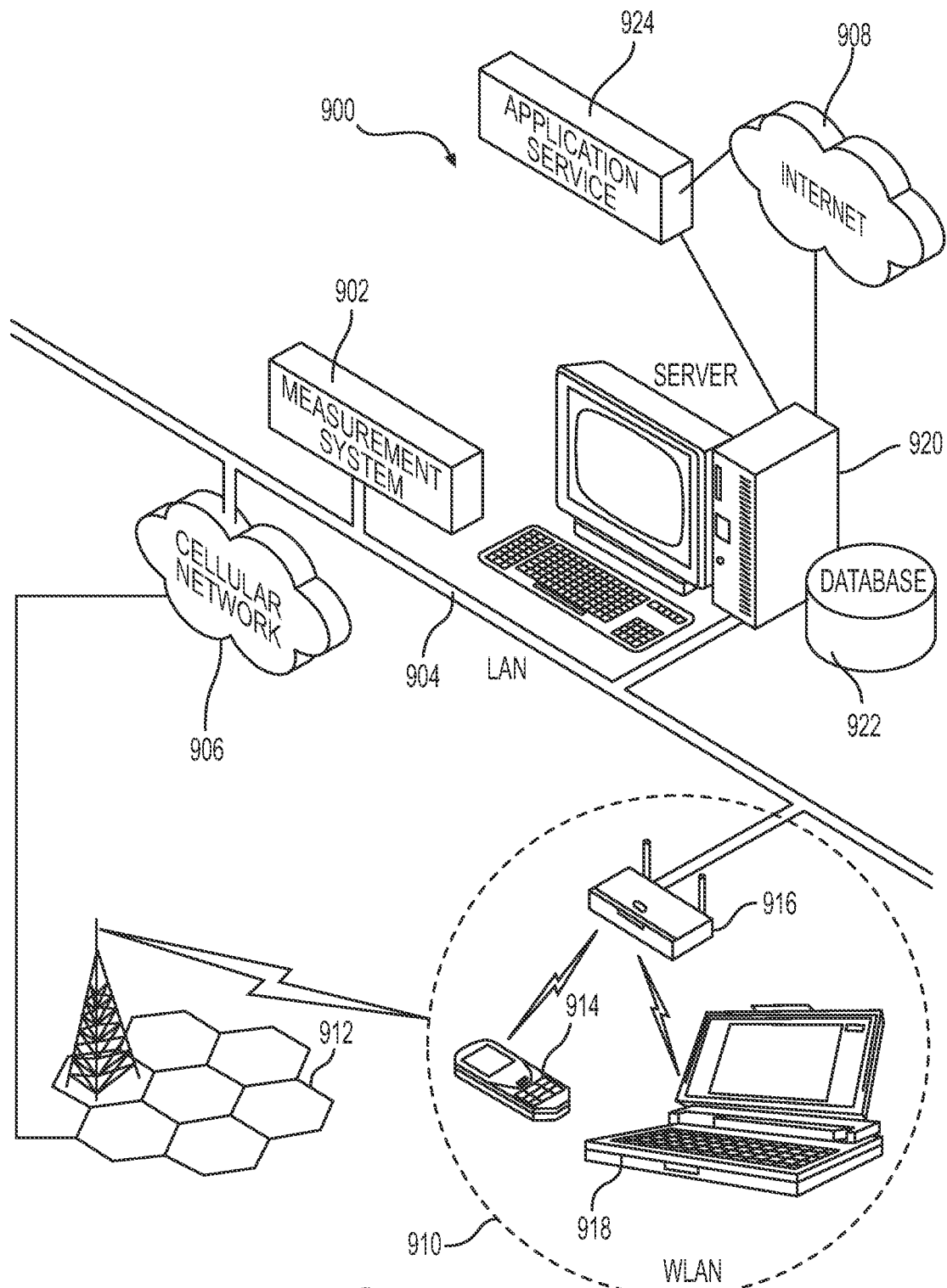
FIG. 34 is an illustration of a communication network for measurement and reporting in accordance with an exemplary embodiment.

FIG. 34 is an illustration of a communication network 900 for measurement and reporting in accordance with an exemplary embodiment. Briefly, the communication network 900 expands broad data connectivity to other devices or services. As illustrated, the measurement and reporting system 902 can be communicatively coupled to the communications network 900 and any associated systems or services.

As one example, measurement system 902 can share its parameters of interest (e.g., angles, load, balance, distance, alignment, displacement, movement, rotation, and accelera-tion) with remote services or providers, for instance, to analyze or report on surgical status or outcome. This data can be shared for example with a service provider to monitor progress or with plan administrators for surgical monitoring purposes or efficacy studies. The communication network 900 can further be tied to an Electronic Medical Records (EMR) system to implement health information technology practices. In other embodiments, the communication network 900 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 900 can provide wired or wireless connectivity over a Local Area Network (LAN) 904, a Wireless Local Area Network (WLAN) 910, a Cellular Network 906, and/or other radio frequency (RF) system (see FIG. 4). The LAN 904 and WLAN 910 can be communicatively coupled to the Internet 908, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 900 can utilize common computing and communications technologies to support circuit-switched and/or packet-switched communications. Each of the standards for Internet 908 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 906 can support voice and data services over a number of access technologies such as GSM-GPRS, EDGE, CDMA, UMTS, WiMAX, 2G, 3G, WAP, software defined radio (SDR), and other known technologies. The cellular network 906 can be coupled to base receiver 912 under a frequency-reuse plan for communicating with mobile devices 914.

The base receiver 912, in turn, can connect the mobile device 914 to the Internet 908 over a packet switched link. The internet 908 can support application services and service layers for distributing data from the measurement system 902 to the mobile device 914. Mobile device 914 can also connect to other communication devices through the Internet 908 using a wireless communication channel. The mobile device 914 can also connect to the Internet 908 over the WLAN 910. Wireless Local Access Networks (WLANs) provide wireless access within a local geographical area. WLANs are typically composed of a cluster of Access Points (APs) 916 also known as base stations. The measurement system 902 can communicate with other WLAN stations such as laptop 918 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 900, the measurement system 902 can establish connections with a remote server 920 on the network and with other mobile devices for exchanging data. The remote server 920 can have access to a database 922 that is stored locally or remotely and which can contain application specific data. The remote server 920 can also host application services directly, or over the internet 908.

Figure 35:
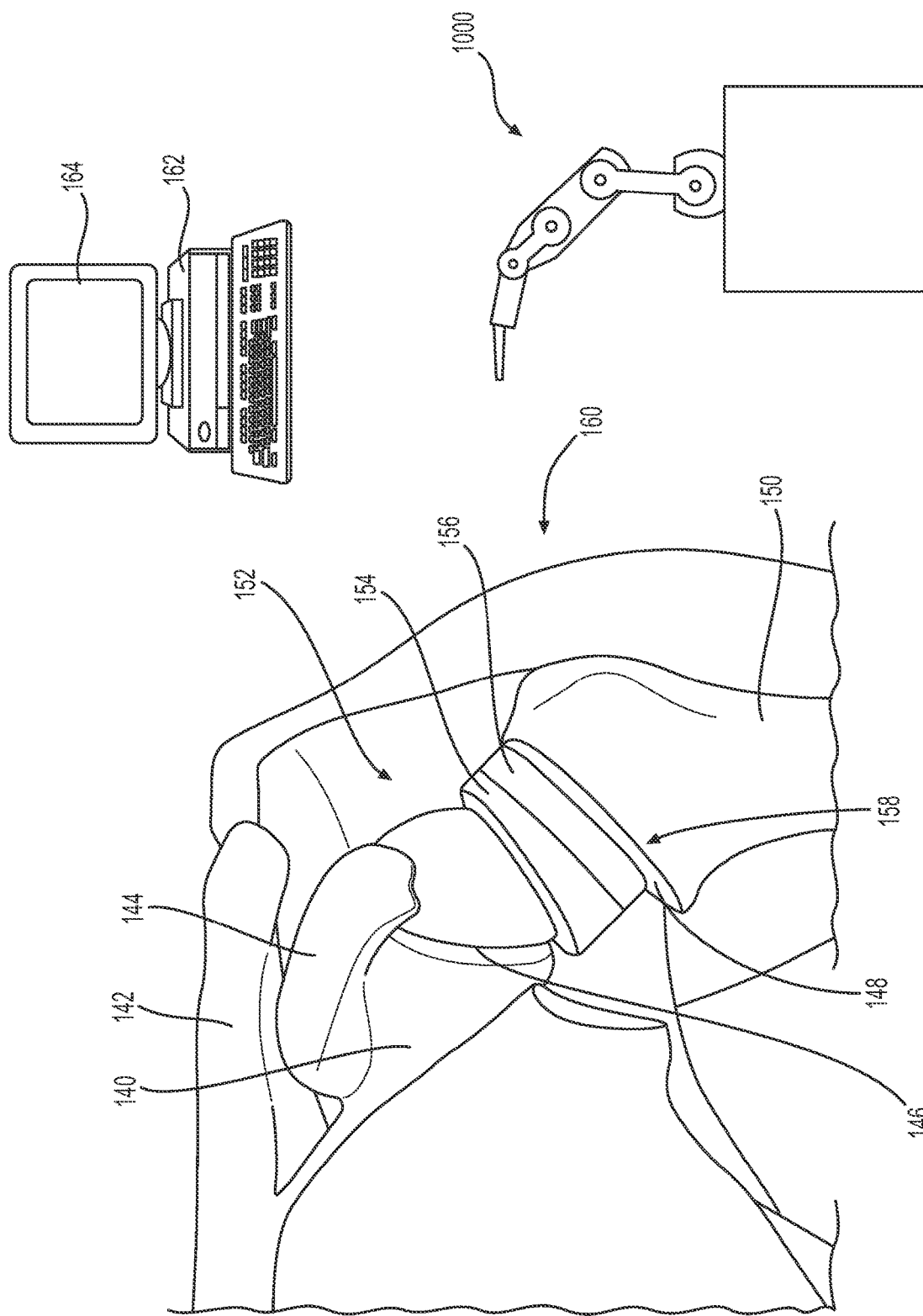
FIG. 35 is a diagram of a robot supporting installation of a shoulder joint in accordance with an example embodiment.

FIG. 35 is a diagram of a robot 1000 supporting installation of a shoulder joint in accordance with an example embodiment. In general, a robot can support or assist in the installation of the shoulder joint under control of a surgeon. In the example embodiment, measurement device 154 can be coupled to robot 1000. One example of the robot is the Robodoc surgical robot with a robotic assisted joint installation application. Robot 1000 can also include surgical CNC robots, surgical haptic robots, surgical tele-operative robots, surgical hand-held robots, or any other surgical robot. Measurement device 154 can be automated to couple to and work with robot 1000 thereby replacing direct hand control by the surgeon. The actions taken by robot 1000 in control of measurement device 154 can be smoother and more accurate by having robot 1000 use the measurement data in real-time and providing feedback to measurement device 154 for subsequent steps. An added benefit can be shortening the time of surgery that reduces the time a patient is under anesthesia.

Robot 1000 can be configured to perform computer-assisted surgery and more specifically shoulder surgery with measurement device 154. Typically, robot 1000 and measurement device 154 is used for computer-assisted surgery to improve performance, alignment, stability, range of motion, reduce surgical time, and minimize impingement in the installation of a prosthetic joint and more specifically a shoulder joint. In one embodiment, robot 1000 can distract, perform bone cuts, align prosthetic components, reposition prosthetic components, adjust loading, perform tissue releases, perform range of motion, and improve stability using the real-time measurement data sent from measurement device 154.

In general, measurement data from measurement device 154 can be wirelessly transmitted to a computer of robot 1000. Alternatively, the measurement data can be hard wired to robot 1000. Examples of measurement data from measurement device 154 can be range of motion for predetermined movements, impingement, load magnitude, position of load, position, and motion to name but a few. The measurement data received by robot 1000 can be further processed to calculate and display measurement data needed by the surgeon for the preparation of the bone surfaces or installation of the final prosthetic components based on the quantitative measurement data. The prepared bone surfaces will receive a prosthetic component that supports proper alignment for optimal range of motion and stability. In one embodiment, the computer in robot 1000 includes one or more algorithms that are used at various stages of the surgery. The measurement data from measurement device 154 is input to the algorithms of robot 1000 and the algorithms can convert the data into information displayed on the display for robotic actions that are used to make bone cuts, pin placements, prosthetic component sizing, etcetera or provide feedback on actions that the surgeon may take. The feedback may take the form of audible, visual, or haptic feedback that guides the surgeon on the distraction or subsequent steps taken by the robot to support or resist an action based on the measurement data. The feedback can also smooth or prevent motions by a user that could be detrimental to the surgery. Furthermore, the status of the measurement data can be used to generate a workflow that is subsequently implemented by a surgeon or automatically by robot 1000 to enhance performance and reliability of the shoulder joint installation.

Figure 36:
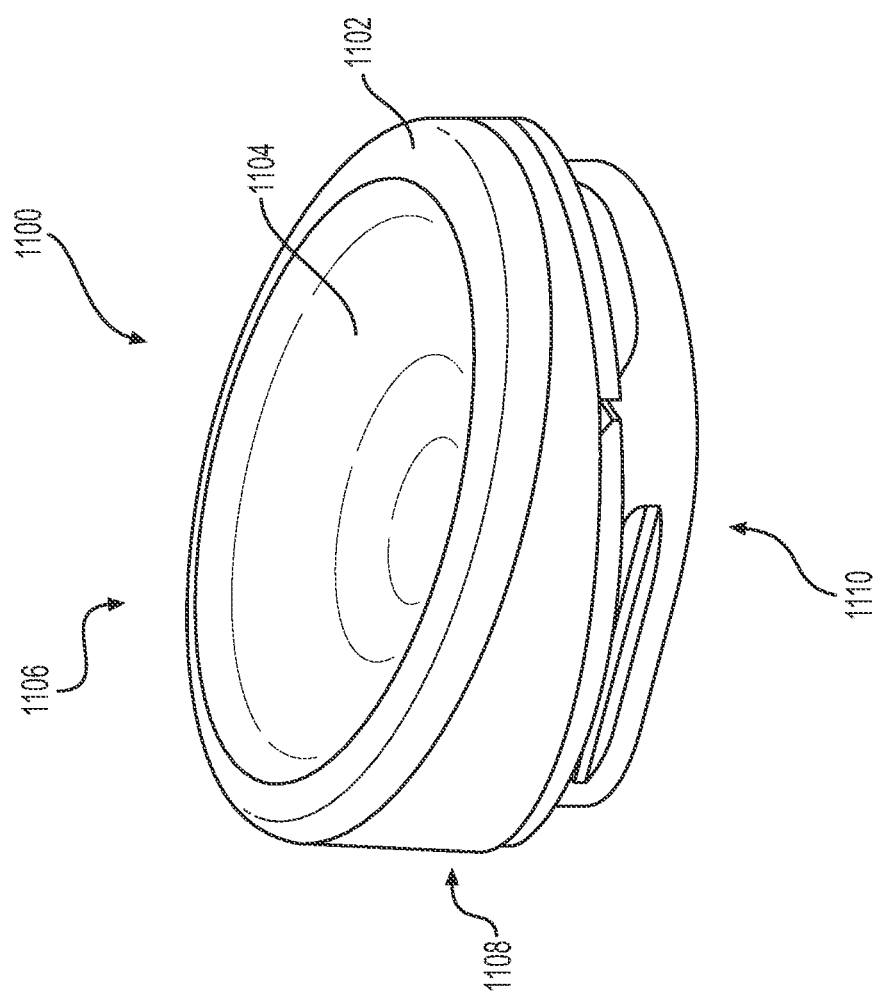
FIG. 36 is a measurement device in accordance with an example embodiment.

FIG. 36 is an illustration of a measurement device 1100 in accordance with an example embodiment. Measurement device 1100 houses electronic circuitry and at least one sensor identical to measurement device 154 as shown in FIGS. 3-21. Measurement device 1100 transmits measurement data to a computer in proximity to display measurement data in real-time. Measurement data from measurement device 1100 can be provided on a GUI 380 as shown in FIGS. 22A-FIG. 27A as disclosed herein above. In the example, measurement device 1100 is configured for a shoulder implant. In general, measurement device 1100 can be adapted for use in the musculoskeletal system such as bones, tissue, ligaments, tendons, or joints. As shown, measurement device 1100 is configured to couple to a humeral prosthesis for measuring range of motion, stability, impingement, load, and position of load of the shoulder joint. A glenoid sphere of the shoulder joint is configured to couple to an external curved surface 1104 of measurement device 1100. Moreover, embodiments or uses stated for measurement device 154 herein above can be applied to measurement device 1100.

Measurement device 1100 comprises an upper housing 1106 and a bottom housing 1108. Upper housing 1106 and bottom housing 1108 couple together to form a hermetically sealed enclosure that houses the electronic circuitry, power source, and sensors. Upper housing 1106 has a rim 1102 and external curved surface 1104. Measurement device 1100 further includes a shim 1110 configured to couple to bottom housing 1108. Shim 1110 is a removable structure of measurement device 1110 that is configured to couple to a humeral tray of the humeral prosthesis. A plurality of shims are provided with measurement device 1100 to change a height of measurement device 1100. In one embodiment, increasing the height of measurement device 1100 using a shim can be used to increase loading applied by the muscles, tendons, or ligaments of the shoulder joint. Conversely, decreasing the height of the measurement device 1100 using a shim of a lessor height can decrease loading applied by the muscles, tendons, or ligaments of the shoulder joint. In one embodiment, a plurality of shims can be provided that change an angle that measurement device 1100 presents to the glenoid sphere when coupled in the shoulder joint.

Figure 37B:
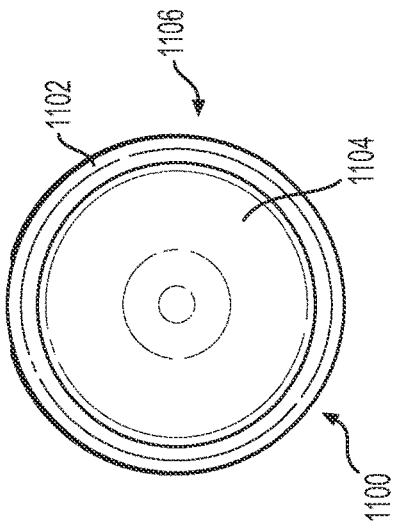
FIG. 37B is a view of the measurement device illustrating the external curved surface in accordance with an example embodiment.
Figure 37D:
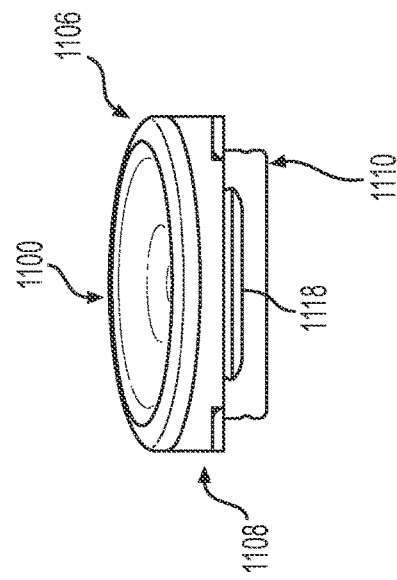
FIG. 37D is an anterior view of the measurement device illustrating an under-cut formed in a shim in accordance with an example embodiment.
Figure 37A:
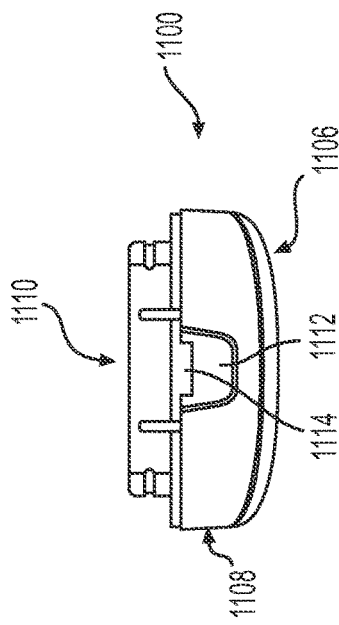
FIG. 37A is a superior view of the measurement device in accordance with an example embodiment.

FIG. 37A is a superior view of measurement device 1100 in accordance with an example embodiment. As mentioned previously, shim 1110 removably couples to bottom housing 1108. This allows different shims to be rapidly coupled to or removed from measurement device 1100 during a shoulder joint installation to determine an optimal fit or placement of the humeral prosthesis in the shoulder joint using quantitative measurement data. A cut out 1112 is shown in bottom housing 1108. In one embodiment, a ledge or protrusion is formed on bottom housing 1108 that underlies retaining feature 1114. Retaining feature 1114 is a tab extending from shim 1110. In one embodiment, retaining feature 1114 couples to the ledge or protrusion of bottom housing 1108 under force to retain shim 1110 to bottom housing 1108. In one embodiment, retaining feature 1114 is flexible such that retaining feature 1114 can be forced away from the ledge or protrusion of bottom housing 1108 to release shim 1110 from bottom housing 1108. Cutout 1112 in bottom housing 1108 allows access to facilitate flexing of retaining feature 1114 away from bottom housing 1108.

FIG. 37B is a view of measurement device 1100 illustrating external curved surface 1104 in accordance with an example embodiment. In general, upper housing 1106 of measurement device 1100 includes rim 1102 and external curved surface 1104. As mentioned previously, a glenoid sphere couples of the shoulder joint couples to external curved surface 1104 of measurement device 1100. In one embodiment, the plurality of sensors underlie external curved surface 1104 and are configured to measure a force, pressure, or load applied at each location where a sensor is placed. The measurement data from the plurality of sensors is provided to a computer to calculate a load magnitude applied to external curved surface 1104 by the glenoid sphere of the shoulder joint and the location of the applied load by the glenoid sphere.

Figure 37C:
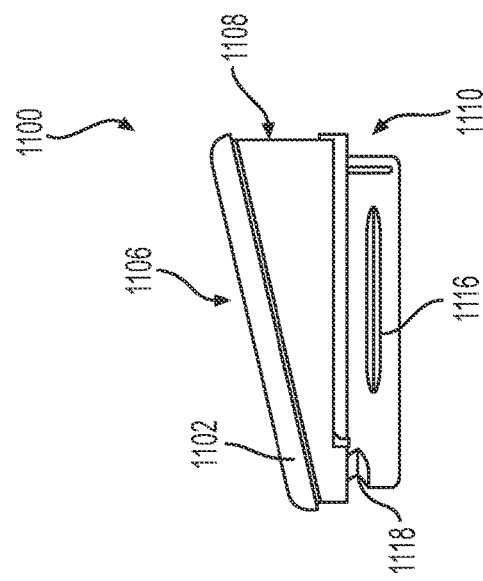
FIG. 37C is a side view of the measurement device in accordance with an example embodiment.

FIG. 37C is a side view of measurement device 1100 in accordance with an example embodiment. Upper housing 1106 is coupled to bottom housing 1108. Shim 1110 is coupled to bottom housing 1108. The side view illustrates under-cut 1116 and under-cut 1118 in shim 1110. In one embodiment, under-cut 1118 is also on the opposing side of shim 1110. Under-cuts 1116 and 1118 are used to retain and align measurement device 1100 to an implant tray of the humeral prosthesis. In one embodiment, corresponding features formed in the implant tray couple to under-cuts 1116 and 1118.

FIG. 37D is an anterior view of measurement device 1100 illustrating under-cut 1118 formed in shim 1110 in accordance with an example embodiment. Under-cut 1118 is used to retain and align measurement device 1110 to the implant tray of the humeral prosthesis.

Figure 38:
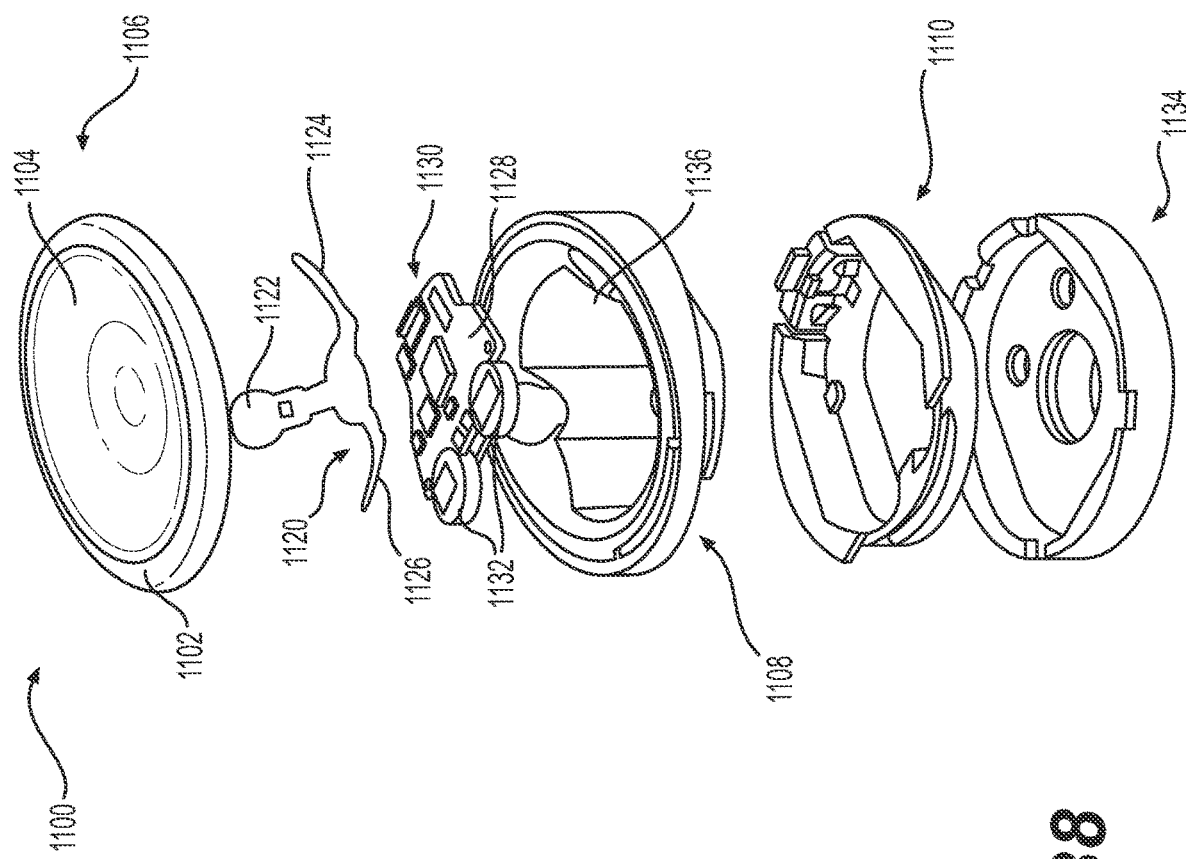
FIG. 38 is an exploded view of the measurement device in accordance with an example embodiment.

FIG. 38 is an exploded view of measurement device 1100 in accordance with an example embodiment. A flexible interconnect 1120 is configured to couple a plurality of sensors to electronic circuitry 1130. The plurality of sensors can be formed in or on flexible interconnect 1120. In one embodiment, the plurality of sensors comprises a sensor 1122, a sensor 1124, and a sensor 1126. In one embodiment, sensors 1122, 1124, and 1126 are formed in flexible interconnect 1120. Alternatively, sensors can be coupled to flexible interconnect 1120. In one embodiment, one or more reference sensors are formed in flexible interconnect 1120. In one embodiment, sensors 1122, 1124, and 1126 and interconnect in flexible interconnect 1120 are shielded. Sensors 1122, 1124, and 1126 are configured to couple to external curved surface 1104.

Electronic components and power source 1132 are coupled to a printed circuit board 1128. Printed circuit board 1128 includes one or more levels of interconnect to connect the electronic components to form electronic circuitry 1130 that is configured to control a measurement process and transmit measurement data. In one embodiment, power source 1132 comprises batteries for powering measurement device 1100. Printed circuit board 1128 can be a rigid printed circuit board that includes a connector for coupling to flexible interconnect 1120. Electronic circuitry 1130, flexible interconnect 1120, and sensors 1122, 1124, and 1126 are placed in a cavity 1136 of bottom housing 1108. Upper housing 1106 couples to bottom housing 1108 to form a housing for electronic circuitry 1130, flexible interconnect 1120, and sensors 1122, 1124, and 1126. In one embodiment, sensors 1122, 1124, and 1126 are placed at predetermined locations between upper housing 1106 and bottom housing 1108 to support a load magnitude and position of applied load measurement where a glenoid sphere couples to external curved surface 1104 of measurement device 1100 for the shoulder joint. As mentioned previously, the electronic circuitry 1130, the reference sensor, a position measurement system (e.g. IMU), and sensors 1122, 1124, and 1126 operate similarly to that described for measurement device 154 (see FIG. 3) and will not be disclosed in detail for brevity. Furthermore, measurement device 1100 will transmit measurement data to computer 162 and have measurement data displayed on display 164 as disclosed herein above. The measurement data can be displayed on GUI 380 in graphical form to speed assimilation of the measurement data in the same manner as discussed for measurement device 154.

A shim 1110 couples to bottom housing 1108 to add height to measurement device 1100. A plurality of shims are provided with measurement device 1100 where each shim of the plurality of shims has a different thickness. Thus, shim 1110 can be removed and replaced with one of the other shims from the plurality of shims to change the height of measurement device 1100 by a predetermined amount. Upper housing 1106, bottom housing 1108, and shim 1110 can be formed from a biological compatible material such as a composite material, a polymer, plastic, metal, or a metal alloy. In one embodiment, upper housing 1106, bottom housing 1108, and shim 1110 can be molded or 3D printed from a polymer material.

An implant tray 1134 is a component of the humeral prosthesis. In one embodiment, implant tray 1134 couples to the humeral prosthesis. In one embodiment, implant tray 1134 is held in place to the humeral prosthesis by a screw and implant tray 1134 can be removed by removing the screw. Shim 1110 is configured to couple to implant tray 1134 to hold measurement device 1100 in place for generating quantitative measurement data related to the shoulder joint for assessing range of motion, stability, impingement, movement, load, or position of load.

FIG. 39 is a view of cavity 1136 of bottom housing 1108 of measurement device 1100 in accordance with an example embodiment. In the example, placement of components of measurement device 1100 are illustrated. Printed circuit board 1128 with the electronic components is coupled to an interior surface of bottom housing 1108. Printed circuit board 1148 fits within cavity 1136 and is retained by printed circuit board snaps 1142. Printed circuit board snaps 1142 are forced through openings in printed circuit board 1128 to form an interference fit that prevents movement and aligns printed circuit board 1128 within cavity 1136. In one embodiment, printed circuit board snaps 1142 extend from the interior surface of bottom housing 1108 and the heads of printed circuit board snaps 1142 are made larger than the openings in printed circuit board 1128. Printed circuit board 1128 has a connector 1146 that couples to flexible interconnect 1120. In one embodiment, power source 1132 couples to and is retained by printed circuit board 1128. Power source 1132 provides power for electronic circuitry 1130 and sensors 1122, 1124, and 1126 to provide measurement data for a complete shoulder replacement surgery.

Sensors 1122, 1124, and 1126 couple to a surface 1144 on bottom housing 1108 at predetermined locations relative to external surface 1104 of upper housing 1106 (see FIG. 36). In one embodiment, sensors 1122, 1124, and 1126 are located on a radial position of externa curved surface 1106. In one embodiment, sensors 1122, 1124, and 1126 are spaced equidistant from one another. In one embodiment, a reference sensor 1148 can be located centrally on or in flexible interconnect 1120 relative to sensors 1122, 1124, and 1126. Alternatively, more than one reference sensor can be formed on or in flexible interconnect 1120. Sensors 1122, 1124, and 1126 are held in place by sensors snaps 1140. Sensor snaps 1140 couple through openings in proximity to sensors 1122, 1124, and 1126 to align and retain sensors 1122, 1124, and 1126 at the predetermined locations. In one embodiment, a raised region is formed underlying sensors 1122, 1124, and 1126. The raised regions extend above surface 1144 and provide a planar surface to support sensors 1122, 1124, and 1126.

FIG. 40 is a cross-sectional view of measurement device 1100 in accordance with an example embodiment. Upper housing 1104 is shown coupling to bottom housing 1108. In one embodiment, a peripheral groove 1152 is formed circumferentially on bottom housing 1108. A peripheral tongue 1150 is formed circumferentially on upper housing 1106 and is configured to couple to peripheral groove 1152 on bottom housing 1108. In one embodiment, glue or an adhesive can be used in peripheral groove 1152 to seal and retain upper housing 1106 to bottom housing 1108. Alternatively, one or more retaining structures on upper housing 1106 and one or more corresponding retaining structures on bottom housing 1108 can be used to couple upper housing 1106 to bottom housing 1108. Peripheral tongue 1150 can comprise a conformal material that forms a seal when upper housing 1106 couples to bottom housing 1108.

Retaining feature 1114 on a superior side of measurement device 1100 is shown coupling shim 1110 to bottom housing 1108. Although not shown there can be more than one retaining feature coupling shim 1110 to bottom housing 1110. Bottom housing 1108 has a cutout 1156 configured to receive retaining feature 1114. Retaining feature 1114 has a corresponding protrusion 1154 configured to fit in cutout 1156. As mentioned previously, retaining feature 1114 is flexible and can be flexed away from bottom housing 1108 such that protrusion 1154 is outside cutout 1156 allowing shim 1110 to be removed from bottom housing 1108.

Printed circuit board 1130 is retained to or in proximity to the interior surface of bottom housing 1108. Flexible interconnect 1120 is shown coupling to connector 1146 on printed circuit board 1130. Sensor 1122 formed in or placed on flexible interconnect is coupled between upper housing 1106 and bottom housing 1108. In one embodiment, sensor 1122 couples to planar surfaces formed on an interior surface of upper housing 1106 and the interior surface of bottom housing 1108. Sensor 1122 underlies a predetermined location of external surface 1104. The predetermined locations of sensors 1122, 1124, and 1126 are used to calculate a position of applied load and a load magnitude from the measurement data. Note that flexible interconnect 1120 does not undergo any bends that kink the interconnect. Sensor snap 1140 is shown coupling through flexible interconnect 1120 to retain sensor 1120 at the predetermined location.

FIGS. 41A and 41B illustrates measurement device 1100 with two different shims in accordance with an example embodiment. In general, measurement device 1100 includes a plurality of shims. In the example, two different shims are disclosed but more than two can be provided. Shim 1110 is a zero height shim and corresponds to measurement device 1100 at a minimum height. In the example, upper housing 1106 and bottom housing 1108 are coupled together and configured to measure at least one parameter. Shim 1110 is a separate component that couples to bottom housing 1108. Measurement device 1100 is shown with shim 1100 coupled to bottom housing 1110 to form measurement device 1110 at a standard, normal or minimum height.

Shim 1160 is a 2.5 millimeter shim that raises the height of measurement device 1100 2.5 millimeters when compared to zero height shim 1100 of FIG. 41A. In the example, upper housing 1106 and bottom housing 1108 are coupled together and configured to measure at least one parameter. Shim 1160 is a separate component that couples to bottom housing 1108. Measurement device 1100 is shown with shim 1160 coupled to bottom housing 1110 to form measurement device 1110 at a height increased by 2.5 millimeters. As stated previously, measurement device 1100 can be provided with more than two shims of different heights. For example, the shoulder joint when reduced with shim 1110 of FIG. 41A might have a loading when measured by measurement device 1100 that is less than desirable. Shim 1110 can then be removed and replaced with shim 1160. Reducing the shoulder joint with shim 1160 in measurement device 1160 will increase tension on muscles of the shoulder joint thereby increasing the loading applied to measurement device 1100. The tension on the different muscles, ligaments, or tendons can be adjusted to achieve stability, maximize range of motion, minimize impingement, and load the shoulder joint within an acceptable range based on quantitative measurement data. For example, the tension can be adjusted using soft tissue tensioning to adjust the loading within the acceptable range measured by load sensors within measurement device 1100 in real-time.

Figure 42:
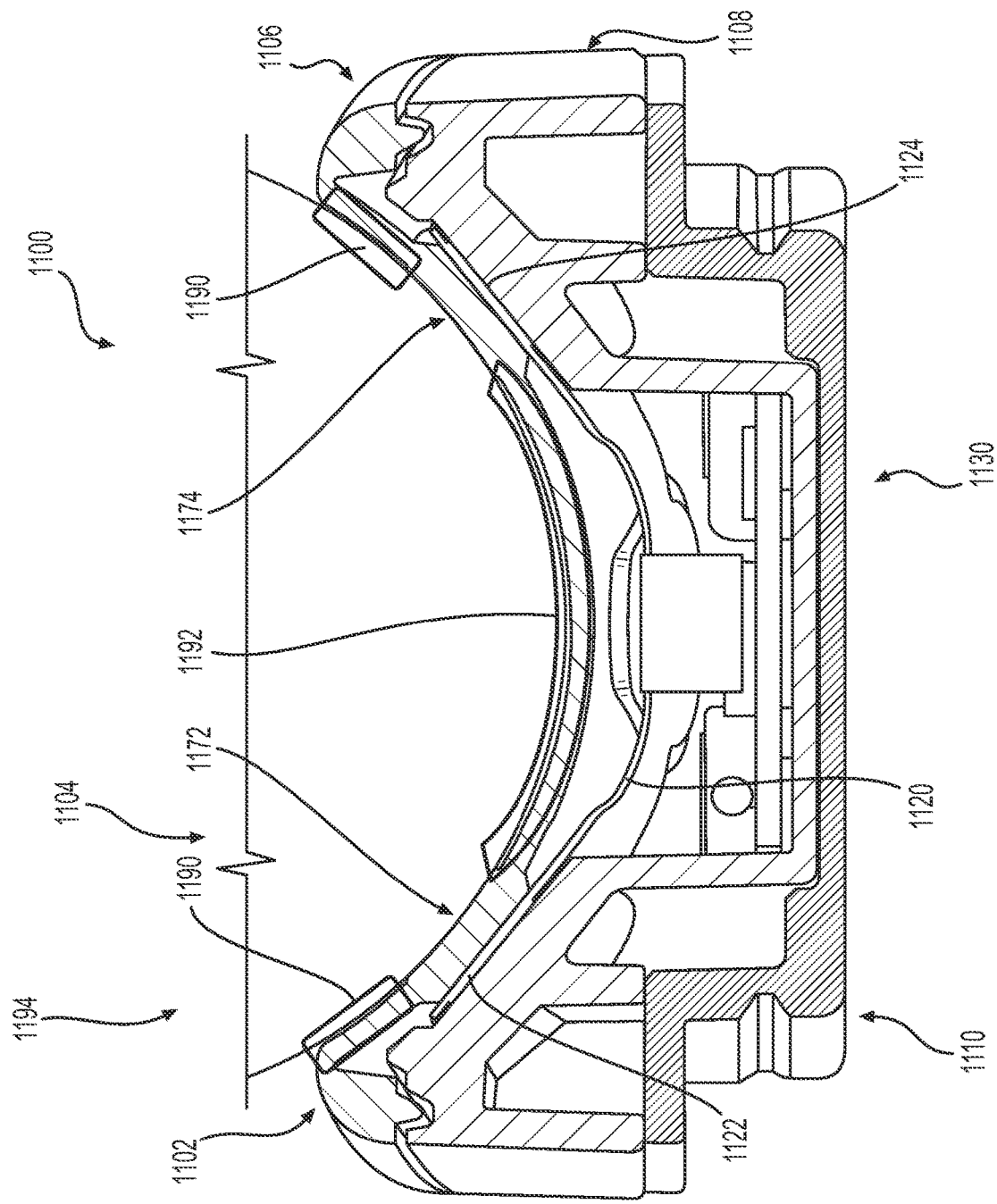
FIG. 42 is a cross-sectional view of the external curved surface of the upper housing that is modified to direct loading to predetermined areas of the external curved surface in accordance with an example embodiment.

FIG. 42 is a cross-sectional view of external curved surface 1104 of upper housing 1106 that is modified to direct loading to predetermined areas of external curved surface 1104 in accordance with an example embodiment. The cross-sectional view shows upper housing 1106 coupled to bottom housing 1108 to form an enclosure to isolate and hermetically seal electronic circuitry 1130, flexible interconnect, 1120, and sensors 1122, 1124, and 1126 from an external environment. Shim 1110 couples to bottom housing 1108. A partial view of glenoid sphere 1194 is shown coupling to external curved surface 1104 of upper housing 1106. In general, loading by glenoid sphere 1194 is directed to the plurality of load sensors underlying external curved surface 1104. In the example, the loading is directed to sensor 1122, sensor 1124, and sensor 1126 (not shown in the illustration). As shown, sensors 1122 and 1124 respectively underlie region 1172 and region 1174 of external curved surface of 1104. Similarly, sensor 1126 will underlie region 1176 of FIG. 42. As previously mentioned, sensors 1122, 1124, and 1126 are located at predetermined radial positions of external curved surface 1104. In one embodiment, sensors 1122, 1124, and 1126 are also spaced equidistant from each other. Sensors 1122, 1124, and 1126 are placed as close to rim 1102 of upper housing 1106 as feasible to maximize the measurement area on external curved surface 1104.

In the example, glenoid sphere 1194 is 38 millimeters in diameter and has a 19 millimeter radius. In one embodiment, external curved surface 1104 has a larger radius than glenoid sphere 1194. In the example, the radius of external curved surface is 38.15 millimeters. External curved surface 1104 is modified such that glenoid sphere 1194 only couples to regions 1172, 1174, and 1176 of external curved surface 1104. Sensors 1122, 1124, and 1126 respectively underlie regions 1172, 1174, and 1176 of external curved surface 1104. Thus, loading applied by glenoid sphere 1194 is directed to sensors 1122, 1124, and 1126 of measurement device 1100 and not to areas of external curved surface 1104 outside regions 1172, 1174, and 1176. In general, there are two regions on external curved surface 1104 that does not couple to glenoid sphere 1194. In one embodiment, a region 1192 of external curved surface 1104 of upper housing 1106 does not couple to glenoid sphere 1194. Note that a gap is shown between glenoid sphere 1194 and external curved surface 1104 in region 1192. Region 1192 corresponds to a load measurement area between sensors 1122, 1124, and 1126. In one embodiment, the gap between glenoid sphere 1194 and external curved surface 1104 in region 1192 is approximately 0.15 millimeters. In one embodiment, region 1192 can be molded having a 0.15 millimeter cutout in region 1192. Alternatively, 0.15 millimeter of material can be removed from region 1192.

In one embodiment, a region 1190 of external curved surface 1104 of upper housing 1106 does not couple to glenoid sphere 1194. Note that a gap is shown between glenoid sphere 1194 and external curved surface 1104 in region 1130. Region 1190 corresponds to the area outside region 1192 and regions 1172, 1174, and 1176 of external curved surface 1104. In one embodiment, the gap between glenoid sphere 1194 and external curved surface 1104 in region 1190 is approximately 0.10 millimeters. In one embodiment, can be molded having a 0.10 millimeter cutout in region 1190. Alternatively, 0.10 millimeter of material can be removed from region 1190.

Figure 43:
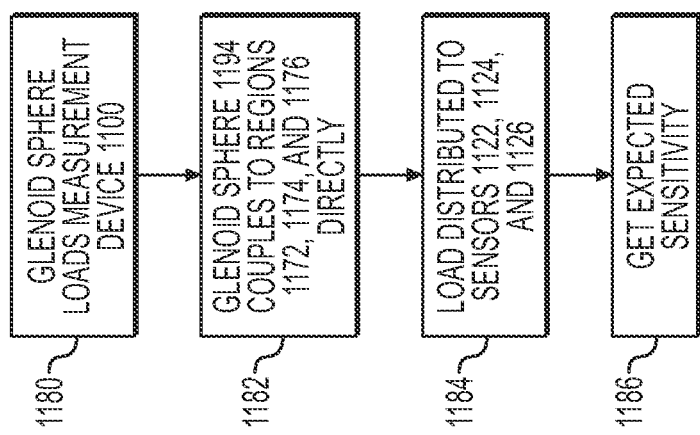
FIG. 43 is a block diagram of loading the measurement device in accordance with an example embodiment.

FIG. 43 is a block diagram of loading measurement device 1100 in accordance with an example embodiment. The method will refer to components listed in FIG. 42. In a step 1180, a glenoid sphere 1194 of a shoulder joint loads measurement device 1100. In the example, the glenoid sphere 1194 couples to the scapula and measurement device 1100 couples to the humeral prosthesis to form the shoulder joint. In a step 1182, glenoid sphere 1194 couples to regions 1172, 1174, and 1176 directly. Sensors 1122, 1124, and 1126 respectively underlie regions 1172, 1174, and 1176 of external curved surface 1104 of upper housing 1106. In one embodiment, glenoid sphere 1194 does not couple to regions 1190 and 1192 of external curved surface 1104 of upper housing 1106. Loading applied by glenoid sphere 1194 is coupled through and distributed among sensors 1122, 1124, and 1126. In a step 1186, by distributing the load through regions 1172, 1174, and 1176 and thereby through sensors 1122, 1124, and 1126 the expected sensitivity of the sensors is correct. In one embodiment, loading applied by glenoid sphere 1194 to measurement device 1100 only couples through sensors 1122, 1124, and 1126.

Figure 44:
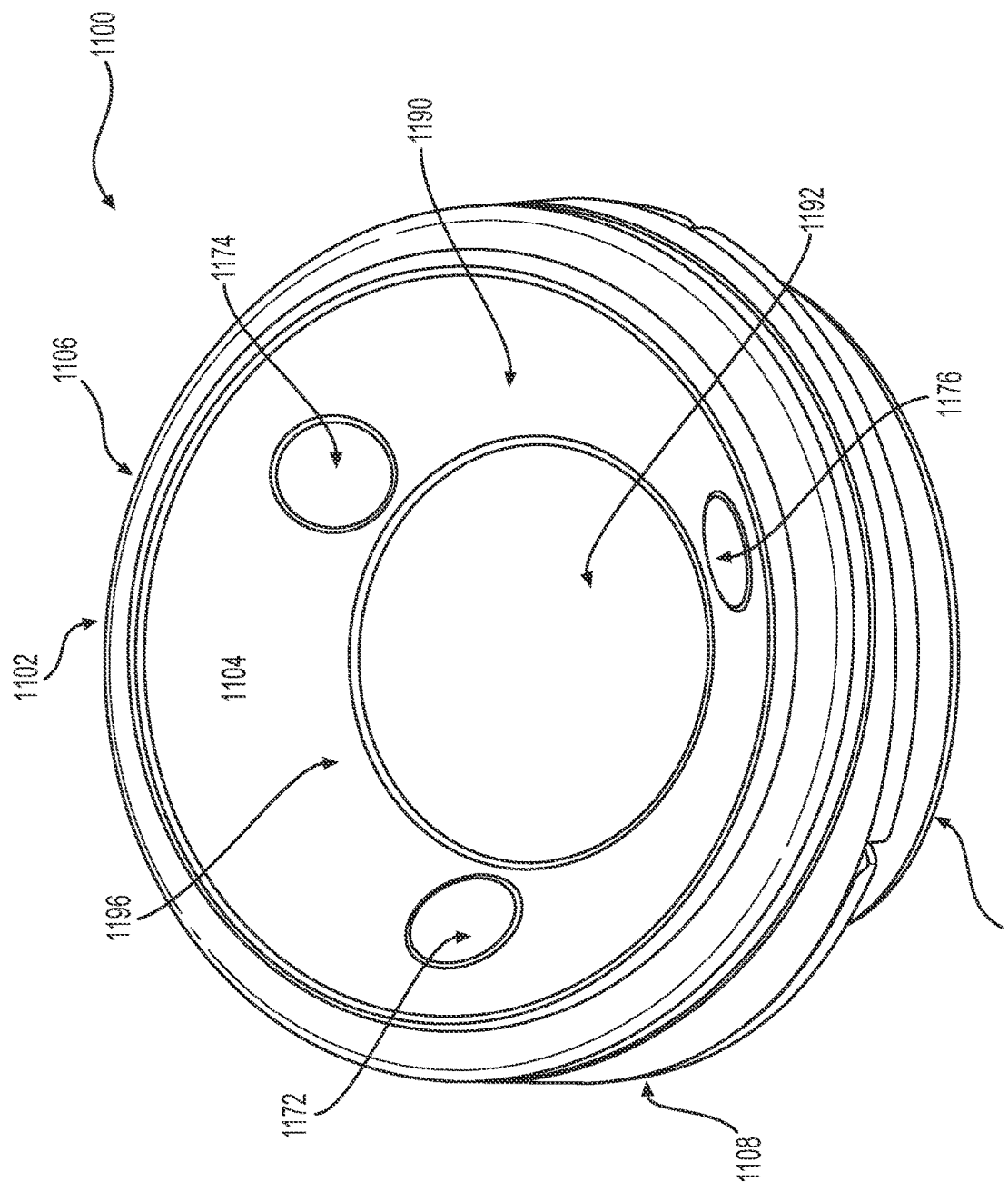
FIG. 44 is an illustration of the measurement device illustrating different regions of the external curved surface of the upper housing in accordance with an example embodiment.

FIG. 44 is an illustration of measurement device 1100 illustrating different regions of external curved surface 1104 of upper housing 1106 in accordance with an example embodiment. In general, external curved surface 1104 has three different regions each having a different surface height. The first regions corresponds to locations of the sensors for measuring a force, pressure, or load applied to external curved surface 1104. The surface height and curvature of the first regions corresponds to a radius configured to receive a spherical prosthetic component. In the example, the glenoid sphere has a radius of 19 millimeters and the radius of the first regions corresponding to the locations of the sensors is 19.075 millimeters. In one embodiment, external curved surface 1104 has a larger radius than spherical prosthetic component that couples to it.

The second region of external curved surface 1104 corresponds to a location of applied load of the spherical prosthetic component to external curved surface 1104. In general, the sensors are located adjacent to or in proximity to rim 1102 of upper housing 1106. Placing the sensors in proximity to the rim 1102 maximizes area in which the sensors can accurately measure the location of applied load. In one embodiment, the sensors are located on a radial position of external curved surface 1104. In one embodiment, the sensors are spaced equidistant from one another. In one embodiment, the second region can be located at or below the sensor locations. In one embodiment, the second region can be an irregular shape. In one embodiment, the second region can comprise more than one second region. In the example, the surface of the second region of external curved surface 1104 is below the surface of the first regions. In one embodiment, the spherical prosthetic component does not couple to the second region when coupled to external curved surface 1104. The spherical prosthetic component couples to the first regions corresponding to the sensor locations.

The third region of external curved surface 1104 corresponds to a location of applied load that is in proximity to the sensors or above the sensors on external curved surface 1104. In one embodiment, the range of motion of the spherical prosthetic component when coupled to external curved surface 1104 does not typically place the position of applied load near rim 1102 of upper housing 1106. In general, the third region corresponds to extremes of the range of motion for the prosthetic joint. In one embodiment, the third region can be located in proximity to or above the sensor locations. In one embodiment, the third region can be an irregular shape. In one embodiment, the third region can comprise more than one third region. In the example, the third region of external curved surface 1104 is outside the second region of external curved surface 1104 but does not include the first regions. In one embodiment, the spherical prosthetic component does not couple to the third region when coupled to external curved surface 1104. The spherical prosthetic component couples to the first regions corresponding to the sensor locations. In the example, the surface of the third region is below the surface of the first regions. In one embodiment, the surface of the second region is below the surface of the third region.

In the example, a circle 1196 is drawn on external curved surface 1104 to define a boundary that identifies a region 1190 and a region 1192. Region 1192 corresponds to the second region of external curved surface 1104 disclosed herein above. Region 1192 is an area of external curved surface 1104 that is within circle 1196. Region 1190 corresponds to the third region of external curved surface 1104. In one embodiment, region 1190 is an area of external curved surface 1104 that is outside of circle 1196 but does not include regions 1172, 1174, and 1176 up to rim 1102. As mentioned previously, sensors 1122, 1124, and 1126 as shown in FIG. 39 respectively underlie regions 1172, 1174, and 1176. In one embodiment, regions 1172, 1174, and 1174 have an area larger than or equal to an area of sensors 1122, 1124, and 1126. In one embodiment, regions 1172, 1174, and 1176 have a curved surface configured to interface with glenoid sphere 1194 of FIG. 42. In the example, regions 1172, 1174, and 1176 have a curved surface corresponding to a radius of 19.075 millimeters whereas the glenoid sphere has a radius of 19 millimeters. A surface of region 1192 of external curved surface 1104 is below the surface of regions 1172, 1174, and 1176. In the example, the surface of region 1192 is 0.15 millimeters below the surfaces of regions 1172, 1174, and 1176 such that glenoid sphere 1194 of FIG. 42 does not couple to region 1192 when glenoid sphere 1194 is coupled to measurement device 1100. A surface of region 1190 of external curved surface 1104 is below the surface of regions 1172, 1174, and 1176. In the example, the surface of region 1190 is 0.10 millimeters below the surfaces of regions 1172, 1174, and 1176 such that glenoid sphere 1194 does not couple to region 1190 when glenoid sphere 1194 is coupled to measurement device 1100. In the example, the surface of region 1190 is above the surface of region 1192 in relation to regions 1172, 1174, and 1176. In one embodiment, having regions 1190, 1192, 1172, 1174, and 1176 of external curved surface 1104 directs loading applied by glenoid sphere 1194 through sensors 1122, 1124, and 1126 which yields an expected sensitivity for the measurement device.

Referring briefly to FIGS. 1-3, a shoulder joint system 160 is disclosed comprising a first shoulder prosthesis and a second shoulder prosthesis. In general, shoulder joint system 160 can be used for a prosthetic reverse shoulder or a normal prosthetic shoulder. The electronic circuitry and sensors can be housed in either a prosthetic component that couples to the humerus, a prosthetic component that couples to the scapula, or both. In one embodiment, the first shoulder prosthesis is a humeral prosthesis 158 configured to couple to humerus 150. Humeral prosthesis 158 comprises a stem 124, a neck 126, and a tray 156. In one embodiment, the second shoulder prosthesis is a glenoid sphere 152 configured to couple to scapula 140. Humeral prosthesis 158 and glenoid sphere 152 each have external curved surfaces configured to mate together to support movement and rotation of the shoulder joint. Alternatively in normal prosthetic shoulder, the first shoulder prosthesis is a glenoid prosthesis 114 and the second shoulder prosthesis is a humeral prosthesis 102.

During a trialing process a humeral liner 128 of humeral prosthesis 158 is removed and a measurement device 154 replaces humeral liner 128 to take one or more measurements to support installation of shoulder joint system 160. Measurement device 154 has an external curved surface configured to mate with glenoid sphere 152 and support movement of the shoulder joint system. In one embodiment, measurement device will be dimensionally identical to the humeral liner that couples to humeral tray 156. Referring briefly to FIGS. 5-21, electronic circuitry and a plurality sensors are shown in measurement device 154. In particular, FIGS. 5 and 6 illustrate measurement device 154 having an upper housing 220 and a bottom housing 222. Three sensors 230 are illustrated that are located at different radial locations beneath external curved surface 224 of upper housing 220. Upper housing 220 couples to bottom housing 222 to form a hermetic seal that houses the electronic circuitry and a plurality of sensors. In one embodiment, the hermetic seal is formed by an O-ring or adhesive that couples between upper housing 220 and bottom housing 222. Referring briefly to FIG. 16, one or more housing snaps 279 are used to couple upper housing 220 to bottom housing 222 of measurement device 154. In one embodiment, a housing snap 278 comprises a protrusions formed on a sidewall 328 of bottom housing 222 and a corresponding opening formed on upper housing 220. The region of upper housing 220 having the openings is configured to flex such that the upper housing 220 can be forcibly pressed onto bottom housing 222 until the opening overlies a corresponding housing snap 278. The one or more housing snaps 278 preloads the plurality of sensors when coupling upper housing 220 to bottom housing 222. Referring briefly to FIG. 29B a plurality of sensors are each located a radial position relative to the external curved surface of measurement device 154. In one embodiment 3 sensors are located at 3 different radial locations. Referring briefly to FIG. 31, force sensors 530, 532, and 534 are oriented such that the reaction forces are directed to a center of rotation of a shoulder prosthesis. A block diagram of electronic circuitry 236 of measurement device 154 is disclosed in FIG. 32. Electronic circuitry 236 operatively couples to the plurality of sensors in measurement device 154. Electronic circuitry 236 controls a measurement process and transmits measurement data.

Referring briefly to FIG. 19, a flexible interconnect 228 couples the plurality of sensors 230 to electronic circuitry 236. Referring briefly to FIG. 14, flexible interconnect 228 couples a support structure 262 to place plurality of sensors 230 in position relative to the external curved surface of upper housing 220. In one embodiment, flexible interconnect 228 couples to an interior surface 244 of bottom housing 222. In one embodiment, flexible interconnect 228 couples to support structure 262 a predetermined angle such that the surface of support structure 262 is non-parallel to interior surface 244 of bottom housing 222. In one embodiment, support structure 262 positions plurality of sensor 230 to couple between upper housing 220 and bottom housing 222. Each sensor of plurality of sensors 230 underlies the external curved surface of upper housing 220 at predetermined locations discussed herein. Each sensor of plurality of sensors 230 respectively couples to a planar surface on the interior of the upper housing and a planar surface of the bottom housing. In one embodiment, the three load sensors are placed equidistant from each other.

Electronic circuitry 236 and the plurality of sensors transmit measurement data to a computer 162 of FIG. 32. Computer 162 is configured to receive the measurement data from the shoulder joint system that includes measurement device 154 but can include sensors in other components of the shoulder joint system. Electronic circuitry 236 of the first shoulder prosthesis and computer 162 can be in two-way communication. In one embodiment, three load sensors are configured to measure loading applied to the first shoulder prosthesis. In one embodiment, computer 162 is configured to calculate a force magnitude and location of applied force using the measurements and locations of the first, second, and third sensors underlying the external curved surface of measurement device 154. In one embodiment, the force applied to the external curved surface of measurement device 154 is normal to the external curved surface. In one embodiment, a display couples to computer 162. The display is configured to show in real-time at least one of a load magnitude applied to the external curved surface of the first shoulder prosthesis. In general, a force applied by the second shoulder prosthesis to the first shoulder prosthesis is normal to the external curved surface of the first shoulder prosthesis. In one embodiment, the plurality of load sensors are oriented such that the reaction forces are directed to a center or rotation.

Referring briefly to FIG. 22a, display 164 coupled to computer 162 is configured to graphically display an external curved surface 384 corresponding to the external curved surface of the upper housing. Computer 162 is configured to receive measurement data from measurement device 154. Computer 162 can perform calculations related to the measurement data from the one or more sensors. Computer 162 further convert the measurement data to a graphic form that allows a surgeon or surgical team to rapidly assimilate measurement data. Display 164 is coupled to computer 162 having a graphical user interface (GUI) 380. GUI 380 is configured to provide an image of external curved surface 384 of measurement device 154 and a rim surrounding the external curved surface 384.

Display 164 is configured to graphically display a contact point 382 of the upper housing where the glenoid sphere couples to the external curved surface of the upper housing in real-time. In one embodiment, glenoid sphere 152 applies a force to measurement device 154 that is normal to external curved surface 224. Furthermore, the display also shows a contact point on the external curved surface of the first shoulder prosthesis. The contact point will move in real-time on the display as the shoulder is moved through different range of motions. In one embodiment, the display and computer is in the operating room to provide the information in real-time to the surgical team. Other measurements that are made with shoulder joint system 160 are motion, position, joint stability, range of motion, or impingement to name but a few. Referring briefly to FIG. 22B, computer 162 is configured to calculate when impingement occurs from the measurement data. In one embodiment, display 164 notifies when impingement occurs by highlighting a rim 520 of the external curved surface of the upper housing. Rim 520 highlights a portion of the rim where the impingement occurs or corresponds to at a terminus of direction of the range of motion where the impingement occurs.

In one embodiment, one or more motion bars are displayed on display 164. The one or more motion bars are configured to graphically indicate a range of motion of the shoulder joint system as it is moved through a predetermined motion. Referring briefly to FIG. 23, four motion bars (400, 402, 404, and 406) are disclosed each corresponding to a specific motion. Each motion bar graphically illustrates a range of motion achieved in the installation of the shoulder joint system for the predetermined motion. Each motion bar has a first end and a second end. The first end and the second end of a motion bar corresponds to a maximum internal rotation for a predetermined movement and a maximum external rotation for the predetermined movement. Between the first end and second end, the motion bar is configured to indicate an acceptable internal range of motion and an acceptable external range of motion for the predetermined movement. The motion bar is also configured to indicate a center of the predetermined movement. In one embodiment, a bar indicates a position of the shoulder during the predetermined movement. For example, a bar 426 of motion bar 402 indicates a position of the shoulder joint in an I/E rotation at 45 degrees adduction. A box 428 on the display indicates loading applied to the external curved surface of measurement device over the predetermined movement via a color map.

Referring briefly to FIG. 25, a range of motion (ROM) overlay 390 on GUI 380 is disclosed. The motion data and load data from the predetermined motions of FIG. 23 are stored in memory. In FIG. 25, GUI 380 graphically displays the movement of contact point 382 to the external curved surface 384 on GUI 380 for each of the four different shoulder joint movement measured in FIG. 23. A trace of a predetermined movement on the external curved surface of the measurement device as shown in FIG. 25 is a ROM overlay. GUI 380 is configured to provide at least one ROM overlay on the image of the external curved surface of the measurement device on the display of the computer. Stated differently a ROM overlay comprises at least one load track corresponding to a predetermined movement of the shoulder joint. In one embodiment, the applied loading can vary significantly at different points on the load track. In one embodiment, the GUI 380 is configured to provide at least one impingement ROM assessment that includes a trace that illustrates the limits of abduction/adduction and horizontal flexion.

In one embodiment, GUI 380 is configured to provide an image of the external curved surface of the measurement device and a rim surrounding the external curved surface. The portion of the rim is highlighted when impingement occurs and corresponds to the direction of movement of the shoulder joint. GUI 380 is configured to provide at least one impingement ROM assessment that includes a trace that illustrates the limits of abduction/adduction and horizontal flexion.

Referring briefly to FIG. 3, a shoulder system 160 is disclosed. Shoulder system 160 comprises a first prosthetic component and a second prosthetic component. Shoulder system 160 is configured to transmit measurement data to a computer 162 and display measurement data on a display 164. The first prosthetic component and the second prosthetic component each have a curved surface configured to couple together to support shoulder system 160. The curved surfaces of the first and second prosthetic component allow for a wide range of motion for the shoulder joint. In one embodiment, the first prosthetic component is a humeral prosthesis 158 configured to couple to humerus 150. In one embodiment, the second prosthetic component is a glenoid sphere 152 configured to couple to scapula 140. Humeral prosthesis 158 comprises a humeral tray 156. A humeral liner or measurement device 154 is configured to couple to humeral tray 156. Referring briefly to FIG. 36, a measurement device 1100 is disclosed. Measurement device 1100 compromises an upper housing 1106, a bottom housing 1108, and a shim 1110. Measurement device 1100 or measurement device 154 is configured to couple to humeral tray 156 for providing measurement data. Shim 1110 is a removable device to adjust a height of measurement device 1100. For example, adding height can increase the force applied to measurement device 1100 when placed in a joint. Conversely, removing the shim or replacing the shim with a thinner shim will reduce the force applied to measurement device 1100 when placed in the joint. In one embodiment, shim 1110 couples to bottom housing 1108 and retains measurement device 1100 to humeral tray 156. Upper housing 1106 has an external curved surface 1104 configured to couple to another prosthetic component to support joint movement. Upper housing 1106 couples to bottom housing 1108 to form a hermetically sealed enclosure. The hermetically sealed enclosure houses at least one sensor and electronic circuitry configured to control a measurement process and transmit measurement data. In one embodiment, shim 1110 is configured to couple bottom housing 1108. In one embodiment, shim 1110 is configured to couple measurement device 1100 to a humeral tray of a humeral prosthesis. Although not shown, for measurement device 154, shim 1110 is used to change the height of measurement device 154 to adjust the load applied to the prosthetic component. In one embodiment, measurement device 1100 with shim 1110 couples to humeral tray 156 of FIG. 3. In one embodiment, a plurality of shims are provided where each shim has a different height for adjusting a height of measurement device 1100. Each shim of the plurality of shims is configured to couple to measurement device 1100. Furthermore, each shim is configured to couple to a tray of the prosthetic component. In one embodiment, each shim of the plurality of shims includes one or more cutouts to retain a shim of the plurality of shims to the tray of the prosthetic component.

In general, everything disclosed for measurement device 154 herein above also applies to measurement device 1100. In other words, electronic circuitry, sensors, or structures of measurement device 154 also apply to measurement device 1100. Although not shown the electronic circuitry disclosed for measurement device 154 herein above is also within measurement device 1100. Thus, figures related to measurement device 154 will be disclosed when discussing structure, electronic circuitry, or sensors for measurement device 1100. Electronic circuitry 236 is disclosed in FIG. 32. Electronic circuitry 236 is placed within the enclosure formed by upper housing 1106 coupling to bottom housing 1108. Referring briefly to FIG. 19 a first sensor, a second sensor, and a third sensor are located within bottom housing 222 corresponding to bottom housing 1108. The first, second, and third sensors correspond to sensors 230. Referring to FIG. 5, upper housing 220 corresponding to upper housing 1106 is shown prior to coupling to bottom housing 222. Coupling upper housing 220 to bottom housing 222 couples the first, second, and third sensors respectively to external curved surface 224 corresponding to external curved surface 1104. More specifically, the first, second, and third sensors respectively couple to external curved surface 224 at a first predetermined radial location, a second predetermined radial location, and a third predetermined radial location upper housing 220 when coupled to bottom housing 222. Referring briefly to FIG. 28, an illustration of sensors 530 and 532 are shown in a cross-sectional view illustrating radial locations. The third sensor (not shown) is spaced such that all three sensors are spaced equidistant. In other words, the first, second, and third predetermined radial locations have an equal radius from the center of curvature. In one embodiment, the first, second, and third radial locations of sensors 530, 532, and 534 on external curved surface 224 has a greater radius than a radius of the external curved surface of the prosthetic component that couples to measurement device 154. In one embodiment, the first, second, and third sensors are located at or near the rim of the external curved surface. In one embodiment, the positions of the first, second, and third sensors have an equal radius relative to the external curved surface.

In general, measurement device 1100 couples to a first prosthetic component for generating measurement data related to a shoulder joint system. Measurement device 1100 of the first prosthetic component couples to an external curved surface of a second prosthetic component as disclosed in FIGS. 1-3. In one embodiment, the external curved surface of the second prosthetic component is configured to couple to the external curved surface of upper housing 220 of the measurement device 154 only at the surfaces of the first, second, and third predetermined radial locations corresponding respectively to the locations of first, second, and third sensors underlying the external curved surface of the upper housing. A force applied by the second shoulder prosthesis to the first shoulder prosthesis is directed thru the first, second, and third sensors. As previously mentioned electronic circuitry 236 couples to the first, second, and third sensors. Electronic circuitry 236 is configured to control a measurement process and transmit measurement data.

Referring briefly to FIG. 44, measurement device 1100 is illustrated disclosing different regions of external curved surface 1104 of upper housing 1006. The regions disclosed herein also correspond to measurement device 154. A plurality of regions correspond to a location of external curved surface 1104 where a force, pressure, or load is measured. In one embodiment, the plurality of regions correspond to a first sensor, a second sensor, and a third sensor that underlies external curved surface 1104. Region 1172, region 1174, and region 1176 correspond to the plurality of regions of external curved surface 1104 and are located at a first, second, and third predetermined radial location. In one embodiment, regions 1172, 1174, and 1176 correspond to surfaces of the first, second, and third predetermined radial locations of the external curved surface 1104 of measurement device 1100. Regions 1172, 1174, and 1176 are equal to or larger than the area of the first, second, or third sensors that underlie the radial locations. A first region of external curved surface 1104 relates to a circle 1196 illustrated on FIG. 44. In one embodiment, a first region is the area within circle 1196 of external curved surface 1104 of measurement device 1100. The first region is illustrated as region 1192. In one embodiment, the surfaces of the first, second, and third predetermined radial locations corresponding to regions 1172, 1174, and 1176 are above a surface of the first region (region 1192) of external curved surface 1104 within circle 1196. A second region of external curved surface 1104 of measurement device 1100 corresponds to a region outside circle 1196 but does not include regions 1172, 1174, and 1176. The second region is illustrated as region 1190. The second region extends from circle 1196 to rim 1102 of measurement device 1100 excluding regions 1172, 1174, and 1176. In one embodiment, the surfaces of the first, second, and third predetermined radial locations corresponding to regions 1172, 1174, and 1176 are above a surface of the second region (region 1190). In one embodiment, the surface of the second region of external curved surface 1104 comprises an area that is above the surface of the first region of external curved surface 1104. In one embodiment, rim 1102 of measurement device is 1100 is a maximum height of external curved surface 1104. Conversely, the first region corresponding to the area of the surface within circle 1196 is the lowest portion of external curved surface 1104 of measurement device 1100.

A method of measurement within a shoulder joint is provided herein below. The steps disclosed can be practiced independently and in any order. The ordering of steps does not indicate an order or sequence but is merely to identify a step. In a first step, a first shoulder prosthesis is coupled to a first bone of a musculoskeletal system. A second shoulder prosthesis is coupled to a second bone of the musculoskeletal system. The first shoulder prosthesis has an external curved surface configured to couple to an external curved surface of the second shoulder prosthesis to support movement of the shoulder joint. In one embodiment, the external curved surface of the first shoulder prosthesis is part of a measurement device configured to measure one or more parameters. The computer includes a display for displaying the measurement data or to graphically display information related to the measurement data. In one embodiment, the first bone can be a humerus and the second bone a scapula. Alternatively, the first bone can be the scapula and the second bone the humerus.

In a second step, a force, pressure, or load from the second shoulder prosthesis is directed through the external surface of the measurement device. Underlying the external curved surface of the measurement device is a first sensor at a first predetermined radial location, a second sensor at a second predetermined radial location, and a third sensor at a third predetermined radial location. In a third step, the first, second, and third sensors are placed equidistant from one another at positions that maximize the radius of circle defined by the sensors. The first, second, and third sensors are oriented such that sensor reaction forces are directed to a center of curvature of the external curved surface of the first shoulder prosthesis. In one embodiment, it is assumed that no frictional forces or negligible frictional forces occur on the external curved surface of the first shoulder prosthesis or at a sensor interface. In one embodiment, reaction force vectors are assumed to be normal to the external curved surface of the measurement device of the first shoulder prosthesis and therefore passes through the center of curvature of the external curved surface of the measurement device.

Reverse total shoulder arthroplasty prosthesis classification systems have been developed to objectively categorize glenoid designs based upon how they position the center of rotation (CoR) and separately categorize humeral designs based upon the position of the humerus. The center of rotation and the position of the humerus are then brought together to account for the combined offset and interaction that corresponds to a geometry of a shoulder joint. A generalized list of prosthesis classifications in the literature are as follows: a glenosphere whose CoR is less than or equal to 5 millimeters lateral to the glenoid fossa is categorized as a medialized glenoid (MG); and a glenosphere whose CoR is greater than 5 millimeters lateral is categorized as a lateralized glenoid (LG). The position of the CoR is determined by the difference between the glenosphere thickness and the radius. For a humeral prosthesis classification: a humeral component offset less than or equal to 15 millimeters is categorized as a medialized humerus (MH); and a humeral component offset greater than 15 millimeters is categorized as a lateralized humerus (LH). Humeral offset is defined as the horizontal distance between the intramedullary canal/humeral stem axis to the center of the humeral liner and is influenced by humeral neck angle, humeral, osteotomy, and a use of an in-lay liner/stem or an on-lay humeral tray/stem design. The combined interaction between these glenoid and humeral design categories drives the rTSA prosthesis classification system known as MG/MH, LG/MH, MG/LH, and LG/LH. The classification system can be further refined by adding components with different geometric considerations thereby providing further options to a surgical team with refinements between or outside MG/MH, LG/MG, MG/LH, or LG/LH that further optimize a selection of components for rTSA specific to a patient.

In general, reverse total shoulder arthroplasty (rTSA) at the time of intra-operative reduction is highly variable based on physician experience, prosthesis design, sizing configuration, and patient factors. Examples of issues that can occur are over-lengthening of the arm that can result in complications such as acromial and scapular stress fractures, polyethylene wear, glenoid loosening, deltoid muscle strain, and brachial plexus injuries. An unknown factor in selection process is optimal soft tissue tensioning for a given patient undergoing rTSA. Too much tension can occur from over-stuffing a patient's joint by the use of too thick of a prosthesis. The choice of humeral liner, glenosphere component, or bonegraft are often used to adjust tension. A shallow humeral osteotomy can result in patient experiencing complications such as pain, reduced range of motion, soft tissue injury, and acromial or scapular bone fractures. Conversely, too little tension from use of an insufficiently thick prosthesis, bone graft, lack of proximal humeral bone, or glenoid/scapula bone can result in a patient experiencing complications such as instability, reduced function or range of motion resulting from lax musculature, or impingement. The ability to measure joint tension over a range of motion can provide quantitative measurement data can be used to select one of the classification systems disclosed herein above and further delineate to a sub system variation of the classification system to support an optimal rTSA implant system for a patient. A selection system comprising measurement device 154 as disclosed herein above can be used to assess rTSA joint tension during intra-operative rTSA surgery. The quantitative measurement data generated by measurement device 154 can support a selection of a specific rTSA glenoid and humeral design categories corresponding to the rTSA classification system. The quantitative measurement data from can further support the selection of a rTSA sub classification system to further refine an optimal rTSA installation specific to a patient based on measurements of the patient shoulder during the rTSA surgery.

Numerous rTSA prosthesis designs and techniques are available to provide joint stability for patients of various ranges of bone morphologies and bone defects. On the humeral side, the most common method to increase joint stability with rTSA is to lateralize the humerus by use of a thicker humeral tray or a thicker humeral liner. For patients with no proximal humeral bone, endoprostheses with lateral build-up have also been proposed. On the glenoid side, the use of bone graft, augmented baseplates, or thicker glenospheres have also been proposed. Modified surgical techniques can also results in differing amounts of joint stability (such as taking a larger or smaller humeral osteotomy or implanting the glenoid higher or lower on the glenoid, or even performing a muscle transfer if the joint is imbalanced in a given plane and/or is soft tissue deficient.

Adjusting different thicknesses of humeral and glenoid implants to fine-tune joint tensioning subjectively for patients during and after the intra-operative reduction step is non-ideal. In one embodiment, it would be preferable for the surgeon to assess joint tensioning prior to an implant selection and bone preparation are performed as disclosed herein below. Although the example disclosed is a reverse shoulder implant installation the system and procedure is adaptable for a standard shoulder and can be implemented to the same benefit. In one embodiment, it would preferable to make an assessment of patient specific joint tensioning at the beginning of the reverse shoulder procedure, after the humeral head osteotomy is performed. A decision can be made after the objective quantification of joint tension to determine which of the humeral or glenoid implants (from the rTSA classification system) is best suited for the patient and the respective offsets and thicknesses of the selected implants to achieve optimal tensioning and functionality of the rTSA. Furthermore, an assessment could also be helpful to identify modifications in the surgical technique, for example if additional humeral head osteotomy is necessary or if the glenoid should be implanted with an inferior shift or, if a standard or augmented glenoid component should be used or if bone graft should be applied, or not.

Figure 45:
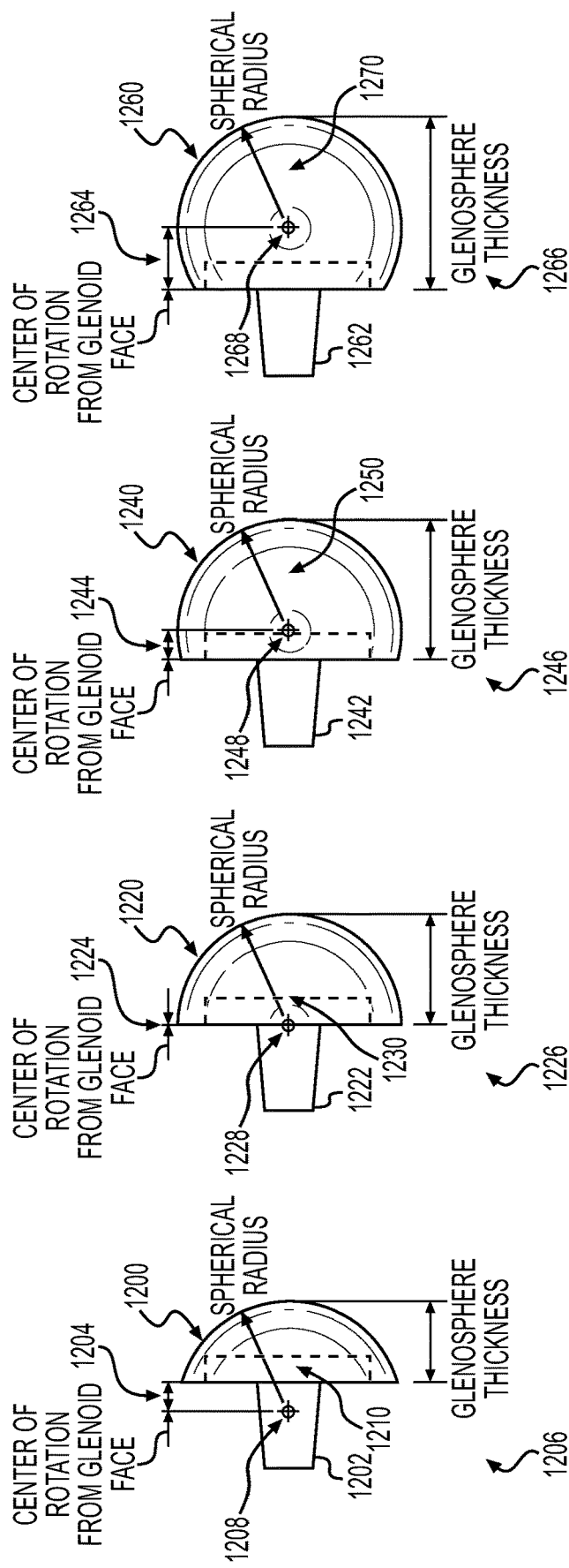
FIG. 45A is an illustration of a glenoid component having a CoR below a surface of a glenoid of a scapula in accordance with an example embodiment.
FIG. 45B is an illustration of a glenoid component having a CoR co-planar to a surface of a glenoid of a scapula in accordance with an example embodiment.
FIG. 45C is an illustration of a glenoid component having a CoR that is within a glenoid hemisphere in accordance with an example embodiment.
FIG. 45D is an illustration of a glenoid component having a CoR within a glenoid hemisphere in accordance with an example embodiment.

FIGS. 45 A, B, C, and D are illustrations of different glenospheres that are adapted for use in a rTSA in accordance with an example embodiment. In general, glenoid designs are based upon how they position the center of rotation (CoR). In one embodiment, the glenoid components of FIGS. 45 A, B, C, and D are glenoid components that are part of a selection system that is used for a selection process of a shoulder surgery to support a selection of at least one prosthetic component that is installed during the shoulder surgery. The glenoid components for the selection process can be temporarily coupled to the scapula. The glenoid components can be reused if a sterilization process is implemented after each use. Alternatively, the glenoid components can be disposable after the selection process. In one embodiment, the glenoid prosthesis classification of a glenoid component having a CoR less than 5 millimeters lateral is categorized as a medialized glenoid (MG). In one embodiment, a glenosphere having a CoR greater than 5 millimeters is categorized as a lateralized glenoid (LG). In one embodiment, the position of the CoR is determined by the difference between the glenosphere thickness and radius. In general, the glenospheres shown in FIG. 45A-D can be glenoid components used in the selection process or final glenoid components. The glenoid components of the selection system are designed to be easily removed and replaced during the selection process of the shoulder joint.

In a shoulder joint, a glenoid prosthetic component couples to a humeral prosthetic component. In one embodiment, the selection system is used in a shoulder surgery prior to the installation of a glenoid prosthetic component or a humeral prosthetic component. Humeral designs are separately categorized based upon an offset that positions the humerus within the shoulder joint. The selection system includes measurement device 154 as shown in FIG. 3 and a ring that replaces the humeral prosthetic component during the selection process. The glenoid components of FIGS. 45 A, B, C, and D are configured to couple to measurement device 154 to generate measurement data over different range of motions of the shoulder joint. In one embodiment, a first humeral component or a second humeral prosthetic component is configured for use in the shoulder joint. The selection system supports the selection of either the first or the second humeral prosthetic component based on measurement data from the measurement system. As previously mentioned, the first or second humeral prosthetic component can be characterized by an offset when installed in the shoulder joint. The offset of the measurement system and ring when coupled to the humerus is between the offset of the first and second humeral prosthetic components being used in the shoulder joint. In one embodiment, the offset of measurement system 154 and the ring when coupled to the humerus is half way between the offsets of the first and second humeral prosthetic components. Measurement data from measurement system 154 is taken over different range of motions. In one embodiment, the measurement data comprises load measurements and position of the shoulder joint that are used to determine a position of applied load to the measurement system 154 and a load magnitude at the position of applied load. In one embodiment, the first prosthetic component is selected if the measurement data is below above a predetermined threshold and the second prosthetic component is selected if the measurement is above the predetermined threshold. Although the example only selects one of two prosthetic components it is understood that more prosthetic components could be added with different offsets and the measurement data would support the selection process. In one embodiment, more than one predetermined threshold or a measurement range could be used to determine which prosthetic component is selected during a selection process. In one embodiment, the glenoid designs and humerus designs can then be combined and identified by the combined offset and interaction within the shoulder joint. In general, the selection system can account for the different variations of the glenoid and humerus designs to generate quantitative measurement data that can be used to support the selection of an optimal prosthetic component for installation for the specific patient.

FIG. 45A is an illustration of a glenoid component 1200 having a CoR below a planar surface of a glenoid of a scapula in accordance with an example embodiment. In one embodiment, the planar surface of glenoid component 1200 couples to the scapula. Glenoid component 1200 can be used during the selection process or as a final glenoid prosthetic component. In the example, glenoid component 1200 is a component of a selection system used in a selection process. Glenoid component 1200 has a curved surface configured to support movement of a shoulder joint over a range of motion. In one embodiment, the curved surface is a sphere, hemisphere, or a partial sphere. The curved surface of glenoid component 1200 is configured to couple to external curved surface 224 of measurement device 154 shown in FIG. 5. The selection process supports removing glenoid component 1200 and replacing the glenoid component with a glenoid component from FIG. 45 B, C, or D to optimize a fit within the shoulder joint if necessary. Glenoid component 1200 can be coupled to an unprepared surface of the scapula during the selection process. Alternatively, the surface of the scapula can be prepared with one or more bone cuts, drilling, shaping, or surfacing procedures prior to receiving glenoid component 1200. In one embodiment, the unprepared or prepared surface is located at the glenoid cavity of the scapula. A stem 1202 couples through an opening made in the glenoid cavity of the scapula such that the planar surface of glenoid component 1200 couples to the prepared or unprepared surface of the scapula. In one embodiment, glenoid component 1200 is temporarily coupled to the scapula with a screw or pin. In one embodiment, the screw or pin can couple through stem 1202. Stem 1202 improves a stability of glenoid component 1200 and acts as an anchor to the scapula. A spherical radius 1210 corresponds to a curvature of the curved surface of glenoid component 1200. A center of rotation 1208 (CoR) of radius 1210 is located in a center of stem 1202 below the planar surface of glenoid component 1200. The planar surface of glenoid component 1200 is coupled to a prepared or unprepared surface of the scapula and will have the CoR inset by a distance indicated by double arrow 1204 within the scapula. The distance of double arrow 1204 is measured from the planar surface of glenoid component 1200 to the center of rotation (CoR) 1208 of glenoid component 1200. Glenoid component 1200 has a thickness as indicated by double arrow 1206. The distance of double arrow 1206 is measured from the planar surface of glenoid component 1200 to an apex of the curved surface of glenoid component 1200. Thus, factors such as glenosphere thickness, CoR, or spherical radius 1210 can be used to characterize and classify a glenoid prosthetic component. In one embodiment, glenoid component 1200 used in the selection process can be provided without stem 1202. Glenoid component 1200 with or without stem 1202 can be coupled to the glenoid of the scapula with a screw, pin, or adhesive and used as a glenoid component during the selection process or a final glenoid prosthetic component.

FIG. 45B is an illustration of a glenoid component 1220 having a CoR co-planar to a surface of a glenoid of a scapula in accordance with an example embodiment. In one embodiment, the planar surface of glenoid component 1220 couples to the scapula. Glenoid component 1220 can be used during the selection process or as a final glenoid prosthetic component. In the example, glenoid component 1220 is a component of the selection system used in the selection process. Glenoid component 1220 has a curved surface configured to support movement of a shoulder joint over a range of motion. In one embodiment, the curved surface is a sphere, hemisphere, or a partial sphere. The curved surface of glenoid component 1220 is configured to couple to external curved surface 224 of measurement device 154 shown in FIG. 5. The selection process supports removing glenoid component 1220 and replacing the glenoid component with a glenoid component from FIG. 45 A, C, or D to optimize a fit within the shoulder joint if necessary. Glenoid component 1220 can be coupled to an unprepared surface of the scapula during the selection process. Alternatively, the surface of the scapula can be prepared with one or more bone cuts, drilling, shaping, or surfacing procedures prior to receiving glenoid component 1220. In one embodiment, the unprepared or prepared surface is located at the glenoid cavity of the scapula. A stem 1222 couples through an opening made in the glenoid cavity of the scapula such that the planar surface of glenoid component 1220 couples to the unprepared or prepared surface of the scapula. In one embodiment, glenoid component 1220 is temporarily coupled to the scapula with a screw or pin. In one embodiment, the screw or pin can couple through stem 1222. Stem 1222 improves a stability of glenoid component 1220 and acts as an anchor to the scapula. A spherical radius 1230 corresponds to a curvature of the curved surface of glenoid component 1220. A center of rotation 1228 (CoR) of radius 1230 is located in a center of stem 1202 that intersects the planar surface of glenoid component 1220. The planar surface of glenoid component 1220 is coupled to a prepared or unprepared surface of the scapula and will have the CoR co-planar to the surface of the scapula and the planar surface of glenoid component 1220 as indicated by double arrow 1224. The distance of double arrow 1224 is measured from the planar surface of glenoid component 1220 to the center of rotation (CoR) 1228 of glenoid component 1220. Note that the distance indicated by double arrow 1224 is zero. Glenoid component 1220 has a thickness as indicated by double arrow 1226. The distance of double arrow 1226 is measured from the planar surface of glenoid component 1220 to an apex of the curved surface of glenoid component 1220. Thus, factors such as glenosphere thickness, CoR, or spherical radius 1230 can be used to characterize and classify a glenoid prosthetic component. In one embodiment, glenoid component 1220 used in the selection process can be provided without stem 1222. Glenoid component 1220 with or without stem 1222 can be coupled to the glenoid of the scapula with a screw, pin, or adhesive and used as a glenoid component during the selection process or a final glenoid prosthetic component.

FIG. 45C is an illustration of a glenoid component 1240 having a CoR that is within a glenoid hemisphere in accordance with an example embodiment. In one embodiment, the planar surface of glenoid component 1240 couples to the scapula. Glenoid component 1240 can be used during the selection process or as a final glenoid prosthetic component. In the example, glenoid component 1240 is a component of the selection system used in the selection process. Glenoid component 1240 has a curved surface configured to support movement of a shoulder joint over a range of motion. In one embodiment, the curved surface is a sphere, hemisphere, or a partial sphere. The curved surface of glenoid component 1240 is configured to couple to external curved surface 224 of measurement device 154 shown in FIG. 5. The selection process supports removing glenoid component 1240 and replacing the glenoid component with a glenoid component from FIG. 45 A, B, or D to optimize a fit within the shoulder joint if necessary. Glenoid component 1240 can be coupled to an unprepared surface of the scapula during the selection process. Alternatively, the surface of the scapula can be prepared with one or more bone cuts, drilling, shaping, or surfacing procedures prior to receiving glenoid component 1240. In one embodiment, the unprepared or prepared surface is located at the glenoid cavity of the scapula. A stem 1242 couples through an opening made in the glenoid cavity of the scapula such that the planar surface of glenoid component 1240 couples to the unprepared or prepared surface of the scapula. In one embodiment, glenoid component 1240 is temporarily coupled to the scapula with a screw or pin. In one embodiment, the screw or pin can couple through stem 1242. Stem 1242 improves a stability of glenoid component 1240 and acts as an anchor to the scapula. A spherical radius 1250 corresponds to a curvature of the curved surface of glenoid component 1240. A center of rotation 1248 (CoR) of radius 1250 is aligned to a center of stem 1202 within a glenosphere of glenoid component 1240. The planar surface of glenoid component 1240 is coupled to a prepared or unprepared surface of the scapula and will have the CoR above the surface of the scapula and the planar surface of glenoid component 1240 as indicated by double arrow 1244. The distance of double arrow 1244 is measured from the planar surface of glenoid component 1240 to the center of rotation (CoR) 1248 within the glenosphere of glenoid component 1240. Glenoid component 1240 has a thickness as indicated by double arrow 1246. The distance of double arrow 1246 is measured from the planar surface of glenoid component 1240 to an apex of the curved surface of glenoid component 1240. Thus, factors such as glenosphere thickness, CoR, or spherical radius 1250 can be used to characterize and classify a glenoid prosthetic component. In one embodiment, glenoid component 1240 used in the selection process can be provided without stem 1242. Glenoid component 1240 with or without stem 1242 can be coupled to the glenoid of the scapula with a screw, pin, or adhesive and used as a glenoid component for the selection process or a final glenoid prosthetic component.

FIG. 45D is an illustration of a glenoid component 1260 having a CoR within glenosphere 1260 in accordance with an example embodiment. In one embodiment, the planar surface of glenoid component 1260 couples to the scapula. Glenoid component 1260 can be used in the selection process or as a final glenoid prosthetic component. In the example, glenoid component 1260 is a component of the selection system used in the selection process. Glenoid component 1260 has a curved surface configured to support movement of a shoulder joint over a range of motion. In one embodiment, the curved surface is a sphere, hemisphere, or a partial sphere. The curved surface of glenoid component 1260 is configured to couple to external curved surface 224 of measurement device 154 shown in FIG. 5. The selection process supports removing glenoid component 1260 and replacing the glenoid component with a glenoid component from FIG. 45 A, B, or C to optimize a fit within the shoulder joint if necessary. Glenoid component 1260 can be coupled to an unprepared surface of the scapula during the selection process. Alternatively, the surface of the scapula can be prepared with one or more bone cuts, drilling, shaping, or surfacing procedures prior to receiving glenoid component 1260. In one embodiment, the unprepared or prepared surface is located at the glenoid cavity of the scapula. A stem 1262 couples through an opening made in the glenoid cavity of the scapula such that the planar surface of glenoid component 1260 couples to the unprepared or prepared surface of the scapula. In one embodiment, glenoid component 1260 is temporarily coupled to the scapula with a screw or pin. In one embodiment, the screw or pin can couple through stem 1262. Stem 1262 improves a stability of glenoid component 1260 and acts as an anchor to the scapula. A spherical radius 1270 corresponds to a curvature of the curved surface of glenoid component 1260. A center of rotation 1268 (CoR) of radius 1270 is aligned to a center of stem 1202 within a glenosphere of glenoid component 1260. The planar surface of glenoid component 1260 is coupled to a prepared or unprepared surface of the scapula and will have the CoR above the surface of the scapula and the planar surface of glenoid component 1260 as indicated by double arrow 1264. The distance of double arrow 1264 is measured from the planar surface of glenoid component 1260 to the center of rotation (CoR) 1268 within the glenosphere of glenoid component 1260. In the example. The distance of double arrow 1264 is greater than the distance of double arrow 1244 of FIG. 45C. Glenoid component 1260 has a thickness as indicated by double arrow 1266. The distance of double arrow 1266 is measured from the planar surface of glenoid component 1260 to an apex of the curved surface of glenoid component 1260. Thus, factors such as glenosphere thickness, CoR, or spherical radius 1270 can be used to characterize and classify a glenoid prosthetic component. In one embodiment, glenoid component 1260 used in the selection process can be provided without stem 1262. Glenoid component 1260 with or without stem 1262 can be coupled to the glenoid of the scapula with a screw, pin, or adhesive and used as a glenoid component for the selection process or a final glenoid prosthetic component.

Figure 46:
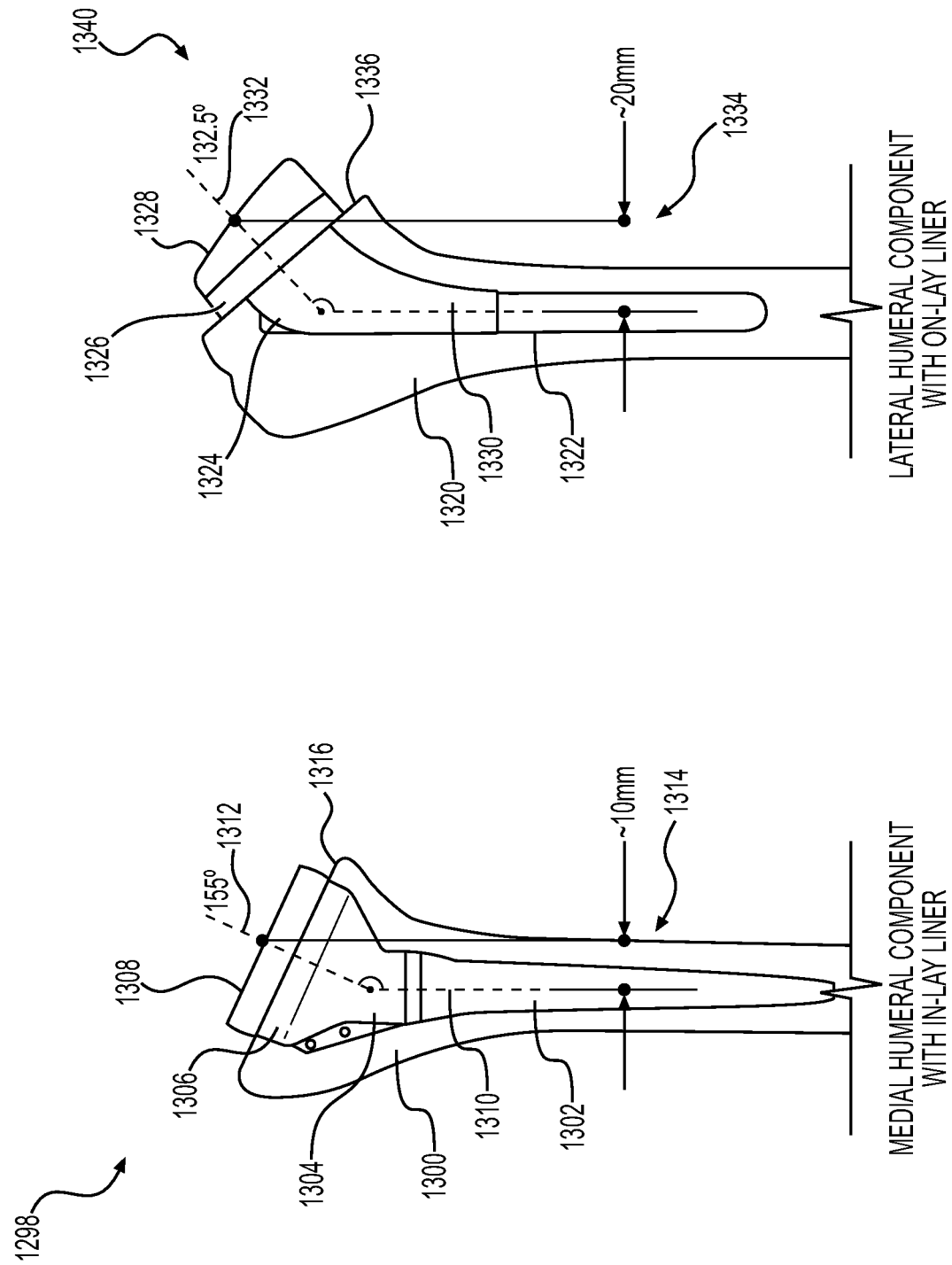
FIG. 46A is an illustration of a humeral component with an in-lay liner in accordance with an example embodiment.
FIG. 46B is an illustration of a humeral component with an on-lay design in accordance with an example embodiment.

FIGS. 46 A and B are illustrations of different humeral prosthetic components adapted for use in a rTSA in accordance with an example embodiment. Although only two types of humeral prosthetic components are illustrated it should be understood that other variations could be provided and accounted for in a selection process. In one embodiment, a humeral prosthesis classification comprises a humeral component offset less than or equal to 15 millimeters is categorized as a medialized humerus (MH). In one embodiment a humeral component having offset greater than 15 millimeters is categorized as a lateralized humerus (LH). Humeral offset is defined as the horizontal distance between the intramedullary canal and humeral stem axis to the center of the humeral liner. The humeral offset is further influenced by humeral neck angle, humeral osteotomy, and use of an in-lay liner/stem or an on-lay humeral tray/stem design. In the example, the selection system has a humeral offset between the types of humeral prosthetic components being considered for the shoulder joint. In one embodiment, the humerus is resected for receiving a humeral selection system of the selection. The resection in combination with the humeral selection system results in an offset of 15 millimeters thereby supporting the selection of an in-lay humeral prosthetic component or an on-lay humeral prosthetic component. In on embodiment, the resection is performed to allow further resection of the humerus to install a humeral prosthetic component. As previously mentioned, the selection system will accommodate the selection of more than two humeral prosthetic components. In general, the offset of the humeral selection system will be between the extremes of the humeral prosthetic components offset being considered for selection. The quantitative measurement data from the humeral selection system is used to determine a humeral prosthetic component for the patient that optimizes performance and reliability.

FIG. 46A is an illustration of a humeral component 1298 with an in-lay liner in accordance with an example embodiment. Humeral component 1298 comprises a stem 1302, a neck 1304, a humeral tray 1306, and a liner 1308. Humeral component 1298 is a final prosthetic component for a rTSA. In one embodiment, stem 1302, neck 1304, and humeral tray 1306 are in-layed in humerus 1300 such that only liner 1308 is outside humerus 1300. Liner 1308 comprises a low friction material that supports movement of a shoulder joint. In one embodiment, liner 1308 is retained by humeral tray 1306. In one embodiment, liner 1308 can be removed and replaced with measurement device 154 as disclosed herein above. Liner 1308 is configured to couple to a glenoid component coupled to a scapula. The glenoid component and liner 1308 each have a curved surface configured to couple together and support movement of the shoulder joint. Similarly, measurement device 154 has external curved surface 224 configured to couple to the glenoid component. Humerus 1300 is modified to accept humeral component 1298 and includes a prepared surface at a predetermined angle. A centerline 1310 of stem 1302 is shown extending into neck 1304 of humeral component 1298. In one embodiment, centerline 1310 also corresponds to a centerline of humerus 1300. Neck 1304 is angled from centerline 1310 of stem 1302. A centerline 1312 of neck 1304 is shown coupled to centerline 1310 of stem 1302. The angle measured between centerline 1310 and centerline 1312 as shown in FIG. 46A measures 155 degrees. Prepared surface 1316 of humerus 1300 is at a 90 degree angle from centerline 1312 of neck 1304. In one embodiment, a line is dropped parallel to centerline 1310 from a point where centerline 1312 intersects a surface of liner 1308. The distance between the line and centerline 1310 is the offset of humeral component 1298. In the example, humeral component 1298 has an offset 1314 of 10 millimeters with an 155 degree angle between centerline 1310 and centerline 1312. Based on the classification disclosed herein above humeral component 1298 is a medialized humerus (MH). The description above is an example and it should be noted that humeral components can be provided with different offsets or angles to adjust the geometry to optimize and improve the performance and reliability of the shoulder joint. In one embodiment, the humeral selection system would have to have an offset greater than 10 millimeters to generate measurement data that can support a selection of humeral component 1298 during a shoulder installation surgery.

FIG. 46B is an illustration of a humeral component 1340 with an on-lay design in accordance with an example embodiment. Humeral component 1340 comprises a stem 1322, a neck 1324, a humeral tray 1326, and a liner 1328. Humeral component 1340 is a final prosthetic component for a rTSA. In one embodiment, stem 1322 and neck 1324 are configured to be placed within humerus 1320. An on-lay humeral component has humeral tray 1326 and liner 1328 outside of humerus 1320. In one embodiment, humeral tray 1326 couples to a prepared bone surface of humerus 1320. Liner 1328 comprises a low friction material that supports movement of a shoulder joint. In one embodiment, liner 1328 is retained by humeral tray 1326. In one embodiment, liner 1328 can be removed and replaced with measurement device 154 as disclosed herein above. The glenoid component and liner 1328 each have a curved surface configured to couple together and support movement of the shoulder joint. Similarly, measurement device 154 has external curved surface 224 configured to couple to the glenoid component. Humerus 1320 is modified to accept humeral component 1340 and includes a prepared surface at a predetermined angle. A centerline 1330 of stem 1322 is shown extending into neck 1324 of humeral component 1340. In one embodiment, centerline 1330 also corresponds to a centerline of humerus 1320. Neck 1324 is angled from centerline 1330 of stem 1322. A centerline 1332 of neck 1324 is shown coupled to centerline 1330 of stem 1322. The angle measured between centerline 1330 and centerline 1332 as shown in FIG. 46B measures 132.5 degrees. Prepared surface 1336 of humerus 1320 is at a 90 degree angle from centerline 1332 of neck 1324. In one embodiment, a line is dropped parallel to centerline 1330 from a point where centerline 1332 intersects a surface of liner 1328. The distance between the line and centerline 1330 is the offset of humeral component 1340. In the example, humeral component 1340 has an offset 1334 of 20 millimeters with a 132.5 degree angle between centerline 1330 and centerline 1332. Based on the classification disclosed herein above humeral component 1298 is a lateralized humerus (LH). The description above is an example and it should be noted humeral components can be provided with different offsets or angles to adjust the geometry to optimize and improve the performance and reliability of the shoulder joint. In one embodiment, the humeral selection system would have to have an offset less than 20 millimeters to generate measurement data that can support a selection of humeral component 1340 during a shoulder installation surgery.

Figure 47:
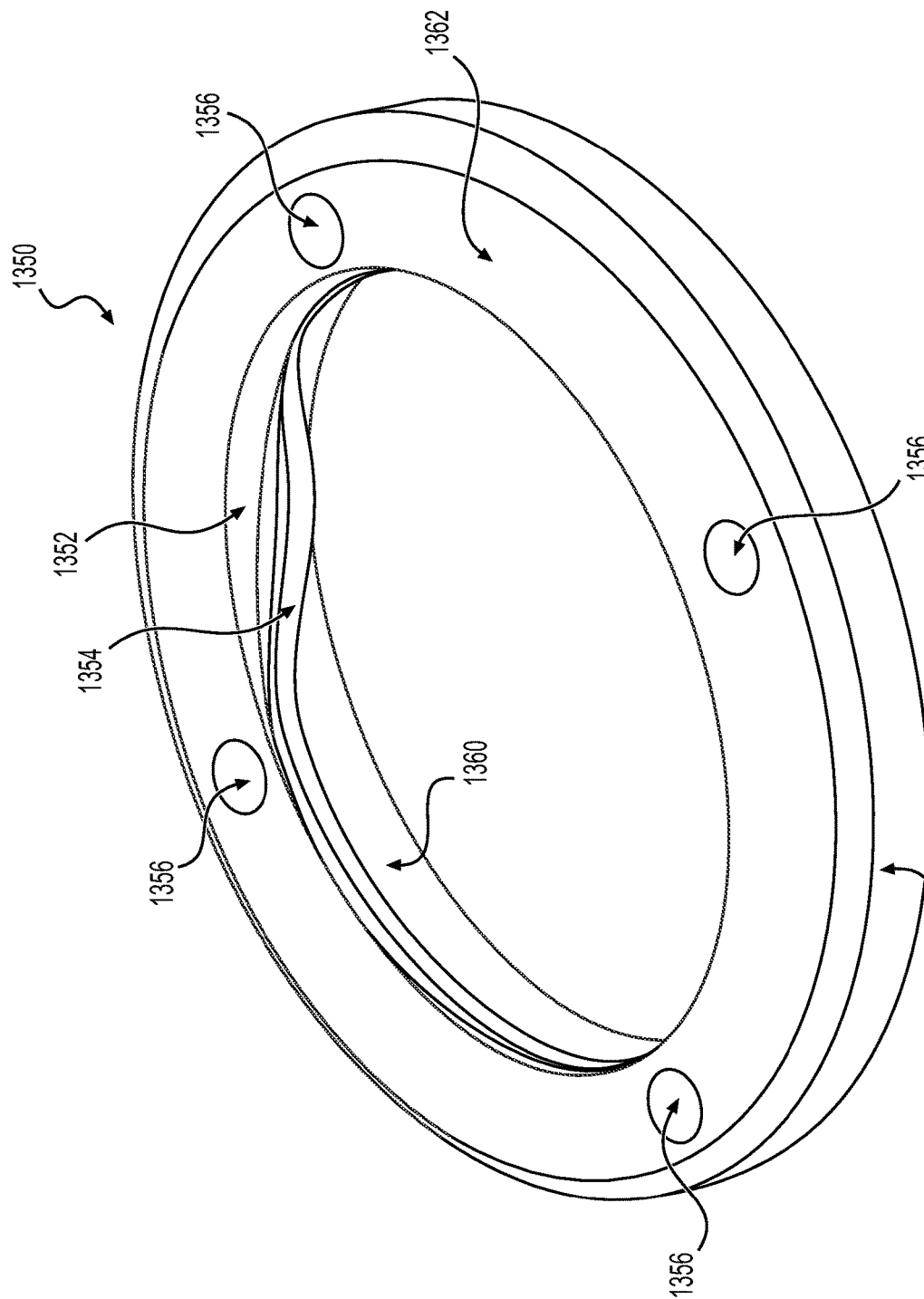
FIG. 47 is an illustration of a ring configured to couple to a bone in accordance with an example embodiment.

FIG. 47 is an illustration of a ring 1350 configured to couple to a bone in accordance with an example embodiment. In the example ring 1350 is a component of the selection system. Ring 1350 is configured to couple to a musculoskeletal system to support selection of a prosthetic component during surgery. In one embodiment, the selection system is used prior to the installation of the final prosthetic components used for the joint installation. More specifically, the selection system generates quantitative measurement data used to support a selection of at least one of the final prosthetic components of the joint of the musculoskeletal system. In the example, ring 1350 is configured for use in a shoulder joint. Ring 1350 is configured to retain measurement device 154. In one embodiment, ring 1350 provides a minimal form factor when coupled to the humerus thereby allowing a minimum amount of bone to be resected to achieve an offset between the extremes of the offsets of the humeral prosthetic components being selected. In the example, the selection system comprises one or more glenoid components, ring 1350, and measurement device 154. Ring 1350 and measurement device 154 corresponds to the humeral selection system herein after. The humeral selection system supports a selection of at least one of a final glenoid prosthetic component or a final humeral prosthetic component for the shoulder joint. The glenoid component and the humeral system are configured to support movement of the shoulder joint without extensive modification to the musculoskeletal system. Measurement device 154 includes one or more sensors configured to measure one or more parameters used to support the selection of the at least one final prosthetic component of the shoulder joint based on quantitative measurement data. In one embodiment, the measurement data is taken over at least one range of motion of the shoulder joint. The measurement data collected during the selection process by the humeral selection system supports the selection of a final glenoid prosthetic component or a final humeral prosthetic component. The quantitative measurement data can include but is not limited to alignment, position, range of motion, loading, rotation, contact point, impingement, and other parameters used to assess performance and reliability of a joint installation.

In the example, ring 1350 is configured to couple to a humerus. In one embodiment, at least one bone cut is made to the humerus to provide a prepared surface to which ring 1350 will couple. The at least one bone cut to the humerus is made to leave sufficient bone for one or more subsequent bone cuts to support installation of the selected final humeral prosthetic component. Ring 1350 is configured to retain measurement device 154 disclosed in detail herein above. Measurement device 154 has external curved surface 224 configured to couple to the curved surface of the glenoid component coupled to the scapula during the selection process. In one embodiment, at least two humeral prosthetic component types are provided each requiring a different bone cut to the humerus. The at least two humeral prosthetic component types will have different offsets. Examples of different humeral component types are a medial humeral component with an in-lay liner and a lateral humeral component with an on-lay liner. In one embodiment, there can be variations on the medial humeral component with the in-lay liner and the lateral humeral component with the on-lay liner that results in different shoulder geometries. Similarly, there will be at least two glenoid components that are used for the selection process. The at least two glenoid components can have different center of rotation or a different glenosphere thickness. In one embodiment, the glenoid components can be easily removed and replaced with another glenoid component having a different geometry. Thus, an optimal solution that improves performance and reliability of the shoulder joint can be determined by trying different combinations of the selection components and generating quantitative measurement data that support the selection of the final prosthetic components that will be installed after the selection process is completed.

Ring 1350 is configured to temporarily measurement device 154 to the humerus. In one embodiment, the humerus is resected to provide a prepared surface at a predetermined angle. In one embodiment, ring 1350 is circular in shape having an exterior sidewall 1364 and an interior sidewall 1360. In one embodiment, the height of ring 1350 is minimized to minimize the resection to the humerus to support further bone cuts for the installation of the final humeral prosthetic component. Alternatively, ring 1350 can have a non-circular shape. Similarly, the interior opening of ring 1350 can be non-circular such to simplify positioning of measurement device 154 to couple to ring 1350. Ring 1350 can be formed of biocompatible material a metal, a metal alloy, plastic, or a polymer material. Ring 1350 can be machined, molded, or formed through 3D printing using the biocompatible material. In one embodiment, ring 1350 is configured to be held to the humerus using nails, pins, or screws. Nails fit though openings 1356 in top surface 1362 of ring 1350 to couple to bone. In the example, four nails, pins, or screws temporarily hold ring 1350 to the humerus. Similarly, a glenoid component is coupled to a scapula for the selection process. In one embodiment, the glenoid component is screwed to the scapula. The glenoid component can be selected in a pre-operative plan. The glenoid component that is selected is carefully considered prior to the surgery but the selection process supports changes to the shoulder geometry based on actual measurements with the selection system. In one embodiment, the glenoid component can be removed during the selection process and changed with a glenoid component having a different geometry.

Ring 1350 includes a retaining feature comprising a groove 1352 and a retaining structure 1354. The retaining feature is configured to couple to a corresponding retaining structure of measurement device 154 to temporarily retain measurement device 154 to the humerus during the selection process. Groove 1352 is a circumferential groove in interior sidewall 1360. In one embodiment retaining structure 1354 is a flexible retaining wire of a predetermined shape. The flexible retaining wire can be made of spring steel to support the retaining wire returning to the predetermined shape after measurement device 154 is removed from ring 1350. As shown, the predetermined shape of retaining structure 1354 includes a portion of the flexible retaining wire when fitted in groove 1352 extends outside the groove. Alternatively, retaining structure 1354 can be a wire of a polymer or plastic material with similar properties to spring steel. In one embodiment, retaining structure 1354 is configured to flex or bend within the groove 1352 when measurement device 154 is placed within ring 1350. In one embodiment, measurement device 154 will have a corresponding groove that aligns to groove 1352 of measurement device 154. Retaining structure 1354 is configured to expand outward to the predetermined shape within the corresponding groove of measurement device 154 is seated and aligned with groove 1352 within sidewall 1360 of ring 1350. In one embodiment, retaining structure 1354 will resist measurement device 154 being pulled apart from ring 1350 up to a point. Retaining structure 1354 will flex or bend back into groove 1352 with sufficient separation force pulling measurement device 154 from ring 1350 thereby separating measurement device 154 from ring 1350.

Figure 48:
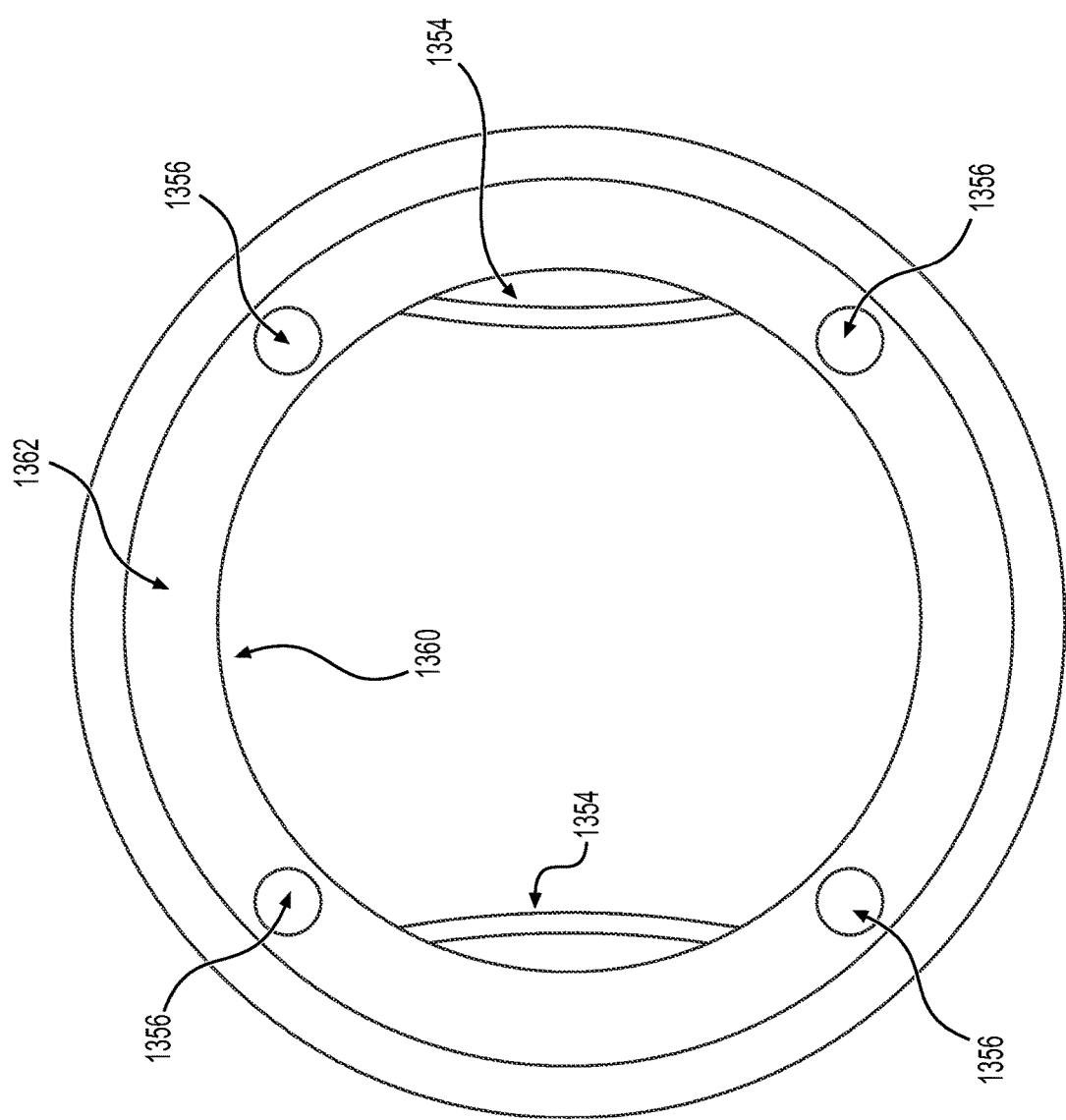
FIG. 48 is an illustration of the ring of FIG. 47 showing the retaining feature extending out of the groove on two sides in accordance with an example embodiment.

FIG. 48 is an illustration of ring 1350 showing retaining feature 1354 extending out of groove 1352 of FIG. 47 on two sides in accordance with an example embodiment. The top view of ring 1350 shows top surface 1362 having openings 1362 for receiving screws or nails to retain ring 1350 to a bone of a musculoskeletal system. Groove 1352 is shown in FIG. 47 as a circumferential groove on interior sidewall 1360 of ring 1350. Retaining structure 1354 couples within groove 1352 but extends outside groove 1352 on two sides as shown in FIG. 48. Retaining structure 1354 is configured to flex when measurement device 154 is inserted into ring 1350. In one embodiment, inserting measurement device 154 into ring 1350 forces retaining structure 1354 to flex into groove 1352 of FIG. 47 as measurement device 154 is pushed into ring 1350. In one embodiment, when a bottom surface measurement device 154 and bottom surface of ring 1350 are co-planar, retaining structure 1354 will align with grooves on a sidewall of measurement device 154. Retaining structure 1354 will expand outward into the grooves in the sidewall of measurement device 154 to retain measurement device 154 to ring 1350.

Figure 49:
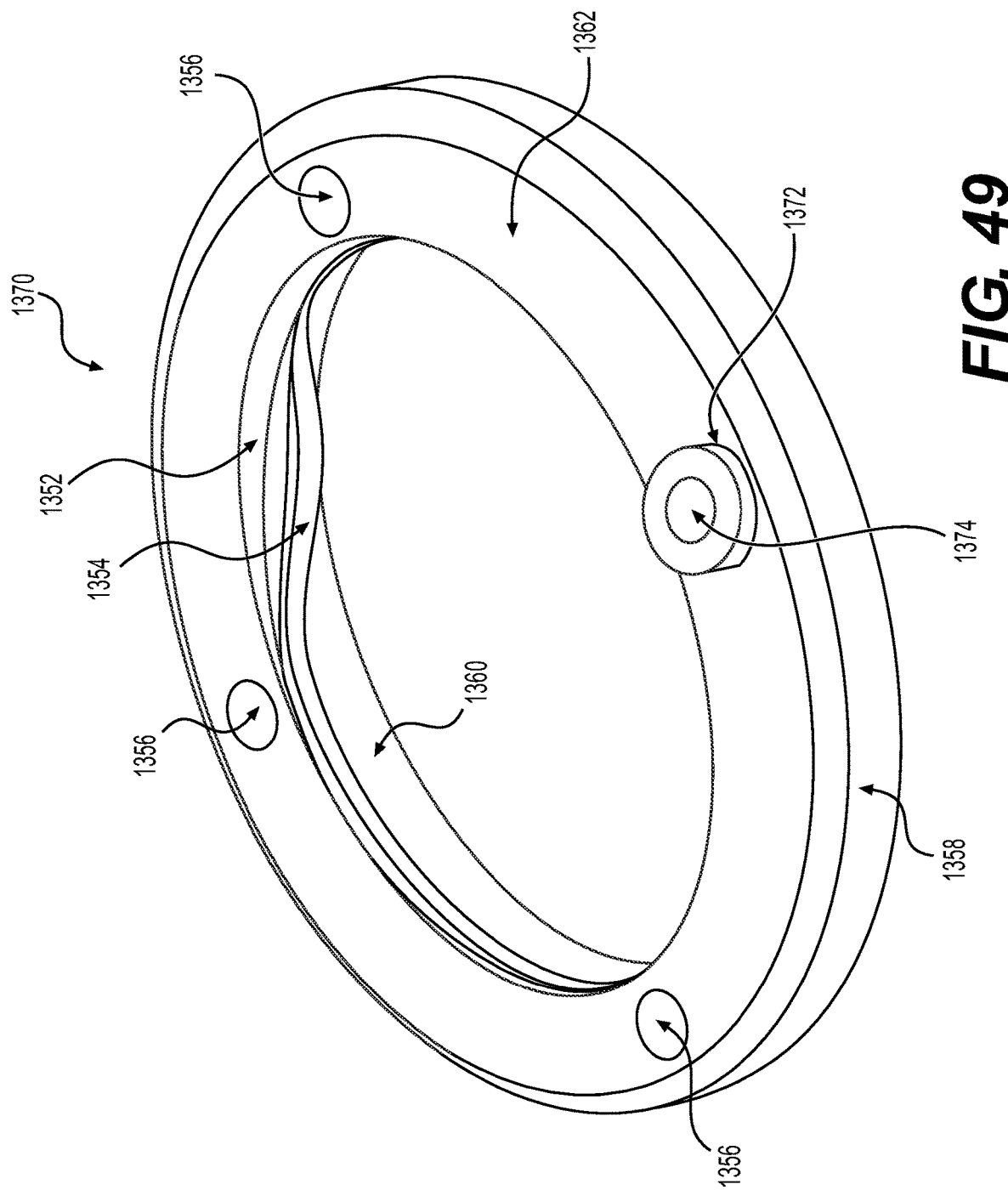
FIG. 49 is an illustration of a ring configured to couple to a humerus with a canal rod in accordance with an example embodiment.

FIG. 49 is an illustration of a ring 1370 configured to couple to a humerus with a canal rod in accordance with an example embodiment. In one embodiment, the humerus is resected leaving a prepared surface for receiving ring 1370. Ring 1370 is similar in operation to ring 1350 of FIG. 47 except that ring 1370 is also adapted for a canal rod to couple to the humerus. Thus, any disclosure related to ring 1350 also applies to ring 1370. Ring 1370 comprises an exterior sidewall 1358, an interior sidewall 136 and a top surface 1362. In one embodiment, openings 1356 are visible from top surface 1362 and couple through ring 1370. Nails, screws, or pins are used to couple ring 1370 through openings 1356 to the humerus. In one embodiment, openings 1356 are at a 90 degree angle to surface 1362. In one embodiment, a flange 1372 of ring 1370 is configured to receive the canal rod through opening 1374. In one embodiment, opening 1374 is angled differently than openings 1356. Opening 1374 is angled to position the canal rod to couple through the medullary cavity of the humerus. The canal rod retains, aligns, and stabilizes ring 1370 to the humerus. Ring 1370 includes groove 1352 having retaining structure 1354 configured to retain measurement device 154 to ring 1370. Retaining structure 1354 is configured to flex within groove 1352 as measurement device 154 is inserted into ring 1370. In one embodiment, measurement device 154 is inserted into ring 1370 until a bottom surface of measurement device 154 is co-planar to a bottom surface of ring 1370. Measurement device 154 will have corresponding grooves that allows retaining structure 1354 to expand into the grooves of measurement device 154 thereby retaining measurement device 154 to ring 1370.

Figure 50:
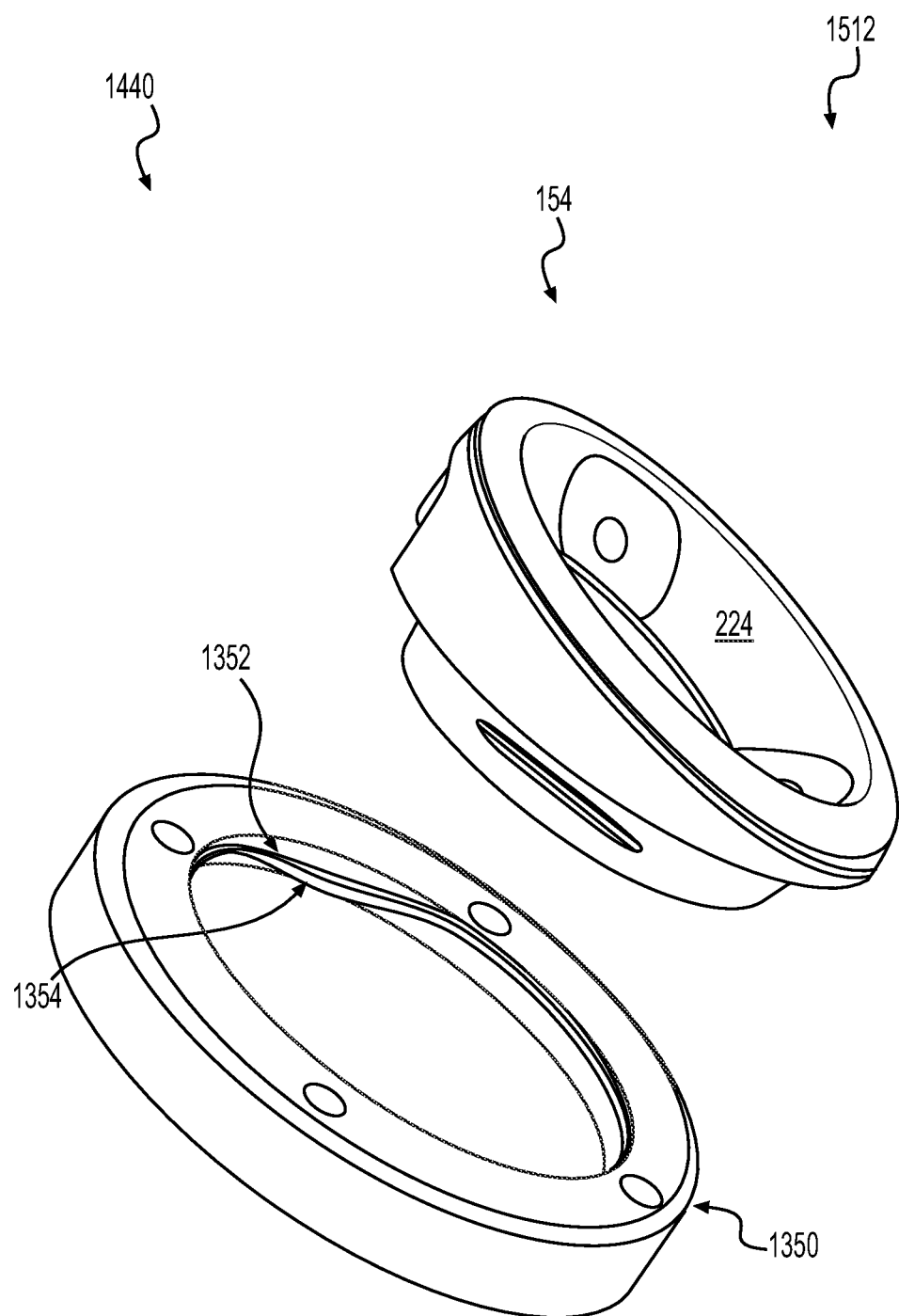
FIG. 50 is an illustration of the ring and the measurement device in accordance with an example embodiment.

FIG. 50 is an illustration of ring 1350 and measurement device 154 in accordance with an example embodiment. Selection system 1512 comprises one or more glenoid components and humeral selection system 1440. In the example, humeral selection system 1440 comprises ring 1350 and measurement device 154. Ring 1350 is configured to temporarily couple to a bone of a musculoskeletal system such as a humerus. In one embodiment, the humerus is resected to provide a prepared surface at a predetermined angle for receiving humeral selection system 1440. Humeral selection system 1440 has a predetermined offset that corresponds to the offsets of the humeral prosthetic components being selected. In the example, an in-lay humeral prosthetic component having an offset of 10 millimeters and an on-lay humeral prosthetic component having an offset of 20 millimeters is being considered for use in the shoulder surgery. The predetermined offset of ring 1350 and measurement device 154 is between 10 millimeters and 20 millimeters to generate quantitative measurement data to support the selection process. In one embodiment, the predetermined offset is selected to be a midpoint between the offset extremes being selected. In the example, the predetermined offset is 15 millimeters which is the midpoint between the 10 millimeter offset of the in-lay humeral prosthetic component and 20 millimeter offset of the on-lay humeral prosthetic component.

Ring 1350 is coupled to the humerus with screws or nails. Measurement device 154 is coupled to ring 1350. In general humeral selection system 1440 provides measurement data prior to selecting the prosthetic components for a shoulder joint. Measurement device 154 has external curved surface 224 configured to couple to a glenoid component of selection system 1512. In one embodiment, measurement device 154 has three load sensors configured to measure loading applied by the glenoid component at three known radial positions on external curved surface 224. In one embodiment, a position of applied load and the load magnitude at the position of applied load on measurement device 154 corresponds to the measurement data used during the selection process. Measurement device 154 further includes an inertial measurement unit (IMU) configured to measure position and movement. Measurement data from measurement device 154 is transmitted and displayed in real-time to a computer and display within the operating room. Moreover, the measurement data can be reviewed as the shoulder joint is moved through a range of motion. The measurement data can be stored in memory of the computer and analyzed using software in the computer to support the selection process. In the example, a plurality of glenoid components are provided as part of selection system 1512 such as glenoid components 1200, 1220, 1240, and 1260 respectively of FIGS. 45A, 45B, 45C, and 45D. The glenoid components can be removed and replaced during the selection process to change a geometry of the shoulder joint, generate measurement data, and determine a geometry that provides the best performance and reliability based on quantitative measurement data. In one embodiment, measurement device 154 has at least one retaining feature configured to retain, align, and couple measurement device 154 to ring 1350. The computer in the operating calculates the position of applied load on external curved surface 224 and the load magnitude at the position of applied load.

Figure 51:
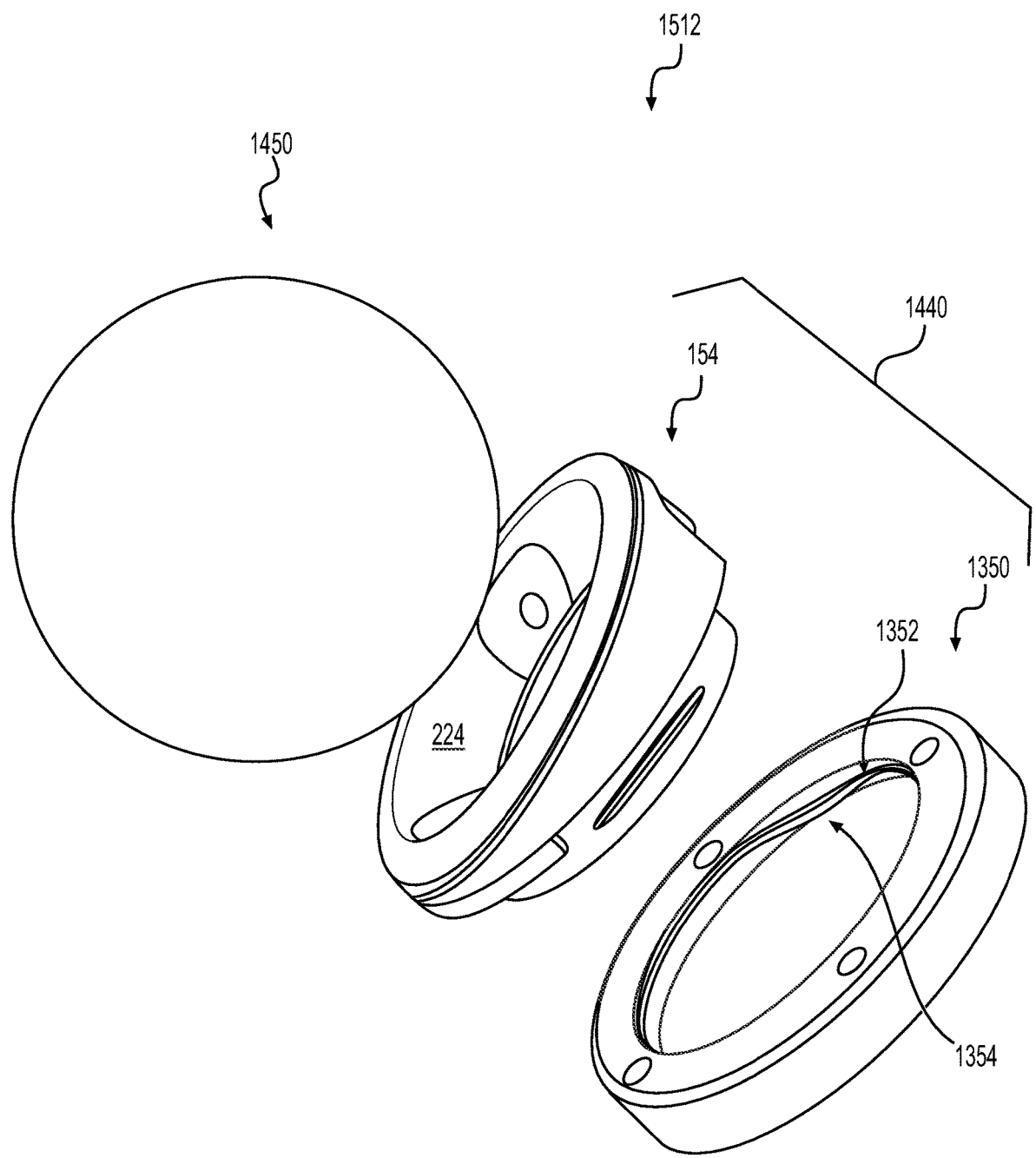
FIG. 51 is an illustration of a selection system in accordance with an example embodiment.

FIG. 51 is an illustration of the selection system in accordance with an example embodiment. Selection system 1512 comprises a glenoid component 1450, measurement device 154, and ring 1350. As disclosed in FIG. 50, humeral selection system 1440 comprises measurement device 154 and ring 1350. In the example, glenoid component 1450 is a sphere. The sphere can be coupled between the glenoid cavity of a scapula and external surface 224 of measurement device 154. Ring 1350 couples to a resected humerus. Measurement device 154 couples to ring 1350 such that humeral selection system 1440 presents a predetermined offset in the shoulder joint. In one embodiment, a plurality of measurement device 154 can be provided with different external curved surfaces 224 each configured to couple to a sphere having a different radius. Measurement device 154 can be removed from ring 1350 and replaced with a measurement device having a different external curved surface. The sphere is also replaced at this time to couple to the replaced measurement device thereby changing a geometry of the shoulder joint. The selection process supports a selection of a glenoid component and a humeral prosthetic component for optimal performance and reliability.

Figure 52:
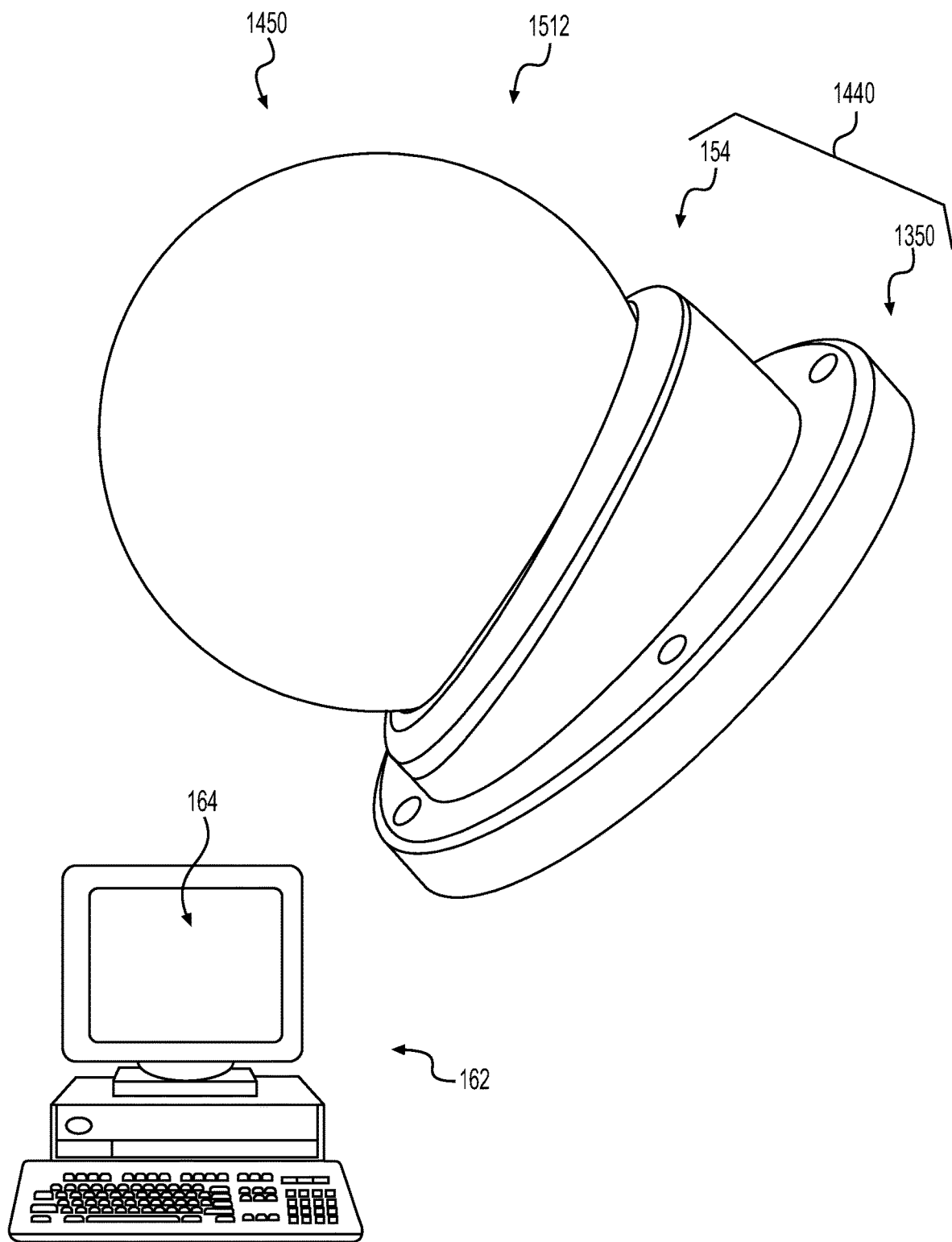
FIG. 52 is an illustration of the selection system coupled together in accordance with an example embodiment.

FIG. 52 is an illustration of selection system 1512 coupled together in accordance with an example embodiment. Selection system 1512 comprises glenoid component 1450 and humeral selection system 1440. Humeral selection system 1440 comprises ring 1350 and measurement device 154. In one embodiment, glenoid component 1450 can be selected during a pre-operative plan for the total shoulder arthroplasty (TSA) or the reverse total shoulder arthroplasty (rTSA). Alternatively, a plurality of glenoid components can be provided with glenoid component 1450 to change the geometry of the shoulder joint during the selection process. As previously mentioned, the humerus is resected to provide a surface for receiving ring 1350. The resection of the humerus is done to leave sufficient bone to support further resection of the humerus to install any of the humeral prosthetic components being contemplated for the selected during the selection process. The offset presented by humeral selection system 1440 is designed to be in a range related to the humeral prosthetic component having the least offset and the humeral prosthetic component having the most offset. The measurement data from measurement device will support selection of the humeral prosthetic component at the extremes of the range and any others having offsets between the extremes.

Ring 1350 is nailed or screwed to the prepared surface of the humerus to be temporarily coupled to the humerus and removed after the selection process is completed. Measurement device 154 is inserted and retained by ring 1350. Glenoid component 1450 can be coupled to the scapula using a pin or a screw. Glenoid component 1450 is coupled between the glenoid cavity and the external curved surface of measurement device 154. The curved surface of glenoid component 1450 supports movement of the humerus in conjunction with the external curved surface of measurement device 154. Selection system 1512 sends measurement data to a computer 162 for processing and calculation. Measurement data is then displayed on display 164 coupled to computer 162 for viewing in real-time by the surgeon or surgical team to support selection of a final glenoid prosthetic component or a final humeral prosthetic component to be installed in the shoulder joint after the selection process. The quantitative measurement data can suggest that the geometry of the shoulder joint be adjusted or optimized. The geometry of the shoulder joint can be adjusted by changing glenoid component 1450. For example, the glenoid components disclosed in FIGS. 45A, 45B, 45C, and 45D can be used in place of glenoid component 1450 for making adjustments to the shoulder geometry. In one embodiment, the adjustment can increase or decrease loading measured by measurement device 154, change range of motion, or the contact point for different movements of the shoulder joint. In one embodiment, the adjustment can improve range of motion or prevent impingement of the shoulder joint. Although not typically done during the selection process, changes can also comprise adjustments that affect the measurement data but not the selection of the final glenoid prosthetic component or the final humeral prosthetic component such as one or more bone cuts to the musculoskeletal system, measurement device 154 rotation, tissue tensioning, or some other modification.

FIG. 53 is an illustration of selection system 1512 in accordance with an example embodiment. Selection system 1512 is placed in shoulder joint 1500 to support the selection process that generates measurement data to choose at least one prosthetic component for the shoulder joint. Selection system 1512 comprises a plurality of glenoid components, measurement device 154, and ring 1350. In one embodiment, the plurality of glenoid components comprises glenoid components as shown in FIGS. 45A, 45B, 45C, and 45D. Glenoid component 1220 is used initially in selection system 1512. In the example, glenoid component 1220 does not have a stem and is configured to couple to scapula 1502 with a screw.

The selection of a glenoid component can be determined in a pre-operative assessment of the shoulder joint. Similarly, a suitable offset range can be determined for the humeral prosthetic component. At least two humeral prosthetic components are selected that correspond to the extremes of the offset range. In the example, an in-lay humeral prosthetic component having a 10 millimeter offset and an on-lay humeral prosthetic component has a 20 millimeter offset can be used in the rTSA. Thus, the offset range is from 10 millimeter to 20 millimeters for the example humeral prosthetic components. Other humeral prosthetic components can be provided for selection if their offsets are within the offset range (10 millimeters to 20 millimeters). The pre-operative assessment can include taking one or more images of the shoulder joint or modeling the shoulder joint. In one embodiment, the selection process can include generating measurement data over different range of motions of the shoulder joint. Note that during the selection process at least one of the final glenoid prosthetic component or the final humeral prosthetic component has not been determined yet.

In the example, glenoid component 1220 is configured to couple to a glenoid cavity of scapula 1502. Glenoid component 1220 is configured to couple to a glenoid cavity in a manner that is temporary. The surface of the glenoid cavity can be prepared for receiving glenoid component 1220. In the example, glenoid component 1220 does not have a stem and is coupled to the glenoid cavity by screw 1560. Alternatively, a final glenoid prosthetic component can be coupled to scapula 1502 if the surgeon or surgical team believes that the selection process need only determine the final humeral prosthetic component being used in the shoulder joint.

In one embodiment, a proximal end of humerus 1504 is resected having a prepared surface 1506 at a predetermined angle. The one or more bone cuts to the humerus are configured to allow installation of humeral selection system 1440 while leaving sufficient bone on humerus 1504 for subsequent bone cuts to install a final humeral prosthetic component such as an in-lay humeral prosthetic component of a first offset or an on-lay humeral prosthetic component of a second offset. Ring 1350 can be coupled to humerus 1504 by nail or screw. In the example, ring 1350 is held to humerus 1504 by nails 1508. It should be noted that ring 1350 is configured to be removed after the selection process is completed. In one embodiment, ring 1350 can be aligned and retained to humerus with a canal rod. Measurement device 154 is configured to couple to ring 1350 by a retaining feature as disclosed herein above. In one embodiment, a bottom surface of measurement device 154 is co-planar to a bottom surface of ring 1350 when coupled together. The external curved surface of measurement device 154 is configured to couple to glenoid component 1220 to support movement of the shoulder joint. Ring 1350, measurement device 154, and the resected humerus in combination have a predetermined offset relative to the first offset and the second offset respectively of the in-lay humeral prosthetic component and the on-lay humeral prosthetic component. In the example, the predetermined offset is between the first offset of the in-lay humeral prosthetic component and the second offset of the on-lay humeral prosthetic component. In one embodiment, measurement device 154 includes three sensors configured to measure loading applied to predetermined locations on the external curved surface of measurement device 154. The measurement data is transmitted to computer 162. Computer 162 is configured to calculate a position applied load to the external curved surface of measurement device 154 and the load magnitude at the position of applied load. Measurement device 154 further includes an inertial measurement unit (IMU) that outputs measurement data to computer 162 related to position. The IMU supports tracking a position of the humerus relative to the scapula. The measurement data is used to note the position of the humerus and the loading applied to measurement device 154 at points within a range of motion. In one embodiment, the measured loading by measurement device 154 is a determining factor on the selection of the final humeral prosthetic component.

The geometry of the shoulder joint can be altered if the measurement data from measurement device 154 indicates an issue or that the performance or reliability of the shoulder joint can be improved by changing a glenoid component during the selection process. In one embodiment, the geometry can be altered by removing the glenoid component 1220 and replacing it with a glenoid component having a different center of rotation or glenosphere thickness. In general, replacing the first glenoid component with a second glenoid component during the selection process will result in a change in the measurement data transmitted from measurement device 154. The measurement data from the second glenoid component will be reported by computer 162 and displayed on display 164 in real-time to the surgeon or surgical team. In one embodiment, computer 162 can have a program or workflow that assesses the measurement data with the second glenoid component in the shoulder joint and provides the measurement data in a form that illustrates if the measurement data improves performance and reliability versus the measurement data from the first glenoid component.

Alternatively, the surgeon or surgical team can review the measurement data on display 164 to determine if the changes are appropriate. Although not typically done during the selection process further changes can be made to improve performance or reliability that results in changes to the measurement data from measurement device 154 but does not require changing the glenoid component. The surgeon can then make adjustments such as soft tissue tensioning, cutting a bone surface, changing position of the implant, rotating an implant, or other modifications that affect the measurement data from measurement device 154. After satisfactory results are achieved, a final glenoid prosthetic component and a final humeral prosthetic component are selected based on quantitative measurement data.

As mentioned previously, there are at least two humeral prosthetic components to choose from during the selection process. The offset of humeral selection system 1440 coupled to the resected humerus is selected to be between the humeral prosthetic component having the least offset and the humeral prosthetic component having the most offset from the humeral components being selected. In one embodiment, the offset of humeral selection system 1440 is selected to be half way between the humeral prosthetic component having the least offset and the humeral prosthetic component having the most offset. The position of applied load and the load magnitude at the position of applied load can be calculated by computer 162 from measurement data from measurement device 154 in real-time over a range of motion and displayed on display 164. In one embodiment, the surgeon or surgical team can use the measurement data to determine which humeral prosthetic component will best load the shoulder joint over different range of motions. Additional corrections or adjustments can be contemplated using the measurement data to improve the shoulder joint after the selection process has been completed and the selected final glenoid prosthetic component and the final humeral prosthetic component are installed.

After completing the selection process, the final glenoid prosthetic component and the final humeral prosthetic component are installed in the final shoulder joint. In one embodiment, a liner from the final humeral prosthetic component is removed. The liner provides a bearing surface to the final glenoid prosthetic component to support movement of the final shoulder joint. In one embodiment, measurement device 154 is also configured to replace the liner in the final humeral prosthetic component. Measurement data in a final shoulder joint is generated and sent to computer 162 and displayed on display 164. The measurement data from the final shoulder joint can be used to verify the measurement data from the selection process. The measurement data form the final shoulder joint can also be used to make further adjustments or changes to the final shoulder joint that improves reliability or performance of the final shoulder joint. Measurement device 154 is then removed from the final humeral prosthetic component and the liner is replaced to complete the rTSA.

Figure 54:
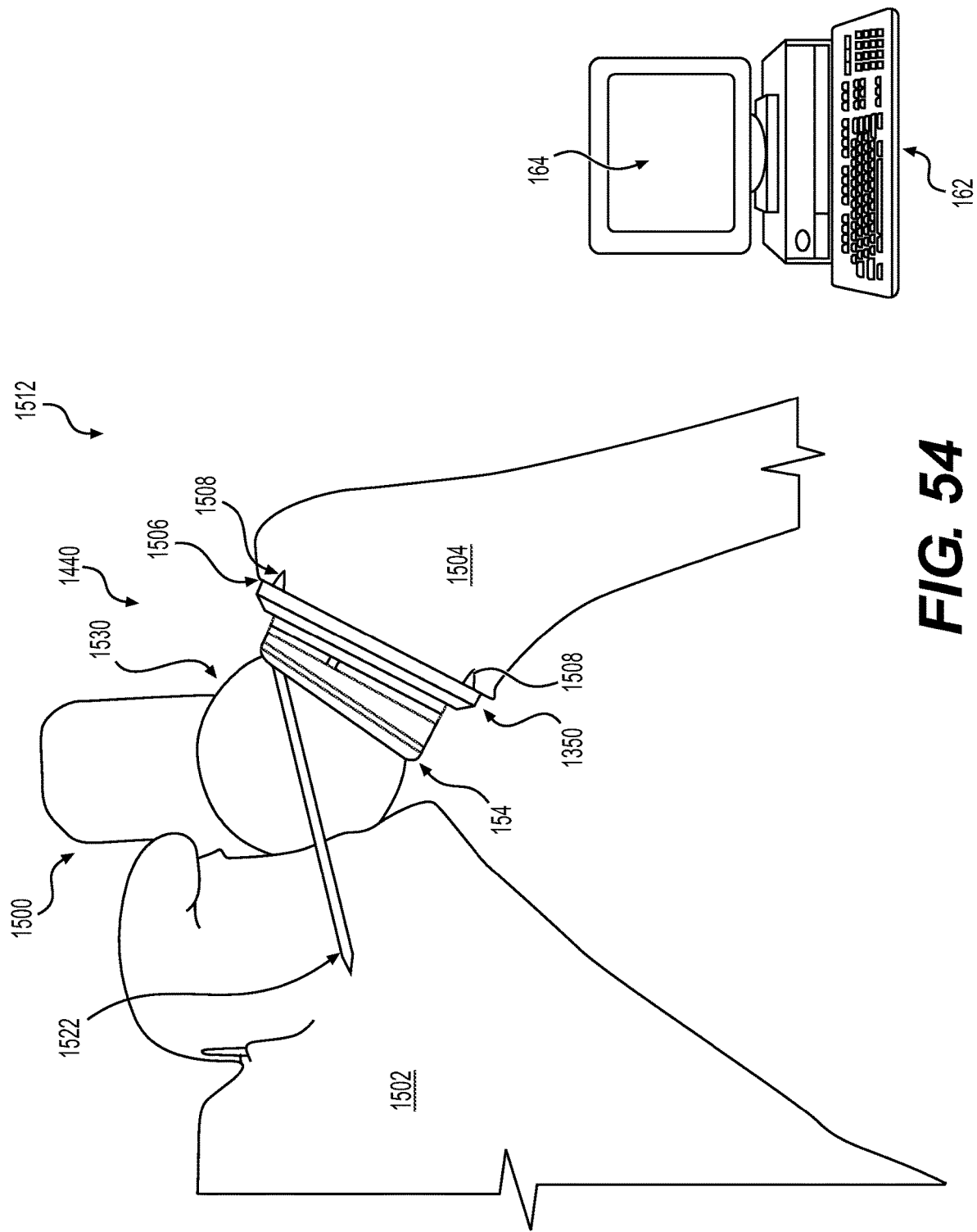
FIG. 54 is an illustration of the selection system including a glenoid component in accordance with an example embodiment.

FIG. 54 is an illustration of selection system 1512 including a glenoid component 1530 in accordance with an example embodiment. Selection system 1512 is installed in shoulder joint 1500. Selection system 1512 comprises glenoid component 1530 and humeral selection system 1440. Glenoid component 1530 is coupled to a glenoid cavity of scapula 1502. Glenoid component 1530 is a glenoid sphere that is temporarily coupled to scapula 1502. Glenoid component 1530 has a thru hole that allows a pin 1522 to be inserted and coupled to scapula 1502 to retain glenoid component 1530 to scapula 1502. Operation of selection system 1512 with glenoid component 1530 is similar to the selection process disclosed in FIG. 53 and anything stated in FIG. 53 can be applied to selection system 1512 with glenoid component 1530.

The selection of a glenoid component can be determined in a pre-operative assessment of the shoulder joint. Similarly, a suitable offset range can be determined for the humeral prosthetic component. At least two humeral prosthetic components are selected that correspond to the extremes of the offset range. In the example, an in-lay humeral prosthetic component having a 10 millimeter offset and an on-lay humeral prosthetic component has a 20 millimeter offset can be used in the rTSA. Thus, the offset range is from 10 millimeter to 20 millimeters for the example humeral prosthetic components. Other humeral prosthetic components can be provided for selection if their offsets are within the offset range (10 millimeters to 20 millimeters). The pre-operative assessment can include taking one or more images of the shoulder joint or modeling the shoulder joint. In one embodiment, the selection process can include generating measurement data over different range of motions of the shoulder joint. Note that during the selection process at least one of the final glenoid prosthetic component or the final humeral prosthetic component has not been determined yet.

In the example, glenoid component 1530 is configured to couple to a glenoid cavity of scapula 1502. Glenoid component 1530 is configured to couple to a glenoid cavity in a manner that is temporary. In one embodiment, the surface of the glenoid cavity is not prepared for receiving glenoid component 1530. In the example, glenoid component 1530 is coupled to scapula 1502 by pin 1522 during the selection process. In one embodiment, glenoid component 1530 does not change during the selection process. The selection process is limited to determining the appropriate humeral prosthetic component for the rTSA. Glenoid component 1530 could be replaced during the selection process if glenoid spheres of different radiuses were available. Using glenoid spheres with different radiuses would require different measurement devices to be used with corresponding external curved surfaces that match the radius of the glenoid sphere.

In one embodiment, a proximal end of humerus 1504 is resected having a prepared surface 1506 at a predetermined angle. The one or more bone cuts to the humerus are configured to allow installation of humeral selection system 1440 while leaving sufficient bone on humerus 1504 for subsequent bone cuts to install a final humeral prosthetic component such as an in-lay humeral prosthetic component having a first offset or an on-lay humeral prosthetic component having a second offset. Ring 1350 is coupled to humerus 1504 by nail or screw. In the example, ring 1350 is held to humerus 1504 by nails 1508. It should be noted that ring 1350 is configured to be removed after the selection process is completed. Measurement device 154 is configured to couple to ring 1350 by a retaining feature as disclosed herein above. In one embodiment, a bottom surface of measurement device 154 is co-planar to a bottom surface of ring 1350 when coupled together. The external curved surface of measurement device 154 is configured to couple to glenoid component 1530 to support movement of the shoulder joint. Ring 1350, measurement device 154, and the resected humerus in combination have a predetermined offset relative to the first offset and the second offset respectively of the first in-lay humeral prosthetic component and the on-lay humeral prosthetic component. In the example, the predetermined offset is between the first offset of the in-lay humeral prosthetic component and the second offset of the on-lay humeral prosthetic component. In one embodiment, measurement device 154 includes three sensors configured to measure loading applied to predetermined locations on the external curved surface of measurement device 154. The measurement data is transmitted to computer 162. Computer 162 is configured to calculate a position applied load to the external curved surface of measurement device 154 and the load magnitude at the position of applied load. Measurement device 154 further includes an inertial measurement unit (IMU) that outputs measurement data to computer 162 related to position. The IMU supports tracking a position of the humerus relative to the scapula. The measurement data is used to note the position of the humerus and the loading applied to measurement device 154 at points within a range of motion. In one embodiment, the measured loading by measurement device 154 is a determining factor on the selection of the final humeral prosthetic component.

In one embodiment, glenoid component 1530 is not replaced with another glenoid component during the selection process. The selection process supports the selection of a final humeral prosthetic component. In the example, the selection comprises the in-lay humeral prosthetic component and the on-lay humeral prosthetic component. Alternatively, glenoid component 1530 could be changed with glenoid components each having a different radius. Measurement devices would have to be provided having external curved surfaces corresponding to the different radiuses of the glenoid components being provided. In one embodiment, computer 162 can have a program or workflow that assesses the measurement data from selection system 1512 in the shoulder joint. Computer 162 provides the measurement data in a form on display 164 that illustrates support for the selection of the in-lay humeral prosthetic component or the on-lay humeral prosthetic component. Although not typically done during the selection process further changes can be made to improve performance or reliability that results in changes to the measurement data from measurement device 154 but does not require changing the glenoid component. The surgeon can then make adjustments such as soft tissue tensioning, cutting a bone surface, changing position of the implant, rotating an implant, or other modifications that affect the measurement data from measurement device 154. After satisfactory results are achieved, a final glenoid prosthetic component and a final humeral prosthetic component are selected based on the quantitative measurement data.

In general, there are at least two humeral prosthetic components to choose from during the selection process. The offset of humeral selection system 1440 coupled to the resected humerus is selected to be between the humeral prosthetic component having the least offset and the humeral prosthetic component having the most offset from the humeral components being selected. In one embodiment, the offset of humeral selection system 1440 is selected to be half way between the humeral prosthetic component having the least offset and the humeral prosthetic component having the most offset. The position of applied load and the load magnitude at the position of applied load can be calculated by computer 162 from measurement data from measurement device 154 in real-time over a range of motion and displayed on display 164. In one embodiment, the surgeon or surgical team can use the measurement data to determine which humeral prosthetic component will best load the shoulder joint over different range of motions.

After completing the selection process, the final glenoid prosthetic component and the final humeral prosthetic component are installed in the final shoulder joint. In one embodiment, a liner from the final humeral prosthetic component is removed. The liner provides a bearing surface to the final glenoid prosthetic component to support movement of the final shoulder joint. In one embodiment, measurement device 154 is also configured to replace the liner in the final humeral prosthetic component. Measurement data in a final shoulder joint is generated and sent to computer 162 and displayed on display 164. The measurement data from the final shoulder joint can be used to verify the measurement data from the selection process. The measurement data form the final shoulder joint can also be used to make further adjustments or changes to the final shoulder joint that improves reliability or performance of the final shoulder joint. Measurement device 154 is then removed from the final humeral prosthetic component and the liner is replaced to complete the rTSA.

Figure 55:
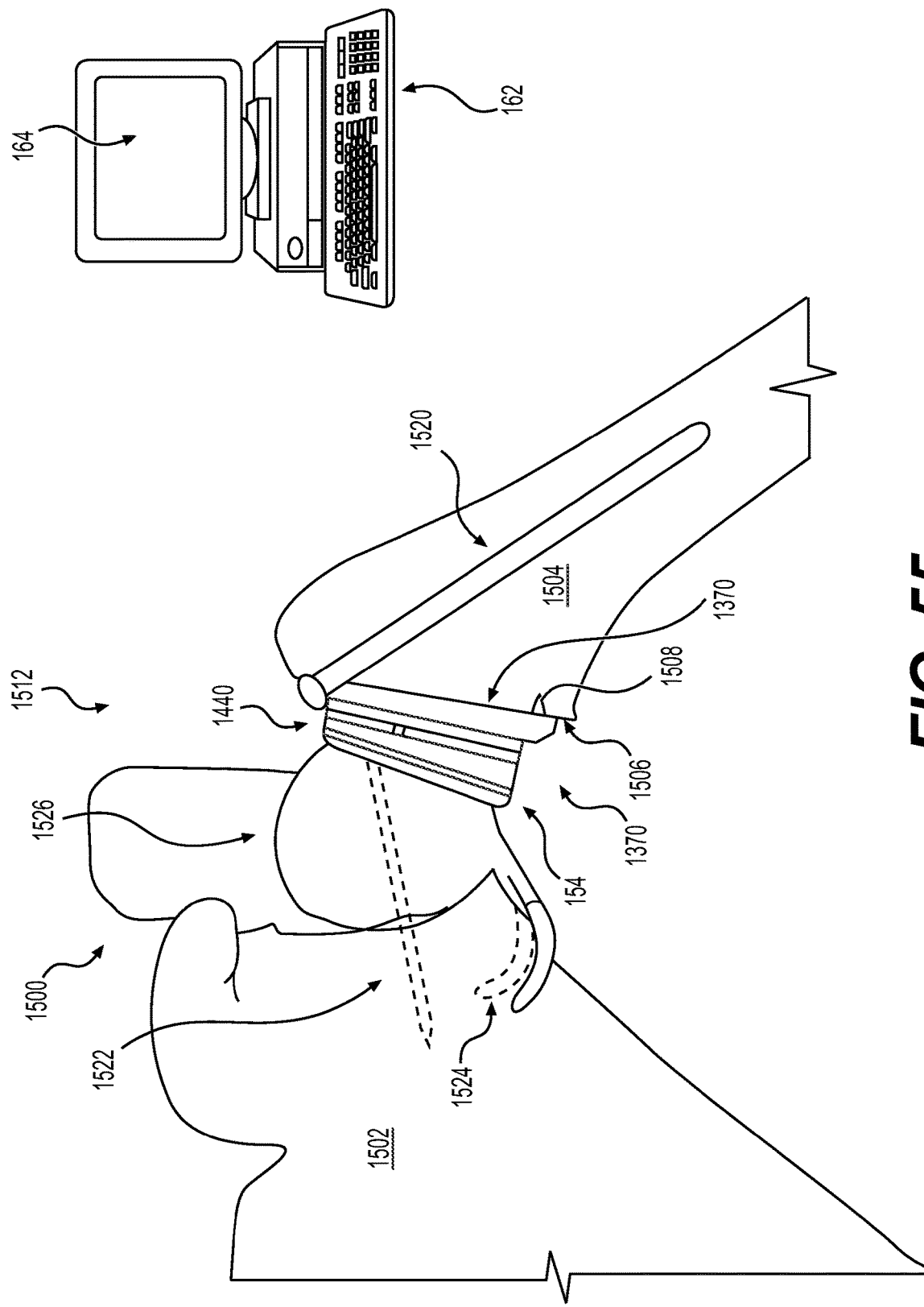
FIG. 55 is an illustration of the selection system including a glenoid component having lateral support in accordance with an example embodiment.

FIG. 55 is an illustration of selection system 1512 including a glenoid component 1526 having lateral support in accordance with an example embodiment. Selection system 1512 is installed in shoulder joint 1500. Selection system 1512 comprises glenoid component 1526 and humeral selection system 1440. Selection system 1512 can include a plurality of glenoid components for adjusting a geometry of shoulder joint 1500. Glenoid component 1526 is coupled to a glenoid cavity of scapula 1502. The glenoid cavity can have a prepared or unprepared surface for receiving glenoid component 1526. Glenoid component 1526 is a glenoid hemisphere that is temporarily coupled to scapula 1502 that includes lateral support 1524. In the example, a pin 1522 couples glenoid component 1526 to scapula 1502. In one embodiment, lateral support 1524 are two arms that extend from glenoid component 1526 to couple to either side of scapula 1502. The arms are configured to align, stabilize, and provides lateral support to glenoid component 1526. Glenoid component 1526 has a thru hole that allows a pin 1522 to be inserted and coupled to scapula 1502 to retain glenoid component 1526 to scapula 1502. In one embodiment, the plurality of glenoid hemispheres provided in selection system 1512 will differ in center of rotation and glenoid thickness as disclosed in FIGS. 45A, 45B, 45C, and 45D but each will have lateral support 1524 and a thru hole for receiving a pin. Operation of selection system 1512 with glenoid component 1526 is similar to the selection process disclosed in FIG. 53 and FIG. 54 and anything stated in FIG. 53 and FIG. 54 can be applied to selection system 1512 with glenoid component 1526.

In one embodiment, a proximal end of humerus 1504 is resected having a prepared surface 1506 at a predetermined angle. The one or more bone cuts to the humerus are configured to allow installation of humeral selection system 1440 while leaving sufficient bone on humerus 1504 for subsequent bone cuts to install a final humeral prosthetic component such as an in-lay humeral prosthetic component of a first offset or an on-lay humeral prosthetic component of a second offset. Ring 1370 can be coupled to humerus 1504 by nail or screw. In the example, ring 1370 is held to humerus 1504 by nails 1508. It should be noted that ring 1370 is configured to be removed after the selection process is completed. In one embodiment, ring 1370 is aligned and retained to humerus with a canal rod 1520. Measurement device 154 is inserted into ring 1370 and retained by a retaining feature. In one embodiment, a bottom surface of measurement device 154 is co-planar to a bottom surface of ring 1370 when coupled together. The external curved surface of measurement device 154 is configured to couple to glenoid component 1526 to support movement of the shoulder joint. Ring 1370, measurement device 154, and the resected humerus in combination have a predetermined offset relative to the first offset and the second offset respectively of the in-lay humeral prosthetic component and the on-lay humeral prosthetic component. In the example, the predetermined offset is between the first offset of the in-lay humeral prosthetic component and the second offset of the on-lay humeral prosthetic component. In one embodiment, the predetermined offset will be half way between the first and second offsets.

In one embodiment, measurement device 154 includes three sensors configured to measure loading applied to predetermined locations on the external curved surface of measurement device 154. The measurement data is transmitted to computer 162. Computer 162 is configured to calculate a position applied load to the external curved surface of measurement device 154 and the load magnitude at the position of applied load. Measurement device 154 further includes an inertial measurement unit (IMU) that outputs measurement data to computer 162 related to position. The IMU supports tracking a position of the humerus relative to the scapula. The measurement data is used to note the position of the humerus and the loading applied to measurement device 154 at points within a range of motion. In one embodiment, the measured loading by measurement device 154 is a determining factor on the selection of the final humeral prosthetic component.

The geometry of the shoulder joint can be altered if the measurement data from measurement device 154 indicates an issue or that the performance or reliability of the shoulder joint can be improved by changing a glenoid component during the selection process. In one embodiment, the geometry can be altered by removing the glenoid component 1526 and replacing it with a glenoid component having a different center of rotation or glenosphere thickness. In general, replacing glenoid component 1526 with a second glenoid component during the selection process will result in a change in the measurement data transmitted from measurement device 154. The measurement data from the second glenoid component will be reported by computer 162 and displayed on display 164 in real-time to the surgeon or surgical team. In one embodiment, computer 162 can have a program or workflow that assesses the measurement data with the second glenoid component in the shoulder joint and provides the measurement data in a form that illustrates if the measurement data improves performance and reliability versus the measurement data from glenoid component 1526.

As mentioned previously, there are at least two humeral prosthetic components to choose from during the selection process. The offset of humeral selection system 1440 coupled to the resected humerus is selected to be between the humeral prosthetic component having the least offset and the humeral prosthetic component having the most offset from the humeral components being selected. In one embodiment, the offset of humeral selection system 1440 is selected to be half way between the humeral prosthetic component having the least offset and the humeral prosthetic component having the most offset. The position of applied load and the load magnitude at the position of applied load can be calculated by computer 162 from measurement data from measurement device 154 in real-time over a range of motion and displayed on display 164. In one embodiment, the surgeon or surgical team can use the measurement data to determine which humeral prosthetic component will best load the shoulder joint over different range of motions. Additional corrections or adjustments can be contemplated using the measurement data to improve the shoulder joint after the selection process has been completed and the selected final glenoid prosthetic component and the final humeral prosthetic component are installed.

After completing the selection process, the final glenoid prosthetic component and the final humeral prosthetic component are installed in the final shoulder joint. In one embodiment, a liner from the final humeral prosthetic component is removed. The liner provides a bearing surface to the final glenoid prosthetic component to support movement of the final shoulder joint. In one embodiment, measurement device 154 is also configured to replace the liner in the final humeral prosthetic component. Measurement data in a final shoulder joint is generated and sent to computer 162 and displayed on display 164. The measurement data from the final shoulder joint can be used to verify the measurement data from the selection process. The measurement data form the final shoulder joint can also be used to make further adjustments or changes to the final shoulder joint that improves reliability or performance of the final shoulder joint. Measurement device 154 is then removed from the final humeral prosthetic component and the liner is replaced to complete the rTSA FIGS. 1-56 will be discussed herein below. Although each figure may not be called out directly, components within each figure may be disclosed. It is understood that the description of a component as described herein will apply to the component wherever it is disclosed in the specification. A selection system 1512 is disclosed herein that is configured to couple within a joint of the musculoskeletal system. In the example, selection system 1512 is coupled with a shoulder joint prior to a selection of at least one shoulder prosthetic component. Selection system 1512 is configured to generate measurement data used to support the selection of the at least one shoulder prosthetic component. In the example, selection system 1512 is provided for a rTSA (reverse total shoulder arthroplasty). The system disclosed herein can be adapted for a TSA (total shoulder arthroplasty). In one embodiment, the measurement device in the TSA would be couple to the humerus similar to the rTSA. Alternatively, selection system 1512 can comprise a sensored component coupled to the scapula, a sensored component coupled to a humerus, or both. Selection system 1512 transmits measurement data from sensors to a computer 162 having a display 164 for providing the measurement data in real-time to a surgeon or surgical team. In the rTSA example, measurement device 154 has an external curved surface configured to receive a sphere or hemisphere. Conversely, the measurement device for the TSA could be an external curved surface shaped like a sphere or hemisphere.

A surgical shoulder system is disclosed herein that is used before the installation of the TSA or the rTSA. The surgical shoulder system includes a selection system 1512 includes a measurement device 154 that is placed in the shoulder joint to generate measurement data in real-time. Selection system 1512 comprises at least one glenoid component and a humeral selection system 1440. In one embodiment, a plurality of glenoid components can be provided for a selection process. Selection system 1512 is configured to couple within a shoulder joint prior to an installation of the shoulder joint prosthetic components. Selection system 1512 supports movement of the shoulder joint. Selection system 1512 is configured to generate measurement data during the selection process to support the selection of at least one prosthetic component to be installed in the shoulder joint. The measurement data from selection system 1512 is transmitted to a computer 162 within the operating room. The computer 162 can include one or more software programs for processing the measurement data and a graphical user interface on a display 164 for reviewing the measurement data in real-time to the surgeon or surgical team.

In general, a plurality of glenoid components is provided in selection system 1512. The plurality of glenoid components can comprise glenoid spheres, glenoid hemispheres, or glenoid partial spheres. In the example, the plurality of glenoid components can comprise glenoid components 1200, 1220, 1240, and 1260. Glenoid components 1200, 1220, 1240, and 1260 have different center of rotations or different glenosphere thickness. In one embodiment, glenoid components 1200, 1220, 1240, and 1260 can have lateral support 1524 similar to glenoid component 1526. In one embodiment, glenoid components 1200, 1220, 1240, and 1260 can include a through hole to pin glenoid components 1200, 1220, 1240, and 1260 to the scapula. In one embodiment, the glenoid components can comprise at least one glenoid sphere. Glenoid components 1200, 1220, 1240, and 1260 can be coupled to the scapula with a screw or pin. Glenoid components 1200, 1220, 1240, and 1260 can be provided respectively with stems 1202, 1222, 1242, and 1262.

In general, a ring 1350 and a measurement device 154 are provided in selection system 1512. Ring 1350 is configured to couple to a bone of the musculoskeletal system and retain measurement device 154 during the selection process. In the example, humeral selection system 1440 comprises a ring 1350 and measurement device 154. Ring 1370 can also be provided in humeral selection system 1440. Ring 1370 is used in conjunction with canal rod 1520 that is used to stabilize, align, and retain ring 1370 to the humerus. In the example, ring 1350 couples to the humerus. Ring 1350 can be temporarily coupled to bone by nails 1508 or screwed to the bone. Measurement device 154 is coupled to ring 1350. Ring 1350 includes a retaining structure 1354 configured to retain measurement device 154 during the selection process. A bottom surface of measurement device 154 is co-planar to a bottom surface of ring 1350 when coupled together. As mentioned previously, the humerus is resected at a predetermined angle having a planar surface. The bottom surface of ring 1350 couples to the planar surface of the humerus. Similarly, the bottom surface of measurement device 154 is coupled to the planar surface of the humerus when coupled to ring 1350.

Selection system 1512 placed in the shoulder joint comprises a glenoid component coupled to the scapula and a humeral selection system 1440 coupled to the humerus. The curved surface of the glenoid component is configure to couple to external curved surface 224 of measurement device 154 to support movement of the shoulder joint. Measurement device 154 includes electronic circuitry and one or more sensors to measure one or more parameters. In one embodiment measurement device 154 has three sensors located at radial positions relative to an external curved surface. Measurement device 154 further includes an IMU and electronic circuitry couple to the three sensors. The electronic circuitry is configured to control a measurement process and transmit measurement data. Measurement device 154 transmits measurement data to computer 162 during the selection process. Computer 162 is configured to receive measurement data from measurement device 154. Computer 162 processes the measurement data. A display 164 couples to computer 162 in the operating room during surgery for viewing measurement data in real-time for use by a surgeon or surgical team to support a selection of at least one prosthetic component for the shoulder joint. Computer 162 uses the measurement data to calculate position of the humerus, a position of applied load to measurement device 154, and the load magnitude at the position of applied load to measurement device 154. Selection system 1512 in the shoulder joint can be moved through a range of motion to see how the shoulder joint is loaded.

In the example, a final humeral prosthetic component is selected for the rTSA during the selection process. Two humeral prosthetic components are being selected in the example, an in-lay humeral prosthetic component or an on-lay humeral prosthetic component. More than two humeral prosthetic components can be chosen from for the selection. In general, the two humeral prosthetic components are provided having two different offsets. In the example, the in-lay humeral prosthetic component 1298 has an offset of 10 millimeters. The on-lay humeral prosthetic component 1340 has an offset of 20 millimeters. The 10 millimeter and 20 millimeter offsets respectively of in-lay humeral prosthetic component 1298 and on-lay humeral prosthetic component 1340 are correspond to the extreme offsets of the prosthetic components being selected. The resection of the humerus and the installation of ring 1350 and measurement device to the humerus is designed to have a predetermined offset in the shoulder joint. In general, the predetermined offset is between the extreme offsets of the prosthetic components being selected. In the example, the predetermined offset is between 10 and 20 millimeters. In one embodiment, the predetermined offset of the resection with ring 1350 and measurement device 154 installed is 15 millimeters or half way between the offset extremes of the prosthetic components being selected. Measurement data is generated with selection system 1512 in the shoulder joint. In general, a first prosthetic component is selected if selection system 1512 measures above a predetermined threshold. Conversely, a second prosthetic component is selected if selection system 1512 measures below the predetermined threshold. As previously mentioned, measurement device 154 measures a load magnitude applied by the glenoid component to external curved surface 224 of measurement device 154. In the example, the predetermined threshold is a force or a load applied to the measurement device 154. In the example, the predetermined threshold is 20 lbs. In one embodiment, a range can be used to determine the prosthetic component being selected. For example, measurement data from measurement device 154 within a range of 0-20 lbs. supports the selection of on-lay humeral prosthetic component 1340. Conversely, measurement data from measurement device 154 with a range of 20-40 lbs. supports a selection of in-lay humeral prosthetic component 1298. The shoulder joint can be further optimizing by changing the glenoid component. For example, a surgeon can increase or decrease loading applied to measurement device 154 by selecting from glenoid components 1200, 1220, 1240, and 1260 during the selection process.

The selection process results in a final glenoid component and a final humeral prosthetic component being selected for installation in the shoulder joint. As previously mentioned at least one of the final glenoid component or the final humeral prosthetic component is selected using measurement data from measurement device 154 during the selection process. In one embodiment, the final glenoid prosthetic component and the final humeral prosthetic component are installed in a final shoulder joint. The final humeral prosthetic component has a liner that has a bearing surface to support movement of the final shoulder joint. In on embodiment, the liner is removed from the final humeral prosthetic component. Alternatively, a humeral tray and the liner can be removed from the final humeral prosthetic component. Measurement device 154 is then coupled to the final humeral prosthetic component and measurement data generated for the final shoulder joint. In one embodiment, the measurement data generated with the final prosthetic components is verified against the measurement data generated with selection system 1512. In one embodiment, further adjustments can be made to the final shoulder joint to optimize the installation. Measurement data generated by measurement device 154 with the final prosthetic components is used to measure the optimization in real-time. Measurement device 154 is removed after the verification or optimization is completed. The liner can then be reinstalled to the final humeral prosthetic component, the final shoulder joint reassembled, and the wound sealed to complete the shoulder joint surgery.

Selection system 1512 is configured to support selection of at least one shoulder prosthetic component during surgery. Selection system 1512 comprises at least one glenoid component, a ring 1350, and measurement device 1370. Ring 1350 is configured to couple to a bone of a shoulder joint. Measurement device 154 has a plurality of sensors located at radial positions relative to an external curved surface 224 of measurement device 154. Measurement device 154 is configured to couple to ring 1350. Selection system 1512 generates measurement data configured to support the selection of the at least one shoulder prosthetic component during surgery. Measurement data from measurement device 154 is transmitted to computer 162. Display 164 is configured to couple to computer 162. In one embodiment, computer 162 and display 164 are in the operating room where the shoulder surgery is being performed to provide the measurement data in real-time to a surgeon or a surgical team. Computer 162 is configured to process the measurement data and display the measurement data on display 164.

In general, ring 1350 is configured to couple to a bone of the musculoskeletal system for retaining measurement device 154. In the example ring 1350 couples to a humerus. In one embodiment, the humerus is resected leaving a planar surface 1506 for receiving ring 1350. Ring 1350 can be held to the humerus by nails 1508 or screws. Alternatively, ring 1370 can be coupled to the humerus. Ring 1370 can be coupled to the humerus with nails 1508 and canal rod 1520. Canal rod 1520 stabilizes, aligns, and retains ring 1370 to the humerus. Measurement system 154 couples to ring 1350. In one embodiment, rings 1350 or 1370 have at least one retaining feature. The at least one retaining feature is configured to retain measurement system 154 to ring 1350 or 1370. In one embodiment, a bottom surface of ring 1350 is co-planar to a bottom surface of measurement device 154 when coupled and retained. In the example of the resected humerus with planar surface 1506, the bottom surface of ring 1350 and the bottom surface of measurement device 154 will both couple to planar surface 1506.

At least one glenoid component is used in selection system 1512. The glenoid component can be a glenoid sphere, glenoid hemisphere, or a glenoid partial sphere. In the example, glenoid components 1200, 1220, 1240, and 1260 are included with selection system 1512. Glenoid components 1200, 1220, 1240, and 1260 have different center of rotations or different glenosphere thickness or height. In one embodiment, glenoid components 1200, 1220, 1240, and 1260 can have lateral support 1524 similar to glenoid component 1526. In one embodiment, glenoid components 1200, 1220, 1240, and 1260 can include a through hole to pin glenoid components 1200, 1220, 1240, and 1260 to the scapula. In one embodiment, the glenoid components can comprise at least one glenoid sphere. Glenoid components 1200, 1220, 1240, and 1260 can be coupled to the scapula with a screw or pin. Glenoid components 1200, 1220, 1240, and 1260 can be provided respectively with or without stems 1202, 1222, 1242, and 1262. Glenoid components 1200, 1220, 1240, and 1260 can be readily changed during the selection process to improve loading, range of motion, and geometry of the shoulder joint.

In one embodiment, selection system 1512 is configured to generate quantitative measurement data to support the selection of at least one prosthetic shoulder component during shoulder surgery. In the example, selection system 1512 is configured to rapidly determine if an in-lay humeral prosthetic component 1298 having a first offset 1314 (10 millimeters) or an on-lay humeral prosthetic component 1340 having a second offset 1334 (20 millimeters) is suited for placement within the shoulder joint. Humeral selection system 1440 coupled to the humerus has a predetermined offset. The predetermined offset is chosen to be between the highest and lowest offsets of a plurality of humeral prosthetic components being provided for the shoulder surgery. In the example, the predetermined offset of humeral selection system 1440 is between the first offset 1314 and the second offset 1334 respectively of in-lay humeral prosthetic component 1298 and on-lay humeral prosthetic component 1340. In on embodiment, the predetermined offset is set half way between the extreme offsets such as 15 millimeters in the example. In one embodiment, the measurement data from measurement device 154 includes the position of the humerus, the position of applied load to external curved surface 224 of measurement device 154, and the load magnitude at the position of applied load to external curved surface 224 of measurement device 154. The measurement data is received by computer 162 and displayed on display 164 for viewing by the surgeon or surgical team. A predetermined threshold can be used to indicate a selection of a prosthetic component. Computer 162 can compare the measurement data from measurement device 154 to the predetermined threshold. The predetermined threshold can be determined by clinical studies of previous shoulder joint installations. In general, measurement data above the predetermined threshold indicates a selection of a first prosthetic component whereas measurement data below the predetermined threshold indicates a selection of a second prosthetic component. In the example, the predetermined threshold is a load value in which in-lay humeral prosthetic component 1298 is selected if the load value from measurement device 154 is above the predetermined threshold and on-lay humeral prosthetic component 1340 is selected if the load value from measurement device 154 is below the threshold. For example, the predetermined threshold can be 20 lbs. of loading based on clinical trials. The predetermined threshold corresponds to a load magnitude at the position of applied load to external surface 224 of measurement device 154. As mentioned previously, selection system 1512 supports movement of the shoulder joint and generates measurement data over a range of motion in real-time. The selection process can also be reviewed over a range of motion where many load values are measured over the range of motion of selection system 1512. The predetermined threshold can be expanded to a range to support selection of one prosthetic component over the other. In the example, on-lay humeral prosthetic component is selected if the measurement data from measurement device 154 is within a range of 0-20 lbs. The in-lay humeral prosthetic component is selected if the measurement data from measurement device 154 is within a range of 20 to 40 lbs. The ranges could be used over a range of motion. Measurement data greater outside the range could require an adjustment or a change in geometry of the shoulder joint by changing the glenoid component in selection system 1512 to a glenoid component with a different center of rotation or glenosphere thickness thereby increasing or decreasing the measurement data or range of motion.

In general, measurement device 154 is placed directly on, within, or above a resected humeral osteotomy in order to simulate different humeral offsets associated with different humeral implant types, such as an in-lay or on-lay humeral stem. Alternatively, if multiple stem options are available, the measurement device 154 can be provided in an offset that is directly between the offsets of the 2 prosthesis design styles and used to assess joint tensioning so that the assessment can inform the surgeon if they want to select an in-lay/inset style humeral stem or an on-lay/on-set humeral stem style, as each prosthesis prepares the bone differently and are not forward or backwards compatible. This can be achieved by attaching with a humeral selection system 1440. For example, a ring 1350 or 1370 with fixation spikes can be secured to the bottom of measurement device 154 to couple to the humeral osteotomy. The surgeon then performs a baseline joint tissue assessment. In one embodiment, the surgeon can select to use a humeral stem design with less inherent offset such as the in-lay/inset style humeral component if the quantified load is above a predetermined threshold. Conversely, the surgeon can select a humeral stem design style with more inherent offset such as an on-lay/on-set style humeral component if the quantified load is less than the predetermined threshold. It should be noted that if additional fixation is required for this sensor, the modular fixation ring which couples to measurement device 154 can also include a stem portion to help maintain its position during this baseline assessment. In one embodiment, a modular stem portion aligns with the position of the eventual or final humeral stemmed implant. In one embodiment, the selected final humeral stemmed implant will not require any additional bone cutting when replacing the trial system configured for measurement. In on embodiment, a small bone reamer can inset measurement device 154 to provide alternative baseline tensioning assessments. In one embodiment, measurement data can be generated without glenoid preparation, with a use of an instrument that would couple under the inferior glenoid rim and mate with measurement device 154. In one embodiment, measurement device 154 can be used after glenoid preparation. The surgeon can operate on the glenoid component first and install a glenosphere or a glenosphere trial as it may be advantageous to do so if the patient has medial glenoid wear and the glenoid needs to be bone grafted first or have an augmented baseplate and glenosphere secured to make this assessment. In one embodiment, measurement device 154 is used later in the procedure as a final assessment during the trial reduction as a surrogate for the final implant. In doing so, the same measurement device is used at the beginning and end of the procedure to first inform the baseline tension of the patient and at the end to validate the tension of the reconstructed joint with the appropriately selected rTSA prosthesis design, given that patients unique requirements for boney morphology, soft tissue tension, and overall joint stability/mobility.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does not yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact measurement device or surgical apparatus may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A method, comprising:
   performing a resection of a first bone of a shoulder joint of a patient to produce a resected surface;
   coupling a coupling device directly to the resected surface,
      wherein the coupling device is coupled to the resected surface using at least one of at least one nail or at least one screw;
   coupling a prosthetic device to a second bone of the shoulder joint,
      wherein the second bone is opposite the first bone;
   coupling a measurement device directly to the coupling device,
      wherein the measurement device includes an external surface that is configured to articulate with the prosthetic device;
   moving the shoulder joint through a range of motion,
      wherein the measurement device measures at least one force within the shoulder joint while the shoulder joint is moved through the range of motion; and
   selecting at least one of (a) the prosthetic device that is coupled to the second bone of the shoulder joint or (b) a further prosthetic device configured to be coupled to the first bone of the shoulder joint based at least on the measured at least one force.

2. The method of claim 1, wherein the coupling device comprises a ring.

3. The method of claim 2, wherein a bottom surface of the ring is co-planar to a bottom surface of the measurement device when the measurement device is coupled to the coupling device.

4. The method of claim 1, wherein the measurement device comprises a plurality of sensors located at radial positions relative to an external curved surface.

5. The method of claim 1, wherein the prosthetic device is selected if the measured at least one force is above a predetermined threshold, and wherein the further prosthetic device is selected if the measured at least one force is below the predetermined threshold.

6. The method of claim 1, wherein the prosthetic device is selected if the measured at least one force is below a predetermined threshold, and wherein the further prosthetic device is selected if the measured at least one force is above the predetermined threshold.

7. The method of claim 6, wherein the prosthetic device is an on-lay humeral prosthetic component, and wherein the further prosthetic device is an in-lay humeral prosthetic component.

8. The method of claim 7, wherein the predetermined threshold is 20 pounds.

9. The method of claim 1, wherein the first bone is a humerus.

10. The method of claim 1, wherein the step of coupling the coupling device directly to the resected surface further comprises coupling the coupling device to the resected surface using a canal rod.

11. The method of claim 1, further comprising:
    removing the measuring device from the coupling device;
    coupling a liner to the coupling device; and
    placing the measuring device in the joint to record verification data.

* * * * *

UNITED STATES PATENT AND TRADEMARK OFFICE
CERTIFICATE OF CORRECTION

PATENT NO. : 11,992,424 B2  
APPLICATION NO. : 16/951771  
DATED : May 28, 2024  
INVENTOR(S) : Chris Roche et al.

Page 1 of 1

It is certified that error appears in the above-identified patent and that said Letters Patent is hereby corrected as shown below:

On the Title Page

Item (73) (Assignees), Line 1 (Residence of 1st Assignee), Delete "Mahwa," and insert --Mahwah--.

Signed and Sealed this
Twenty-second Day of July, 2025

Coke Morgan Stewart
*Acting Director of the United States Patent and Trademark Office*